(12) United States Patent
Chudy et al.

(10) Patent No.: US 11,756,669 B2
(45) Date of Patent: *Sep. 12, 2023

(54) SYSTEM AND APPARATUS FOR ITEM MANAGEMENT

(71) Applicant: CHUDY GROUP, LLC, Powers Lake, WI (US)

(72) Inventors: Duane S. Chudy, Lincolnshire, IL (US); Larry Montgomery, Butternut, WI (US); James Spernow, Grayslake, IL (US)

(73) Assignee: Chudy Group, LLC, Powers Lake, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,679

(22) Filed: May 3, 2022

(65) Prior Publication Data

US 2022/0270743 A1    Aug. 25, 2022

Related U.S. Application Data

(63) Continuation of application No. 17/117,512, filed on Dec. 10, 2020, now Pat. No. 11,348,675, which is a
(Continued)

(51) Int. Cl.
*G16H 20/60* (2018.01)
*G07F 17/00* (2006.01)
(Continued)

(52) U.S. Cl.
CPC ............ *G16H 20/60* (2018.01); *A61J 7/0069* (2013.01); *B65B 5/04* (2013.01); *B65G 1/02* (2013.01);
(Continued)

(58) Field of Classification Search
CPC .. G06F 19/3462; G06F 17/00; G06F 19/3475; A61J 7/0069; A61J 7/04;
(Continued)

(56) References Cited

U.S. PATENT DOCUMENTS

| 4,685,271 A | 8/1987 | Ringer et al. |
| 4,695,954 A | 9/1987 | Rose et al. |

(Continued)

FOREIGN PATENT DOCUMENTS

| CA | 2609055 | 12/2006 |
| CA | 2628789 | 8/2009 |

(Continued)

OTHER PUBLICATIONS

"Bastian Material Handling, LLC, Indianapolis. Indiana, www.bastiansolutions.com. "Controls and Automation Interfaces" brochure. 11 pages. Date: Undated."

(Continued)

*Primary Examiner* — Michael Collins
(74) *Attorney, Agent, or Firm* — Myers Bigel, P.A.

(57) ABSTRACT

Item-management systems, apparatus, and methods are described, preferably for management of items such as medicaments. In embodiments, an item-management system comprises a container defining plural cells, a docking station configured to receive the container, sources of visible information to indicate the cell(s) into which an item is to be loaded, and at least one controller operable to control the visible information sources to indicate the cell into which the item is to be received.

16 Claims, 95 Drawing Sheets

Related U.S. Application Data continuation of application No. 16/871,435, filed on May 11, 2020, now Pat. No. 11,264,124, which is a continuation of application No. 15/610,083, filed on May 31, 2017, now Pat. No. 10,650,921, which is a continuation of application No. 13/841,724, filed on Mar. 15, 2013, now Pat. No. 9,672,327, which is a continuation-in-part of application No. 13/766,092, filed on Feb. 13, 2013, now Pat. No. 9,002,510, which is a continuation of application No. 12/033,957, filed on Feb. 20, 2008, now Pat. No. 8,380,346.

(51) Int. Cl.

| | | |
|---|---|---|
| *A61J 7/00* | (2006.01) | |
| *G06Q 10/08* | (2023.01) | |
| *G07F 11/62* | (2006.01) | |
| *G16H 20/13* | (2018.01) | |
| *G06Q 50/22* | (2018.01) | |
| *B65G 1/02* | (2006.01) | |
| *G06F 17/00* | (2019.01) | |
| *B65B 5/04* | (2006.01) | |
| *G16H 40/20* | (2018.01) | |
| *G16H 20/10* | (2018.01) | |
| *A61J 1/03* | (2023.01) | |
| *A61J 7/04* | (2006.01) | |

(52) U.S. Cl.
CPC ............ *G06F 17/00* (2013.01); *G06Q 10/08* (2013.01); *G06Q 50/22* (2013.01); *G07F 11/62* (2013.01); *G07F 17/0092* (2013.01); *G16H 20/10* (2018.01); *G16H 20/13* (2018.01); *G16H 40/20* (2018.01); *A61J 1/03* (2013.01); *A61J 7/04* (2013.01); *A61J 2205/10* (2013.01); *A61J 2205/20* (2013.01); *A61J 2205/60* (2013.01)

(58) Field of Classification Search
CPC ....... A61J 1/03; A61J 2205/10; A61J 2205/20; A61J 2205/60; G16H 20/10; G16H 40/20; G16H 20/60; G16H 20/13; G06Q 10/08; G06Q 50/22; G07F 11/62; G07F 17/0092; B65G 1/02; B65G 5/04; B65B 5/04
USPC ....... 700/242, 244, 231, 232, 236, 240, 243; 221/2, 5, 6
See application file for complete search history.

(56) References Cited

U.S. PATENT DOCUMENTS

| | | | |
|---|---|---|---|
| 4,763,810 A | 8/1988 | Christiansen | |
| 4,771,912 A | 9/1988 | Van | |
| 4,838,453 A | 6/1989 | Luckstead | |
| 5,408,443 A | 4/1995 | Weinberger | |
| 5,502,944 A | 4/1996 | Kraft et al. | |
| 5,915,589 A | 6/1999 | Lim | |
| 6,011,999 A | 1/2000 | Holmes | |
| 6,021,392 A | 2/2000 | Lester et al. | |
| 6,021,918 A | 2/2000 | Dumont et al. | |
| 6,102,855 A | 8/2000 | Kehr et al. | |
| 6,170,699 B1 | 1/2001 | Kim | |
| 6,294,999 B1 | 9/2001 | Yarin et al. | |
| 6,338,007 B1 | 1/2002 | Broadfield et al. | |
| 6,349,848 B1 | 2/2002 | Uema et al. | |
| 6,457,611 B1 | 10/2002 | Koehler | |
| 6,581,356 B2 | 6/2003 | Kim | |
| 6,658,322 B1 | 12/2003 | Frederick et al. | |
| 6,702,146 B2 | 3/2004 | Varis | |
| 6,705,487 B2 | 3/2004 | Kim | |
| 6,762,681 B1 | 7/2004 | Danelski | |
| 6,779,663 B1 | 8/2004 | Pocsi | |
| 6,925,783 B1 | 8/2005 | Pearson | |
| 6,975,922 B2 | 12/2005 | Duncan et al. | |
| 6,994,409 B2 | 2/2006 | Godlewski | |
| 7,142,944 B2 | 11/2006 | Holmes et al. | |
| 7,177,721 B2 | 2/2007 | Kirsch et al. | |
| 7,178,688 B2 | 2/2007 | Naufel et al. | |
| 7,195,156 B2 | 3/2007 | Venema et al. | |
| 7,203,571 B2 | 4/2007 | Kirsch et al. | |
| 7,228,988 B2 | 6/2007 | Inamura | |
| 7,369,919 B2 | 5/2008 | Vonk et al. | |
| 7,472,526 B2 | 1/2009 | Pearson | |
| 7,515,981 B2 | 4/2009 | Ryznar et al. | |
| 7,516,848 B1 | 4/2009 | Shakes et al. | |
| 7,537,155 B2 | 5/2009 | Denenberg et al. | |
| 7,587,878 B2* | 9/2009 | Kim | A61J 7/0069 53/51 |
| 7,657,344 B2 | 2/2010 | Holmes et al. | |
| 7,779,614 B1 | 8/2010 | McGonagle et al. | |
| 7,809,470 B2 | 10/2010 | Shoenfeld | |
| 7,818,950 B1 | 10/2010 | McGonagle et al. | |
| 7,848,846 B2 | 12/2010 | Uema et al. | |
| 7,856,794 B2 | 12/2010 | Zieher | |
| 7,886,506 B2 | 2/2011 | Knoth et al. | |
| 7,922,037 B2 | 4/2011 | Ohmura et al. | |
| 7,946,101 B1 | 5/2011 | McGonagle et al. | |
| 7,950,202 B2 | 5/2011 | Kodama et al. | |
| 7,971,414 B1 | 7/2011 | McGonagle et al. | |
| 7,997,417 B2 | 8/2011 | Saether | |
| 8,261,939 B2 | 9/2012 | Knoth | |
| 8,301,294 B1 | 10/2012 | Shakes et al. | |
| 8,380,346 B2 | 2/2013 | Chudy et al. | |
| 8,744,620 B2 | 6/2014 | Shavelsky et al. | |
| 9,002,510 B2 | 4/2015 | Chudy | |
| 9,477,816 B2 | 10/2016 | Dent et al. | |
| 9,626,822 B2* | 4/2017 | Yuyama | G07F 11/004 |
| 9,672,327 B2* | 6/2017 | Chudy | A61J 7/0069 |
| 10,621,306 B2 | 4/2020 | Dent et al. | |
| 10,650,921 B2* | 5/2020 | Chudy | G16H 20/60 |
| 11,264,124 B2* | 3/2022 | Chudy | G16H 20/60 |
| 11,348,675 B2* | 5/2022 | Chudy | G07F 17/0092 |
| 2003/0057231 A1* | 3/2003 | Kim | G07F 17/0092 221/92 |
| 2004/0129716 A1* | 7/2004 | Naufel | G07F 11/62 221/9 |
| 2004/0134043 A1 | 7/2004 | Uema et al. | |
| 2005/0145644 A1 | 7/2005 | Mori et al. | |
| 2006/0021900 A1 | 2/2006 | Feodoroff | |
| 2006/0184271 A1 | 8/2006 | Loveless | |
| 2007/0073560 A1 | 3/2007 | Walker et al. | |
| 2009/0014461 A1 | 1/2009 | Omura et al. | |
| 2009/0044489 A1 | 2/2009 | Siegel | |
| 2009/0120042 A1* | 5/2009 | Zieher | B65B 35/06 53/494 |
| 2009/0152291 A1* | 6/2009 | Ohmura | G07F 17/0092 221/197 |
| 2009/0188937 A1 | 7/2009 | Kim | |
| 2009/0281657 A1 | 11/2009 | Gak et al. | |
| 2012/0209422 A1 | 8/2012 | Wagner | |
| 2013/0126545 A1 | 5/2013 | Chudy et al. | |
| 2013/0158706 A1 | 6/2013 | Chudy et al. | |
| 2013/0319902 A1 | 12/2013 | Tufi | |
| 2014/0261883 A1 | 9/2014 | Dent et al. | |
| 2017/0017775 A1 | 1/2017 | Dent et al. | |
| 2020/0342972 A1 | 10/2020 | Chudy et al. | |
| 2021/0090713 A1 | 3/2021 | Chudy et al. | |

FOREIGN PATENT DOCUMENTS

| | | |
|---|---|---|
| DE | 102006007136 | 12/2006 |
| EP | 1433457 | 6/2004 |
| EP | 2093722 A1 | 8/2009 |
| JP | 2007209600 A | 8/2007 |
| JP | 2007297066 A | 11/2007 |
| WO | 2004088463 A2 | 10/2004 |
| WO | 2006128443 A1 | 12/2006 |

(56) References Cited

FOREIGN PATENT DOCUMENTS

| WO | 2007091375 A1 | 8/2007 |
|---|---|---|
| WO | 2014159697 A1 | 10/2014 |

OTHER PUBLICATIONS

"Bastian Material Handling, LLC, Indianapolis, Indiana, www.bastiansolutions.com. Exacta Acculight "Pick to Light (PTL) Technology" from Bastian Material Handling. 6 pages. Date: Copyright 2008."

"Chudy Group, LLC, Powers Lake, WI. "The ATP-Series Automated Tablet Packaging Solutions" brochure. pp. 5 and 8. Date: Jul. 2010."

"European Search Report. EPO Application No. 09152723.4. Date: Jun. 16, 2009. 6 pages.".

"Innovative Picking Technologies, Inc., Ixonia, Wisconsin, www.ipti.net. "Pick-Max 2" brochure. 5 pages. Date: Undated."

"Innovative Picking Technologies, Inc., Ixonia, Wisconsin, www.ipti.net. IEcono-Pick." 2 pages. Date: Undated.

"Lighthouse Selection, LLC, Manchester, New Hampshire, www.lighthouseselection.com. web page. 2 pages. Date: Copyright 2006."

"Photograph of medicament loading device including medicaments. Date: 2007 and earlier."

"Photograph of medicament loading device not including medicaments. Date: 2007 and earlier."

"Tosho, Tokyo, Japan. "U2 Xana-4001 U2" brochure. Date: Undated. 4 pages."

"Warehouse Equipment, Inc., Elk Grove, Illinois, www.weinet.com. WEI Material Handling Solutions webpage. 1 page. Date: Copyright 2005."

\* cited by examiner

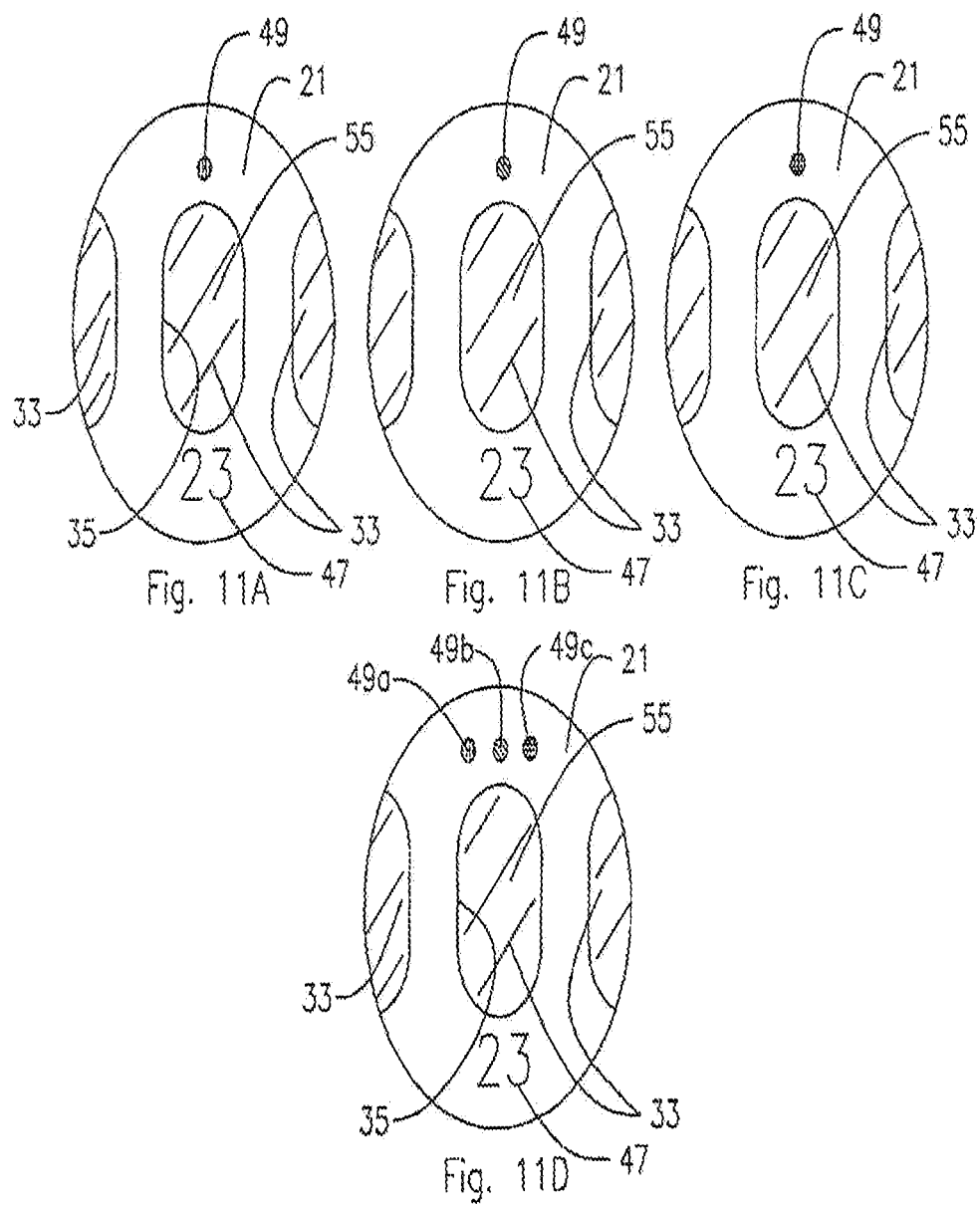

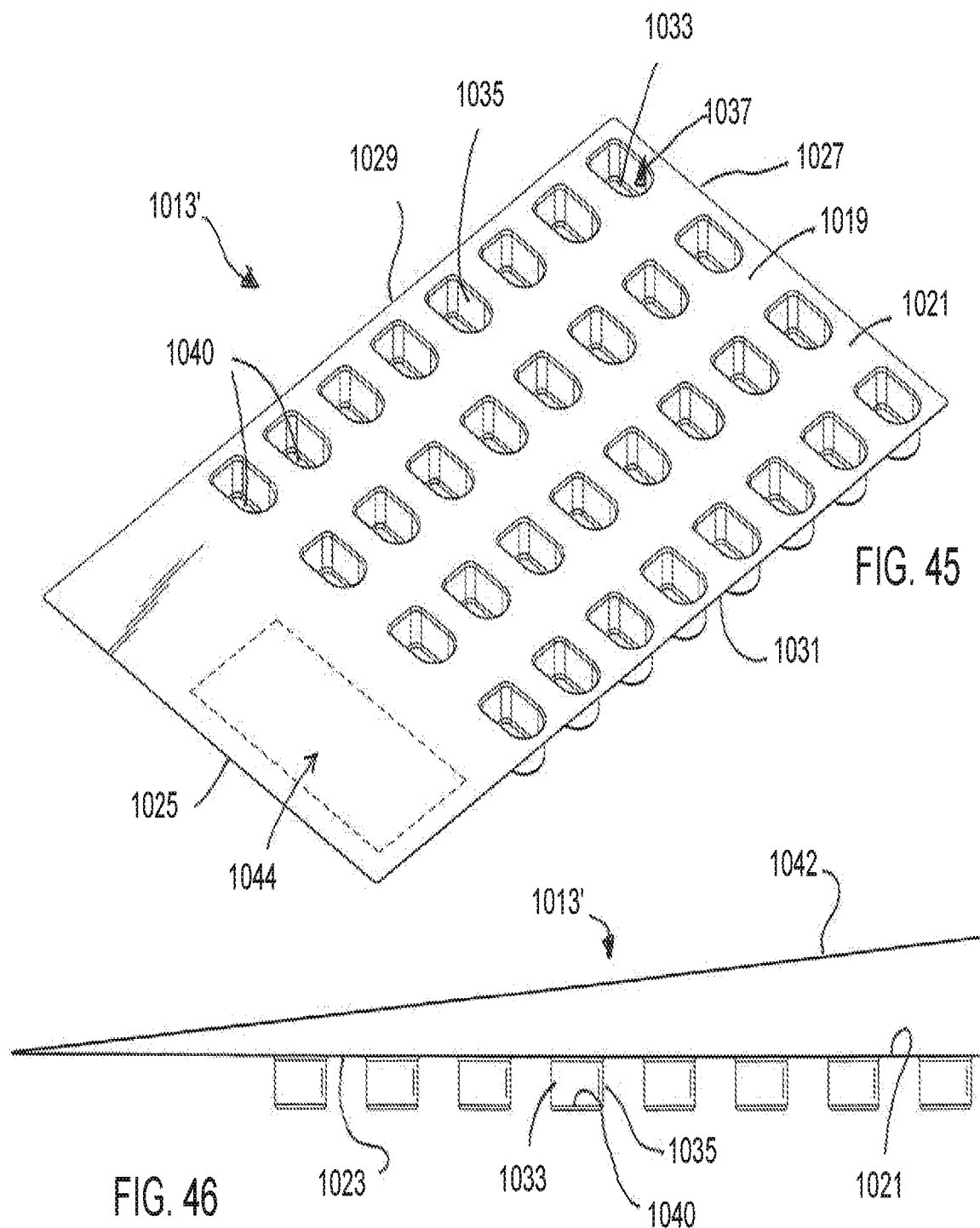

SYSTEM AND APPARATUS FOR ITEM MANAGEMENT

CROSS REFERENCE TO RELATED APPLICATIONS

This application is a continuation of and claims priority to U.S. patent application Ser. No. 17/117,512, filed Dec. 10, 2020, which is a continuation of and claims priority to U.S. patent application Ser. No. 16/871,435, filed May 11, 2020, now U.S. Pat. No. 11,264,124, which is a continuation of and claims priority to U.S. patent application Ser. No. 15/610,083, filed May 31, 2017, now U.S. Pat. No. 10,650,921, issued May 12, 2020, which is a continuation of and claims priority to U.S. patent application Ser. No. 13/841,724, filed Mar. 15, 2013, now U.S. Pat. No. 9,672,327, issued Jun. 6, 2017, which is a continuation-in-part of U.S. patent application Ser. No. 13/766,092, filed Feb. 13, 2013, now U.S. Pat. No. 9,002,510, issued Apr. 7, 2015 which is a continuation of U.S. patent application Ser. No. 12/033,957, filed Feb. 20, 2008, now U.S. Pat. No. 8,380,346, issued Feb. 19, 2013. U.S. patent application Ser. Nos. 13/841,724, 13/766,092 and 12/033,957 are incorporated herein by reference in their entirety to provide continuity of disclosure.

FIELD

The field relates generally to item management and, more particularly, to item management providing for improved efficiency in item distribution.

BACKGROUND

Personnel involved in handling of items are routinely required to manage and organize the items for delivery to an appropriate user or process. An item as used herein, means or refers to a separate article, object, or product. Care is required to ensure that the correct item is delivered to the user or process. Examples of such item-management tasks involve handling of medicament or nutriceutical items ultimately intended for use by a patient, consumer, or other user. A medicament means or refers to a medication product while a nutriceutical can represent a dietary supplement which provides health or medical benefits. (e.g., a vitamin, a mineral, or a supplement.)

Items such as medicaments and nutraceuticals are provided in various physical forms, such as solid or substantially solid forms, granular forms, gel forms, and liquid forms. Solid or substantially solid medicament and nutriceutical items may be shaped into small solid tablets in the physical form of capsules, spheres, ovals, disks, multiangles, squares, triangles, and ellipses. Gel, granular, or liquid-form items may be packaged in the form of small capsules and gel caps (for oral consumption), or ampules containing a liquid. Medicament and nutriceutical items may also be provided which differ in strength of the active chemical constituent. For example, a single medicament or nutriceutical item may be provided with a concentration of 1, 5, or 10 milligrams of the active chemical constituent.

One way in which the foregoing types of items are managed for delivery to the ultimate user is through automated dispensing machines. Automated dispensing machines are frequently utilized by pharmacies, hospitals, long-term care facilities, and others in the health-care field for purposes of automatically dispensing medicaments required to fulfill patient prescription orders and to dispense medicaments administered to patients in hospitals and long-term care facilities, such as nursing homes. Automated dispensing machines can also be used in retail distribution, such as to dispense nutriceutical or food items. Such automated dispensing machines are computer controlled to dispense an appropriate quantity of medicaments and, typically, to package the medicaments. And, automated dispensing machines can typically be programmed to dispense and package all medicaments required to fulfill all prescription orders and dispense requests for a given eight-hour work shift. The automated dispensing machine will proceed to automatically execute the instructions until all requested medicaments have been output.

Automated dispensing machines typically store and dispense a plurality of different medicament types. Medicaments which are frequently prescribed or utilized, referred to as "fast-moving" medicaments, are stored within the automated dispensing machines in large quantities as loose, bulk form items within cassettes, cells, canisters, magazines, racks, or other storage apparatus. A single medicament type is stored in each storage apparatus.

Medicaments which are less frequently prescribed or utilized are referred to as "slow-moving" medicaments. Medicament types which are infrequently required may be stored in the automated dispensing machine in what is referred to as an "exception storage apparatus," a type of storage apparatus which derives its name merely from being an alternative to the medicament storage apparatus used for the faster moving medicaments. Slow-moving medicaments could include medicament types with unusual chemical constituents or with unusual active-constituent concentrations. An exception storage apparatus stores small quantities of the less-frequently used medicaments which could not be efficiently stored in large bulk quantities. Unlike the cassettes, cells, canisters, magazines, racks, or other storage apparatus for the faster moving medicaments, more than one medicament type can be stored in a single exception storage apparatus.

An exception storage apparatus can be provided, for example, as a drawer, or as a tray-like device, which pulls out from the automated dispensing machine and which includes a plurality of medicament-holding cells, or compartments, for holding one medicament item or a small quantity of medicaments. In certain automated dispensing machine types, the cells of the exception storage apparatus are movable along a track. The cells can be indexed forward along the track toward an opening so that the cell contents fall serially (i.e., one-after-the-other) through a cell bottom opening for packaging by the machine. Any number of cells can be provided in the exception storage apparatus. For example, an exception storage apparatus could include 64 total cells grouped in four rows of 16 cells all movable along the track. More than one exception storage apparatus may be provided.

The exception storage apparatus offers the operator an opportunity to increase the range of dispensing options because more than one type of medicament can be stored in such storage apparatus. For example, the medicaments can be arranged in the exception storage apparatus to dispense medicaments for a particular patient according to the order in which the medicaments are to be taken by the patient (e.g., breakfast, lunch, and dinner) or can be loaded to meet the medicament requirements of more than one patient.

Upon activation, the automated dispensing machine automatically meters out from the appropriate storage apparatus the desired quantity of medicament(s) called for by the prescription order or dispense request. The medicament item or items are directed from the storage apparatus to the packaging apparatus by means of gravity through a chute or other guide apparatus, or by mechanical means such as an auger. The packaging device may then load the dispensed medicaments into one or more packages. The type of package utilized is based on the capability of the particular type of automated dispensing machine. By way of example only, automated dispensing machines may load the medicaments into containers such as vials, bottles, blister packages, or pouch packages. The medicament or medicaments, once packaged in the container type utilized by the automated dispensing machine, may then be delivered to the patient or other designated user.

Loading or replenishment of the cassettes, cells, canisters, or other storage apparatus for the fast moving medicaments is relatively easy. All that is required is placement of a loaded storage apparatus into the machine (e.g., in place of a depleted storage apparatus) or the pouring of a quantity of the bulk-form medicaments into a depleted storage apparatus.

However, loading or replenishment of the cells or compartments of the exception storage apparatus is more problematic because a human being must manually load or replenish the cells or compartments. In a pharmacy, hospital, or long-term care facility, the human is a pharmacy technician or a registered pharmacist. The technician or pharmacist must manually load the medicament items directly into the exception storage apparatus cells. Alternatively, the medicament items can be placed into the cells of a "loading device." A loading device is a device with cells or compartments that correspond to the cells of the exception storage apparatus. The loading device can be loaded at a workstation and carried to the automated dispensing machine so that the medicament contents of the loading device can be transferred into the appropriate cells of the exception storage device. By way of example only, a busy pharmacy might use dozens of different loading devices to load the exception storage apparatus during a given work shift.

The exception storage apparatus loading process is tedious and time consuming, irrespective of whether the medicament items are placed directly into the exception storage apparatus cells or are placed into the cells of a loading device for transfer to the exception storage apparatus. As can be appreciated, the loading process must be undertaken in a deliberate and considered manner to ensure that the correct medicament is placed in the correct cell or compartment. Placement of the correct medicament in the correct cell or compartment can be difficult because the cells or compartments of a typical exception storage apparatus or loading device are relatively small and are in close proximity to each other. The chance of an inadvertent error may be increased because certain medicaments have similar shapes, sizes, and appearances.

Typically, printed paper instructions are generated which direct the technician or pharmacist to place the required medicament into a designated cell or compartment. At a minimum, valuable time is required to follow the instructions. The instructions may require complex ordering of different medicament types among the cells raising the possibility, no matter how slight, that the wrong medicament could be placed in a cell or compartment. And, because the technician or pharmacist must take her eyes off the exception storage apparatus or loading device to read the instructions, and because the cells typically look alike, there is also a slight possibility that the wrong medicament item could be placed in the cell. And, since more than one loading device could be used by a pharmacy, there is a possibility, no matter how remote, that an incorrect loading device could be used to load the exception storage apparatus.

If a pharmacist is required to inspect a loading device or exception storage apparatus before use to verify that the medicaments were loaded correctly, then the pharmacist must essentially repeat the loading process to confirm that the correct medicament was received in the correct cell.

A skilled pharmacist's time is extremely valuable. Time spent loading an exception storage apparatus is time that could be spent counseling patients. And, an automated dispensing machine must typically be deactivated or taken "off line" in order to load the exception storage apparatus. Any time spent loading an exception storage apparatus can represent lost productive time in which the automated dispensing machine cannot be used to fulfill prescription orders or dispense requests, thereby decreasing efficiency and increasing costs to the operator.

Problems similar to those described for operators of automated medicament dispensing machines can exist for operators of other types of automated dispensing machines in which both fast and slow moving items must be dispensed from a single machine. For instance, the same issues would face the operator of an automated dispensing machine used to dispense nutriceutical products or other retail food products.

Problems identical to those described above exist with respect to loading of medicaments and other items into other types of containers with plural cells or compartments, particularly if different types of medicaments or items are to be loaded into the same container. Blister packages represent such a container into which plural medicaments or items may be loaded. A blister package is a type of pre-formed container used for holding medicaments, nutraceuticals, or other small goods and items.

The primary component of a blister package is a plurality of cells made from a thin web of formable material. Any number and arrangement of the cells can be provided. Each cell has an upper opening through which one or more item is placed in the cell. A closure of paperboard, or a seal of aluminum foil or plastic may be placed over all of the cells to close the blister package container. The closed blister package container is then ready for delivery to the patient.

Certain blister packages are referred to as push-through-packs. In a push-through-pack, the material in which the cells are formed is collapsible by pushing with a human finger. The seal is breakable so that the item within the cell can be pushed through the seal and out of the blister package container for use.

Blister packages may be used as compliance containers by printing the days of the week above each cell. Such an arrangement ensures that the medicaments may be taken one-after-another at the correct date and time.

A disadvantage of blister packages is that they cannot be easily used as compliance containers if more than one type of medicament is required to be in the container. This is because the blister package is typically loaded with the same type of medicament by means of a form-fill-seal machine.

To load the blister package with different types of medicaments in an order in which the medicaments are to be taken would require hand-loading by a human. Such a process would require use of instructions to determine which cell a medicament is to be placed into. Repeated manual tasks of hand-loading would be required to load different types of medicaments in a single blister package. From a human factors standpoint, such a process would be tedious and subject to potential error. Errors could occur, for example, because of the number of repetitive actions required, the look-alike nature of medicament-type items, and the look-alike nature of the cells. Any error in loading one or more cells of the blister package, for example with the wrong medicament, or the wrong medicament for the date and time of administration, could harm the patient and must be avoided.

An additional problem with any repetitive hand-loading of any container, including the aforementioned "loading devices" and blister packages, is the lack of any positive feedback confirming that the medicament or other item has been loaded into the correct cell. The aforementioned container-loading systems lack any type of feedback to instantaneously confirm and verify that the correct medicament or other item has been placed into the correct cell. Providing such feedback could help assure that the correct medicament is provided for the patient, thus overcoming some of the human-factors limitations of any hand-loading operation.

There is a need for an item-management system, apparatus and methods which would improve the item management and distribution process, which would facilitate more accurate item management and distribution, and which would reduce the time needed to manage items, thereby freeing personnel for other important tasks and improving the quality of care which can be offered.

SUMMARY

Item-management systems, apparatus and methods are described. The systems, apparatus, and methods facilitate management and organization of items, such as medicaments. The systems, apparatus, and methods may be used, for example, to ensure that the correct item is provided to a user or other process.

The systems, apparatus, and methods are described in the preferred context of management of medicament-type items but can have application with respect to management of other items, such as nutraceuticals.

In embodiments, a medicament-management system is provided. The system enables a pharmacy user to rapidly and accurately load medicament container cells with medicaments. The loading is preferably performed by hand-loading. A system may include one or more portable medicament containers, a docking station, indicators or visible information sources which communicate visible information to a user, and at least one controller.

In embodiments, the containers are portable medicament containers. Each container preferably has plural cells and each cell has a cell upper opening through which a medicament is hand-loaded. In an embodiment, the containers are used to transfer medicaments to an automated dispensing machine. In other embodiments, the container or containers may be blister packages.

In embodiments, a container may be temporarily docked at the docking station while being hand-loaded. A second of the containers is temporarily docked after the first container is removed from the docking station. The docking station may include circuitry enabling control of visible information proximate the cells indicating "yes" and "no" states of the cells.

If the container is a blister package, it is preferred that the docking station include structure into which the blister package nests when docked. In embodiments, the docking station may include cell-receiving pockets which receive the blister package cell walls to enable the nesting. Nesting may provide improved support for a container of a blister-package type.

In embodiments, the indicators communicate the visible information to the user. The "yes" state information indicates the cell into which the medicament is to be loaded. In embodiments, the visible information may be viewable directly on the docked container proximate the cells. In certain embodiments, the indicators may include light pipes. The indicators may radiate light. The indicators may include an energizable light source. The light source may be multi-colored and there may be plural indicators associated with each cell of the docked container.

In embodiments, a sensor guide may be provided to detect passage of a medicament toward a cell. A preferred sensor guide may be associated with the docking station and operably connected to the at least one controller. The sensor guide may having plural openings with an opening being associated with each cell. The detection may be implemented to detect whether the medicament is placed into an expected cell. The at least one controller may generate a signal alerting a user to a possible error if the medicament is placed in other than the expected cell.

BRIEF DESCRIPTION OF THE DRAWINGS

Exemplary item-management systems, apparatus, and methods may be understood by reference to the following description taken in conjunction with the accompanying drawings, in which like reference numerals identify like elements throughout the different views. For convenience and brevity, like reference numbers are used for like parts amongst the embodiments. The drawings are not necessarily to scale, emphasis instead being placed upon illustrating the principles of the invention. In the accompanying drawings:

FIGS. 11A-11C are enlarged fragmentary views of region 11 of FIGS. 3, 6, and 9 provided to illustrate an alternative indicator embodiment comprising a multi-colored lamp which may be used with the holders or guide of FIGS. 3, 6, and 9;

FIG. 11D is an enlarged fragmentary view of region 11 of FIGS. 3, 6, and 9 provided to illustrate a further alternative indicator embodiment comprising a tri-lamp indicator which may be used with the holders or guide of FIGS. 3, 6, and 9;

FIGS. 21A-21C show an exemplary sequence for loading the contents of the holder into the exception tray;

FIG. 45 is a perspective view of the exemplary holder of FIG. 37;

FIG. 46 is a side elevation view of the exemplary holder of FIG. 45;

Figure 1:
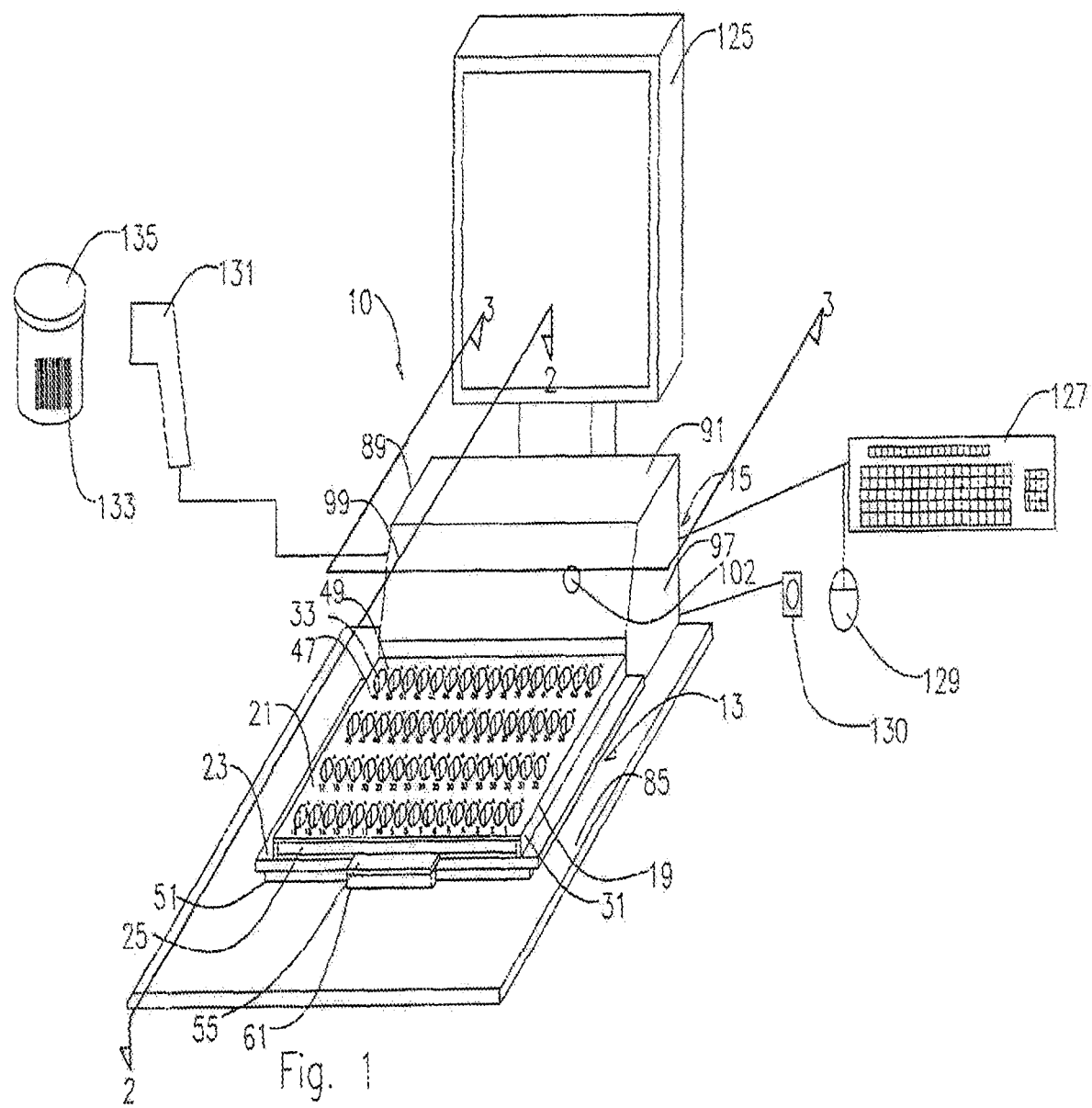
FIG. 1 is a perspective view of a representative holder docked at a docking station.

While the systems, apparatus, and methods are susceptible to various modifications and alternative forms, specific embodiments thereof have been shown by way of example in the drawings and are herein described in detail. It should be understood, however, that the description herein of specific embodiments and methods is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Referring first to FIGS. 1-9 and 12A, there are shown embodiments of an exemplary system 10 for management of items. The embodiments are described in the context of a preferred item-management system for management of medicament 11 items. System 10, preferably includes holder 13, docking station 15 to which holder 10 may be temporarily docked, and controller 17 which may include one or more controls capable of operating system 10. The term "at least one controller," therefore, means or refers to embodiments in which controller 17 includes one or more controller components. Controller 17 may include components internal and/or external to docking station 15. In a further exemplary system 10' (FIG. 12B), controller 17 is illustrated as being entirely within docking station 15. System 10 may be configured and arranged based on the needs of the pharmacy, hospital, long-term care facility or other operator. While it is envisioned that embodiments of system 10 or 10' will be utilized in the health-care industry, it should be understood that such systems and others may have application in fields outside of the health-care industry for dispensing of items other than medicaments 11.

Figure 5:
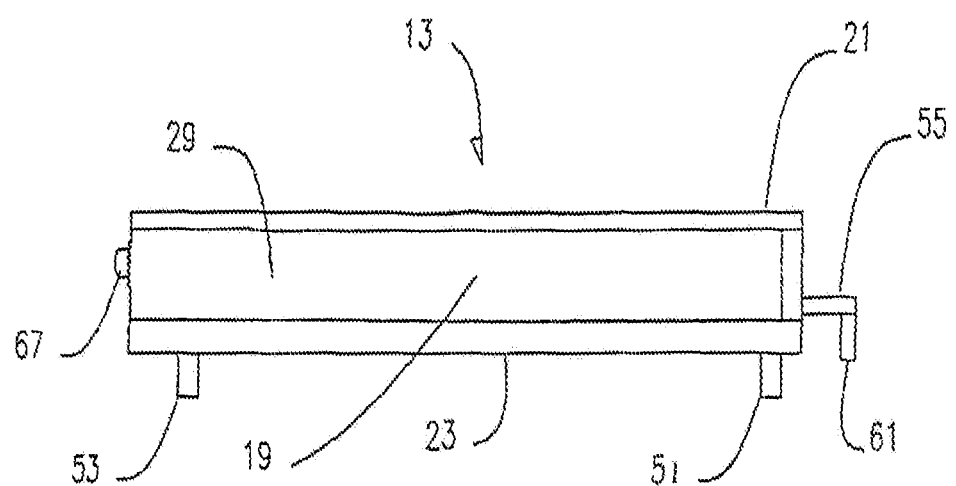
FIG. 5 is a left side elevation view of the representative holder of FIG. 1.
Figure 6:
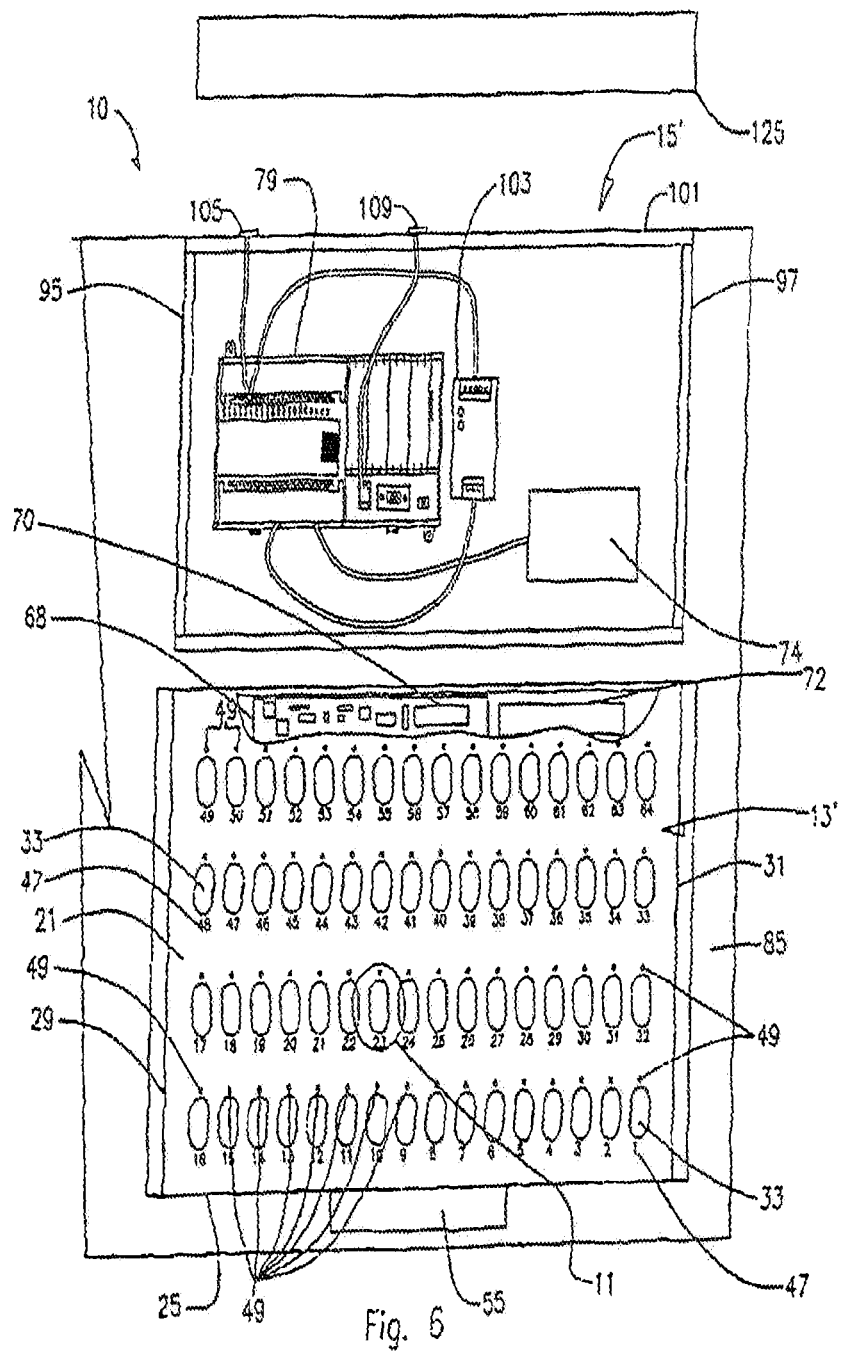
FIG. 6 is a schematic top sectional view of a representative wireless-type holder docked at a docking station taken along a section, such as section 3-3 of FIG. 1 with certain holder portions cut away to facilitate understanding.

Referring then to FIGS. 1-5, there is shown an exemplary holder 13 for managing and organizing medicaments. A further exemplary holder 13' is illustrated in FIG. 6. The word "holder" means or refers to apparatus which holds one or more items. Holder 13' is a wireless-type holder but is otherwise identical to holder 13. For simplicity and brevity, like reference numbers of holder 13 and docking station 15 are used to identify like parts of holder 13' and docking station 15' and the description of holder 13 and docking station 15 are incorporated by reference with respect to holder 13' and docking station 15'.

Exemplary holder 13, 13' has a tray-like appearance in that holder 13, 13' is a flat, shallow container used for carrying, holding, and organizing items which are preferably medicaments 11. However, other holder configurations may be utilized depending on the needs of the user.

For simplicity and brevity, like reference numbers of holder 13 and docking station 15 are used to identify like parts of holder 13' and docking station 15' and the description of holder 13 and docking station 15 are incorporated by reference with respect to holder 13' and docking station 15'.

Exemplary holder 13, 13' includes a body 19, a top and a bottom 21, 23, a front and a rear side 25, 27, and a left and a right side 29, 31. Holder 13, 13' further includes cells, of which cell 33 is representative. Each cell 33 is defined by a wall 35, of which wall 35 is representative. For purposes of simplicity and brevity, each cell 33 of holder 13, 13' is indicated by reference number 33 and each wall is indicated by reference number 35.

Each wall 35 defines a cell 33 upper opening, or inlet 37, and a cell lower opening, or outlet 39. As shown in the examples, the cell inlets 37 extend through, and are included in and along, the body top 21 while the cell outlets 39 extend through, and are included in and along, the body bottom 23. In the embodiments, medicaments 11 are loaded into each cell 33 through inlet 37 and are discharged from cell 33 through outlet 39 as described in detail below.

In the embodiments, each cell 33 is identical and, as noted, reference number 33 indicates each identical cell 33. However, it is possible that cells 33 of holder 13, 13' may have a structure which is not identical and which may differ depending on the needs of the user.

Referring to FIGS. 1-6 each exemplary holder 13, 13' shown includes sixty four total cells 33 organized into four rows of sixteen cells. In the examples, the organization of cells 33 is identical to the organization of cells 41 of exception storage apparatus 43 shown pulled out from automated dispensing machine 45 in FIGS. 18-21C. Exemplary holder 13, 13' is configured and arranged such that each cell 33 outlet 39 is in registry with (i.e., aligned with) a corresponding cell 41 of exception storage apparatus 43 permitting direct movement of medicaments 11 from holder 13, 13' into exception storage apparatus 43 as shown in the example of FIGS. 21A-21C. Holder top 21 is preferably provided with human-readable indicia 47 identifying each cell 33. In the examples, indicia 47 is an integer from 1 to 64 proximate each cell 33. Other types of indicia 47 may be used, such as alpha-numeric indicia.

Holder 13, 13' further includes at least one indicator 49 for each cell 33, of which indicator 49 is representative. For purposes of simplicity and brevity, each indicator of holder 13, 13' is indicated by reference number 49. An indicator 49 is located on holder 13, 13' top side 21 next to each cell 33. Each indicator 49 could be located inside body 19 if body is translucent. One indicator 49 is provided for each cell 33 for a total of sixty four indicators 49 in these examples. Each indicator 49 may be a visible indicator in the form of a selectively-operable lamp (i.e., an artificial light source). Energizing of each lamp-type indicator 49 indicates the cell 33 into which the medicament 11 or other item is to be loaded. Preferably, each indicator 49 is a light-emitting diode (LED), although it is envisioned that other types of lamp-type indicators 49 may be used.

Controller 17 is operable to selectively operate each indicator 49 when holder 13 is docked at docking station 15.

Selective operation of an indicator 49 proximate to a cell 33 prompts the technician or pharmacist to place each medicament 11 into the cell 33 associated with the activated indicator 49 or indicators 49. Collectively, the indicators 49 comprise a type of pick-to-light system. Thus, if a medicament 11 is to be loaded in the cells 33 designated by human-readable indicia 47 as cells 1, 3, 6, 9, 12, 15, 18, 21, 24, and 27, each of the indicators 49 next to such cells 33 may be activated communicating to the technician or pharmacist the specific cells 33 which should contain that medicament 11. Use of a pick-to-light system of indicators 49 advantageously communicates information to the technician or pharmacist without resort to a set of written instructions. A pick-to-light system is far superior to written instructions because the person responsible for loading or verification of holder 13, 13' need not take his or her eyes off of holder 13, 13' to read the instructions thereby increasing accuracy and reducing the time required to load or verify the medicaments 11 that should be in the holder 13, 13'.

As illustrated in yet a further embodiment illustrated in FIGS. 11A, 11B, and 11C, indicator 49 could comprise a single multi-colored indicator 49 for each cell 33. For example a multi-colored LED lamp could be used as indicator 49. As is known, changing the voltage to a multi-colored LED or selectively activating one of plural LED anodes causes the LED to emit a different color as represented in FIGS. 11A-11C. Each different color can be used to communicate a different type of information to the technician loading the holder 13, 13'. For example, a red color signal from indicator 49 (FIG. 11A) could indicate that one medicament 11 is to be loaded into that cell 33. A green-color signal from indicator 49 (FIG. 11B) could indicate that more than one medicament 11 is to be loaded in that cell 33. A yellow-color signal from indicator 49 (FIG. 11C) could indicate that a half-size medicament is to be loaded in that cell 33.

A further indicator 49 embodiment is illustrated in FIG. 11D. In the example of FIG. 11D, a plural-lamp indicator 49 could be provided for each cell 33 for purposes of communicating information to the technician or pharmacist. In FIG. 11D, a plural-lamp indicator 49 consisting of three lamps is provided adjacent each cell 33. Any number of lamps could be used. Each lamp of indicator 49 could, for example, consist of an LED lamp of a different color, such as red 49a, green 49b, or yellow 49c. Each color could indicate a different type of information as described in connection with the multi-colored LED example of FIGS. 11A-11C. Energizing of only the red-color indicator 49a could indicate that one medicament 11 is to be loaded into that cell 33. Energizing of only the green-color indicator 49b could indicate that more than one medicament 11 is to be loaded in that cell 33. Energizing of only the yellow-color indicator 49c could indicate that a half-size medicament is to be loaded in that cell 33. Alternatively, the lamps may all be of the same color and the number of activated indicator lamps 49 proximate each cell 33 could indicate the quantity of medicaments to be placed in each cell 33. Alternatively, the indicator 49 could have a blink pattern indicating the medicament 11 to be loaded into the cell 33. A constant blink could indicate that one medicament 11 is to be loaded into the cell, two blinks could indicate that more than one medicament 11 is to be loaded in that cell 33, and three blinks could indicate that a half-size medicament is to be loaded in that cell 33. Operation of the indicators 49 as described can also be used for verification of medicaments received in each cell 33.

Holder 13, 13' further includes a pair of legs 51, 53 depending from holder 13, 13' bottom side 23. Legs 51, 53 may be provided to support holder 13 on a surface (such as counter top 85). Referring to FIGS. 1 and 5, bottom side 23 may extend outwardly from holder sides 29, 31 for a purpose described below.

Referring to FIGS. 1-6 and 21A-21C, exemplary holder 13, 13' further includes a planar shuttle member 55 positioned in planar track 57 in holder proximate each cell 33 outlet 39. Shuttle member 55 includes openings 59 and a pull 61 which permits the technician or pharmacist to grasp shuttle member 55 with his or her hand and to pull or push shuttle member 55.

In the example, shuttle member 55 is movable between a first position in which shuttle member 55 covers and closes each cell 33 outlet 39 as shown in FIG. 21A and a further position in which the shuttle member 55 openings 59 are in alignment with each cell 33 outlet 39, thereby opening each cell outlet 39 permitting medicaments 11 to drop from each cell 33 into a corresponding cell of exception storage apparatus 43 as shown in FIG. 21C. The first position of shuttle member 55 is referred to herein as a "cell-closed position" and the further position of shuttle member 55 is referred to herein as a "cell-opened position." In between these positions, the cells 33 are partially open permitting medicaments to start to fall from cells 33 as shown in FIG. 21B.

In the embodiments, shuttle member 55 serves as a gate, opening and closing each cell 33 as shuttle member 55 moves between the cell-closed (FIG. 21A) and cell-opened positions (FIG. 21C). Shuttle member 55 thereby blocks each cell outlet 39 in the cell-closed position permitting a medicament 11 to be loaded into each cell 33 for organizing and storage and further opens each cell outlet 39 permitting each medicament 11 to be discharged from holder 13, 13' for loading into exception storage apparatus 43 as described below.

Figure 3:
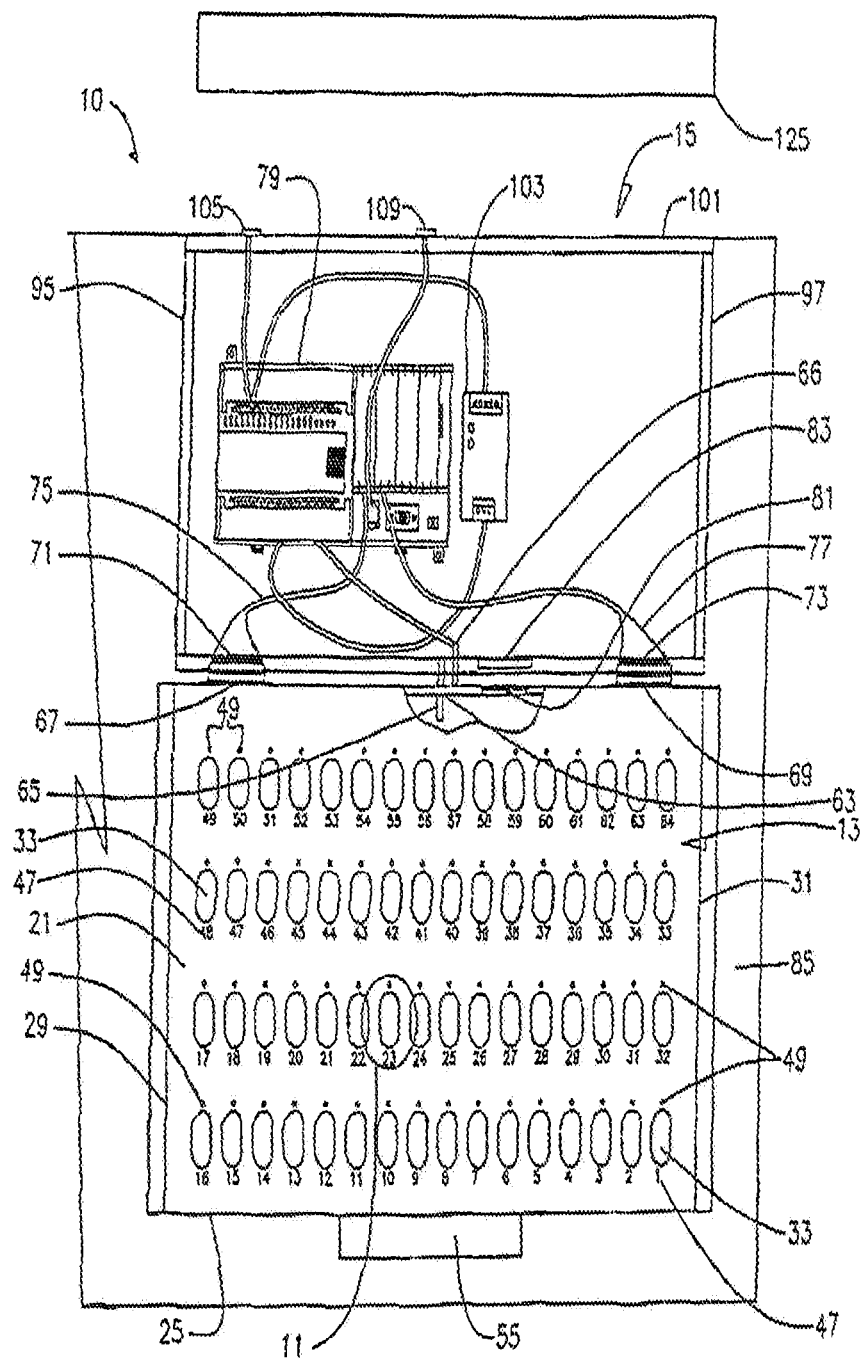
FIG. 3 is a schematic top sectional view of a representative holder docked at a docking station taken along section 3-3 of FIG. 1 with certain holder portions cut away to facilitate understanding.
Figure 4:
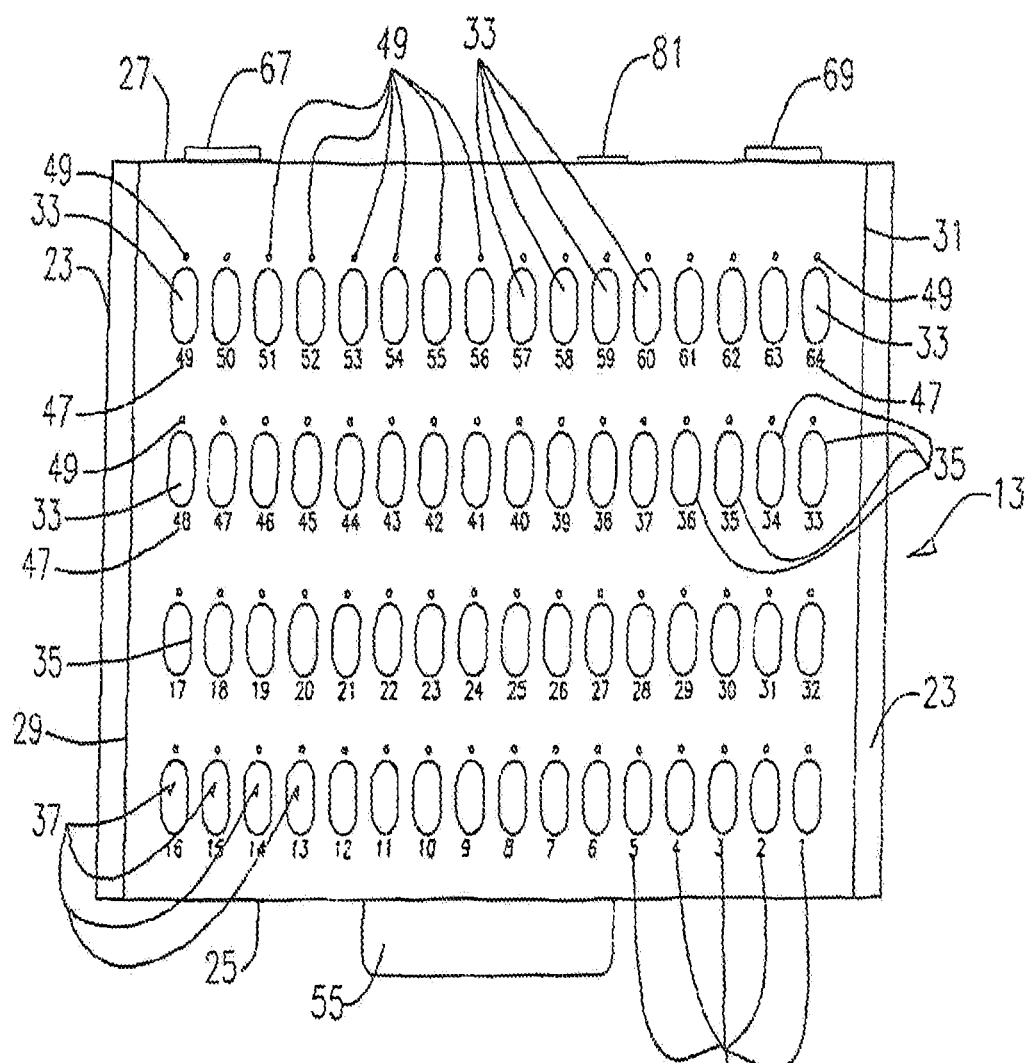
FIG. 4 is a top side view of the representative holder of FIG. 1.

Referring to FIG. 3, holder 13 and docking station 15 may include structure configured to enable or facilitate docking of holder 13 with docking station 15. In the embodiment, holder 13 is provided with a female alignment pin receiver 63 and docking station 15 is provided with a male alignment pin 65 which is inserted into and seated in receiver 63 when holder 13 is docked with docking station 15. The mechanical interconnection of receiver 63 and pin 65 properly locates holder 13 at docking station 15. A contact-switch-type proximity detector 66 may be provided to indicate to controller 17 that holder 13 is properly docked at docking station 15. Holder 13' and docking station 15' may be provided with receiver 63, pin 65, and detector 66.

FIGS. 1-5 and FIG. 6 are provided to show exemplary types of connections between a holder and a docking station. Referring first to FIGS. 1-5, an exemplary electro-mechanical connection between holder 13 and docking station 15 is shown. In the example, holder 13 body 19 is provided with a pair of electrical contacts 67, 69 permitting control over operation of indicators 49 through docking station 15 and controller 17. Two contacts 67, 69 are not required as any number of contacts will suffice. When holder 13 is properly docked with docking station 15, contacts 67, 69 are brought into operable connection with corresponding contacts 71, 73 on docking station. Contacts 71, 73 are connected by suitable electrical conductors 75, 77 to programmable logic controller 79 of controller 17. Contacts 67, 69 are operably connected to indicators 49 through appropriate conductors (not shown) permitting selective energizing and operation of indicators 49 to indicate the cell 33 into which each medicament 11 is to be loaded. Examples of representative contacts 67, 69, 71, 73 for a holder 13 with sixty four indicators 49 are Amplimite™ 37 position, size 4 HD-20 male and female contacts available from Tyco Electronics of Harrisburg, Pa.

Referring now to FIG. 6, the holder 13' embodiment shown therein includes structure enabling wireless connection between holder 13', docking station 15,' and controller 17. Holder 13' includes a control circuit board 68, with a wireless transmitter/receiver 70 powered by a battery 72 associated with holder 13'. Board 68 is operably connected to indicators 49 through appropriate conductors (not shown) permitting selective energizing and operation of indicators 49 to indicate the cell 33 into which each medicament 11 is to be loaded or to permit verification of medicaments 11 received in cells 33. Transmitter/receiver 70 sends and receives signals with docking station 15' transmitter/receiver 74 permitting selective operation of indicators 49 through docking station 15' and controller 17.

In the examples of FIGS. 1-5 and FIG. 6, exemplary holder 13, 13' and docking station 15, 15' are provided with apparatus 81, 83 for uniquely identifying holder 13, 13' to docking station 15, 15' and system 10 or 10' as shown schematically in FIG. 3. Positive identification of holder 13, 13' enables the user to precisely control loading of appropriate medicaments 11 into holder 13 and 13' permits the user to maintain more accurate records of medicaments 11 which have been dispensed. In such embodiments, holder 13, 13' may include an identification element 81 and docking station 15, 15' may include an identification element detector 83 as shown in FIG. 3. The identifier element 81 may, for example, consist of a radio frequency identification tag (RFID) and the detector 83 may be an RFID tag reader (i.e., an interrogator) on docking station 15. The exemplary RFID tag 81 may be re-writable or read-only, as desired. Exemplary RFID reader 83 provided on docking station 15, 15' detects information embedded on the RFID tag 81. Information embedded in RFID tag 81 identifying holder 13, 13' may be used by system 10, 10' to control the medicament-dispensing process.

Figures 19, 19A:
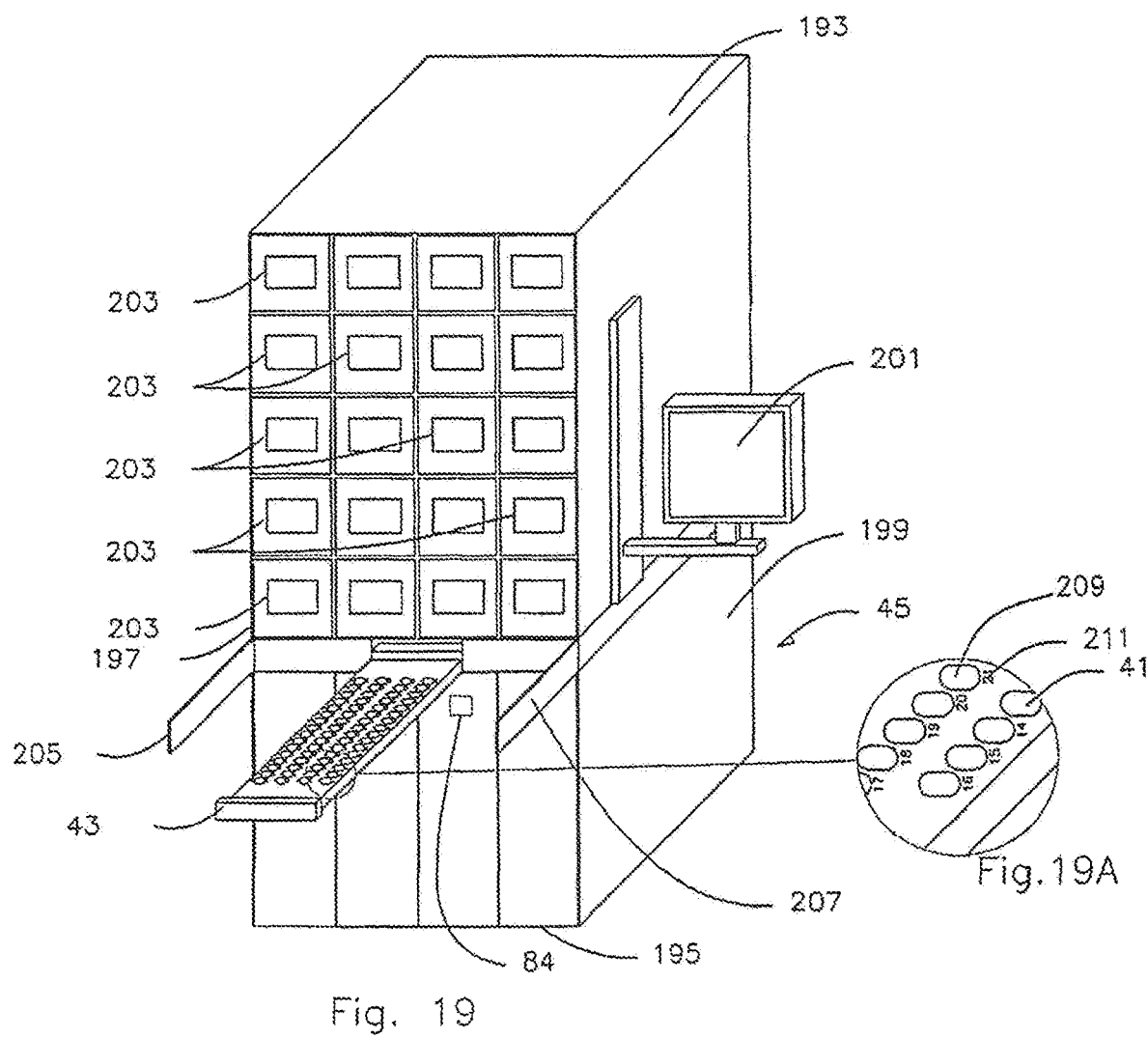
FIG. 19 is a perspective view of the exemplary automated medicament dispensing machine of FIG. 18, but with one exemplary exception storage apparatus in an outwardly-extended position ready to receive medicaments.
FIG. 19A is an enlarged fragmentary view of a portion of the exemplary exception storage apparatus of FIG. 19.
Figure 20:
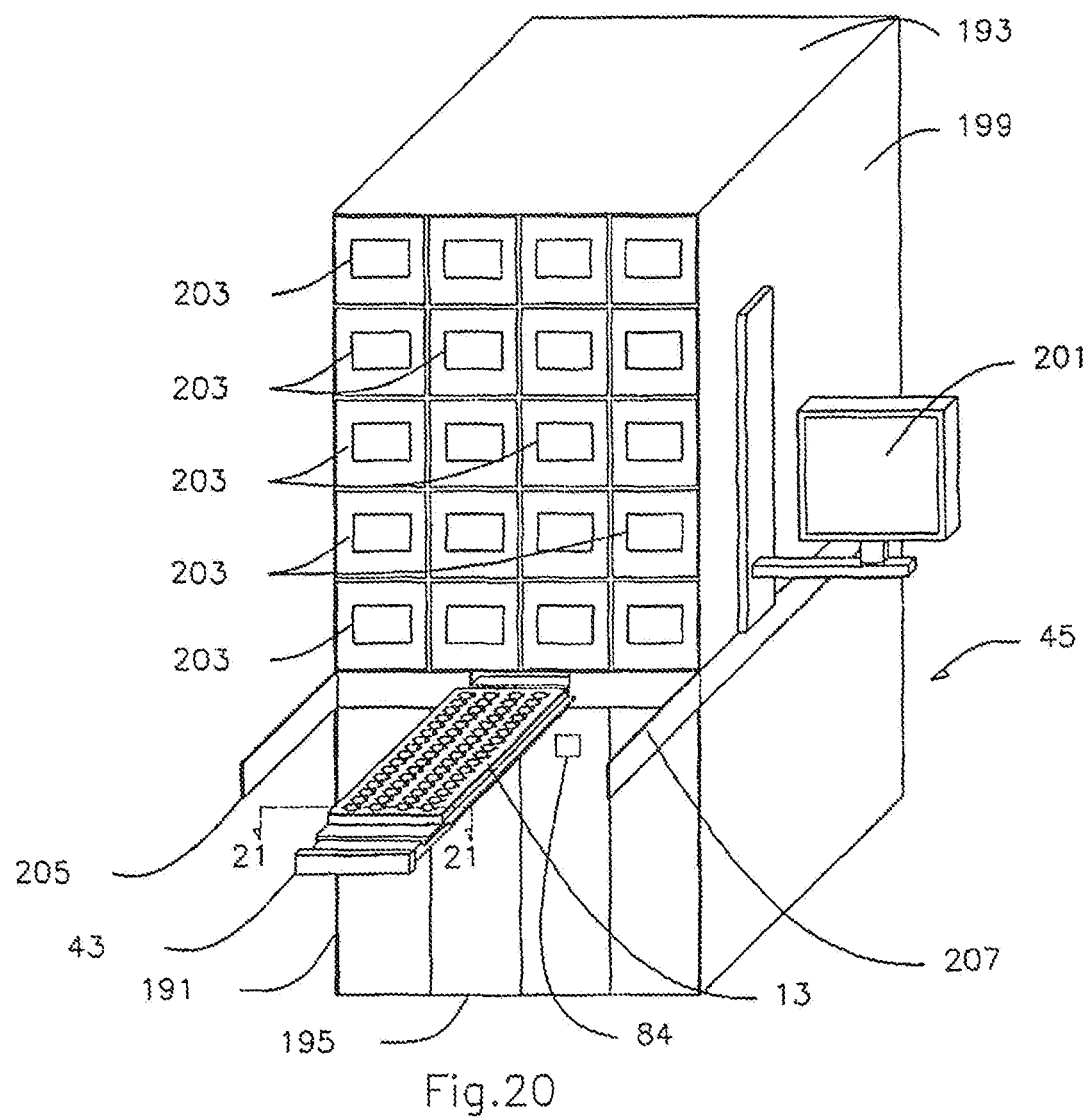
FIG. 20 is a perspective view of the exemplary automated medicament dispensing machine of FIGS. 18 and 19 but with the representative holder of FIGS. 1-10 positioned on the exemplary exception storage apparatus.
Figure 21A:
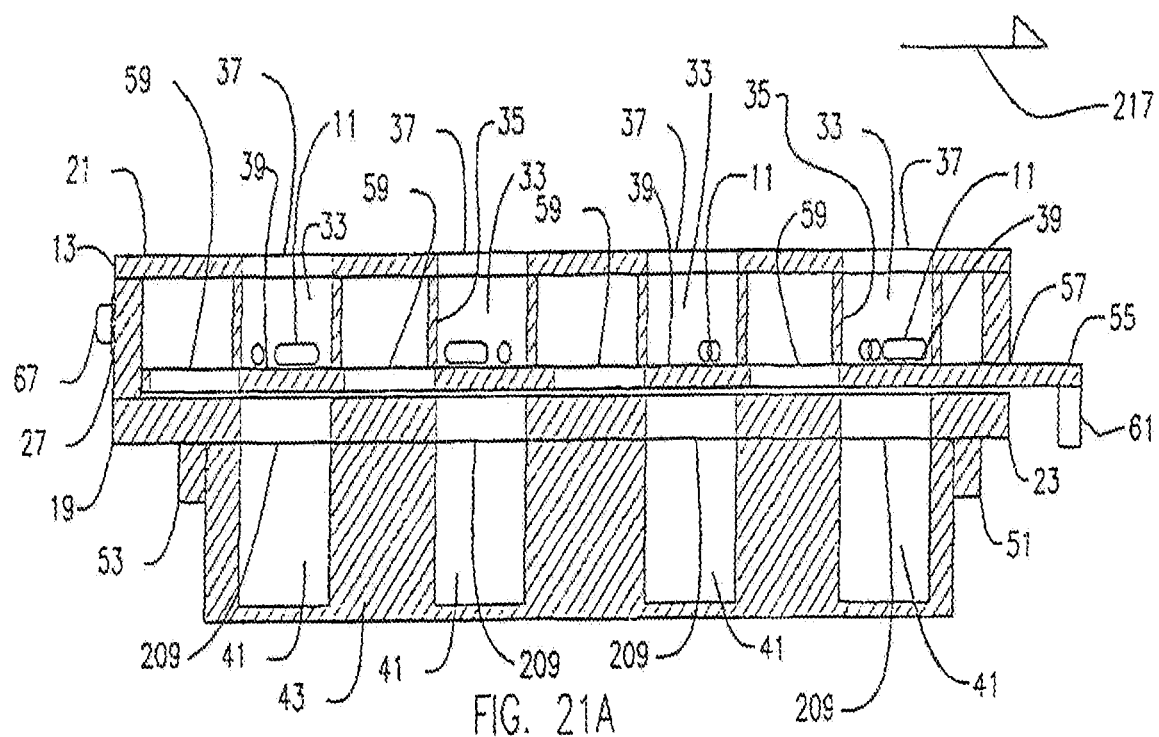
FIGS. 21A-21C are schematic side sectional views of the representative holder of FIGS. 1-5 and exception storage apparatus of FIGS. 19-20 taken along section 21-21 of FIG. 20.
Figure 21B:
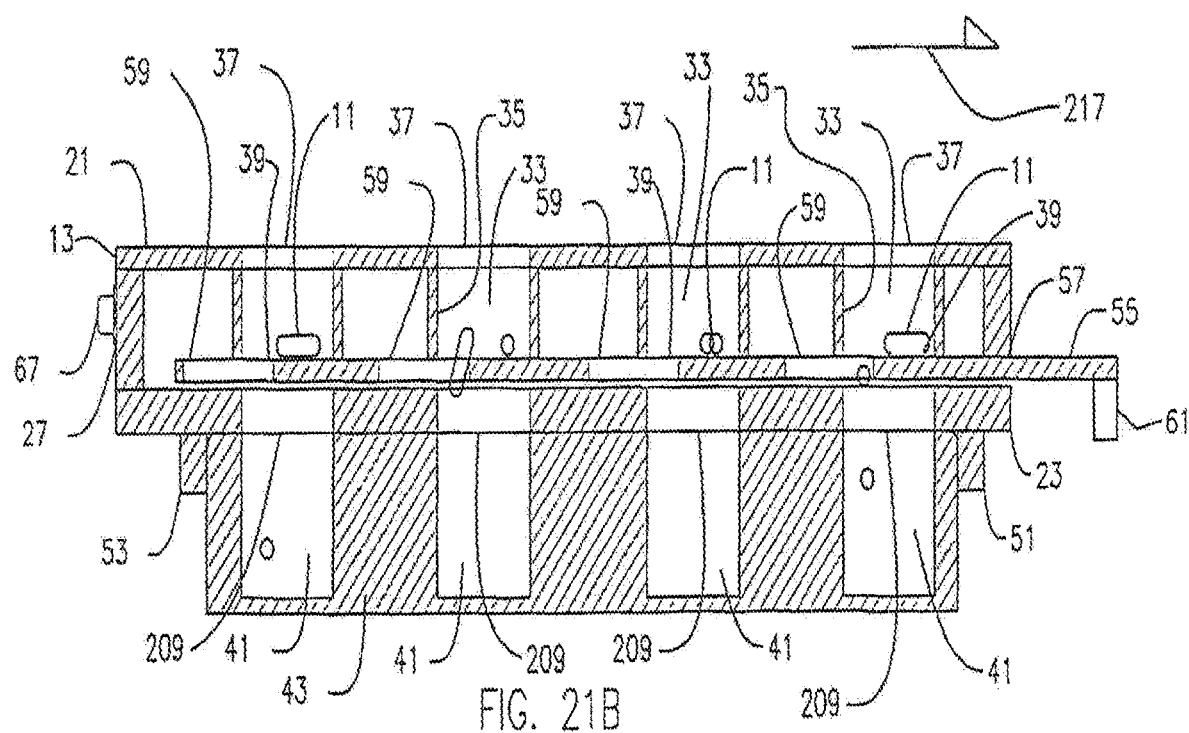
Figure 21C:
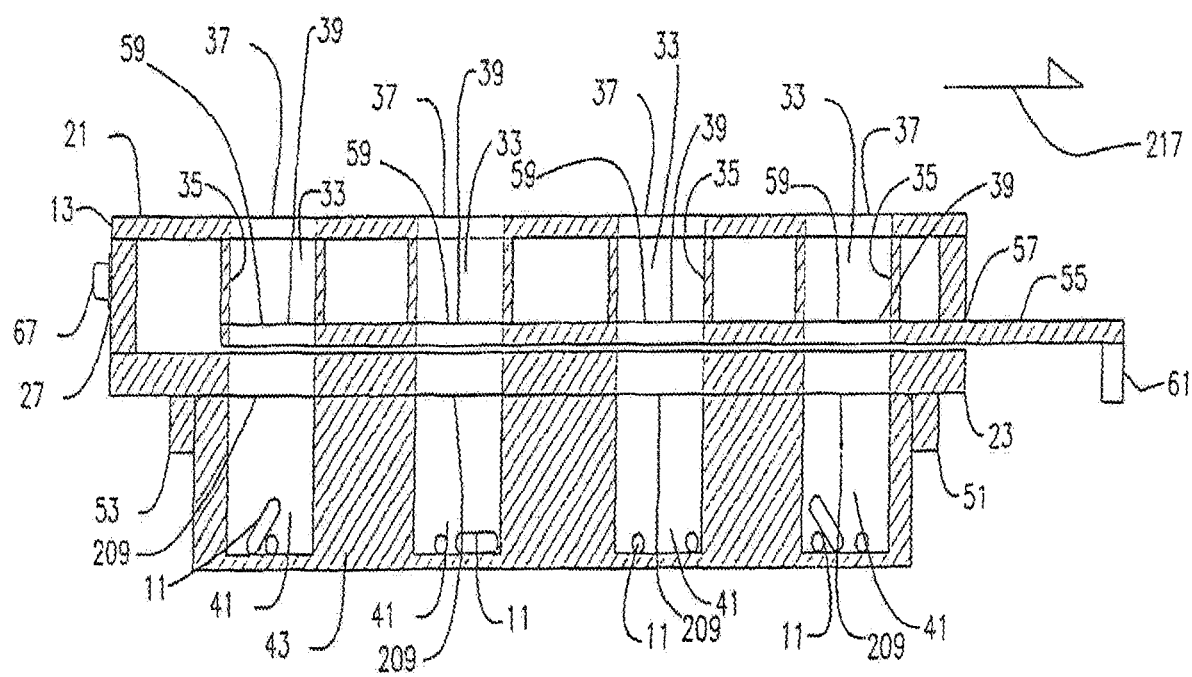

An identification element detector 84 may be provided on automated dispensing machine 45 (FIGS. 19, 20). In the example utilizing RFID tags, detector 84 may comprise an RFID reader. If the correct holder 13, 13' identification element 81 is detected by detector 84, the technician or pharmacist is prompted to transfer medicaments 11 from holder 13, 13' to exception storage apparatus 43. Conversely, if an incorrect holder identification element 81 is detected by detector 84, the technician or pharmacist is prompted to not load the exception storage apparatus 43.

Holder 13, 13' may be made of any suitable material or combination of materials. Preferably, body 19 is made of plastic material construction for reasons of ease of manufacture, low weight, ease of cleaning, and cost. Indicators 49 are preferably LED-type lamps but may comprise other types of visible indicators.

Referring next to FIG. 1-3, and FIG. 6 there are shown embodiments of docking stations 15, 15' capable of use with a respective exemplary holder 13, 13'. Each docking station 15, 15' may be placed on a counter top 85, such as the counter top 85 at a workstation in a pharmacy, long-term care facility, hospital, or other facility. A mounting bracket 87 may be provided to mechanically secure docking station 15, 15' to counter top 85.

Each exemplary docking station 15, 15' preferably includes housing 89 including top and bottom walls 91, 93, left and right side walls 95, 97 and front and rear walls 99, 101. Indicator 102 is provided on front wall 99. Indicator 102 is preferably an LED lamp which is activated if a holder 13 is properly docked at docking station 15, 15' and is recognized as an authorized holder 13 by system 10, 10' by means of identifier element 81.

In the embodiments of FIGS. 1-3 and FIG. 6, housing 89 encloses a programmable logic controller (PLC) 79 and a power supply 103. In such embodiments, PLC 79 is a component of controller 17. Power-supply port 105 is provided for connection to a suitable 120 Volt electrical power source by means of an electrical cord (not shown) to supply electrical power to PLC 79. PLC 79 includes instructions permitting selective closing and opening of relays within PLC 79 corresponding to the indicator(s) 49 of holder 13, 13' which are to be selectively operated to indicate the cell 33 into which each medicament 11 is to be placed. Power supply 103 preferably provides 5 Volt DC power to selected ones of LED-type indicators 49 once the appropriate relays of PLC 79 are selectively closed, thereby providing selective energizing and operation of indicators 49. In embodiments utilizing a multi-color LED-type indicator 49 (FIGS. 11A-11C) PLC 79 may also regulate the voltage to each indicator 49 or selectively energize the anodes to change the color emitted by the multi-colored LED. In wireless holder embodiments 13', control circuit board 68 (e.g., a controller on board 68) activates indicator 49 responsive to signals generated by PLC 79 to transmitter/receiver 74. An exemplary PLC 79 suitable for use as a component of controller 17 is a Model 06 Koyo Electronics PLC available from Automation Direct, Inc. of Cumming, Ga.

Figure 12A:
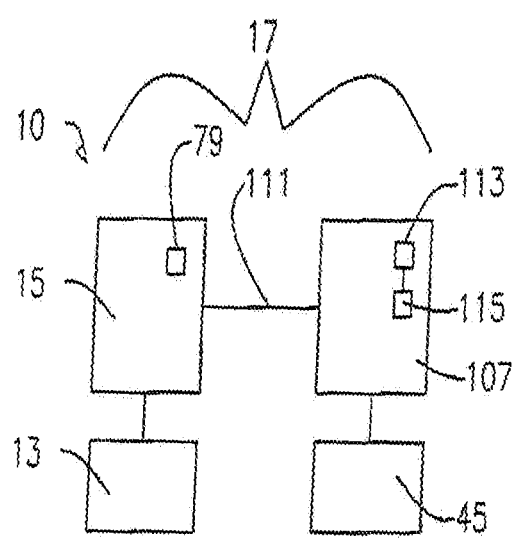
FIG. 12A is a schematic illustration of an exemplary system including a docking station and computer external to the docking station.

Referring to the embodiment of FIG. 12A, system 10 may include a server 107 operably connected to PLC 79 via data port 109 and communication link 111. In the embodiment, controller 17 includes both PLC 79 and server 107 operatively connected thereto. Server 107 may include memory 113 with a program of instructions 115 residing in memory 113. Server 107 is representative of any data management system operated by a pharmacy, hospital, long-term care facility, or other operator for proposes of managing information related to dispensing of medicaments 11. Communication link 111 may be any link capable of transmitting data and other information. Link 111 may, for example, comprise a dedicated land line, wireless link, ethernet, internet, intranet, local area network (LAN), or other suitable connection enabling data transmission between PLC 79 and server 107. Server 107 is preferably an off-the-shelf computer representative of any suitable data-management controller. It is envisioned that holder 13 can be connected directly to server 107 without a docking station 15, for example through a suitable communication link.

Figure 12B:
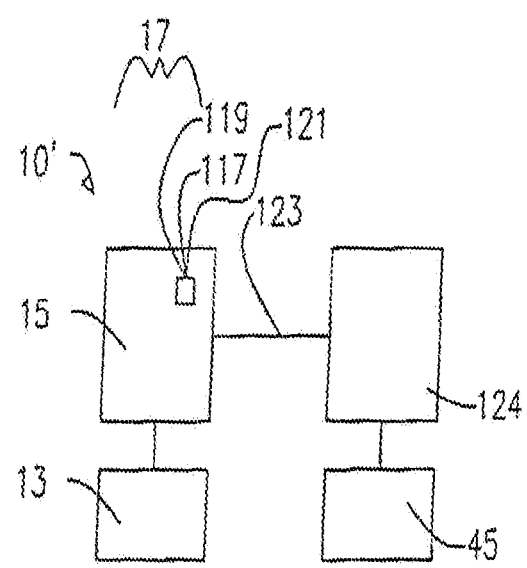
FIG. 12B is a schematic illustration of a further exemplary system including a docking station and computer internal to the docking station.

In a further illustrative embodiment represented by FIG. 12B, system 10' includes an on-board computer 117 within docking station 15, 15' housing 89 and computer 117 serves as controller 17. Computer 117 includes a program of instructions 119 residing in memory 121 which are operable to selectively energize and operate the indicators 49 to indicate the cell 33 into which one or more medicament(s) is/are to be placed. In this embodiment, computer 117 is linked to automated dispensing machine 45 via communication link 123 and server 124. Communication link 123 may be of the type as described previously in connection with link 111 and server may be a pharmacy information system server provided to manage pharmacy workflow generally. Overall activation of indicators 49 is provided by computer 117 in this example. System 10' is otherwise identical to system 10 and the description of system 10 is incorporated by reference with respect to system 10'.

Each docking station 15, 15' further preferably includes a video display 125, keyboard 127, and mouse 129 permitting a technician or pharmacist to input and receive information from server 107 or computer 117 of controller 17. A biometric identification device 130 may be provided to permit the technician or pharmacist to be identified to the system 10 or 10', particularly when logging on to the system. The biometric device 130 may be a fingerprint reader, retina scanner, or other suitable device. A bar code scanner 131 is preferably operably connected to controller 17. Video display 125 is preferably a touch screen display permitting a technician to input information to controller 17 by simply touching her finger on a desired portion of the display 125. Bar code scanner 131 may be any off-the-shelf scanner capable of reading a bar code 133 on a container 135 provided to hold medicaments 11. Keyboard 127 may be an off-the-shelf QWERTY-type keyboard 127 permitting a technician to input information to controller 17 and system 10, 10'.

FIGS. 7, 8, 9, and 10 illustrate a further holder 13" and docking station 15" embodiment suitable for use with an item-management system, such as system 10 or 10'. For simplicity and brevity, like reference numbers of holders 13, 13' and docking stations 15, 15' are used to identify like parts of holder 13" and docking station 15" and the description of holders 13, 13' and docking stations 15, 15' are incorporated by reference with respect to holder 13" and docking station 15". The embodiment of FIGS. 7-10 differs from the embodiments of FIGS. 1-6 because the indicator or indicators 49 which are selectively-operable to indicate the holder cell 33 into which an item is to be loaded are located on a guide 136 associated with docking station 15". Use of guide 136 with indicators 49 located thereon enables use of the item-management system with a holder 13" which does not include indicators 49 thereon, typical of holders presently in use.

Referring further to FIGS. 7-10, holder 13" includes body 19, top and bottom sides 21, 23, sides 25-31, cells 33 (including inlet and outlet openings 37, 39), legs 51, 53, shuttle member 55. An identification element 81 of the type previously described is preferably provided on body 19. An alignment pin receiver 63 may be provided to receive pin 65 of docking station 15" to position holder 13" at docking station 15". Exemplary docking station 15" includes detector 83, housing 89 with walls 91-101, lamp 102, power supply 103, and ports 105, 109, and is provided with a video display 125, keyboard 127, mouse 129, biometric identification device 130, and bar code scanner 131 for the purposes described in connection with docking stations 15, 15'.

Docking station 15" includes a guide 136 attached to housing front wall 99. Guide 136 is preferably a planar member located in a plane above a holder 13" docked at docking station 15" beneath guide 136. Guide 136 is provided with openings, each of which is identified by reference number 138 for brevity. In the example, guide 136 is provided with 64 total openings 138 grouped in four rows of openings 138. This opening 138 pattern is identical to the pattern of cells 33 in holder 13". This opening 138 pattern is such that the openings 138 in guide 136 are in registry and alignment with the corresponding cells 33 of holder 13" when holder 13" is docked at docking station 15". This arrangement allows a technician to rapidly and accurately load each cell 33 of holder 13" by inserting a it through the appropriate opening 138 in guide and into the corresponding cell 33 during holder 13" loading.

Indicators 49 on guide 136 are proximate each opening 138 to indicate to the technician, upon activation, which opening 138 a medicament 11 or other item is to be inserted. Indicators 49 may, for example, be a single lamp (preferably an LED) as illustrated in FIGS. 1, 3-4, 6-7, and 9, a multi-colored LED as illustrated in FIGS. 11A-11C, or plural indicators 49 as illustrated in FIG. 11D, or another indicator type. Human-readable indicia 140 is preferably provided on guide 136 so that each opening 138 on guide 136 has the same indicia 140 as indicia 47, 211 on holder 13" and exception storage apparatus 43. Indicia 140 further assists the technician to ensure that the correct medicament 11 is loaded into the correct guide 136 opening 138. Guide 136 indicators 49 are connected to PLC 79 through appropriate conductors (not shown) permitting selective energizing and operation of indicators 49 to indicate the opening 138 through which each medicament 11 is to be loaded. Guide 136 may be made of any suitable material such as metal, plastic, laminate or a combination of materials.

Docking station 15" is otherwise identical to docking station 15 previously described and illustrated and the description of docking station 15 is incorporated by reference. Controller 17, as previously described, controls operation of docking station 15" and indicators 49 on guide 136 and holder 13", docking station 15", and controller 17 may be used as part of an item-management system, such as system 10 or 10' (FIGS. 12A, 12B).

FIGS. 14-17 are exemplary screen displays of a type which could be displayed to a technician or pharmacist on display 125 for purposes of implementing system 10 or 10' using holder 13, 13', or 13" and docking station 15, 15', or 15". The screen displays of FIGS. 14-17 are intended to represent non-limiting examples as the type and number of screen displays can be modified and the information provided in the screen displays may be customized to meet the needs of the particular pharmacy, hospital, long-term care facility or other operator. For convenience and brevity, the screen displays of FIGS. 14-17 are described in connection with system 10 including holder 13 and docking station 15, it being understood that the screen displays and methods of implementing system 10 are applicable for use with system 10' or with holder 13', 13" and docking station 15', 15".

Referring to the screen displays of FIGS. 14-17, a technician or registered pharmacist initiates use of system 10 by logging on to the system 10, preferably at docking station 15. Preferably, loading of holder 13 is performed by a technician while verification of the loaded holder 13 is performed by a registered pharmacist.

Figure 14:
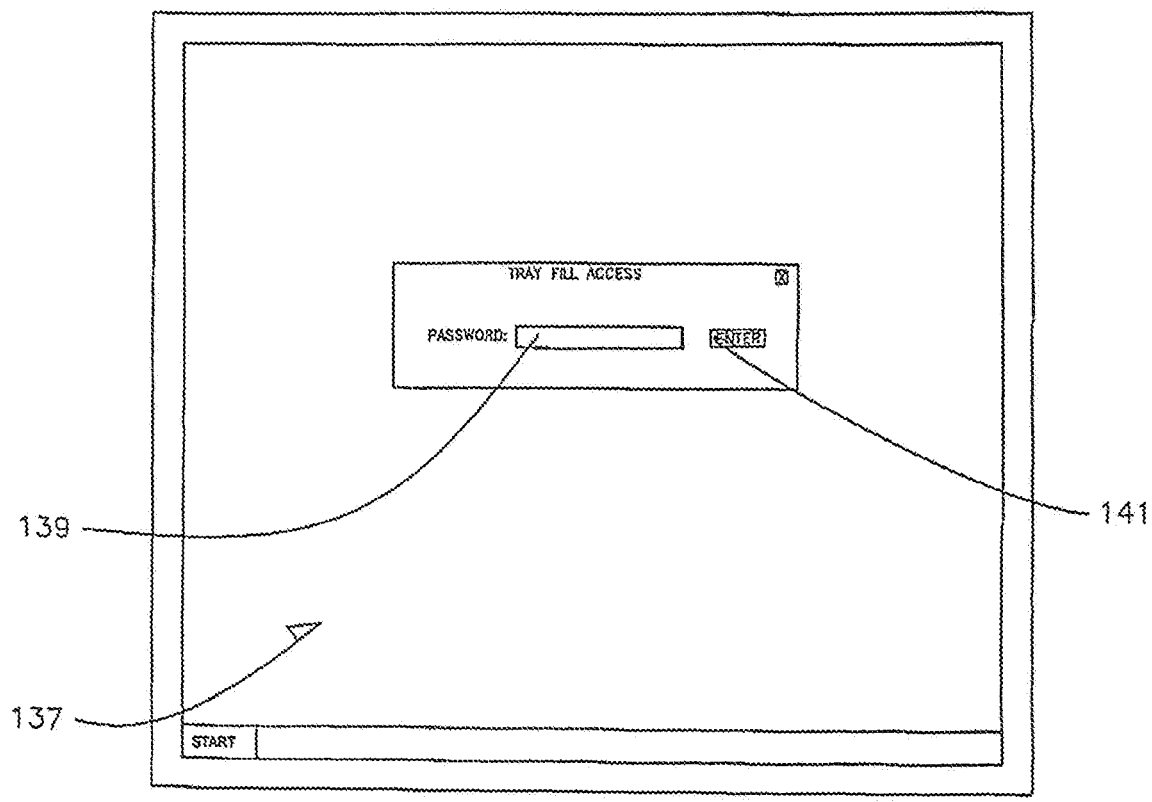
FIG. 14 is an exemplary log-on screen display.

Referring to FIG. 14, the technician is initially presented with a log-on screen 137 displayed on video display 125. The technician logs on to the system 10 by keying his or her password into the password field 139 using keyboard 127 and selecting the ENTER icon 141. Alternatively, the technician could utilize biometric device 130 to identify herself to the system 10. The technician's password information is transmitted to server 107 (or server 124 in system 10'), whereupon it is determined that the technician is an authorized user.

Figure 2:
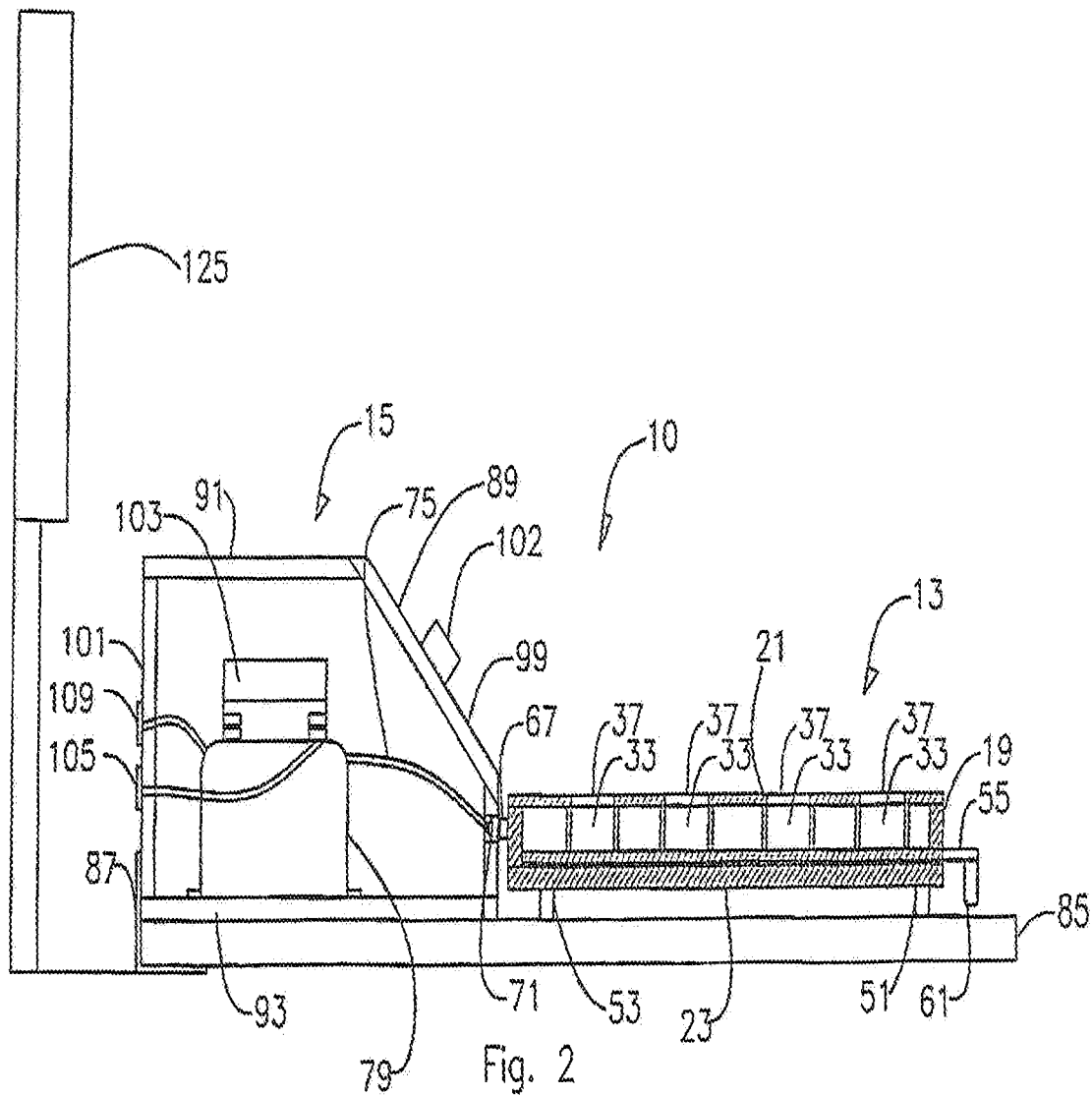
FIG. 2 is a schematic side sectional view of the representative holder and docking station taken along section 2-2 of FIG. 1.

If a holder 13 is not already docked at docking station 15 as shown in FIGS. 1-3 (or is not in wireless communication with docking station 15' as in FIG. 6), a further screen (not shown) may be displayed on video display 125 prompting the technician to dock a holder 13 at docking station 15. In the example of FIGS. 1-3, holder 13 is shown docked at docking station 15 by insertion of pin 65 in receiver 63, thereby positioning holder 13 to form an electrical connection between holder contacts 67, 69 and docking station contacts 71, 73. Identification element detector 83 identifies the unique identifier element embedded in holder 13. Detector 83 preferably detects an RFID-type identification element 81 to identify holder 13 to system. If the docked holder 13 is recognized by system 10 (or if wireless-type holder 13' is recognized by system 10), indicator lamp 102 is activated to inform the technician that the system 10 is in a ready state. Proximity detector 66 may also indicate to controller 17 that holder 13 is properly docked at docking station 15.

Figure 15:
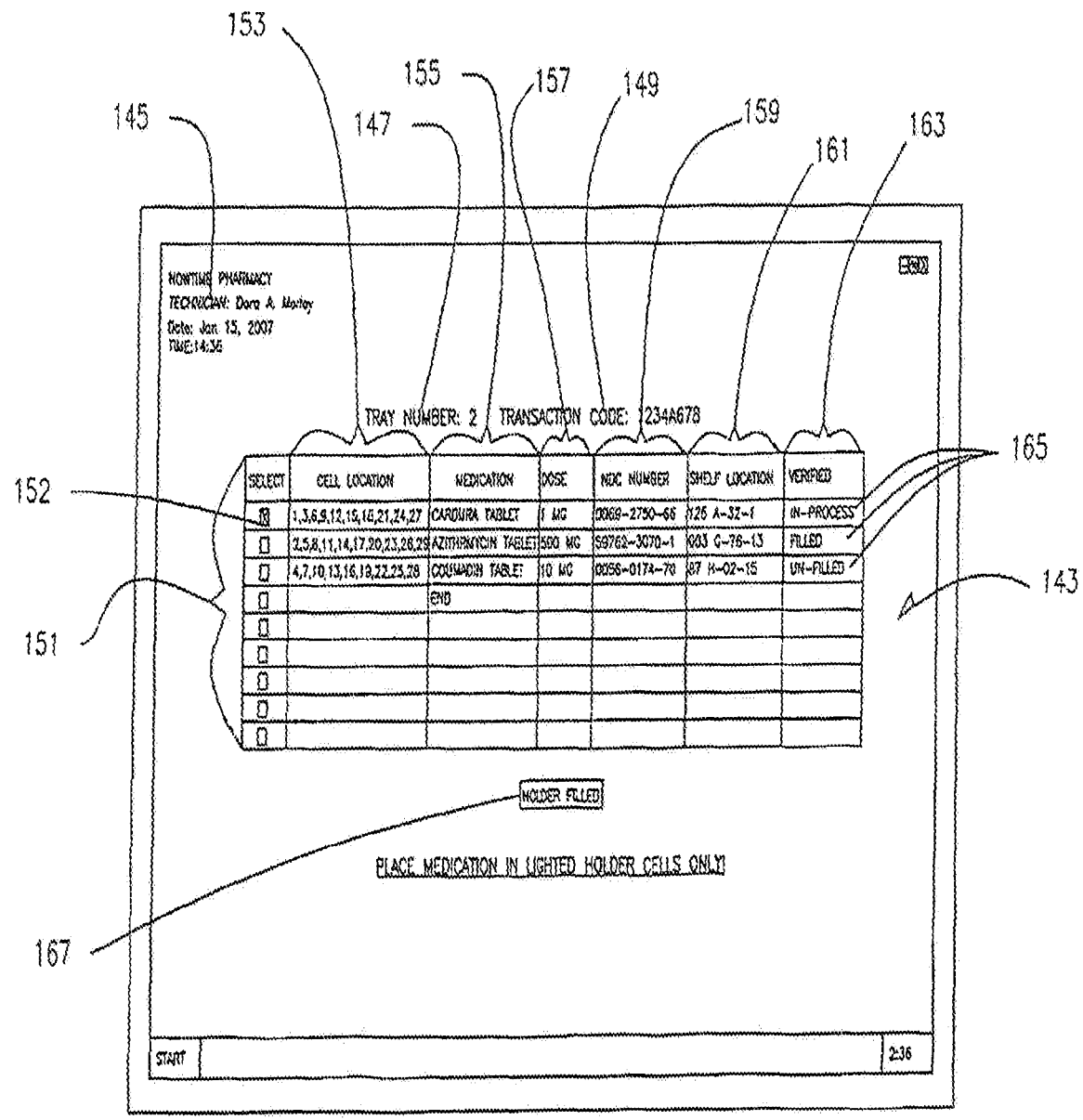
FIG. 15 is an exemplary screen display for loading of a holder.

Referring next to FIG. 15, if the technician is authorized and if holder 13 is docked and recognized, then a holder-loading screen 143 is displayed on video display 125. Holder-loading screen 143 provides information for loading each medicament 11 into the correct cell 33.

Information which may be presented on holder-loading screen 143 can include an identification field 145 identifying the operator name (e.g., Nowtime Pharmacy), technician name, and date and time-of-day on which holder 13 is being loaded. Additional information which may be displayed in connection with screen 143 is the holder identifier 147 and transaction code 149 which indicates the transaction corresponding to loading of the holder 13 for record-keeping purposes. Preferably, the transaction number and all other information relating to loading and verification of holder 13 is stored in a database on server 107 or 124. Holder identifier 147 may be any symbol or group of symbols capable of distinguishing one holder 13 from another holder 13. In the example, holder identifier 137 is identical to the identifier embedded in RFID tag-type identification element 81. In the example, the holder identifier 147 is the number 2. A unique identifier 147 can be important if more than one identical holder 13 is used by the pharmacy, hospital, long-term care provider or other operator.

Referring further to FIG. 15, holder-loading screen 143 includes information 151 required for loading of cells 33 of holder 13. Preferably, information 151 is displayed in the form of a graphical user interface (GUI), thereby facilitating ease of use by the technician. In the example, information 151 includes a select field 152, a cell location field 153, a medication type field 155, a dosage strength field 157, an NDC number 159 field, a shelf location 161 field, and a status 163 field. In the example, information 151 is displayed for each medicament 11 to be loaded into holder 13. In the example of FIG. 15, three medicament 11 types, namely, Cardura tablets, Azithromycin tablets, and Coumadin tablets are to be loaded into holder 13.

The cell location field 153 identifies the cell 33 into which medicament 11 is to be loaded by referencing the human-readable indicia 47 associated with the designated cell 33. In the example, Cardura tablets are to be loaded into cells of holder 13 associated with the human-readable indicia 47 represented by numbers "1, 3, 6, 9, 12, 15, 18, 21, 24, 27" while the other medicaments are to be loaded into the other cells 33 of holder 13 identified in the cell location field 153. The ordering of the medicaments 11 is determined by the order in which the medicaments 11 are required in order to load each container or containers (e.g., a vial, bottle, blister package, or pouch package) for each prescription order or dispense request. For example, server 107 may order the medicaments 11 presented on screen 143 based on the sequence in which prescription orders or dispense requests are to be filled for more than one patient or may order the medicaments 11 presented on screen 143 based on a drug regimen for a single patient, for example, ordering the medicaments by the time of day the medicaments 11 are to be taken by the patient (e.g., breakfast, lunch, and dinner). The slow mover medicaments 11 indicated on screen 143 may be arranged and ordered for serial dispensing (i.e., one-after-the-other) or may be arranged and ordered to alternate with medicaments dispensed from other storage apparatus cassettes, cells, canisters, etc.) within automated dispensing machine 45.

The medication type field 155 and dosage strength field 157 information refers to the type and strength of the medicament 11, while the NDC number field 159 information refers to the 10-digit National Drug Code (NDC) number for the specific medicament 11 called for by the prescription order or dispense request.

The shelf location field 161 information refers to the shelf location of the pharmacy, hospital, long-term care facility, or the like at which the medicament container, for example representative container 135 (FIG. 1), holding a medicament 11 is located. This information is provided to assist the technician in retrieving the container 135 from storage. In the example, fictitious alpha-numeric shelf locations are displayed.

Figure 7:
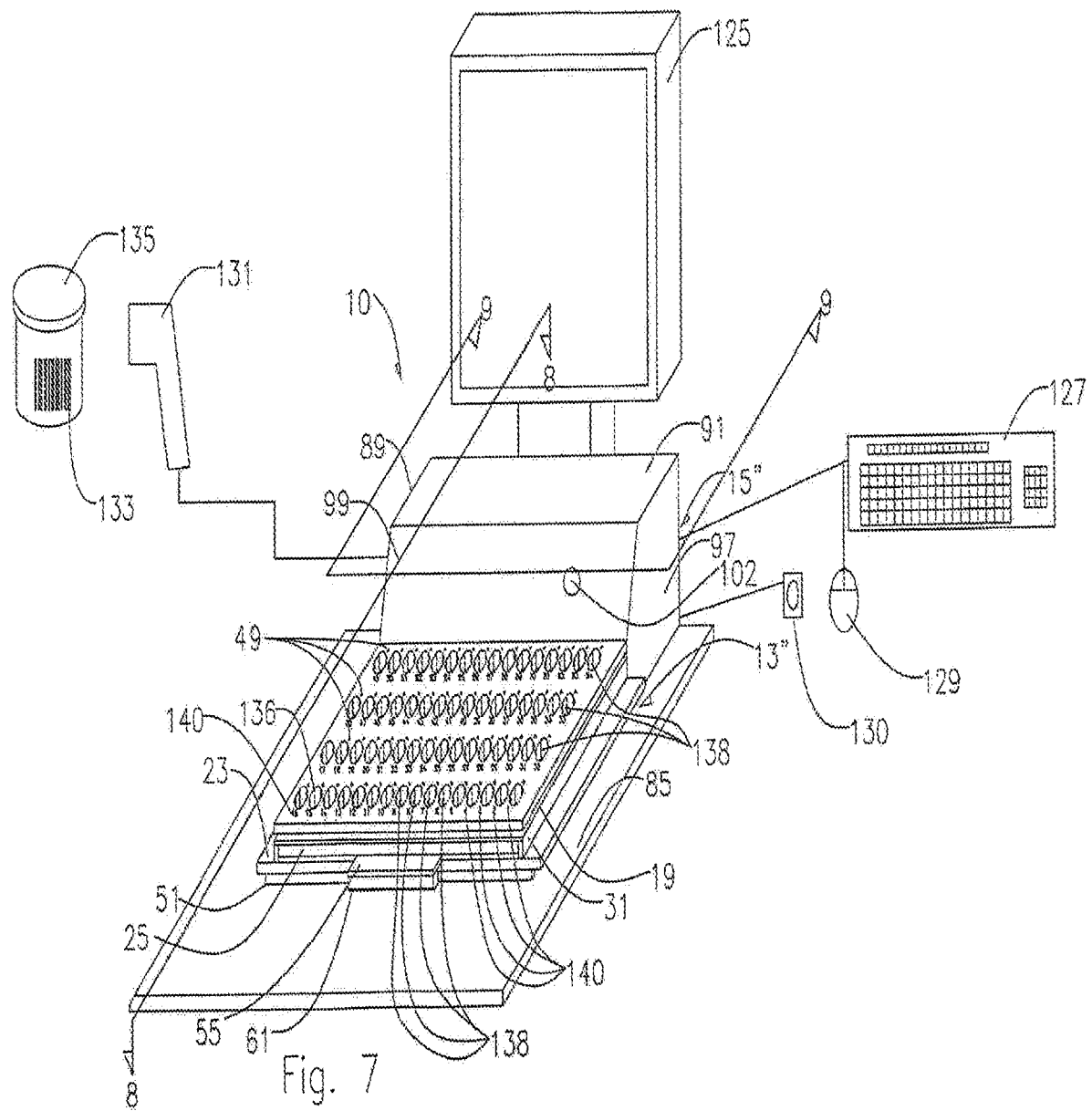
FIG. 7 is a perspective view of a further exemplary embodiment showing a docking station with a guide, and a holder docked at a docking station.
Figure 8:
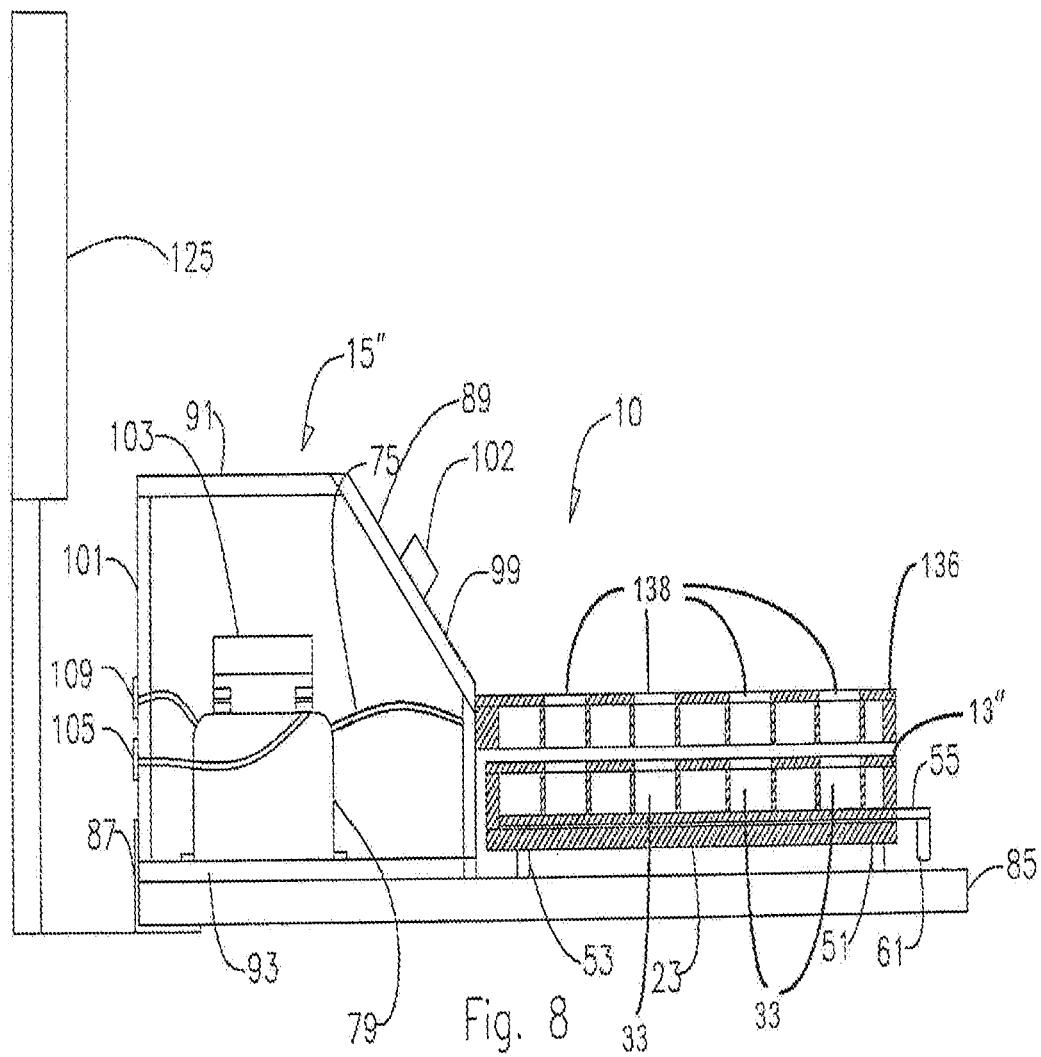
FIG. 8 is a schematic side sectional view of the further exemplary docking station and guide taken along section 8-8 of FIG. 7.
Figure 9:
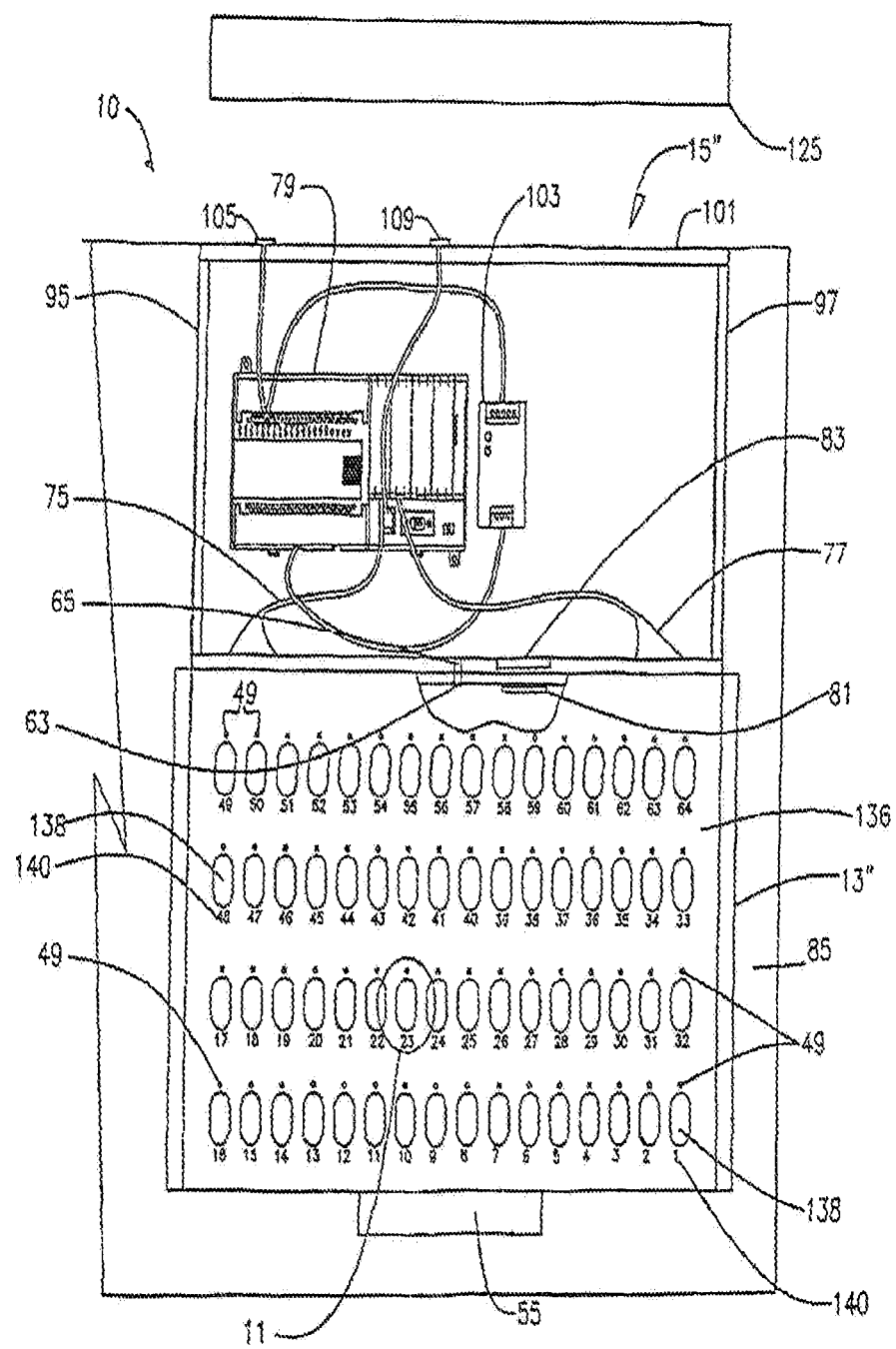
FIG. 9 is a schematic top sectional view of the further exemplary docking station and guide taken along section 9-9 of FIG. 7.
Figure 10:
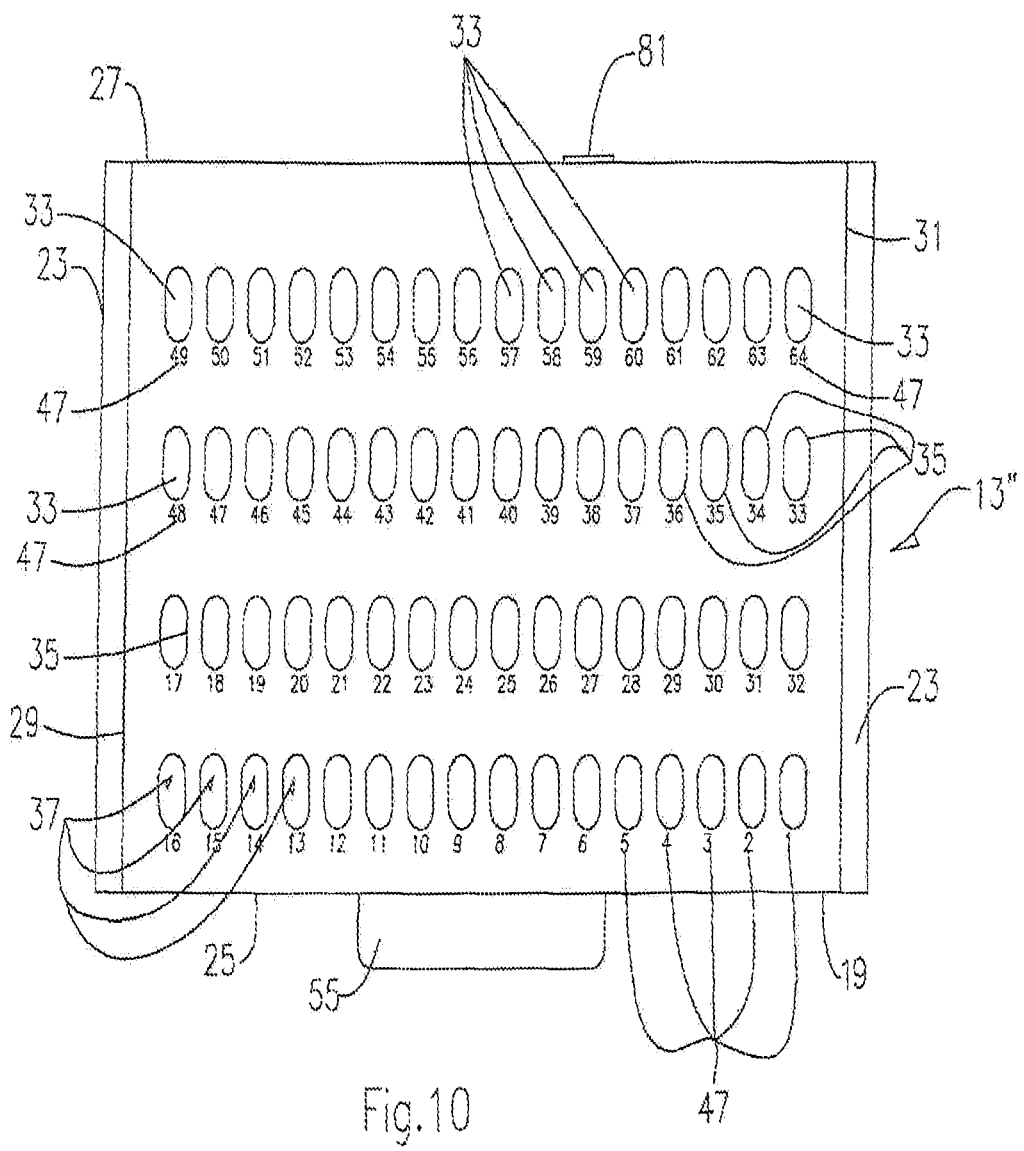
FIG. 10 is a top side view of the holder shown in FIGS. 7-9 shown apart from the docking station.

As illustrated in FIGS. 1 and 7, it is envisioned that the technician will scan the bar code 133 on the container 135 with bar code scanner 131. Program of instructions 115 running on server 107 can then verify that the correct container 135 has been selected from storage based on information contained in bar code 133. The technician can also verify that the correct medicament container 135 has been selected by comparing the medication type 155, strength 157, and human-readable NDC information 159 on the screen 143 with human-readable information on the label for container 135.

The status information field 163 indicates the status of the holder-loading process. Selection of each medicament 11 for loading can be made simply by touching the technician's finger on the row 165 of touch-screen video display 125 associated with one medicament 11 or by selecting the row 165 with another input device, such as keyboard 127 and mouse 129. In the example of FIG. 15, the technician is in the process of loading Cardura tablets into cells 33. This is indicated by the row 165 associated with Cardura tablets having been selected as indicated by the X character in the select field 152 and the IN-PROCESS text in status information field 163. The row 165 associated with the Azithromycin tablets indicates FILLED in the status information field 163 indicating that loading of the Azithromycin tablets has been previously completed. The row 165 associated with the Coumadin tablets has not yet been selected as indicated by the UNFILLED indication in field 153.

PLC 79 (or computer 117 in system 10) selectively activates the indicator 49 for each cell 33 into which the medicament 11 is to be loaded once the appropriate row 165 associated with the medicament is selected. This pick-to-light feature enables the technician to load medicaments 11 without any necessity for reliance on written loading instructions. Thus, in the example of FIG. 15, the indicator 49, preferably an LED lamp, associated with each of cells 33 indicated by the human-readable indicia 47 "1, 3, 6, 9, 12, 15, 18, 21, 24, 27" is energized to tell the technician to load a Cardura tablet into each of these cells 33. Each indicator 49 associated with each other cell 33 of holder 13 is not activated. Activation of only each indicator 49 associated with the cell to be loaded is referred to herein as selective indicator 49 activation or operation.

Once all cells 33 associated with a row 165 are filled, the technician then selects the next row 165 of medicaments to be filled and proceeds to load holder 13 as directed by indicators 49. Selection can again be accomplished by touching the technician's finger on the row 165 of touch-screen video display 125 associated with the next medicament 11 to be loaded in holder 13 or by selecting the row 165 with the keyboard 127 or mouse 129. The indicator or indicators 49 previously activated are deactivated and the appropriate indicators 49 for the next medicament 11 to be loaded are activated. This process is repeated until all medicaments 11 have been loaded in holder 13 as called for by screen 143.

Once all cells 33 of holder 13 are loaded as required by holder-loading screen 143, the technician clicks on, or otherwise selects, the HOLDER FILLED icon 167. Selection of icon 167 sends a signal to server 107 (or server 124 in system 10) indicating that loading of holder 13 has been completed. Each loaded holder 13 can subsequently be verified by a registered pharmacist prior to loading of medicaments 11 from loaded holder 13 into automated dispensing machine 45.

Figure 13:
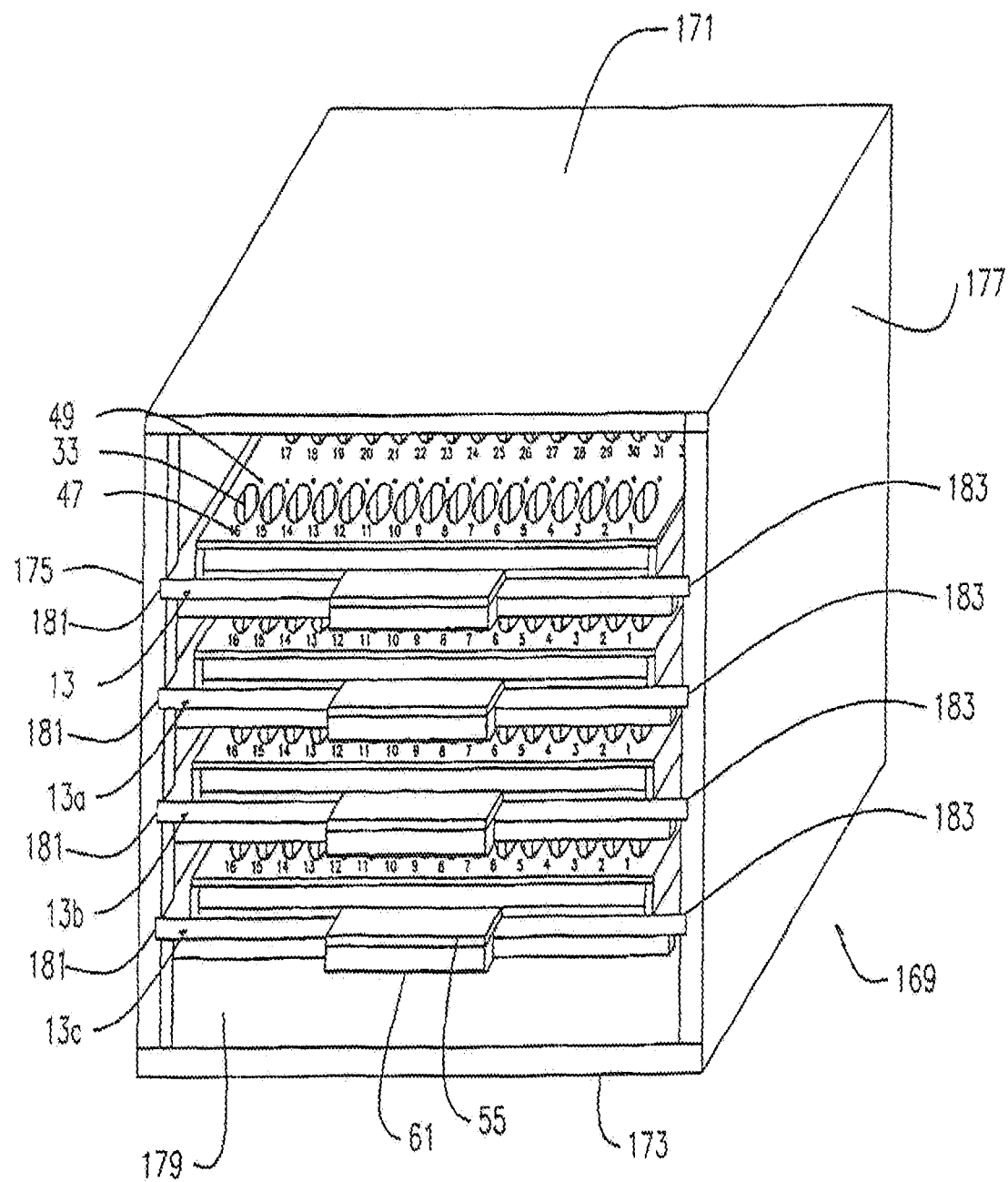
FIG. 13 is a perspective view of a storage cabinet including four representative holders temporarily stored therein.

Referring now to FIG. 13, a storage cabinet 169 may optionally be provided to store one or more holder 13, 13a, 13b, and 13c thereby facilitating loading and verification of multiple holders. In the example, each holder represented by reference numbers 13a, 13b and 13c has structure identical to holder 13. Loaded holders 13, 13a, 13b, and 13c may be stored in cabinet 169 after loading and before verification or may be stored in cabinet 169 after verification by a registered pharmacist and before loading of the verified medicaments 11 into exception storage apparatus 43 of automated dispensing machine 45.

If provided, storage cabinet 169 includes top and bottom walls 171, 173, sidewalls 175, 177, and a front opening 179 through which holders (e.g., holder 13) are placed into cabinet 169. Stacked opposed slot pairs 181, 183 may be provided to receive the bottom 23 of each holder 13 permitting holders 13, 13a, 13b, and 13c to be stored in cabinet 169.

Figure 16:
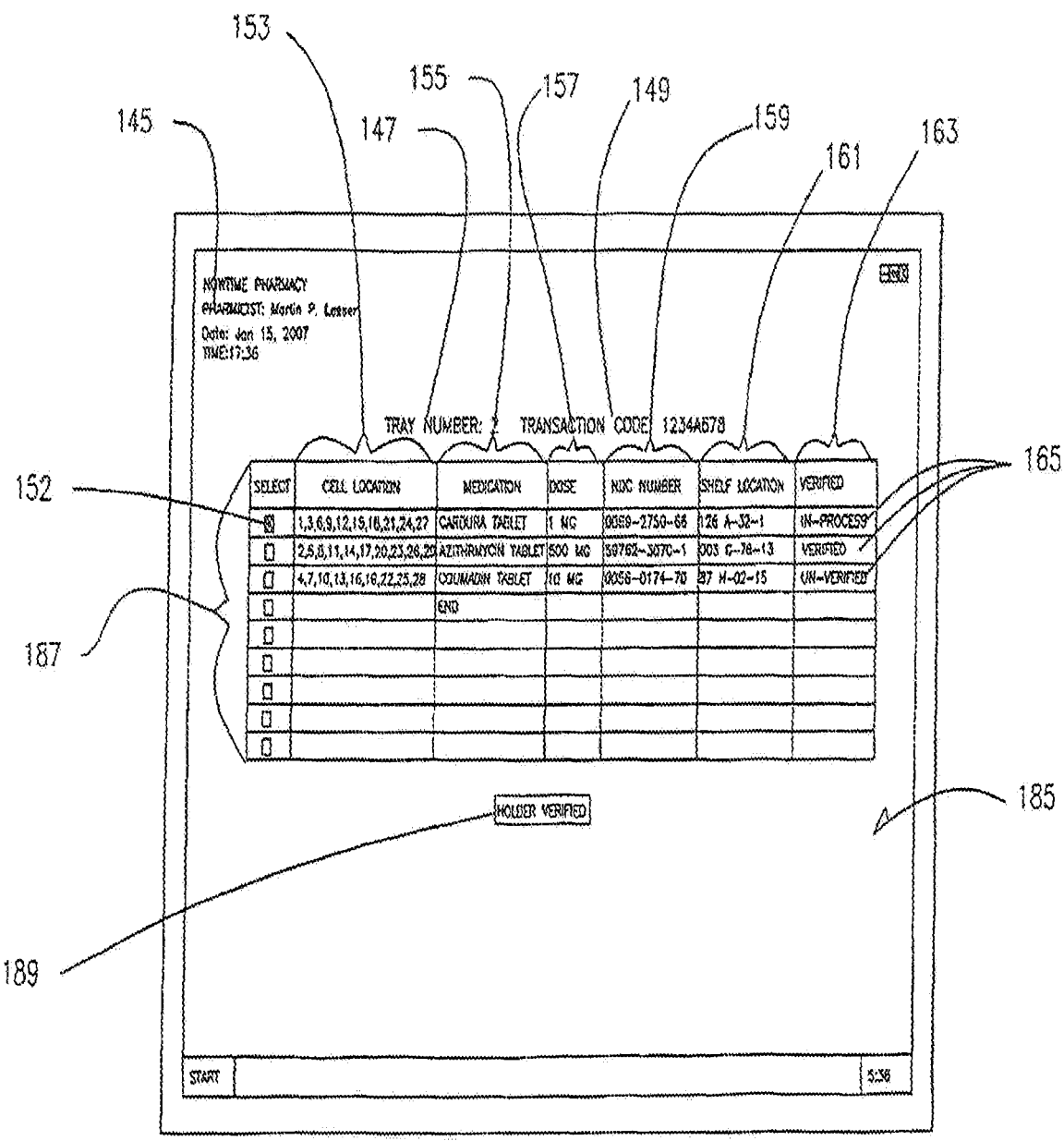
FIG. 16 is an exemplary screen display for verification of the items loaded in the holder.

As already noted, each loaded holder 13 can be verified by a registered pharmacist to ensure that each cell 33 has been loaded with the correct medicament 11. FIG. 16 shows an exemplary holder-verification screen 185 which corresponds to the holder-loading screen 143 for that holder 13. Holder-verification screen 185 includes information 187 required for verification of the medicaments 11 loaded into cells 33 of holder 13. This information is essentially identical to that displayed in connection with holder-loading screen 143. For convenience and simplicity, reference numbers of information displayed on holder-loading screen 143 are used again to identify corresponding fields of information on holder-verification screen 185.

As with the holder-loading screen 143, an identification field 145 can be provided to identify the operator name (e.g., Nowtime pharmacy), name of the pharmacist responsible for medicament 11 verification, and the date and time-of-day on which holder 13 is verified. The holder identifier 147 and transaction code 149 are also preferably displayed for the same purpose as described in connection with the holder-loading screen 143.

Preferably, information 187 is again displayed in the form of a graphical user interface (GUI), thereby facilitating ease of use by the verifying pharmacist. In the example, the displayed information 187 again includes a select field 152, a cell location field 153, a medication type field 155, a dosage strength field 157, an NDC number field 159, a shelf location field 161, and a status information field 163 including the information described in connection with holder-loading screen 143. In the example, information 187 is again displayed for each medicament 11 to be loaded into holder 13. In the example of FIG. 16, the Cardura tablets, Azithromycin tablets, and Coumadin tablets previously loaded into cells 33 of holder 13 are presented for verification by the pharmacist.

In order to verify that each cell 33 holds the correct medicament 11, the pharmacist simply selects the row 165 to be verified. Selection is accomplished by touching the touch screen display 125 on row 165 or by selecting row 165 with the keyboard 127 or mouse 129. The status information field 163 again indicates the status of the holder-verification process.

Referring further to FIG. 16, the screen display 185 shows an example of displayed information for verification that the Cardura tablets have been correctly loaded into the cells 33 indicated by the human-readable indicia 47 "1, 3, 6, 9, 12, 15, 18, 21, 24, 27" located on holder 13. Selection of the Cardura tablets for verification is indicated in the example by the row 165 associated with Cardura tablets having been selected as indicated by the X character in the select field 152 and the IN-PROCESS text in status information field 163. The row 165 associated with the Azithromycin tablets indicates VERIFIED in the status information field 163 indicating that verification of the Azithromycin tablets has been completed. The row 165 associated with the Coumadin tablets has not yet been selected for verification as indicated by the UN-VERIFIED indication in field 163. A selected row 165 can also be highlighted to facilitate identification of the row 165 then being verified.

Figure 17:
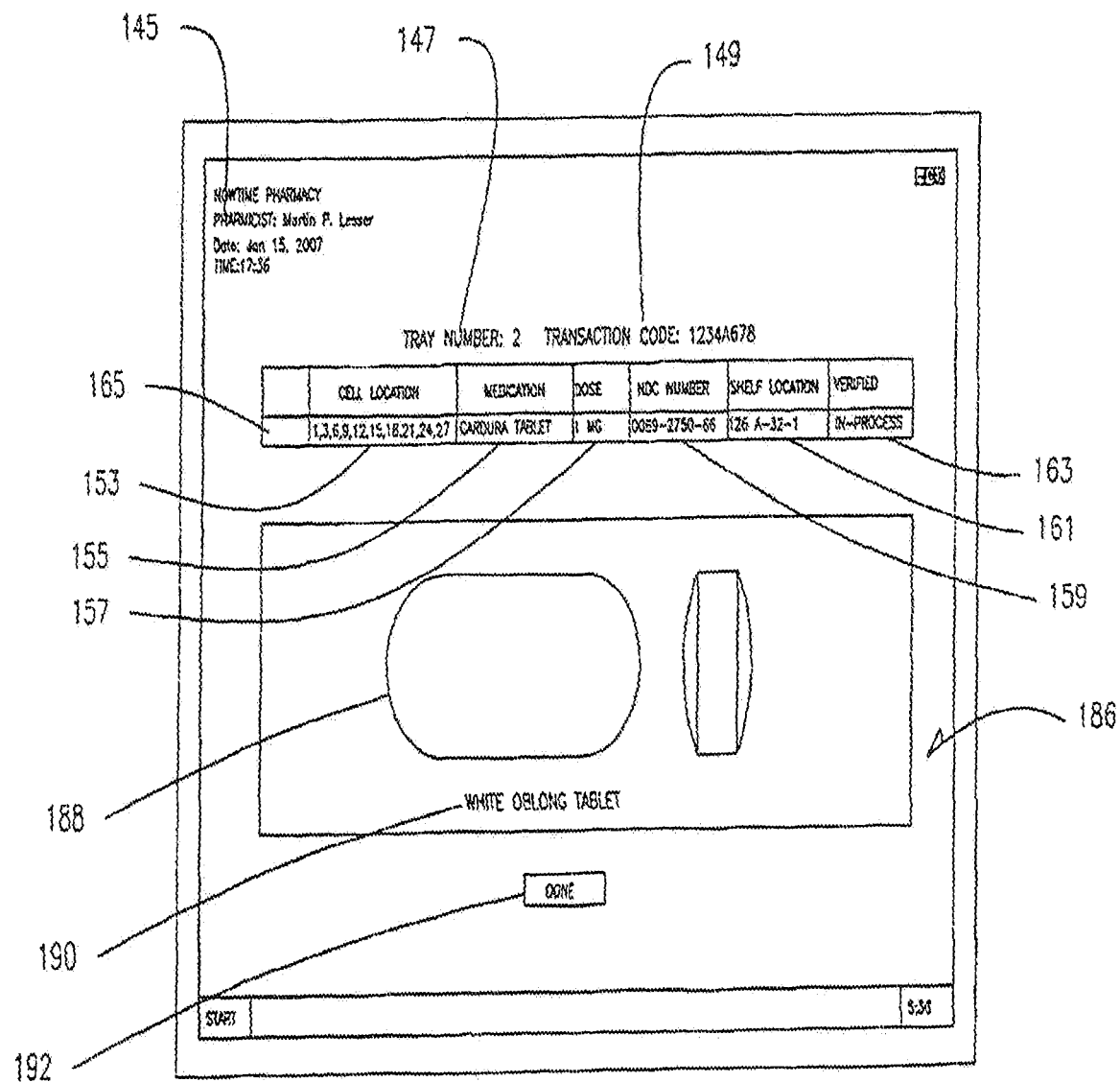
FIG. 17 is an exemplary screen display for verification of the items loaded in the holder including a reference image of a medicament.

Referring next to FIG. 17, a further verification screen display 186 may be provided to assist the pharmacist with the verification process. As each row 165 is selected, a medicament-specific verification screen 186 may be displayed. In the example, screen 186 displays the row 165 being verified including the cell location field 153, medication type field 155, dosage strength field 157, NDC number field 159, shelf location field 161, and status information field 163. Screen 186 also displays a reference image of the physical appearance of the medicament 188 together with a word description 190 of the physical appearance of the medicament 11. In this example of the Cardura medicaments 11, the word description 190 is white oblong tablet. A screen display similar to display 186 of FIG. 17, including a reference image 188 and word description 190, may be displayed to the technician during the holder-loading process associated with screen 143 to assist the technician in placing the correct medicament(s) 11 into each cell 33.

Upon selection of a row 165, PLC 79 of controller 17 again selectively activates each indicator 49, preferably an LED lamp, for each cell 33 to be verified by the pharmacist. As with the loading process, this pick-to-light capability enables the pharmacist to rapidly confirm that the correct medicament 11 has been loaded into the correct cell 33 without the necessity for reliance on written verification instructions. The pharmacist can quickly compare the physical appearance of each medicament 11 in each indicated cell 33 without the necessity of reliance solely on written instructions. This process is facilitated by presentation of screen 186 and the reference image and description information 188, 190 as the pharmacist can quickly compare the appearance of the medicament 11 on screen 186 with the appearance of the medicament(s) 11 in each cell 33 associated with an activated indicator 49.

Thus, in the verification example of FIGS. 16-17, each indicator 49 associated with each of cells indicated by the human-readable indicia 47 "1, 3, 6, 9, 12, 15, 18, 21, 24, 27" into which Cardura tablets was to be loaded, is activated by PLC 79 of controller 17 (or computer 117 in system 10') during the verification process. Each other indicator 49 is inactive.

If screen 186 is provided, selection of the DONE icon 192 returns the pharmacist to screen 185 for selection of the next medicament 11 to be verified.

Once all cells 33 associated with a row 165 are verified, the technician then selects the next row 165 of medicaments to be verified and proceeds to verify the medicament(s) in each cell 33 as directed by indicators 49. The indicator or indicators 49 previously activated are deactivated and the appropriate indicators 49 for the next medicament 11 are activated. This process is repeated until all medicaments 11 have been verified as called for by screen 185.

Once all rows 165 and medicaments 11 are verified, the pharmacist selects the HOLDER VERIFIED icon 189. Selection of icon 189 sends a signal to server 107 of system 10 (or server 124 of system 10') indicating to system 10 that holder 13 has been fully verified and that the medicament 11 contents are in the correct cells 33 ready for use with automated dispensing machine 45. A record may be made of the verified medicament 11 contents of holder 13 cells 33 which may be stored in a database residing on server 107 (or server 124). Such a record is useful in further confirming that the correct medicaments 11 were loaded in holder 13. Each verified holder 13 can then be stored in cabinet 169 awaiting use, or the holder 13 and its medicament 11 contents can be taken directly to automated dispensing machine 45 for immediate loading of medicaments 11 into exception storage apparatus 43.

Figure 18:
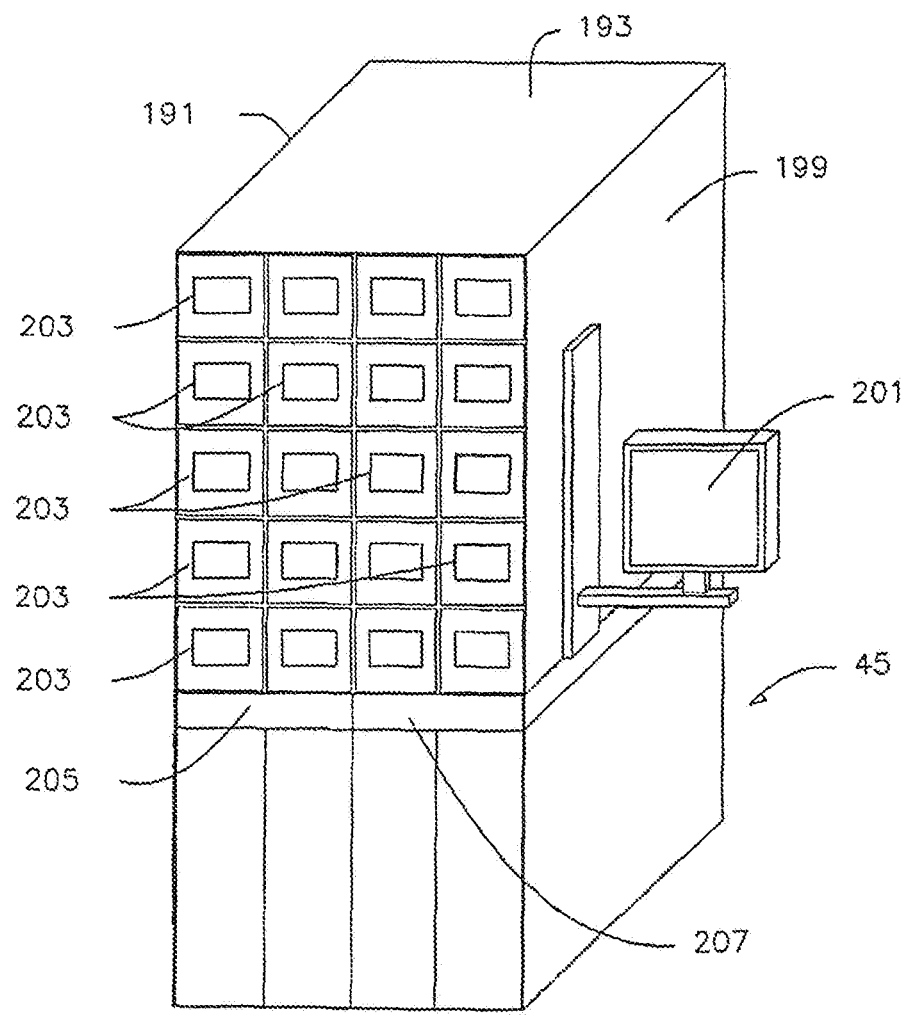
FIG. 18 is a perspective view of an exemplary automated medicament dispensing machine with which the representative holders of FIGS. 1-10 may be utilized.

Referring now to FIGS. 18-20, there is shown an exemplary automated dispensing machine 45 and exception storage apparatus 43 which may be quickly and accurately loaded with medicaments 11 using holder 13 or 13' or 13". Dispensing machine 45 includes a cabinet 191 with top and bottom walls 193, 195 and left and right sidewalls 197, 199. A touch-screen video display 201 is mounted to sidewall 199. Display 201 includes controls permitting a technician or pharmacist to control operation of automated dispensing machine 45 and to receive information about the status of the medicament filling process.

Exemplary automated dispensing machine 45 includes twenty pull-out drawers of which drawers 203 are exemplary. In the example, drawers 203 are organized into five rows of four drawers 203. Each drawer 203 supports a plurality of removable cassette-type storage apparatus (not shown), each of which stores a large quantity of bulk-form medicaments 11. The cassettes can be replenished as medicaments 11 stored therein are depleted.

Exemplary automated dispensing machine 45 further includes a pair of doors 205, 207 which cover exception storage apparatus 43 as shown in FIG. 18 and which can be opened as shown in FIGS. 19-20. As previously described, exception storage apparatus 43 may be provided to store and to dispense "slow mover" medicaments 11 loaded therein. In the example, automated dispensing machine 45 includes a single exception storage apparatus 43. However, any number of exception storage apparatus 43 may be provided based on the needs of the operator.

In the example, exception storage apparatus 43 is a drawer or tray-like device which can be pulled out from cabinet 191 as shown in FIGS. 19-20. When in the state of FIGS. 19-20, automated dispensing machine 45 is temporarily shut down and is out of service and unavailable to fill prescription orders and dispense requests while exception storage apparatus 43 is pulled out from cabinet 191. Therefore, it is important to load exception storage apparatus 43 as promptly as possible to return automated dispensing machine 45 to service.

Figure 22:
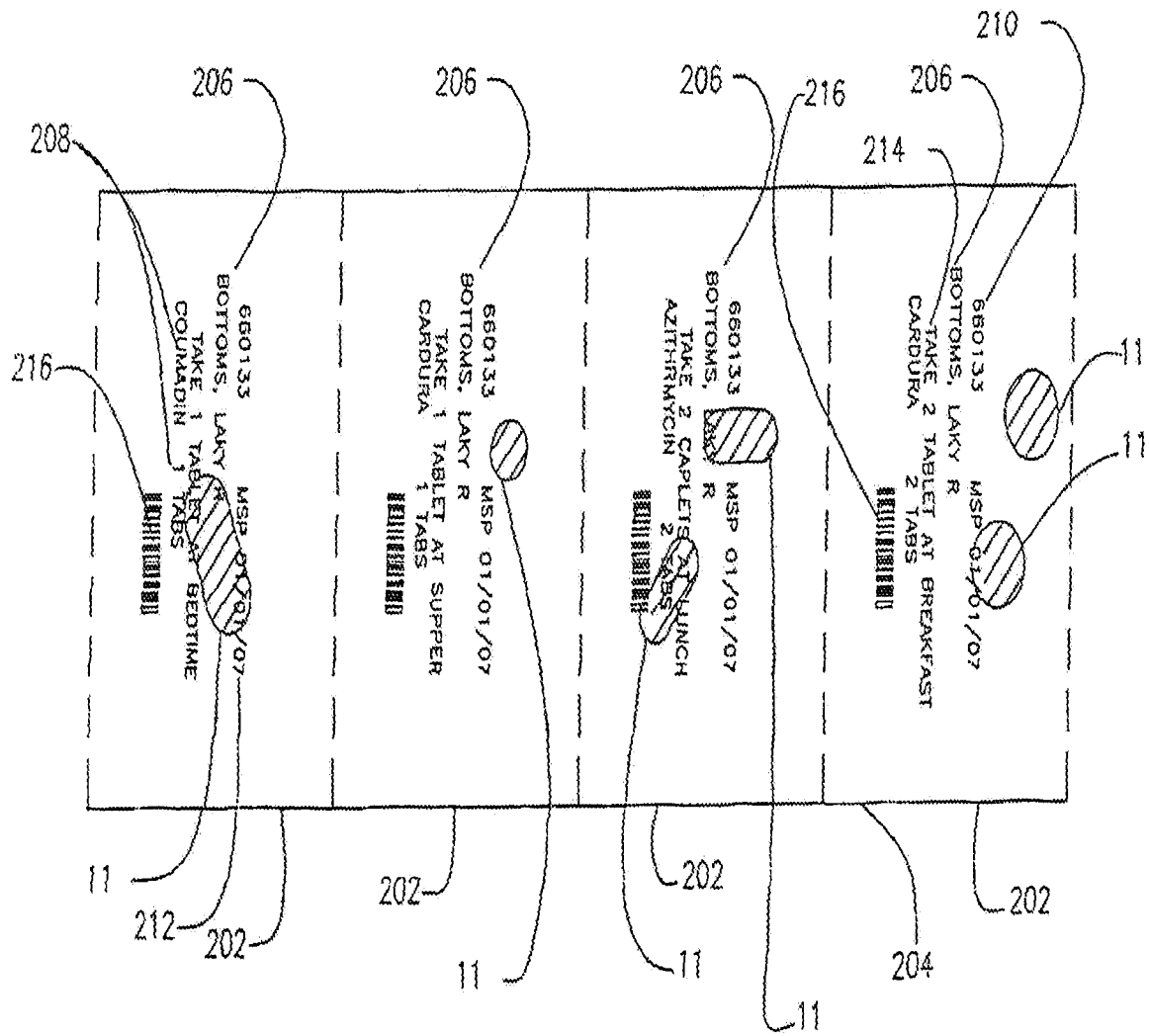
FIG. 22 is an exemplary series of medicament-containing pouch packages of the type produced by the automated dispensing machine of FIGS. 18-20.

The exception storage apparatus 43 shown in FIGS. 19-20 can be described as having a somewhat flat and narrow configuration with a plurality of cells 41 provided therein. Each cell 41 of exception storage apparatus 43 is capable of storing one medicament 11, or a small quantity of medicaments 11 as illustrated in FIGS. 21A-22. In the example, cells 41 include 64 total cells grouped in four rows of 16 cells.

Cells 41 are indexed for movement along a track (not shown) in exception storage apparatus 43. Cells 41 are indexed forward along the track toward an opening (not shown) in the bottom of apparatus 43 so that the contents of each cell 41 fall through a cell bottom opening (not shown) and to a packaging device within automated dispensing machine 45 through chutes, hoppers or other guide structure, or by a mechanical device such as an auger. Medicaments 11 may be discharged from cells 41 by any other suitable means including a movable gate (not shown) over a cell bottom outlet (not shown), or by a solenoid, air-powered actuator, air-jet, or mechanical arm which ejects the medicament through an upper cell inlet 209 of the type shown in FIG. 19A. The medicaments 11 fall via chutes, guides to a packaging device or are directed to packaging device by mechanical means (e.g. an auger).

In the example, automated dispensing machine 45 includes a pouch-package-type packaging apparatus (not shown) within a lower portion of cabinet 191. Alternatively, packaging apparatus capable of packaging medicaments 11 into other container types (e.g., bottles, vial, blister packages) may be utilized. A pouch-package-type packaging device includes a form-fill-seal packaging device. A "form-fill-seal" packaging device forms a package (i.e., a pouch) in a web of packaging material, fills the package with the medicament(s), and seals the package forming a plurality of discrete packages, or pouches.

In the example, one or more medicament 11 discharged from the cassette-type storage apparatus (not shown) or exception storage apparatus 43 is loaded into separate pouches 202 formed (e.g., by heat-sealing or sonic welding) in a web of packaging material 204 as illustrated in FIG. 22. Information can be printed on each pouch 202 by a printer (not shown) associated with automated dispensing machine 45 and such information can include the patient's name 206, medicament name and quantity 208, prescription number 210, date 212, instructions for taking the medicament 214 (such as time of day the medicament is to be taken) and machine-readable indicia 216 (such as a bar code) representative of the aforesaid information. Pouch packages are ideal for use in administering medication regimens because the exact medicaments to be taken at a given time can be packaged together in a single pouch, and the pouches can be organized and labeled in the exact order in which each medicament is to be taken, for example, morning, noon and evening. An exemplary automated dispensing machine 45 is a model ATP 320, 371, or 384 dispensing machine available from Chudy Group, LLC of Powers Lake, Wis.

Transfer of medicaments 11 from holder cells 33 to exception storage apparatus 43 will now be described in connection with FIGS. 21A-21C. In the example, cells 33 of holder 13 are positioned and arranged so that they have a pattern which is identical to that of cells 41 in exception storage apparatus 43. Holder 13, therefore, can be placed directly on top of exception storage apparatus 43 as shown in FIG. 20 and FIGS. 21A-21C with each cell 33 and 41 completely aligned and in registry. In the example, holder 13 and exception storage apparatus 43 each have 64 total cells 33, 41 grouped in four rows of 16 cells. Human-readable indicia 211 is preferably provided on exception storage apparatus 43 (FIG. 19A) so that each cell 33 on holder 13 has the same indicia 47 as indicia 211 on exception storage apparatus 43. The cell 33 pattern and indicia 47 of holder 13 is most preferably identical to the cell 41 pattern and indicia 211 of exception storage apparatus 43.

Referring again to FIGS. 20 and 21A-21C, the verified holder 13 is taken to exception storage apparatus 43 of automated dispensing machine 45 by a technician or pharmacist. Holder 13 is set on top of exception storage apparatus 43. Legs 51, 53 position holder 13 over exception storage apparatus 13 as shown, for example, in FIGS. 21A-21C to ensure that holder 13 is in the correct orientation on exception storage apparatus 43 with correct alignment of cells 33, 41. Once aligned, holder 13 is initially in the position shown in FIG. 21A.

At this point in the process, identification element 81 is detected by detector 84 of automated dispensing machine 45. If the correct holder 13 is positioned over exception storage apparatus 43, the technician/pharmacist is given a prompt signal by video display 201. If an incorrect holder 13 is positioned over exception storage apparatus 43, then display 201 prompts the technician/pharmacist to not transfer the medicaments 11 and may present an error message and/or alarm. In addition, system 10 or 10' may deactivate automated dispensing machine 45 preventing automated dispensing machine 45 operation until the correct holder 13 is in place or the technician/pharmacist overrides the system 10, 10'.

Prior to medicament 11 transfer and as shown in FIG. 21A, shuttle member 55 is in its "closed" position with cell 33 outlets 39 covered by shuttle member 55. Medicaments 11 cannot exit cells 33 in this closed position.

Next, and as shown in FIG. 21B, the technician grasps pull 61 and moves shuttle member 55 in the direction of arrow 217. Movement of shuttle member 55 in the direction of arrow 217 partially opens cell outlets 39 as openings 59 in shuttle member 55 are aligned with cell outlets 39. As a result, medicaments 11 begin to fall by means of gravity into the aligned cells 41 of exception storage apparatus 43.

Finally, and as shown in FIG. 21C, the technician moves shuttle member 55 fully in the direction of arrow 217 by means of pull 61 to fully align openings 59 in shuttle member 55 with cell outlets 39. Cells 33 are fully open in this position causing medicaments 11 in cells 33 to fall into the corresponding cells 41 of exception storage apparatus 43. Exception storage apparatus is now correctly loaded and is ready for dispensing and packaging of the slow mover medicaments 11 stored in cells 41. This loading process shown in FIGS. 21A-21C is very rapid (less than one minute) and enables automated dispensing machine 45 to be quickly returned to service.

Systems 10, 10' accurately and rapidly enable loading of medicaments 11 in the exact order in which the medicaments 11 are to be loaded into exception storage apparatus 43. The medicaments 11 are rapidly verified by the system 10, 10' and docking station 15 in a way which is not possible based solely in reliance on written instructions. This is because selective operation of the indicators 49 permits pharmacy personnel to load and verify the contents of holder 13 without having to take his or her eyes off of the holder 13 to read instructions. Each exemplary system 10, 10' therefore, speeds the holder-loading process while at the same time providing a high confidence level that each cell 33 and 41 has been loaded with the correct medicament 11. Accurate loading of medicaments 11, in turn, provides a better level of care for all patients which, of course, is always the primary objective of any pharmacy, hospital, long-term care facility or other care-giver. And, time required for selecting, verifying, and loading medicaments 11 into the automated dispensing machine is significantly decreased. This frees pharmacists to better serve their patients and enables the automated dispensing machine 45 to be immediately returned to service. The result once again is improved patient care and reduced cost of operation to the pharmacy, hospital, long-term care provider or other operator.

Further Exemplary Embodiments

Referring now to FIGS. 23-53, there are illustrated further exemplary item-management systems 1010, 1010'. As with systems 10, 10', systems 1010, 1010' are described in the context of a preferred item-management system for management of medicament 1011 items.

A sensor guide 1301, 1301' may be used with systems 1010, 1010' to provide heightened accuracy in loading holder 1013, 1013'. Sensor guide 1301, 1301' provides for medicament detection and for positive feedback confirming that the medicament 1011 or other item placed into holder 1013, 1013' was correctly placed into holder 1013, 1013' providing an opportunity to reduce human-factors-related errors as described herein.

System 1010 illustrated in FIGS. 23-36 facilitates accurate and rapid loading of a holder 1013 in the form of a container used in loading an automatic dispensing machine 49. System 1010' illustrated in FIGS. 37-52 facilitates accurate and rapid loading of a holder 1013' in the form of a container known as a blister package.

The terms "holder" and "container" are used interchangeably throughout this document. A "holder" or "container" means or refers to an apparatus which holds one or more items, such as medicaments 1011. Blister packages are a type of holder and container and are identified herein by reference number 1013'.

In the examples, each holder 1013, 1013' is used in conjunction with a respective docking station 1015, 1015' to which holder 1013 or holder 1013' may be temporarily docked. A controller 1017 may include one or more control capable of operating systems 1010, 1010'. As with the above-described embodiments, the term "at least one controller," therefore, means or refers to embodiments in which controller 1017 includes one or more controller components. Controller 1017 may include components internal and/or external to docking station 1015, 1015'.

For simplicity and brevity, like reference numbers of system 1010 are used to identify like or similar parts of system 1010'.

In the example of system 1010, medicaments 1011 are loaded in holder 1013 in the exact order in which medicaments 1011 are to be loaded into exception storage apparatus 43 of automated dispensing machine 45, examples of which are described above. This may be the order in which the medicaments 1011 are to be taken by the patient. Once transferred to exception storage apparatus 43, automated dispensing machine 45 will package the medicaments 1011 into one or more pouch package 202 as described in connection with systems 10, 10' and as illustrated, for example, in FIG. 22. Each pouch package 202 is subsequently delivered to a patient for whom the medicament 1011 is intended. If pouch packages 202 are arranged in the order in which the medicaments 1011 are to be taken, the patient merely opens one pouch 202 after the other and takes the medicament 1011 therein in accordance with the prescription order provided by the patient's physician.

In the example of system 1010', the medicaments 1011 may also be loaded in an order required by a prescription order, for example in the order in which the medicaments 1011 are to be taken by a patient in accordance with the physician's instructions. Automated dispensing machine 45 is not needed for system 1010' because, after closure, holder 1013' becomes the container given to the patient. In embodiments, the patient can merely push against a cell 1033 which then causes the medicament 1011 to be pushed out of the holder 1013' through a closure 1042 (e.g., a foil safety seal) as described herein.

As with the previous embodiments, systems 1010, 1010' utilize visible information to assist pharmacy personnel (e.g., a technician, pharmacist or other user) in the loading and any verification of the contents of holder 1013, 1013' without having to take his or her eyes off of holder 1013, 1013' to read written instructions which may be written on a piece of paper. For each of systems 1010, 1010', the user simultaneously sees the medicament 1011, the cell 1033, sensor guide opening 1317 and visible information at the moment the medicament 1011 is hand loaded into the cell 1033 which improves the accuracy of the prescription fulfillment and minimizes the risk of error.

Systems 1010, 1010' make the tedious, labor-intensive, and time-consuming process of loading holders 1013, 1013' easier and faster, particularly if different types of medicaments 1011 must be loaded into separate cells 1033 of the same holder 1013, 1013'. Each exemplary system 1010, 1010' therefore, provides an opportunity for better patient care because there is an improved confidence level that the correct medicament 1011 is being provided to the patient in accordance with the physician's instructions and because time saved administering medicaments can be allocated to other aspects of patient care provided by the pharmacy, hospital, long-term care facility or other care-giver.

Systems 1010, 1010' may be configured and arranged based on the needs of the pharmacy, hospital, long-term care facility or other operator. While it is envisioned that embodiments of systems 1010, 1010' will be utilized in the health-care industry for loading of medicaments 1011, it should be understood that such systems and others may have application in fields outside of the health-care industry for management and dispensing of items other than medicaments 1011. For example, small parts could be loaded into a holder 1013 or a holder 1013' of a blister-package-type 1013.

Referring next to FIGS. 28-31 and FIGS. 23-25, and 27, exemplary holder 1013 of system 1010 will now be described. Exemplary holder 1013 may be used for loading an automatic dispensing machine 49 in the same manner as described previously in connection with systems 10, 10' and holders 13, 13', 13".

Holder 1013 illustrated in FIGS. 28-31 includes a body 1019, a top and a bottom 1021, 1023, a front and a rear side 1025, 1027, and a left and a right side 1029, 1031. Holder 1013 includes cells 1033, each of which is defined by a wall 1035. In the example of holder 1013, cells 1033 and walls 1035 define an oval shaped cell 1033. The oval shape could match an oval shape of cells 41 of exception storage apparatus 43. For brevity, only certain of the cells 1033 are indicated by reference numbers 1033 and 1035, it being understood that each cell 1033 has the same structure in the examples.

Holder 1013 has a tray-like appearance in that it is a flat, shallow container used for carrying, holding, and organizing items which are preferably medicaments 1011. As illustrated in FIGS. 28-31, holder 1013 is a portable container which can be easily carried by a user from docking station 1015 to automatic dispensing machine 49 for transfer of medicaments 1011 from holder 1013 to exception storage apparatus 43. However, other configurations of holder 1013 may be utilized depending on the needs of the user.

In the examples, each cell wall 1035 of holder 1013 defines a cell 1033 upper opening, or inlet 1037, and a cell lower opening, or outlet 1039. As shown in the examples, the cell inlets 1037 extend through, and are included in and along, the body top 1021 while the cell outlets 1039 extend through, and are included in and along, the body bottom 1023. Medicaments 1011 are loaded into each cell 1033 through inlet 1037 and are discharged from cell 1033 through outlet 1039.

In the examples, each cell 1033 is identical in structure. However, it is possible that cells 1033 of holder 1013 may have a structure which is not identical and which may differ depending on the needs of the user.

Referring again to FIGS. 28-31, the illustrated exemplary holder 1013 is provided with sixty four total cells 1033 organized into four rows of 16 cells 1033. In the examples, the organization of cells 1033 is identical to the organization of cells 41 of exception storage apparatus 43 of automated dispensing machine 45 described above in connection with FIGS. 18-21C. Exemplary holder 1013 is configured and arranged such that each cell 1033 outlet 1039 is in registry with (i.e., aligned with) a corresponding cell 41 of exception storage apparatus 43 permitting direct movement of medicaments 11 from holder 1013 into exception storage apparatus 43 in the same manner as cells 33 are aligned with cells 41 as shown in the example of FIGS. 21A-21C. Cells 1033 can be of any number and need not be arranged in rows and columns as illustrated. For example, cells 1033 could be arranged in any number of rows, columns, or other patterns to correspond to cells 41 of an exception storage apparatus 43 other than as illustrated or for use in transferring medicaments 1011 or items to a device other than exception storage apparatus 43.

Holder top 1021 is preferably provided with human-readable indicia 1047 identifying each cell 1033. In the examples, indicia 1047 is an integer from 1 to 64 proximate each cell 1033. Other types of indicia 1047 may be used, such as alpha-numeric indicia.

Holder 1013 further includes at least one indicator 1049" for each cell 1033, of which indicator 1049" is representative. For purposes of simplicity and brevity, each indicator 1049" of holder 1013, 1013' is indicated by reference number 1049", it being understood that each indicator 1049" has the same structure in the examples. Each indicator 1049" is located through holder 1013 body 1019 from bottom 1023 to top 1021. In the example, indicators 1049" are organized into four rows of 16 indicators 1049" corresponding to the pattern of cells 1033 of holder 1013 and positioned so as to be below each cell 1033 and approximately centered on each cell 1033. One indicator 1049" is provided for each cell 1033 for a total of sixty four indicators 1049" in the example, although other indicator types and arrangements may be provided as described herein.

Each indicator 1049" may be a visible information source in the form of a selectively-operable light pipe. A light pipe means or refers to a light-transmissive device used for transporting or distributing natural or artificial light. The indicators 1049" may be of molded plastic, fiber optics, or other light-communicating materials. Each indicator 1049" (and indicators 1049', 1049' described herein) includes a first end 1054, or inlet, a body 1056, and a second end 1058, or outlet. Light (i.e., visible information) from a light source such as an LED indicator 1049 which enters the inlet 1054, is communicated through body 1056 to outlet 1058. When docked at docking station 1015, indicator 1049" is aligned with docking station indicators 1049, 1049' to receive and communicate light. Indicators 1049, 1049', 1049" communicate light so that the light is visible to a user on holder 1013 top 1021.

Holder 1013 further includes a pair of front legs 1051 and a pair of rear legs 1053 depending from holder 1013 bottom side 1023. Leg pairs 1051, 1053 may be provided to support holder 1013 on a surface (such as workstation counter top 1085).

Figure 31:
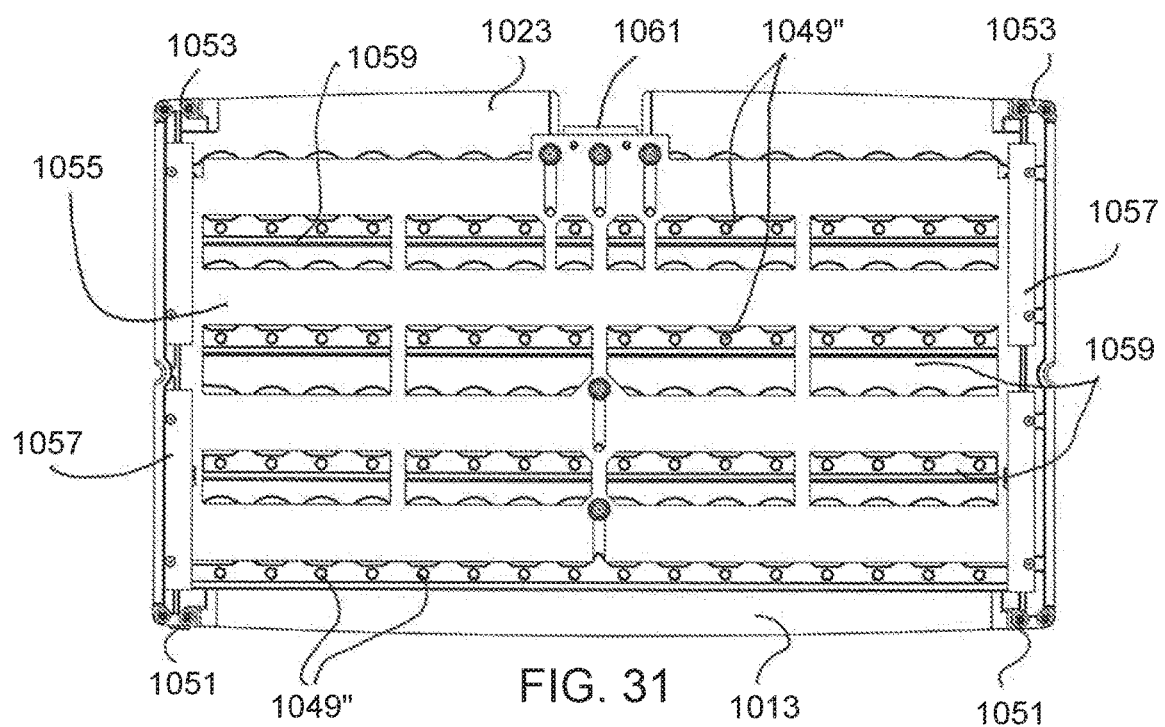
FIG. 31 is a bottom plan view of the exemplary holder of FIG. 29.
Figure 32:
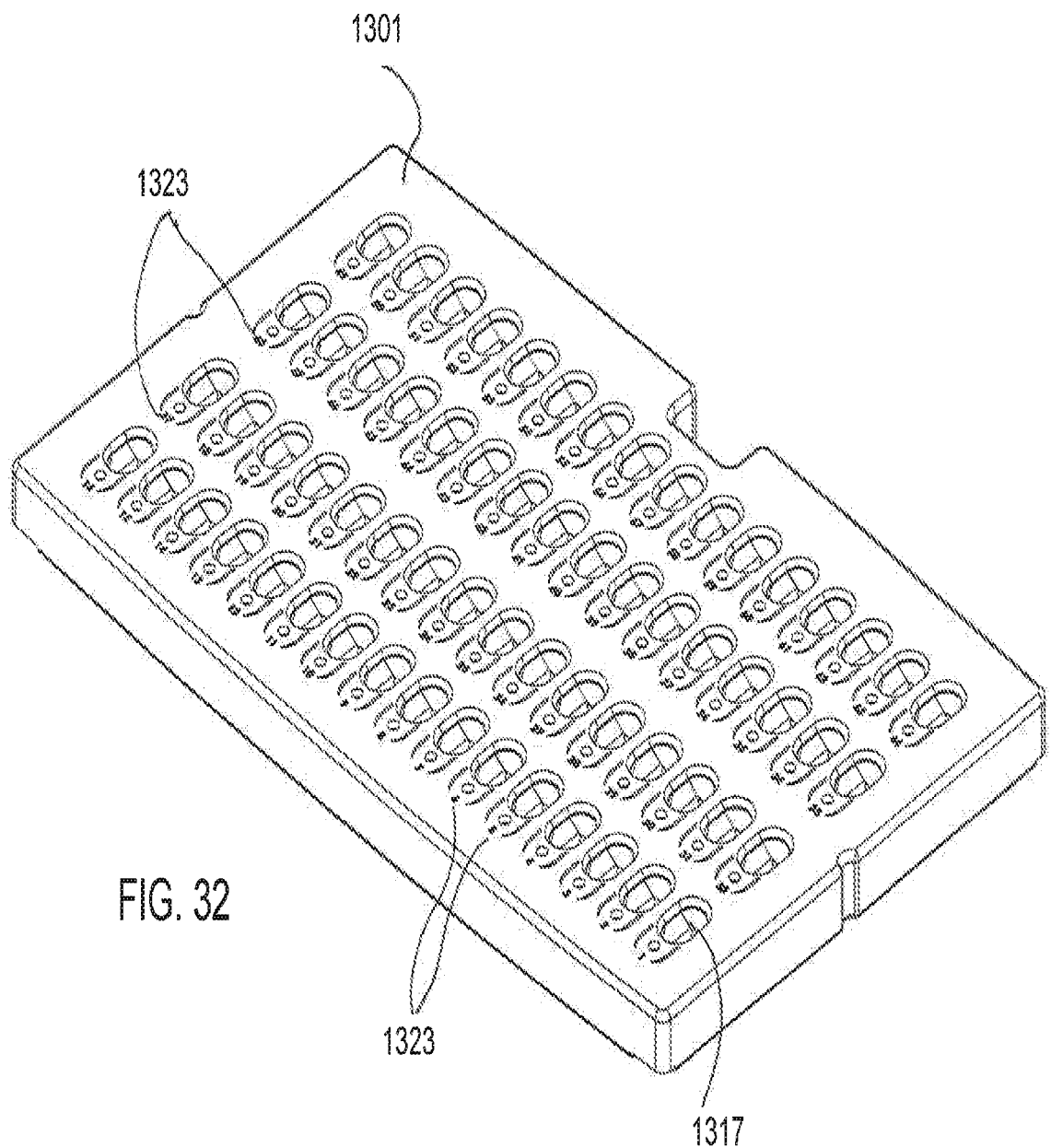
FIG. 32 is a perspective view of an exemplary sensor guide of FIG. 23.
Figure 33:
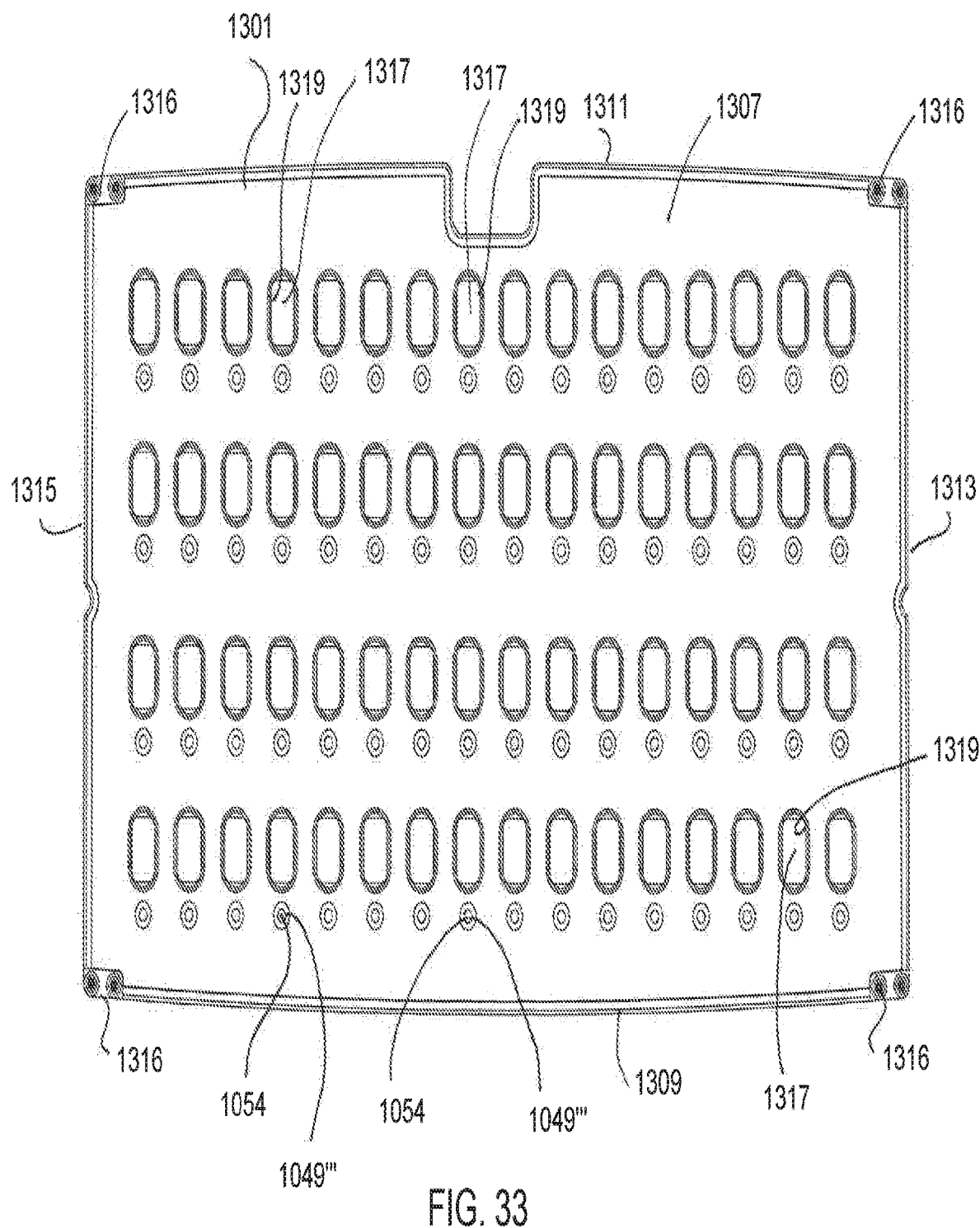
FIG. 33 is a bottom plan view of the exemplary sensor guide of FIG. 23.

Referring to the bottom plan view of FIG. 31, exemplary holder 1013 further includes a planar shuttle member 1055 positioned in planar track 1057 in holder 1013 proximate each cell 1033 outlet 1039. Shuttle member 1055 includes openings 1059 and a pull 1061 which permits the technician or pharmacist to grasp shuttle member 1055 with his or her hand and to pull or push shuttle member 1055.

Figure 28:
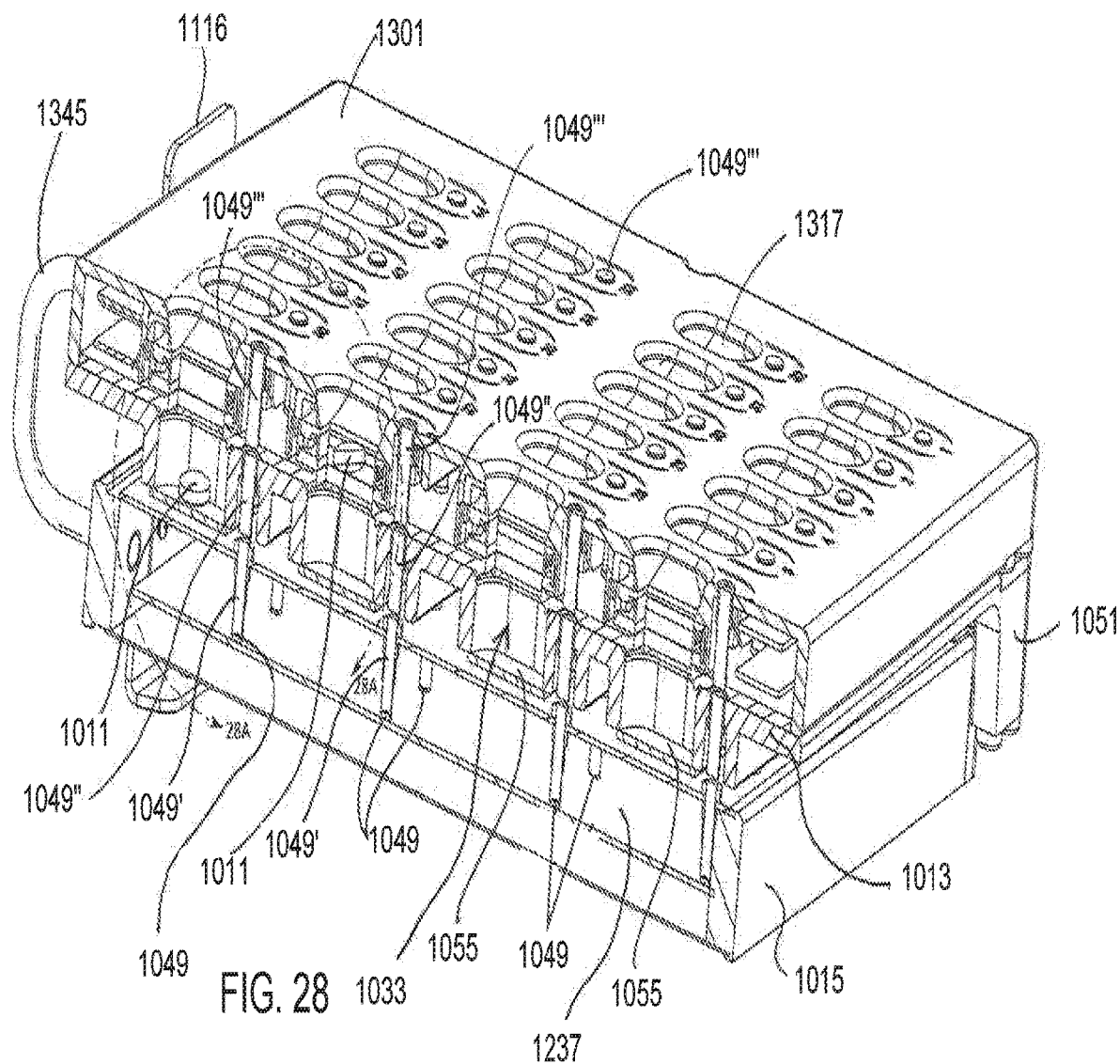
FIG. 28 is a section view of the medicament management system of FIG. 23 taken along section 28-28 of FIG. 26.
Figure 28A:
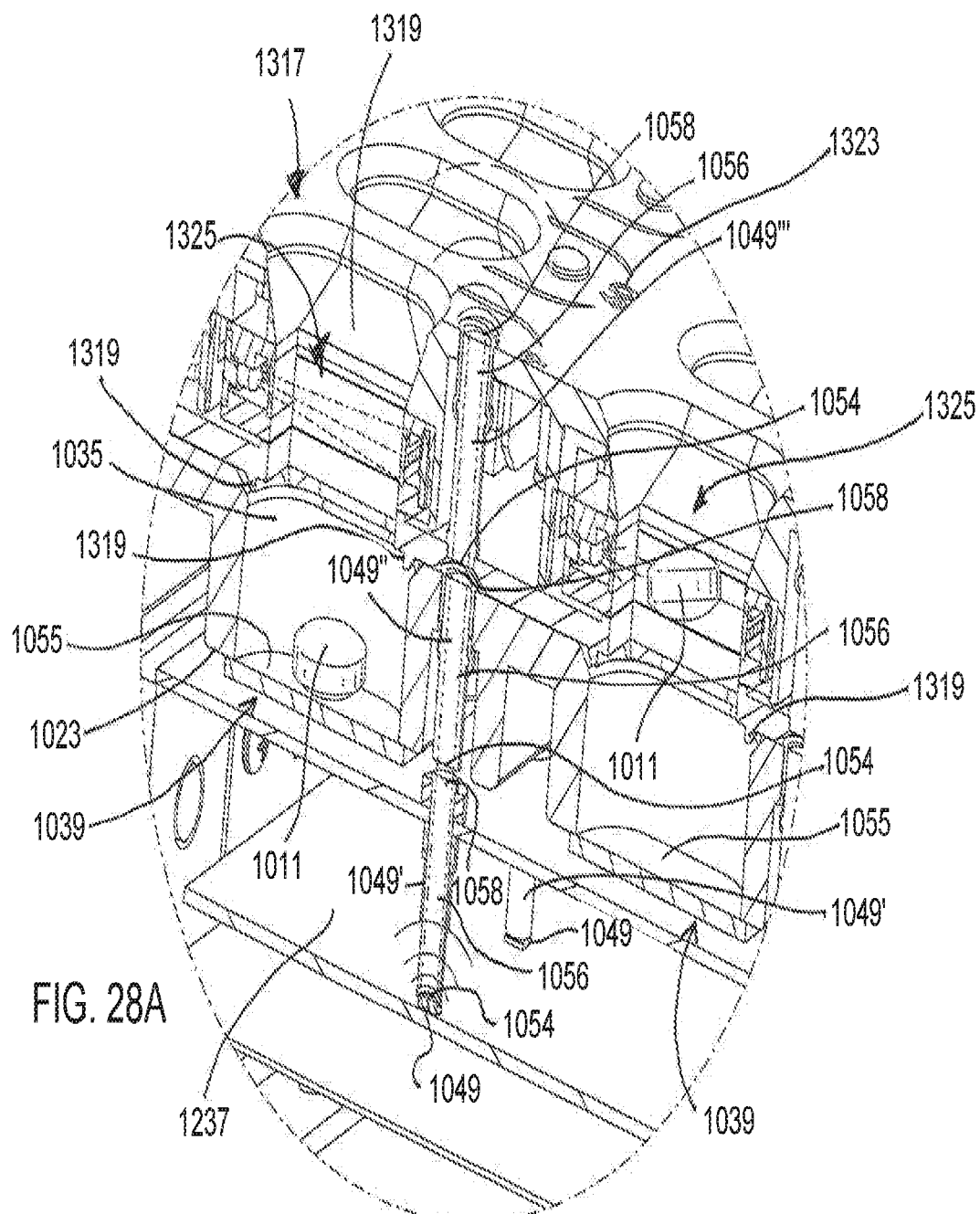
FIG. 28A is an enlarged section view of the medicament management system of FIG. 23 taken along section 28A-28A of FIG. 28.
Figure 29:
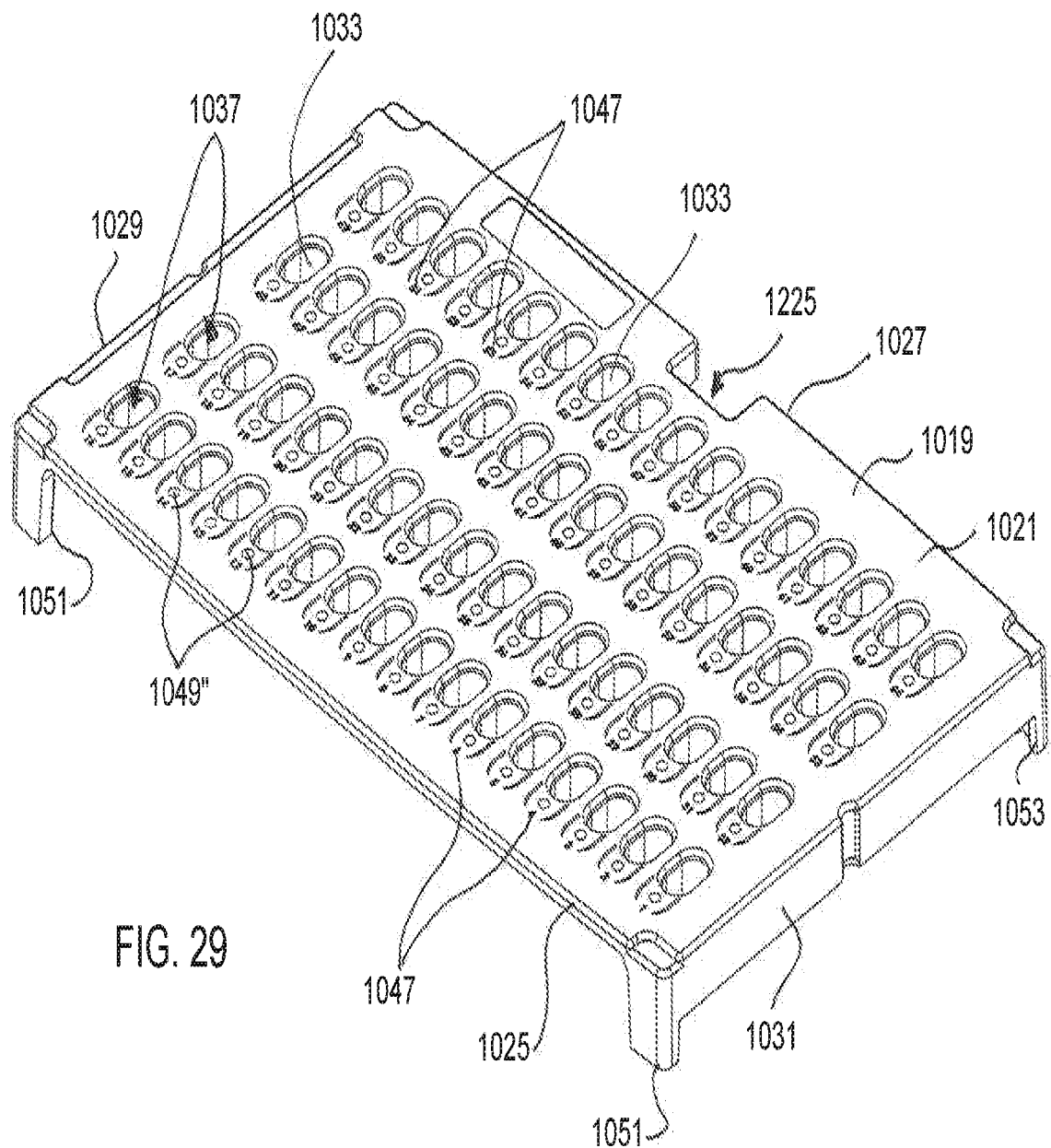
FIG. 29 is a perspective view of an exemplary holder.
Figure 30:
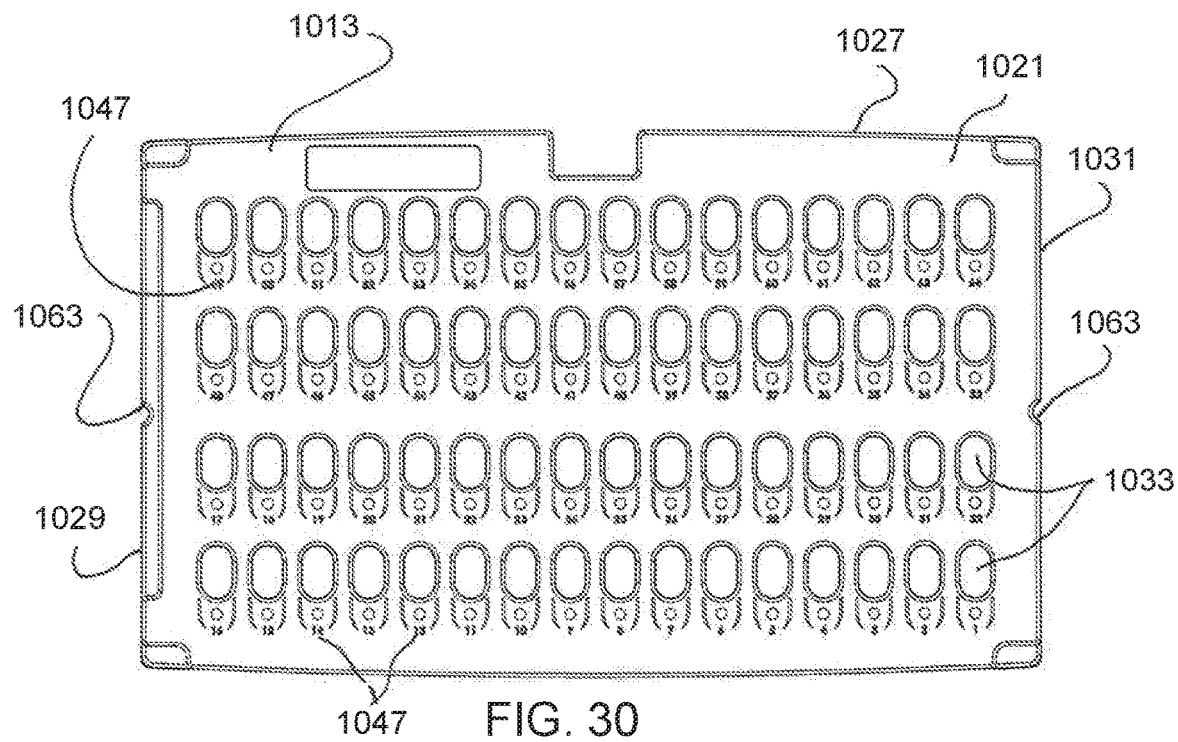
FIG. 30 is a top plan view of the exemplary holder of FIG. 29.

In the example, shuttle member 1055 is movable between a first position shown in FIGS. 28, 28A, and 31 in which shuttle member 1055 covers and closes each cell 1033 outlet 1039 in the same manner as illustrated in FIG. 21A for holder 13 and a further position in which the shuttle member 1055 openings 1059 are in alignment with each cell 1033 outlet 1039, thereby opening each cell outlet 1039 permitting medicaments 1011 to drop from each cell 1033 into a corresponding cell of exception storage apparatus 43 in the same manner as illustrated in FIG. 21C for holder 13. The first position of shuttle member 1055 is referred to herein as a "cell-closed position" and the further position of shuttle member 1055 is referred to herein as a "cell-opened position." In between these positions, the cells 1033 are partially open permitting medicaments 1011 to start to fall from cells 1033. This intermediate position would be the same as for holder 13 illustrated in FIG. 21B.

In the embodiments, shuttle member 1055 serves as a sliding gate or closure, opening and closing each cell 1033 as shuttle member 1055 moves and slides between the cell-closed (e.g., FIG. 21A) and cell-opened positions (e.g., FIG. 21C). Shuttle member 1055 thereby blocks each cell outlet 1039 in the cell-closed position permitting a medicament 1011 to be loaded into each cell 1033 for organizing and storage and further opens each cell outlet 1039 permitting each medicament 1011 to be discharged from holder 1013 for loading into exception storage apparatus 43 in the same manner as described in connection with holder 13 and FIGS. 21A-21C above.

Body 1019 also preferably includes a bar code 1132 (FIG. 24) with a code uniquely identifying holder 1013. Holder 1013 may be made of any suitable material or combination of materials. Preferably, body 1019 is made of plastic material construction for reasons of ease of manufacture, low weight and portability, ease of cleaning, and cost. Indicators 1049" are preferably light pipe-type indicators but may comprise other types of indicators.

Referring now to FIGS. 45-47 and FIGS. 37-39 and FIG. 52, exemplary holder 1013' of system 1010' will next be described. As illustrated, holder 1013' is a portable blister-package-type container for managing and organizing medicaments 1011. In the examples, a loaded holder 1013' can be delivered to a patient as an integrated container including medicaments 1011 as required to fulfill the patient's prescription order. For simplicity and brevity, like reference numbers of holder 1013 are used to identify like parts of holder 1013'.

Exemplary holder 1013' includes a body 1019, a top and a bottom 1021, 1023, a front and a rear side 1025, 1027, and a left and a right side 1029, 1031. Holder 1013' further includes cells, of which cell 1033 is representative. Holder 1013 cells 1033 are referred to by some in industry as "wells" and the terms cells and wells are used interchangeably herein. Each cell 1033 is defined by a wall 1035, of which wall 1035 is representative. In the example of holder 1013', cells 1033 and walls 1035 have an elongate "D" shape (in cross-section), which is a shape employed in certain blister-package-type containers. Other cell 1033 and wall 1035 shapes may be utilized. For purposes of simplicity and brevity, each cell 1033 of blister package 1013 is indicated by reference number 1033 and each wall is indicated by reference number 1035, it being once again understood that each cell 1033 has the same structure in the example. Exemplary holder 1013' has a tray-like appearance in that it is a flat, shallow container used for carrying, holding, and organizing items which are preferably medicaments 1011.

Each wall 1035 defines a cell 1033 upper opening, or inlet 1037 and a cell bottom 1040. As shown in the examples, the cell inlets 1037 extend through, and are included in and along, the body top 1021. In the embodiments, medicaments 1011 are loaded into each cell 1033 through inlet 1037.

In the embodiments, each cell 1033 is identical. However, it is possible that cells 1033 of holder 1013' may have a structure which is not identical and which may differ depending on the needs of the user. For example, certain cells 1033 of holder 1013' could have a depth or a cross-sectional shape which differs from the depth and cross-sectional shape of other cells of holder 1013".

Referring further to FIGS. 45-47 and 37-39 each illustrated exemplary blister package 1013' includes thirty two total cells 1033 organized into eight rows of four cells 1033. The illustrated organization of cells 1033 is merely exemplary. Cells 1033 can be of any number and need not be arranged in rows and columns as illustrated. For example, cells 1033 could be arranged in any number of rows and columns, in a circular pattern, or in any other suitable arrangement.

A closure 1042 may be affixed to body 1019 to cover cell inlets 1037 and provide an integrated and sealed blister-package-type holder 1013'. Closure 1042 may be of a thin foil, paperboard, or other suitable material capable of closing holder 1013'. Closure 1042 may be joined to body 1019 by any suitable means including adhesive(s), sonic bonding (i.e., plastic welding), and heat sealing. Holder 1013' protects medicaments 1011 and other items therein from contact with the outside environment and provides a convenient container with which to deliver the contents of the holder 1013' to the patient or other end user.

Before or after loading of holder 1013', an adhesive-backed label 1044 may be affixed to holder 1013'. Label 1044 may include all information needed for use of holder 1013' as a self-contained, sealed, patient-specific container which may include a course of medicaments 1011 as prescribed by a physician. Alternatively, holder 1013' may include a non-patient-specific label (not shown) generally identifying the medicament 1011 contents so that the holder 1013' can be subsequently delivered to any patient requiring the medicaments 1011.

Label 1044 may include any suitable information including patient name 1046 "John Doe"), physician name 1048 ("Dr. Jane Smith"), medicament name, strength, and NDC number 1050 (e.g., "Naproxen Anaprox 375 mg", 11-digit NDC "00093014801"), instructions 1052 and a unique barcode 1054. In addition or as a substitute for label 1044, the aforementioned information may be printed directly on closure 1042, preferably before joining closure 1042 to body 1019.

Body 1019 may, for example, be made of material capable of having the cells 1033 formed therein by processes such as thermoforming or cold forming. In embodiments, a preferred material for body 1019 is polyvinyl chloride (PVC) sheet. The PVC sheet may be between about 0.008 and about 0.012 inches in thickness, as an example. PVC sheet is inexpensive and can be thermo-formed to form cells 1033. The material selected for body 1019 may be selected so that cells 1033 are collapsible by pushing with a human finger. Closure 1042 is preferably breakable so that a medicament 1011 within cell 1033 can be pushed through closure 1042 and out of holder 1013' for use. In other embodiments, body 1019 may be of a relatively thicker plastic sheet material which does not collapse, thus forming a rigid tray. In such an embodiment, closure 1042 may be of a "peel-off" type to permit access to medicaments 1011 or other items within cells 1033.

Body 1019 may be light-transmissive, and preferably transparent, thereby permitting the contents of each cell 1033 to be seen through bottom 1023 without opening holder 1013'. Body 1019 could also be translucent or opaque as required, for example for ultra-violet light protection of medicaments 1011 therein.

Closure 1042 affixed to holder 1013' may include human-readable indicia (not shown) identifying each cell 1033 and/or providing information to assist the patient comply with the physician's instructions. Closure 1042 is a suitable surface for indicia because it can have a relatively large surface area suitable for printing. For example, indicia on closure 1042 could include a day of the week anchor time at which a particular medicament 1011 is to be removed from blister-package-type holder 1013' and taken by the patient. Other types of indicia and information may be provided or used.

Referring next to FIGS. 23-28A, 36 and FIGS. 37-44B, 50 and 52, there are shown embodiments of docking stations 1015, 1015' capable of use with a respective exemplary holder 1013, 1013'. Each docking station 1015, 1015' may be placed on a counter top 1085, such as the counter top 1085 at a workstation in a pharmacy, long-term care facility, hospital, or other facility.

Each exemplary docking station 1015, 1015' preferably includes housing 1089 including top and bottom walls 1091, 1093, left and right side walls 1095, 1097 and front and rear walls 1099, 1101. As illustrated in FIGS. 23-28A, docking station 1015 may include a pair of rear legs 1102, 1104 attached to rear wall 1101 which raises the rear wall 1101 so that docking station 1015 is angled down toward front wall 1099.

As illustrated in FIGS. 37-39 and 41, exemplary docking station 1015' is supported with a cradle 1106. Cradle 1106 may be made of a single piece of metal sheet or other material and may have a rear leg 1108 which may be elongated to angle docking station 1015' toward front wall 1099, a deck 1110 on which docking station 1015' rests, and a front retainer 1112 against which front wall 1099 rests to retains docking station 1015' on cradle 1106. Angling docking stations 1015, 1015' toward front wall 1099 may help a technician, pharmacist, or other user better see medicaments 1011 or other items at the moment the medicament 1011 enters the holder 1013, 1013' and in an optional subsequent verification process.

As illustrated in FIGS. 24-27, and 37-38 and 41, exemplary docking stations 1015, 1015' may further include structure permitting sensor guide 1301, 1301' to be removed from a holder 1013, 1013' and temporarily stored on docking station 1015, 1015'. Docking station 1015 may include a seat 1114 formed by uprights 1116 and rear legs 1102, 1104. Seat 1114 is provided to temporarily hold sensor guide 1301 upright away from holder 1013. In the example of docking station 1015', sensor guide 1301' may simply be placed on end resting against rear wall 1101 of docking station 1015'. These arrangements permit holder 1013, 1301' to be docked and undocked from docking station 1015, 1015', permit optional verification of a loaded holder 1013, and permit use of systems 1010, 1010' without sensor guide 1301, 1301' as described herein.

In the embodiment of system 1010 illustrated in FIGS. 23-28A, docking station 1015 housing 1089 is generally rectangular in shape, although any shape may be utilized. Housing 1089 has a generally planar top wall 1091 and may include resilient pads (not shown) on which holder 1013 rests when docked at docking station 1015.

Referring to FIGS. 23-27, holder 1013 and docking station 1015 may include locating structure which cooperates to enable or facilitate repeatable docking of holder 1013 with docking station 1015 in a single and identical position. As illustrated in FIGS. 23-27, such locating structure may comprise a pair of female alignment pin receivers 1063 on opposite sides 1029, 1031 of holder 1013 and a pair of male alignment pins 1065 on docking station 1015. Male alignment pins 1065 are received in a respective receiver 1063 when holder 1013 is docked with docking station 1015. The mechanical interconnection of receivers 1063 and corresponding pins 1065 locates holder 1013 at docking station 1015 in a single and identical position and constrains holder 1013 from lateral movement. The exemplary locating structure permits plural different holders 1013 to be repeatedly docked in a single and identical position with a single docking station 1015.

Locating structure for holder 1013 may further include an alignment guide 1223 (FIG. 26) along docking station 1015 housing 1089 rear wall 1101. Alignment guide 1223 is received in recess 1225 provided in holder 1013. Alignment guide 1223 cooperates with alignment pin receivers 1063 and male alignment pins 1065 to limit lateral movement of holder 1013.

In the embodiment of FIGS. 37-39, 41-44B, docking station 1015' housing 1089 is generally rectangular in shape although, as with docking station 1015, any shape may be utilized. In this illustrated embodiment, housing 1089 top wall 1091 is preferably planar and includes a plurality of pockets 1229. For convenience and brevity, select pockets are indicated by reference number 1229, it being understood that the other pockets have the same structure. Pockets 1229 are provided to receive cells 1033 of holder 1013' nested therein for purposes of locating holder 1013' at a known position on docking station 1015'.

In the embodiments, pockets 1229 have an arrangement or pattern which matches the pattern of holder 1013' cells 1033. Each pocket 1229 is defined by a wall 1231, of which wall 1231 is representative. Each wall 1231 defines a pocket upper opening 1233. In the example of docking station 1015', pockets 1229 have an elongate "D" shape (in cross-section) which matches and is complementary to the elongate "D" shape of holder 1013' cells or wells 1033. In the embodiments, the cells 1033 of holder 1013' are inserted into pockets 1229. Walls 1035 defining cells 1033 may be sized to fit snugly within a respective pocket 1229. The complementary elongate "D" shapes of the cells 1033 and pockets 1229 may serve as a type of key which helps to position holder 1013' in a single orientation in docking station 1015'. Preferably, holder 1013' body 1019 and bottom 1023 rest on top wall 1091 of housing 1089 during the process of loading medicaments 1011 into each cell 1033 through cell inlet 1037.

The aforementioned arrangement limits lateral movement of holder 1013' in any lateral direction. Since holder body 1019 and bottom 1023 preferably rest on top wall 1091, holder 1013' is effectively held in place in position to receive the medicaments 1011 or other items therein which is of particular importance when seeking to load holder 1013' accurately. This also locates holder 1013' at a known position which is important so that the location of each cell 1033 is known to system 1010' as previously described in connection with system 1010.

Figure 38:
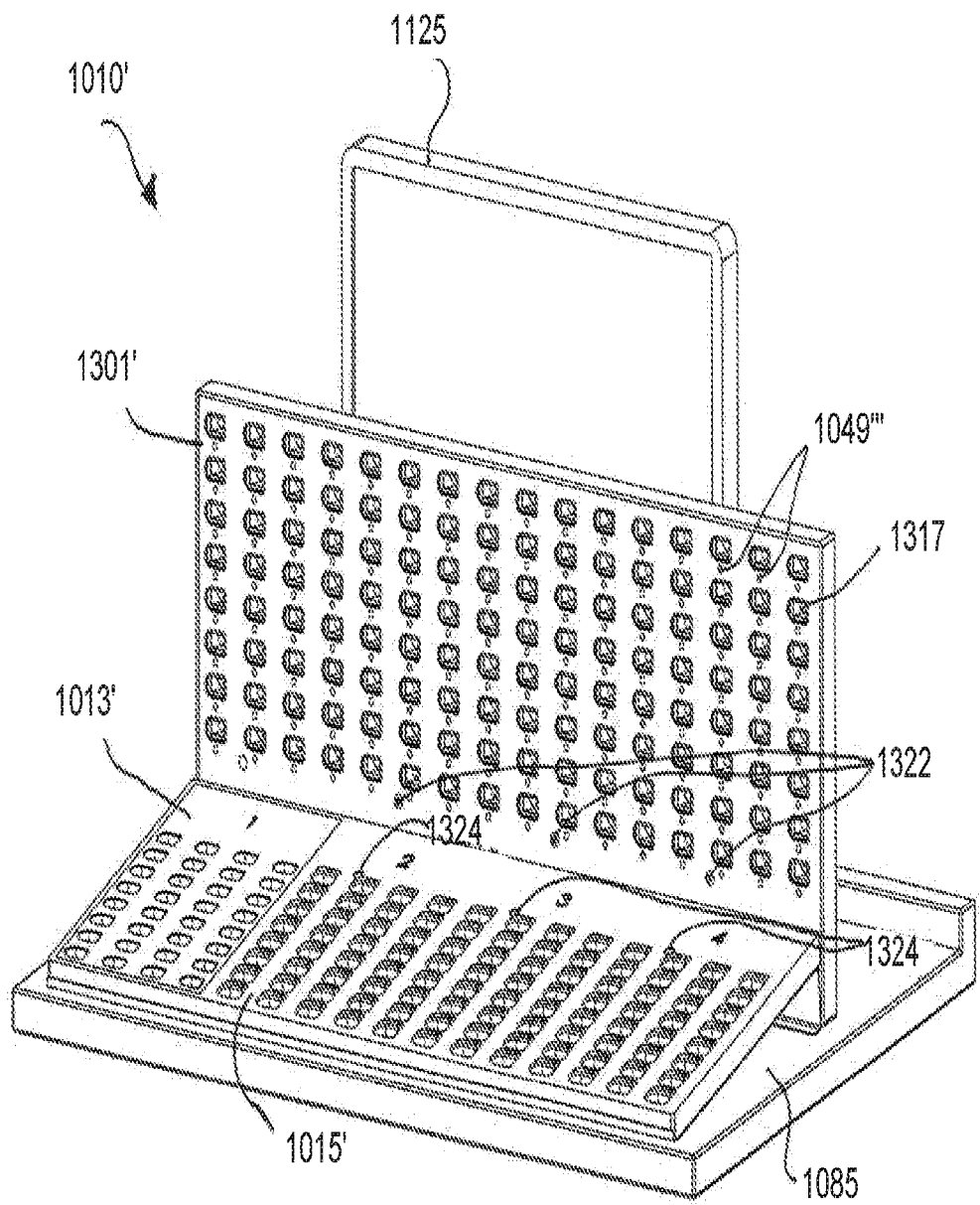
FIG. 38 is a perspective view of the medicament management system of FIG. 37, but with the sensor guide in a storage position.
Figure 39:
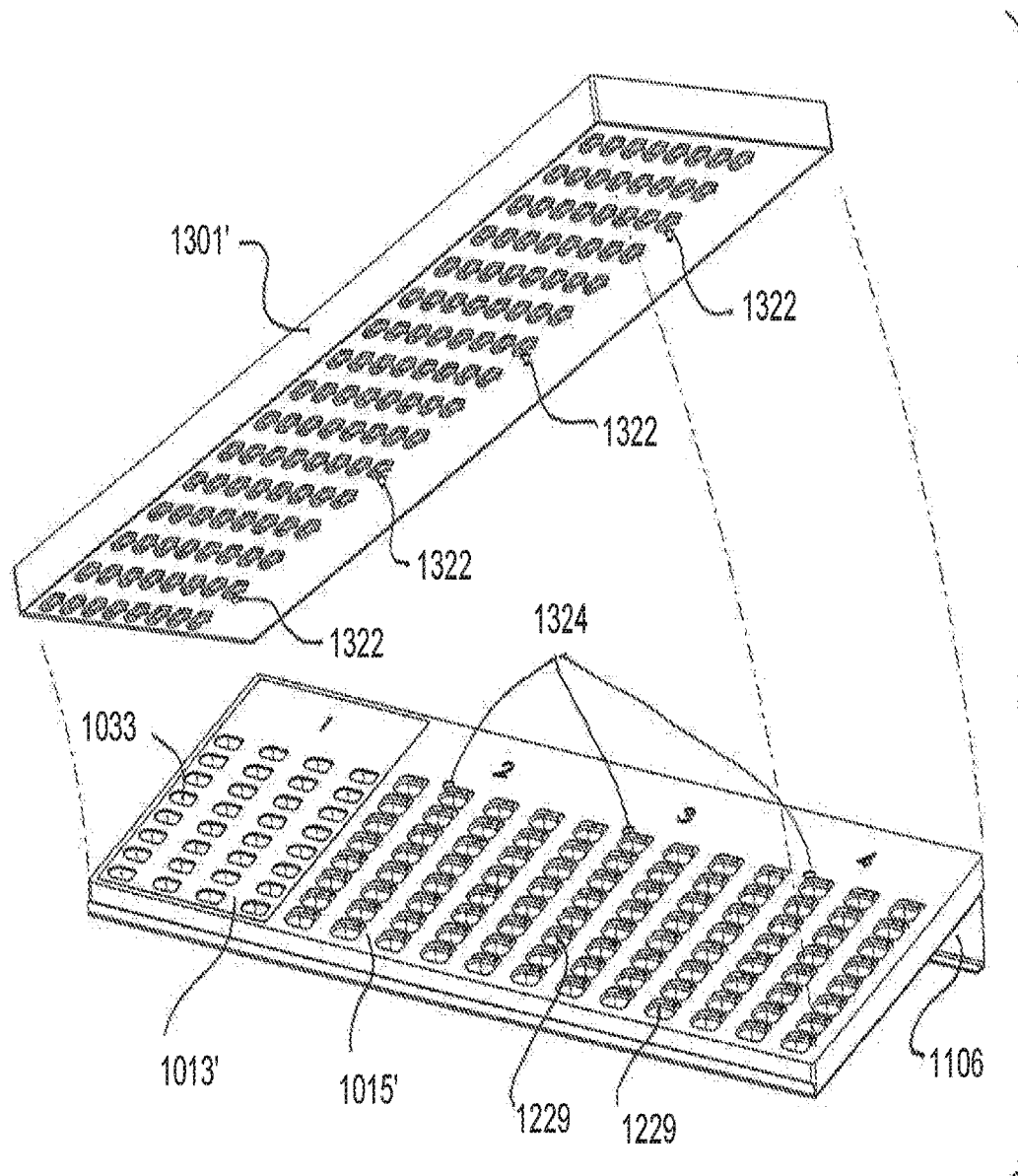
FIG. 39 is a partially exploded view of the medicament management system of FIG. 37 including a docking station, holder, and sensor guide.
Figure 40:
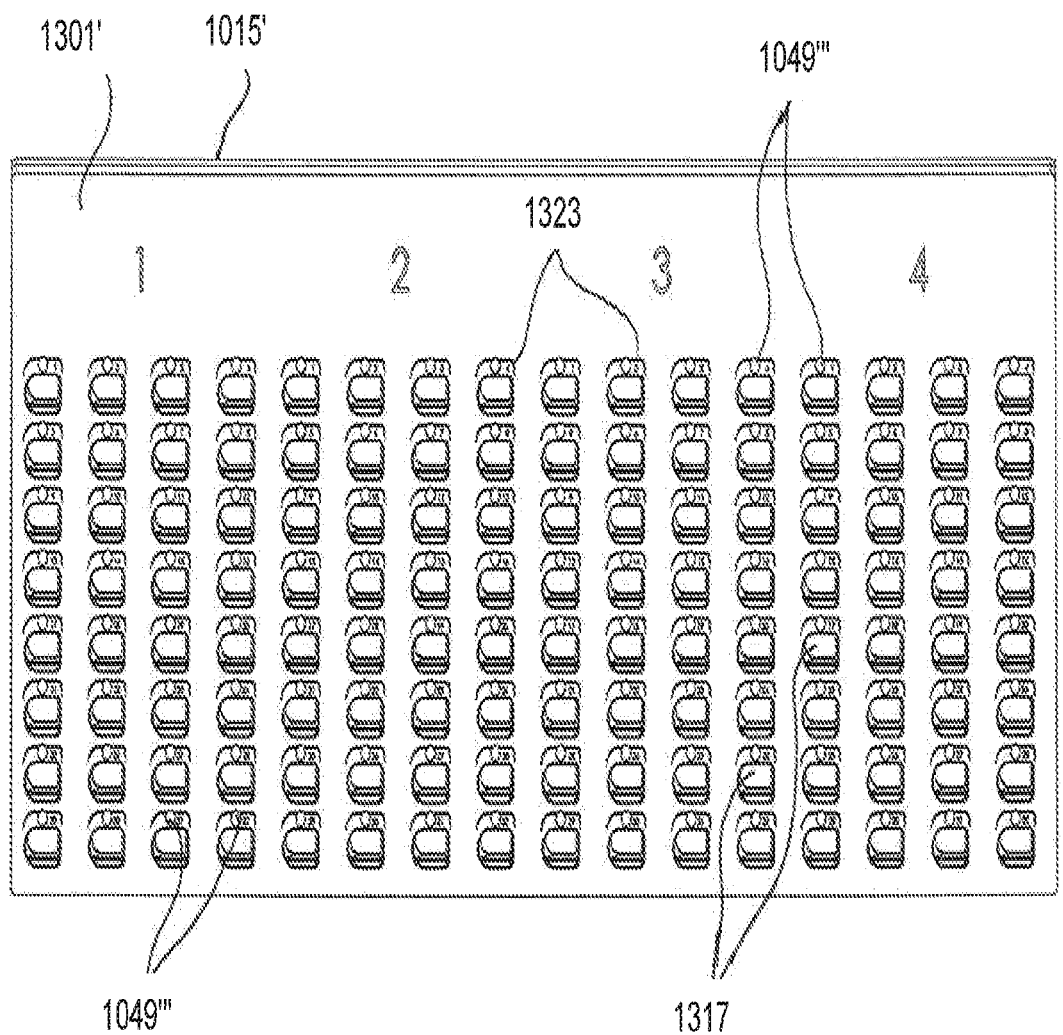
FIG. 40 is a top view of the medicament management system of FIG. 37 including a docking station, holder, and sensor guide.
Figure 41:
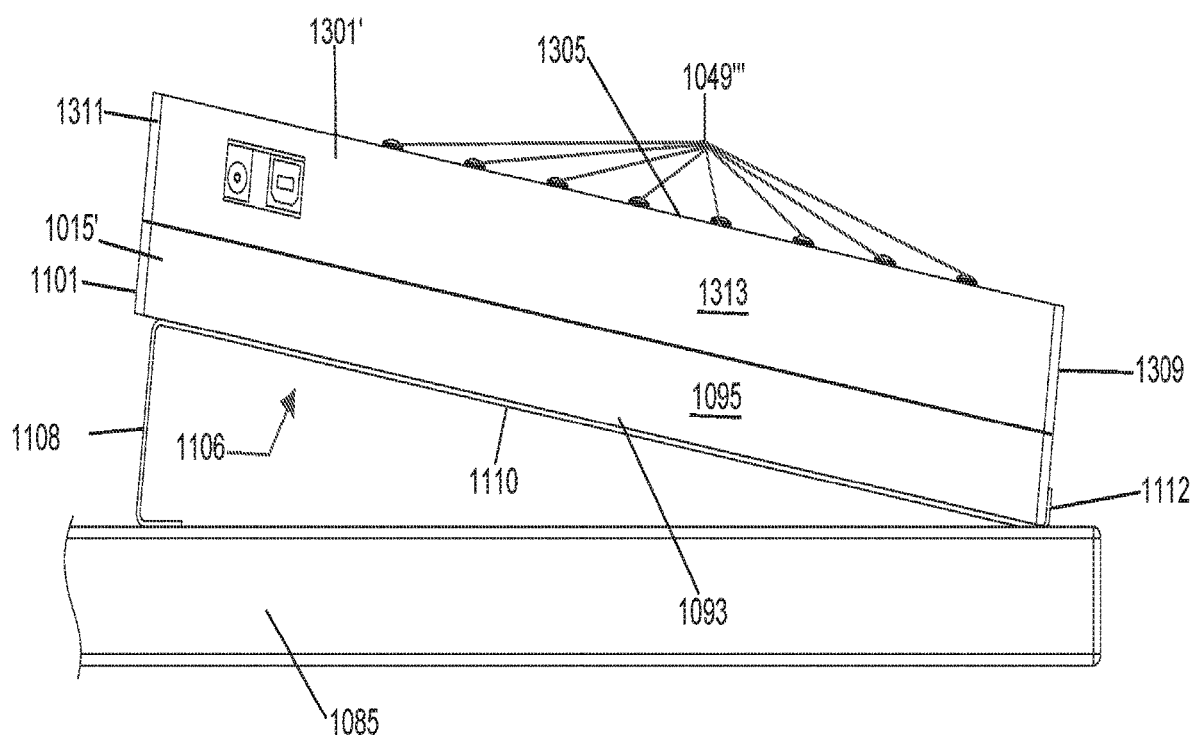
FIG. 41 is a left side elevation view of the medicament management system of FIG. 37 including a docking station, holder, and sensor guide.

In the example, docking station 1015' is configured to simultaneously dock from one to four separate and distinct holders 1013'. Docking station 1015' illustrated in FIGS. 37-39 and 44A-44B includes four groups of thirty two total pockets 1229 for a total of 128 pockets 1229. Each of the four groups is organized into four columns of eight pockets (8 rows.times.4 columns) 1229a, 1229b, 1229c, 1229d to accommodate a holder 1013 having 32 cells 1033 in a pattern which matches that of a group of pockets 1229a-1229d. As illustrated in FIGS. 38-39 and 42A, a holder 1013' is shown nested in one of the groups of pockets 1229a.

Docking station 1015' top wall 1091 is preferably provided with human-readable indicia 1103 identifying each cell pocket 1229. In the examples, indicia 1103 is proximate each pocket 1229 and is an integer from 1 to 32 for each group of pockets 1229. Other types of indicia may be used, such as alpha-numeric indicia.

It can be important that docking station 1015' provide adequate support for holder 1013' during loading of subsequent verification. Providing support can be important because the material used for holder 1013' body 1019 is frequently quite thin and pliant. In the example of docking station 1015' top wall 1091 and pockets 1299, particularly if cells 1033 are snugged against pockets 1229, provide multiple points of support across holder 1013' body 1019 and cells 1033. The support provided by docking station 1015' top wall 1091 and pockets 1229 ensures that such a holder 1013' will not collapse during loading, potentially resulting in loss of costly medicaments 1011.

Figure 42:
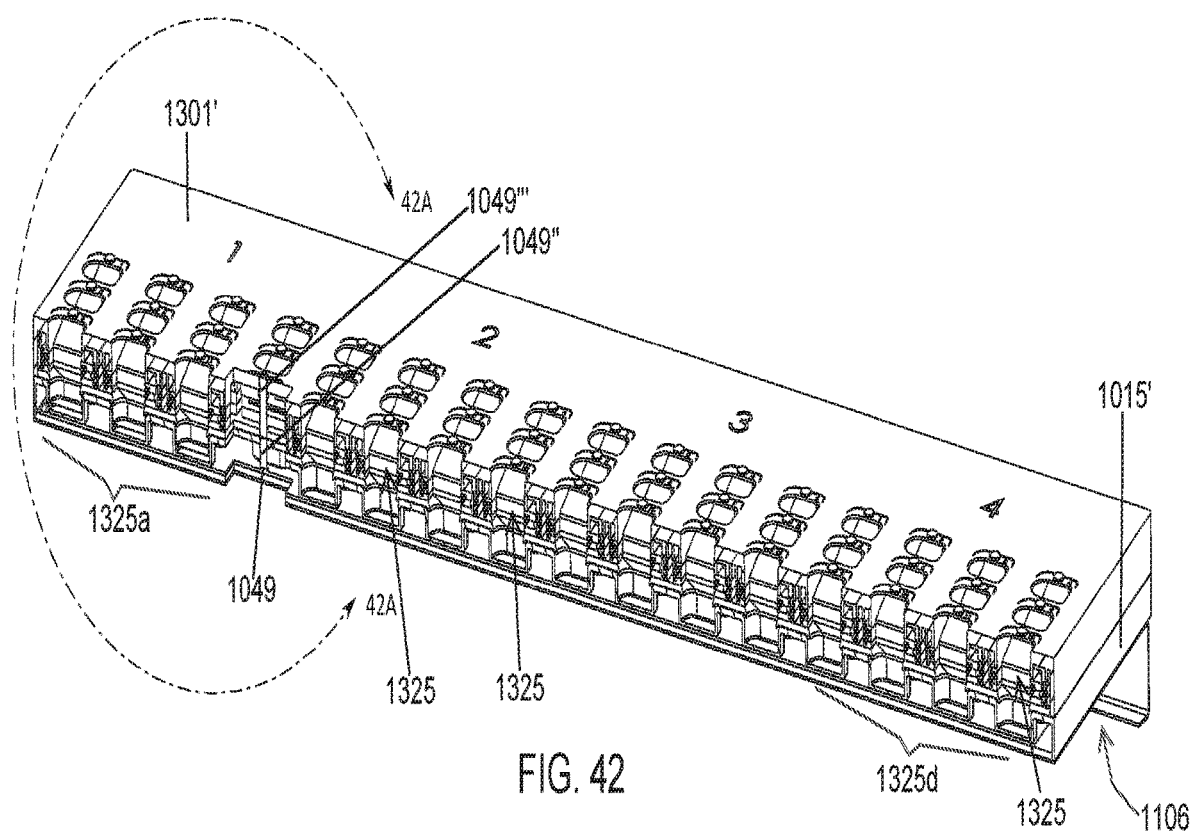
FIG. 42 is a section view of the medicament management system of FIG. 37 taken along section 42-42 of FIG. 37.
Figure 42A:
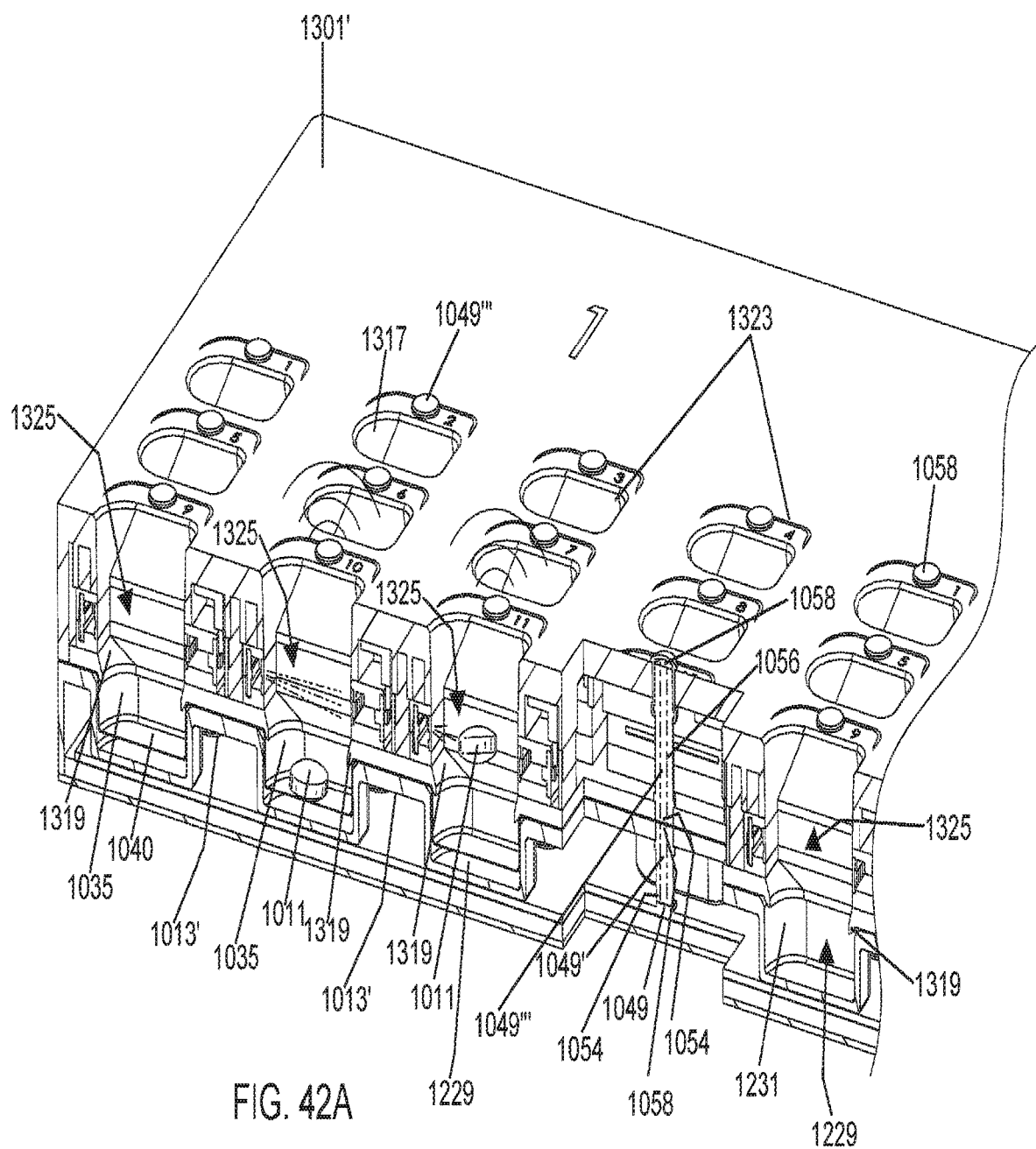
FIG. 42A is an enlarged section view of the medicament management system of FIG. 37 taken along section 42A-42A of FIG. 42.
Figure 43:
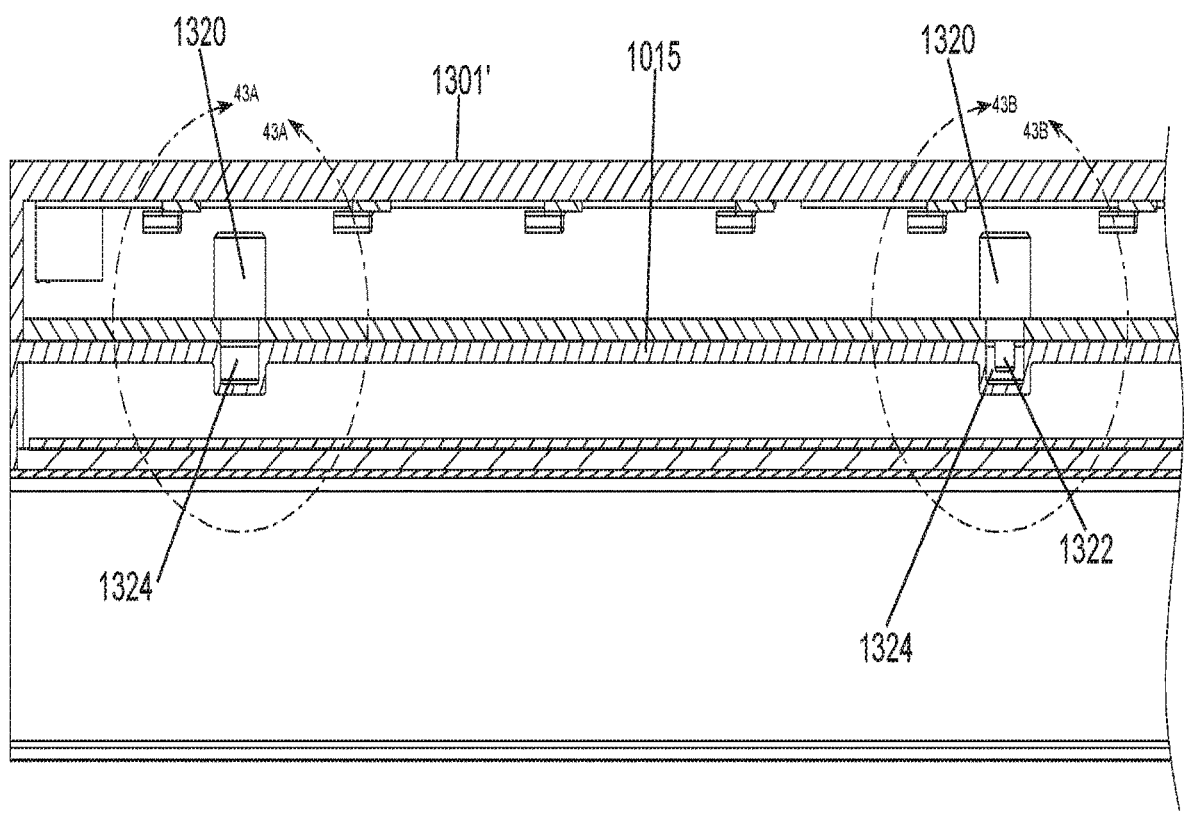
FIG. 43 is a section view taken along section 43-43 of FIG. 37 illustrating exemplary interlock switches.

As illustrated in FIGS. 42-43, yet another benefit of pockets 1229 is that they permit holder 1013' cells 1033 to fit within docking station 1015' with holder 1013' top 1021 flush and essentially co-planar with docking station 1015' top wall 1091. Since holder 1013' is closely against docking station 1015', sensor guide 1301' may be placed closely against holder 1013' to "sandwich" holder 1013' between docking station 1015' and sensor guide 1301' so that the structure of sensor guide 1301' continuously guides medicaments 1011 all the way into the appropriate cell 1033 as described herein. Thus, pockets 1229 serve to locate, potentially support, and permit full seating of holder 1013' with docking station 1015' in the example.

As previously described, it is possible that holder 1013' cells 1033 for the blister-package-type container can have a structure other than the rows and columns illustrated or in which there are differences in structure amongst the cells. Previously-described examples include cells 1033 with different depths or with different cross-sectional shapes. To accommodate these different cell 1033 arrangements and types, holder 1013' pockets 1229 can be sized, shaped, and configured to match the pattern of cells 1033.

In the example, holder 1013' is illustrated with pockets 1229 integrated into housing 1089 so that holder 1013' is a single unit. In other embodiments, docking station 1015' could have a generally planar top wall 1091 and indicators 1049 and/or 1049', but sized, shaped, and configured to receive a removable adapter (not shown) including the pockets 1229 in a pattern which could be identical to the pattern of 128 pockets 1229 illustrated in FIGS. 38-40 and 44A-44B. The adapter could include an indicator identical to indicator 1049' next to each pocket 1229 and in alignment with an indicator 1049 or 1049' when the adapter is mounted on the docking station. Plural different adapters could be utilized interchangeably with the same docking station 1015', each with a pocket 1229 pattern to accommodate a different holder 1013'. It is possible, therefore, that a single docking station 1015' could accommodate multiple different types of holders 1013' by means of an adapter.

Figure 53:
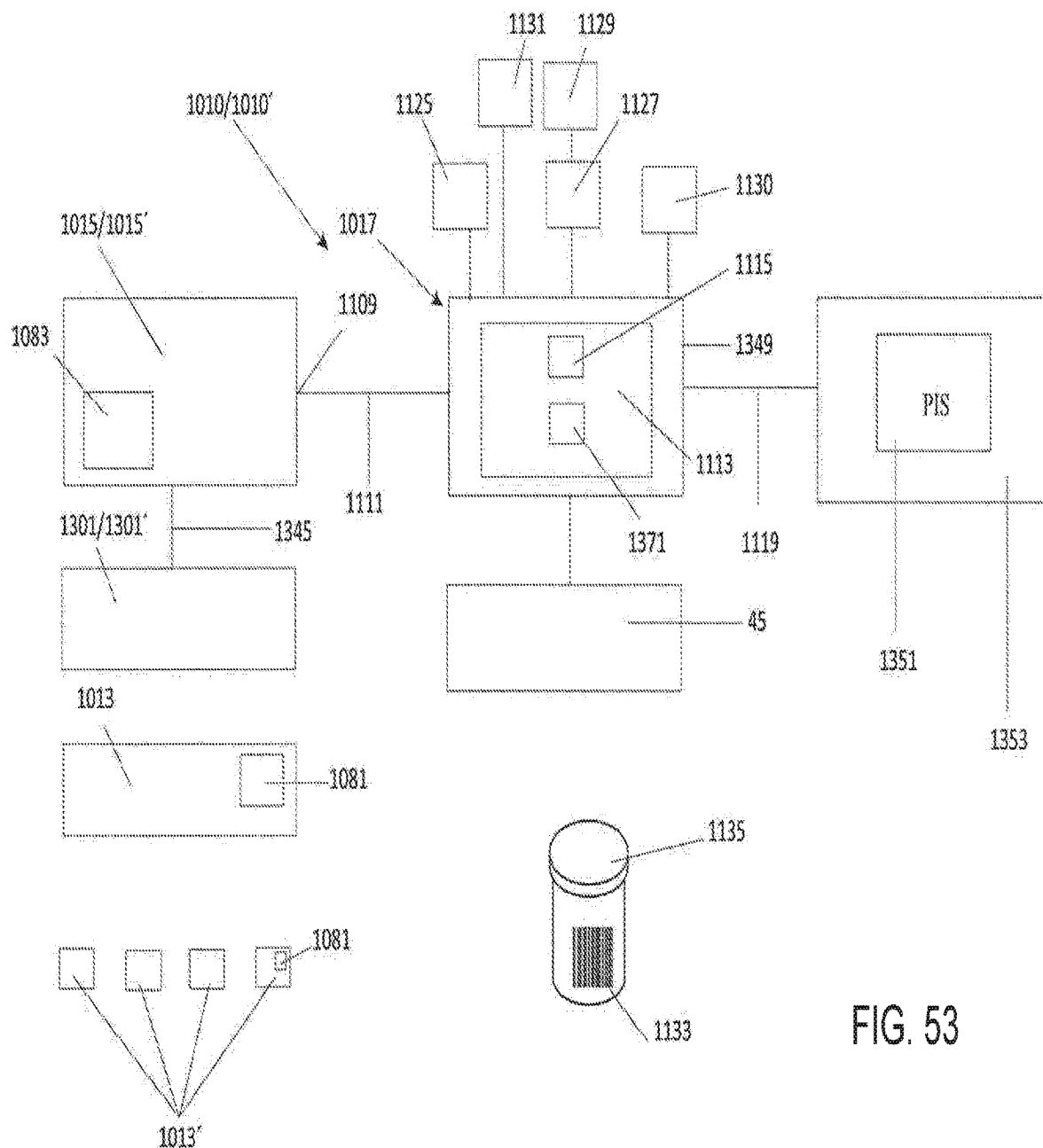
FIG. 53 is a schematic block diagram of exemplary systems for item management.

Referring to the schematic block diagram of FIG. 53, exemplary holder 1013, 1013' and docking station 1015, 1015' may be provided with apparatus for uniquely identifying holder 1013, 1013' to docking station 1015, 1015' and system. Positive identification of holder 1013, 1013' enables the user to precisely control loading of appropriate medicaments 1011 into holder 1013 and 1013' permits the user to maintain more accurate records of medicaments 1011 which have been loaded and dispensed.

In such embodiments, holder 1013, 1013' may include an identification element 1081 and docking station 1015, 1015' may include an identification element detector 1083 as shown in FIG. 53. The identifier element 1081 may, for example, consist of a radio frequency identification tag (RFID) and the detector 1083 may be an RFID tag reader (i.e., an interrogator) on docking station 1015, 1015'. The exemplary RFID tag 1081 may be re-writable or read-only, as desired. Exemplary RFID reader 1083 provided on docking station 1015, 1015 detects information embedded on the RFID tag 1081. Information embedded in RFID tag 1081 identifying holder 1013, 1013' may be used by system 1010, 1010' to control the medicament-dispensing process. The unique identifier of the RFID tag 1081 could be matched to a file for the patient or holder 1013, 1013' in database 1371 to associate such holder with the patient's prescription order. By way of further example, holder 1013, 1013' may include other types of identifier elements, such as a bar code 1132 (FIG. 24) and detector is a barcode scanner 1131 to identify holder 1013, 1013'.

For embodiments utilizing holder 1013', an identification element detector 1083 may be provided apart from docking station 1015, 1015' at any appropriate physical location at which identification of holder 1013' is desired. For example, an identification element detector 1083 could be provided at the patient's bedside to identify holder 1013' and confirm that holder 1013' is for the intended patient. Detection of the identification element 1081 corresponding to the holder 1013' intended for the patient, could be used to prompt the care giver to deliver holder 1013' to the patient. Conversely, if an incorrect holder identification element 1081 is detected by detector 1083, the care giver would not provide the holder 1013' to the patient.

For embodiments utilizing a holder 1013, an identification element detector 84 may be provided on automated dispensing machine 45 (FIGS. 19, 20) as previously described. In the example utilizing RFID tags, detector 84 may comprise an RFID reader. If the correct holder 1013 identification element 1081 is detected by detector 84, the technician, pharmacist, or other user is prompted to transfer medicaments 1011 from holder 1043 to exception storage apparatus 43. Conversely, if an incorrect holder identification element 1081 is detected by detector 84, the technician, pharmacist, or other user is prompted to not transfer medicaments 1011 from holder 1013 to exception storage apparatus 43.

Referring to FIGS. 28-28A and 36 and FIGS. 38-44B and 50-52, exemplary docking stations 1015, 1015' include a plurality of indicators 1049, 1049' within housing 1089. Indicators 1049 may be lamp-type indicators which emit or communicate light energy as indicated in FIGS. 28-28A and 42-42A. Exemplary indicators 1049 separately represent individual light sources and, collectively, represent a light source. Indicators 1049 are preferably directed toward docking station top wall 1091 and are provided in a pattern which matches the pattern of the cells 1033 of holders 1013, 1013' such that at least one indicator 1049 is provided for (i.e., associated with) each cell 1033. Preferably, each indicator 1049 is a light-emitting diode (LED), although it is envisioned that other types of indicators 1049 may be used. Indicators 1049 may all be mounted on a single circuit board 1237 within housing 1089. Circuit board 1237 represents circuitry operatively connected to controller 1017 enabling controller 1017 to selectively control indicators 1049, 1049' as discussed herein.

Referring to FIGS. 28-28A and 36 and FIGS. 42-42A and 44A-44B, exemplary docking stations 1015, 1015' further include a plurality of indicators 1049' within housing 1089 between indicators 1049 and top wall 1091 of housing 1089. In the examples, each indicator 1049' may be a visible indicator in the form of a selectively-operable light pipe of the type described in connection with indicators 1049" of holder 1013 and the description of such indicators 1049" is incorporated herein by reference. Indicators 1049' include first and second ends 1054, 1058, and body 1056. Each indicator 1049' is aligned with an indicator 1049 and receives light from indicator 1049 in first end 1054. Indicator 1049' body 1056 communicates the light through housing 1089 so that light is visible to a user from indicator 1049' second end 1058 at top wall 1091 of docking station 1015, 1015'. In the example of system 1010, light from indicators 1049' is communicated to aligned holder 1013 indicators 1049" when the holder 1013 is docked. In the example of system 1010', light from indicators 1049' is viewable by a user next to, or proximate, a pocket 1229.

In the docking station embodiment 1015, indicators 1049, 1049' are most preferably provided in a pattern which matches the pattern of holder 1013 cells 1033 and indicators 1049" of holder 1013 such that at least one indicator 1049, 1049' is provided for (i.e. associated with) each cell 1033. In the example, indicators 1049, 1049' are organized into four rows of 16 indicators 1049, 1049' corresponding to the pattern of cells 1033 of holder 1013 and positioned so as to be below each cell 1033 and approximately centered on each cell 1033 when a holder 1013 is docked at docking station 1015.

When docked, holder 1013 is seated or docked on docking station 1015 such that indicators 1049" of holder 1013 are in alignment with indicators 1049, 1049' of docking station 1015 and light energy from indicators 1049, 1049' is communicated through a corresponding aligned holder 1013 indicator 1049 to the top wall 1021 of holder 1013.

In the docking station embodiment 1015', holder 1013' is preferably a container of a blister-package-type and does not include indicators 1049". In this embodiment, indicators 1049, 1049' are most preferably provided in a pattern on docking station 1015' which matches the pattern of holder 1013' cells 1033 such that at least one indicator 1049, 1049' is provided for (i.e., associated with) each cell 1033 when a holder 1013' is docked in one of the group of pockets 1229a-1229d. In this example, indicators 1049, 1049' are organized into four groups of 32 total pockets 1229 for a total of 128 indicators 1049, 1049'. Each of the four groups of indicators 1049, 1049' is organized into four rows of eight indicators 1049, 1049', one group corresponding to each group of pockets 1229a, 1229b, 1229c, 1229d. In this example, indicators 1049, 1049' are positioned so as to be above each pocket 1229 and approximately centered on each pocket 1229 with the effect being that indicators 1049, 1049' are positioned slightly above and centered on cells 1033 of a docked holder 1013.

The foregoing examples illustrate that the location of indicators 1049, 1049' is not critical. Indicators 1049, 1049' may be provided in various locations to communicate visible information to assist the technician, pharmacist, or other user to load a medicament 1011 in the correct cell 1033. In other embodiments, it is envisioned that indicators (e.g., indicators 1049) could be located entirely off of docking station 1015, 1015' with the visible information from indicators 1049, projected onto holder 1013, 1013', by for example, lasers, mirrors, projectors, or fiber optics.

Exemplary indicators 1049, 1049', are selectively-operable in that, they selectively communicate light energy, which is a type of visible information. When an indicator 1049 is activated, the aligned indicator 1049' communicates light information to top 1021 of holder 1013'. Conversely, when an indicator 1049 is not activated, the aligned indicator 1049' does not communicate light information to top 1021 of holder 1013. The preferred light energy provided by indicators 1049, 1049' may be viewable to a user on the holder 1013, 1013' proximate each cell 1033 to indicate the cell 1033 into which a medicament 1011 or other item is to be placed.

Preferably, the light energy provided by indicators 1049, 1049' is viewable to a user on holder 1013' of a blister-package-type because holder 1013' body 1019 may be made of a transparent plastic material. The light energy is viewable through the light-transmissive transparent plastic material of body 1019 along top 1021 of holder 1013'. In other embodiments, an opening (not shown) in body 1019 could be provided proximate each cell 1033. Each opening would be in alignment with one of the indicators 1049' when holder 1013' cells 1033 are nested within pockets 1229 of docking station 1015'.

Referring next to FIGS. 23-28A and 32-36 and FIGS. 37-43 and 48-52, a sensor guide 1301, 1301' may optionally be provided to detect the physical presence of medicaments 1011 or other items loaded into cells 1033 of holder 1013, 1013'. In the example, sensor guide 1301, 1301' serves as a guide to aid in correct loading of a holder 1013, 1013'. Sensor guide 1301, 1301' provides positive feedback to controller 1017 indicative that a medicament 1011 or other item has been loaded into the correct cell 1033 of holder 1013, 1013'. Sensor guide 1301, 1301' can provide feedback for a medicament 1011 overcount and undercount. And, sensor guide 1301, 1301' can provide positive feedback indicative that a medicament 1011 or other item has been loaded into an incorrect cell 1033 of holder 1013, 1013'.

Responsive to detection of an erroneous loading of a medicament 1011 by sensor guide 1301, 1301', controller 1017 can generate a signal. The signal may include an error description presented to a user on video display 1125 as described in connection with FIGS. 60-66 and 79-85. The error description may include a description of an overcount, an undercount, and an incorrect cell and can include instructions describing the error and how to correct the error.

The information provided by sensor guide 1301, 1301' to controller 1017 can be used be used for numerous purposes, including to create a record that the holder 1013, 1013' was loaded properly and to make loading more efficient.

In the embodiments illustrated by FIGS. 23-28A and 32-36 and FIGS. 37-43 and 48-52, sensor guide 1301, 1301' may overlie holder 1013, 1013'. Medicaments 1011 or other items are detected as they pass through sensor guide 1301, 1301' during loading into a cell 1033 to alert the user in the event of an error so that corrective action can be taken. In the embodiments, exemplary sensor guides 1301, 1301' have essentially the same structure and operation, except that each sensor guide 1301, 1301' is sized, shaped, and configured to function with the respective holder 1013, 1013' and docking station 1015, 1015'.

Exemplary sensor guide 1301, 1301' may include a body 1303, a top and a bottom 1305, 1307, a front and a rear side 1309, 1311, and a left and a right side 1313, 1315. Exemplary sensor guide 1301, 1301' has a planar, generally rectangular shape which corresponds to docking station 1015, 1015'. Bottom 1307 is preferably generally planar to permit sensor guide 1301, 1301' to abut holder 1013 or 1013' top 1021. Sensor guide 1301, 1301' includes openings 1317, each defined by a wall 1319. For convenience, only certain of openings and walls 1317, 1319 are indicated by reference numbers, it being understood that the other openings and walls are the same in the embodiments.

In the example of sensor guide 1301, openings 1317 and walls 1319 have an oval shape which matches and aligns with the oval shape of holder 1013 cells 1033 and cell inlets 1037. In the example of sensor guide 1301', openings 1317 and walls 1319 have an elongate "D" shape which matches and aligns with the elongate "D" shape of holder 1013' cells 1033 and cell inlets 1037 and pockets 1229 of docking station 1015'. Other shapes of openings 1317 and walls 1319 may be utilized. The aligned cell 1033 walls 1035 and sensor guide opening 1317 walls 1319 form a continuous guide surface from openings 1317 into cell 1033, particularly if holder top 1021 and sensor guide bottom 1307 abut, which constrains medicaments 1011 to enter and stay in the cell 1033 into which they are placed by the user (e.g., a technician or pharmacist).

Sensor guide 1301 may further include four legs 1316, one leg 1316 at each corner of sensor guide 1301. Legs 1316 may be seated in a recess 1318 in holder 1013 top wall 1021 to locate sensor guide 1301 in a single repeatable position on holder 1013 and docking station 1015.

As is well illustrated in FIGS. 28-28A and 42-42A, each sensor guide 1301, 1301" opening 1317 is aligned with a corresponding cell 1033 of a holder 1013 or 1013'. In the embodiments of FIGS. 23-28A and 32-36, sensor guide 1301 is sized for use with a holder 1013 which includes sixty four cells 1033 as previously described. In this example, sensor guide 1301 is provided with 64 openings 1317 organized into a pattern of four rows of 16 openings (4 rows.times.16 columns) 1317 to match the pattern of the sixty four cells 1033 of holder 1013.

In the embodiment of FIGS. 37-52, sensor guide 1301' is sized for use with from one to four holders 1013'. In this example, sensor guide 1301' is provided with 128 openings 1317 organized into a pattern of four groups of 32 openings (8 total rows.times.16 total columns) 1317a, 1317b, 1317c, 1317d to match the pattern of the 128 pockets 1229a-1229d of docking station 1015'.

Sensor guide top 1305 is preferably provided with human-readable indicia 1323 identifying each cell 1033. In the example, indicia 1323 is an integer from 1 to 32 for each group of 32 openings 1317 proximate each cell 1033. Other types of indicia may be used, such as alpha-numeric indicia.

As illustrated in FIGS. 28-28A, exemplary sensor guide bottom 1307 may rest directly against holder 1013 top 1305 with legs 1316 seated in recess 1318 in holder 1013 top wall 1021. As illustrated in FIGS. 37-43, sensor guide 1301' bottom 1307 may rest directly against holder 1013' top 1021. Top 1021 is preferably a flat planar surface in a blister package embodiment. Each sensor guide opening 1317 is in alignment with one of the holder 1013' cells 1033. In other embodiments, sensor guide 1301, 1301' may be spaced from holder 1013 or 1013'. Sensor guide 1301 of system 1010 may include a recess 1225 which receives pull 1061 of holder 1013 when sensor guide 1301 rests on holder 1013.

Figure 43A:
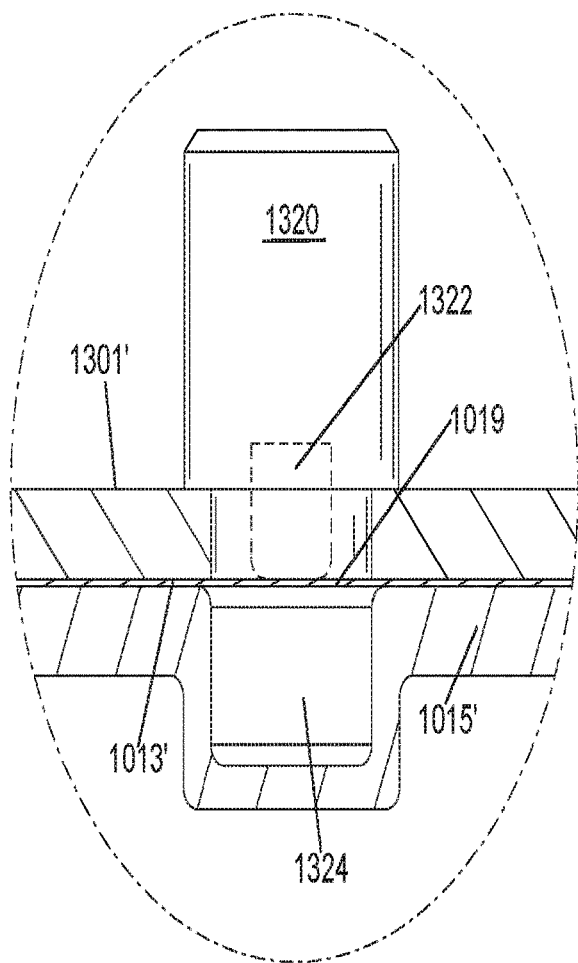
FIGS. 43A and 43B are enlarged section views of the exemplary interlock switches of FIG. 43 taken along sections 43A-43A and 43B-43B of FIG. 43.
Figure 43B:
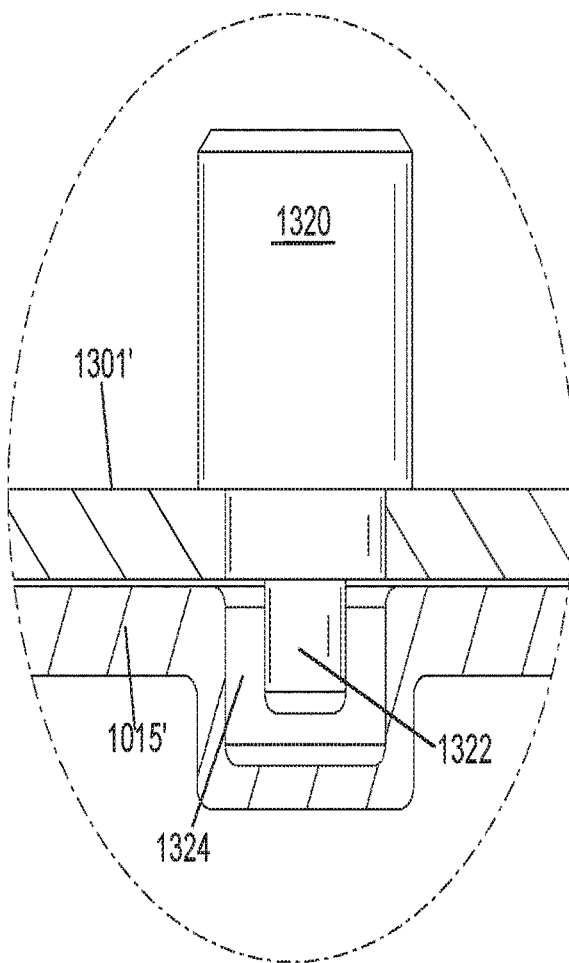
Figure 44A:
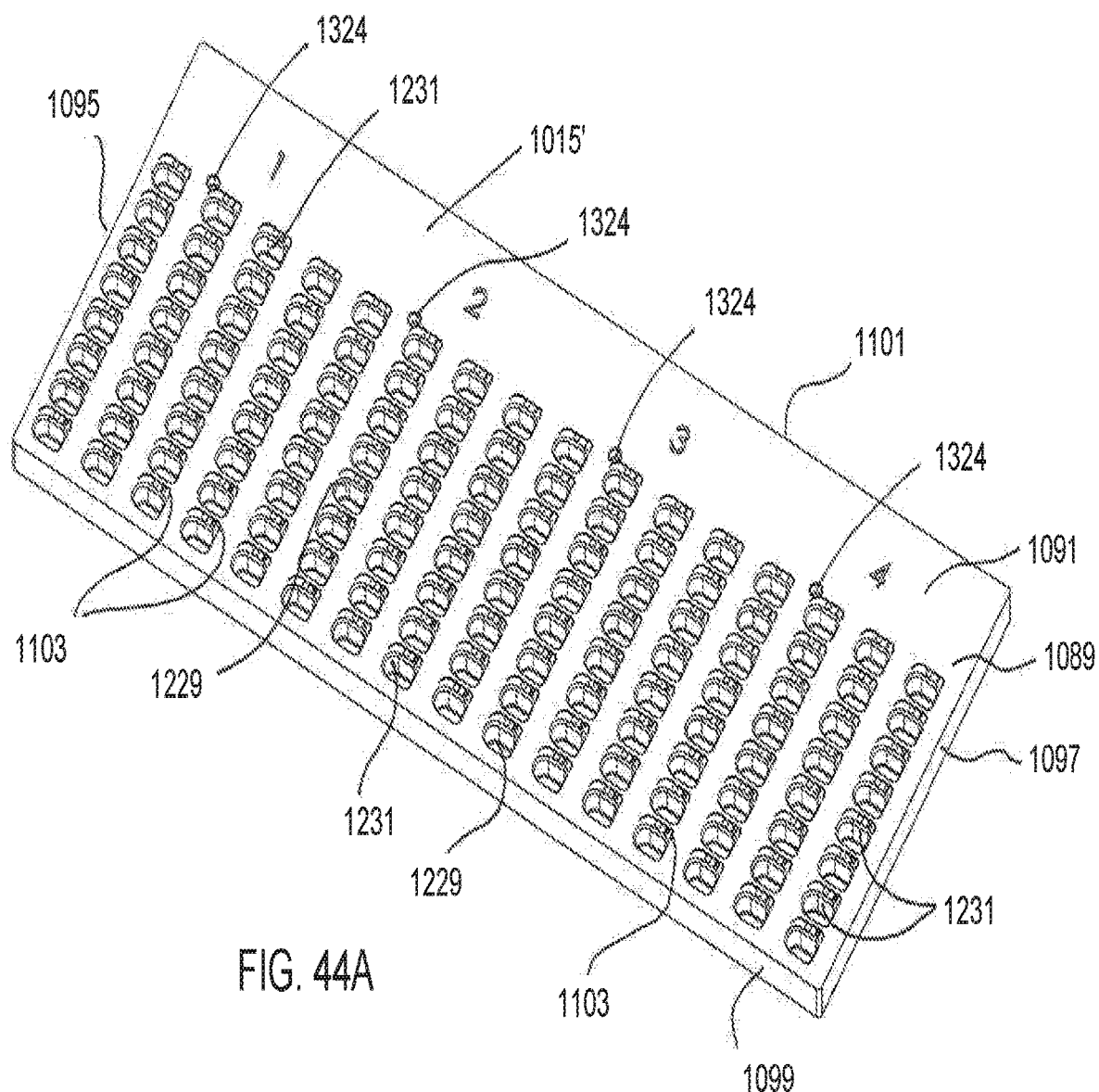
FIGS. 44A-44B are perspective and top plan views of the docking station of FIG. 37.
Figure 44B:
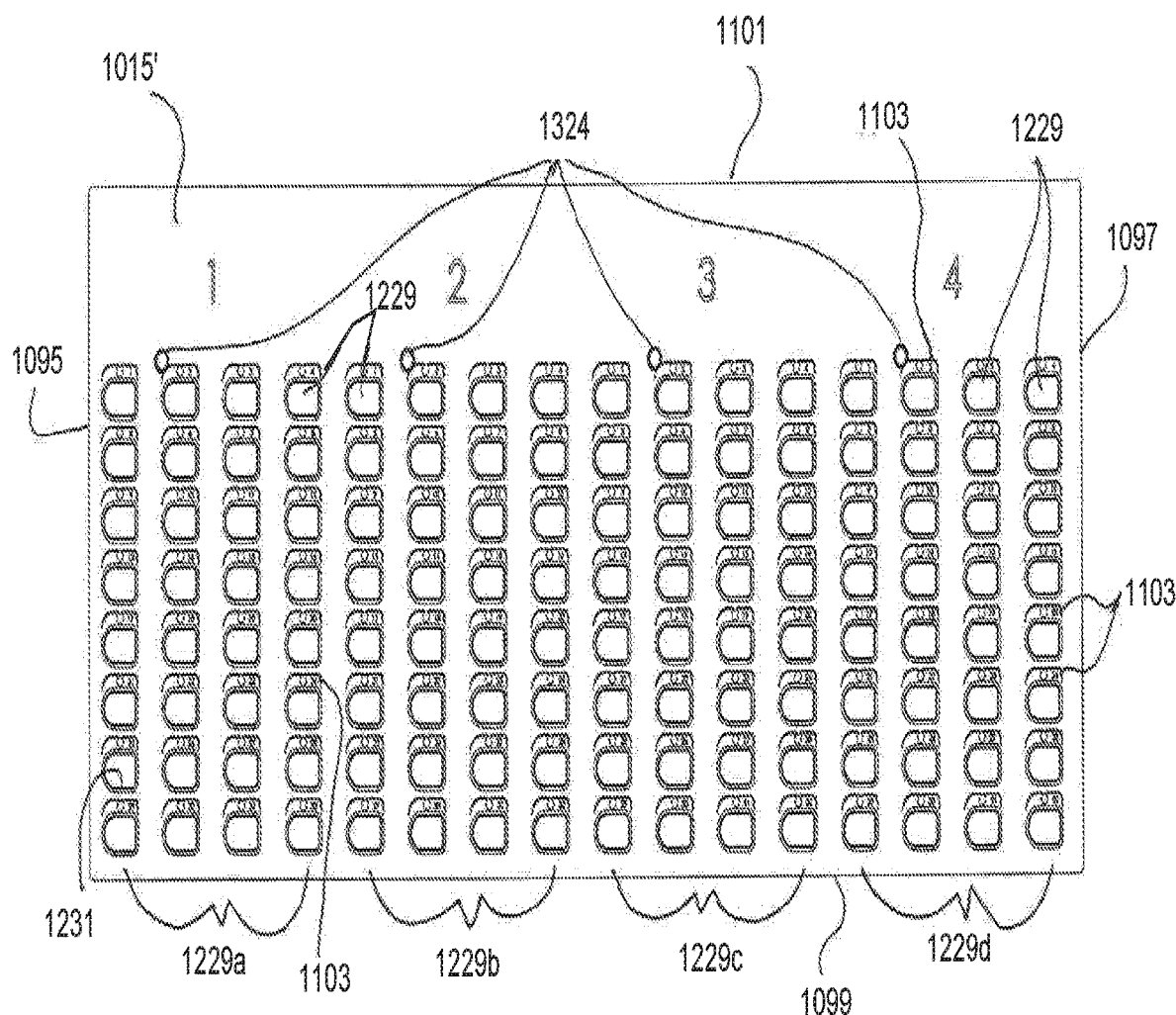
Figure 47:
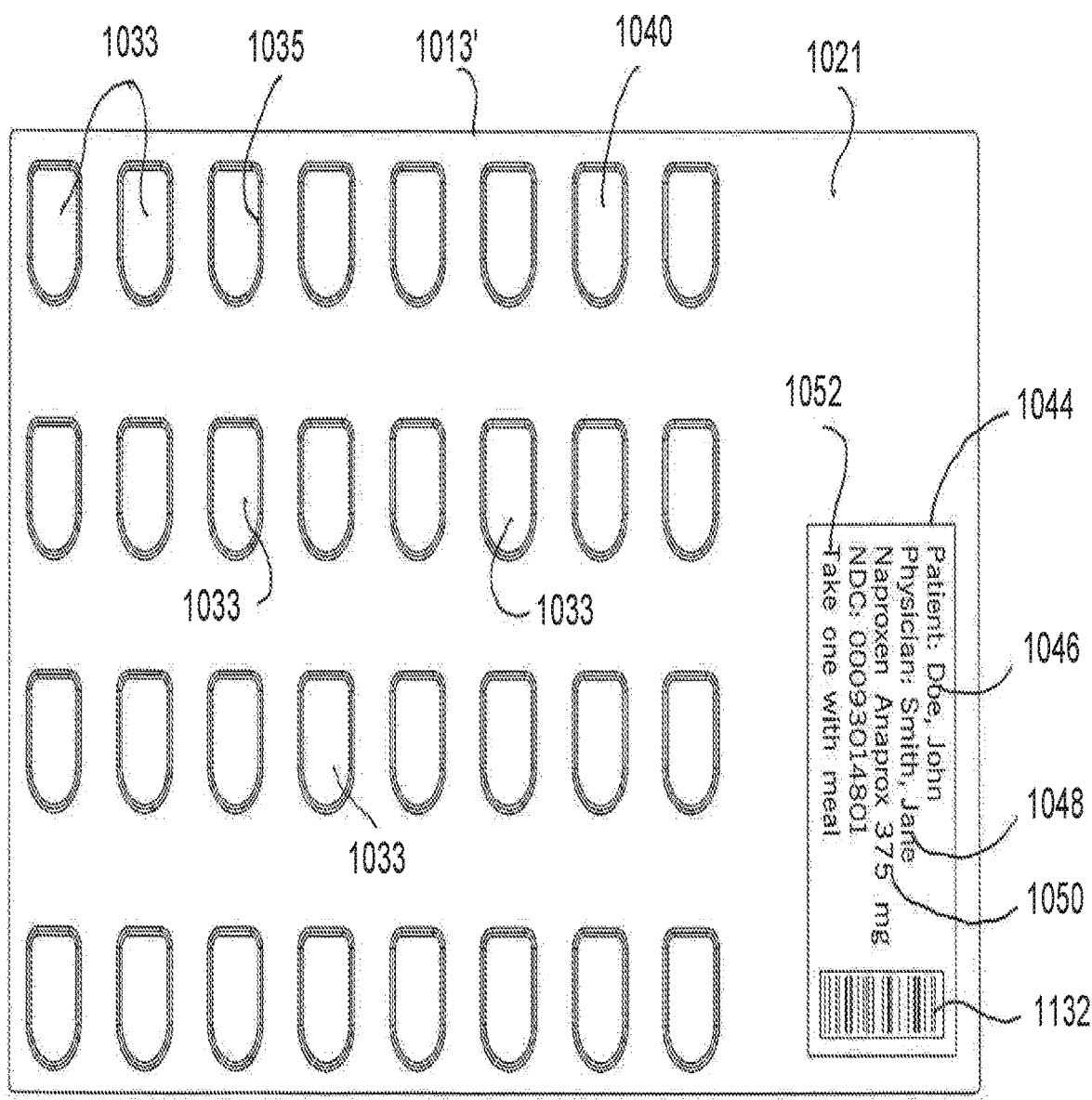
FIG. 47 is a top plan view of the exemplary holder of FIG. 45.
Figure 48:
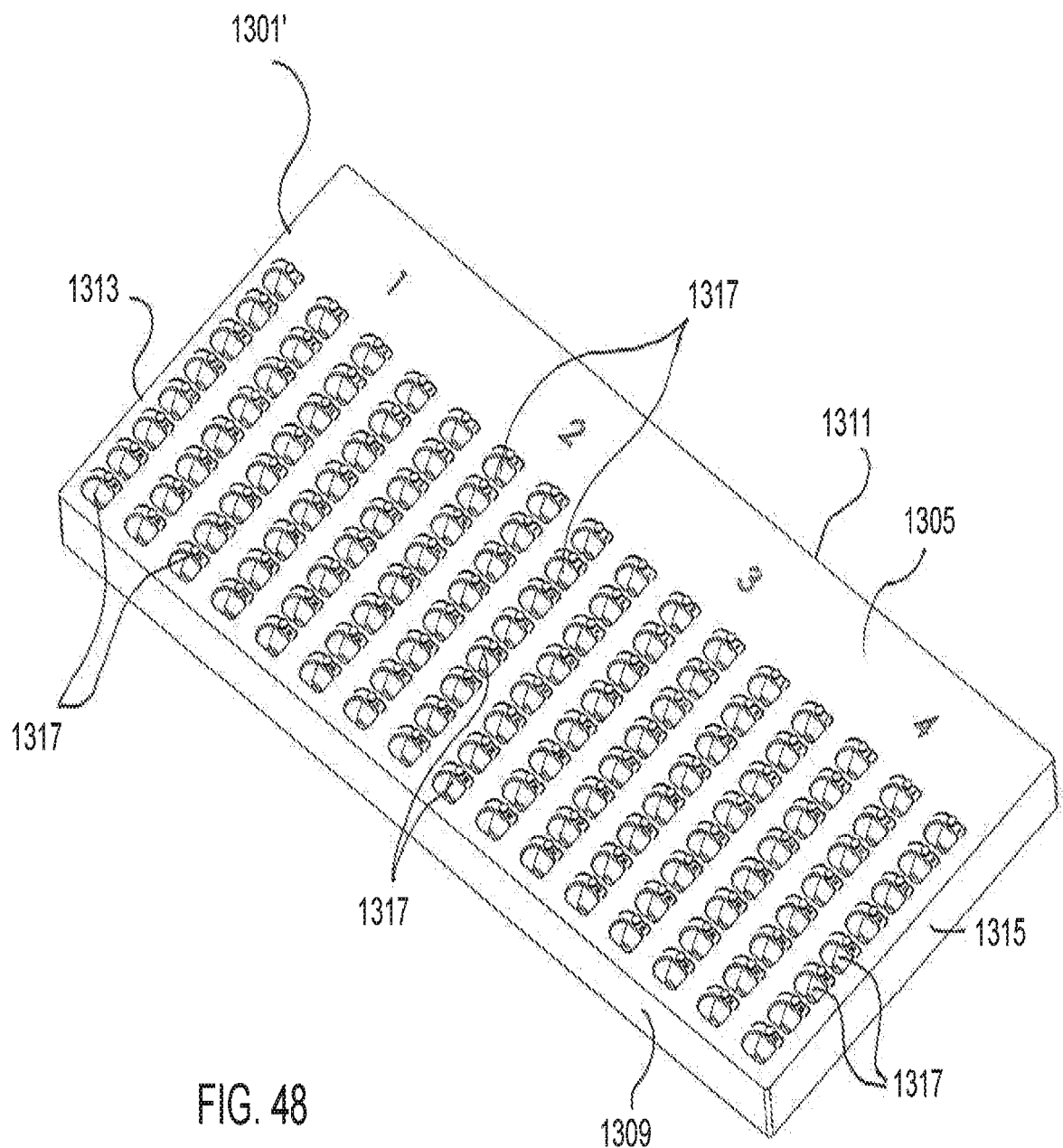
FIG. 48 is a perspective view of the exemplary sensor guide of FIG. 37.
Figure 49A:
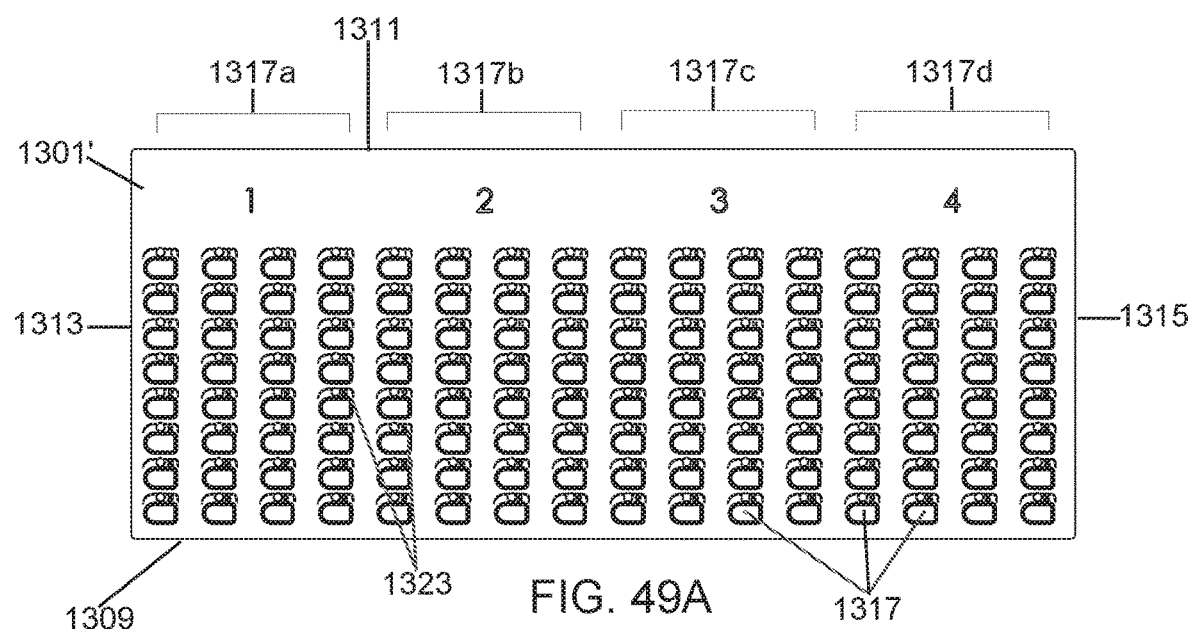
FIGS. 49A and 49B are top and bottom plan views of the exemplary sensor guide of FIG. 37.
Figure 49B:
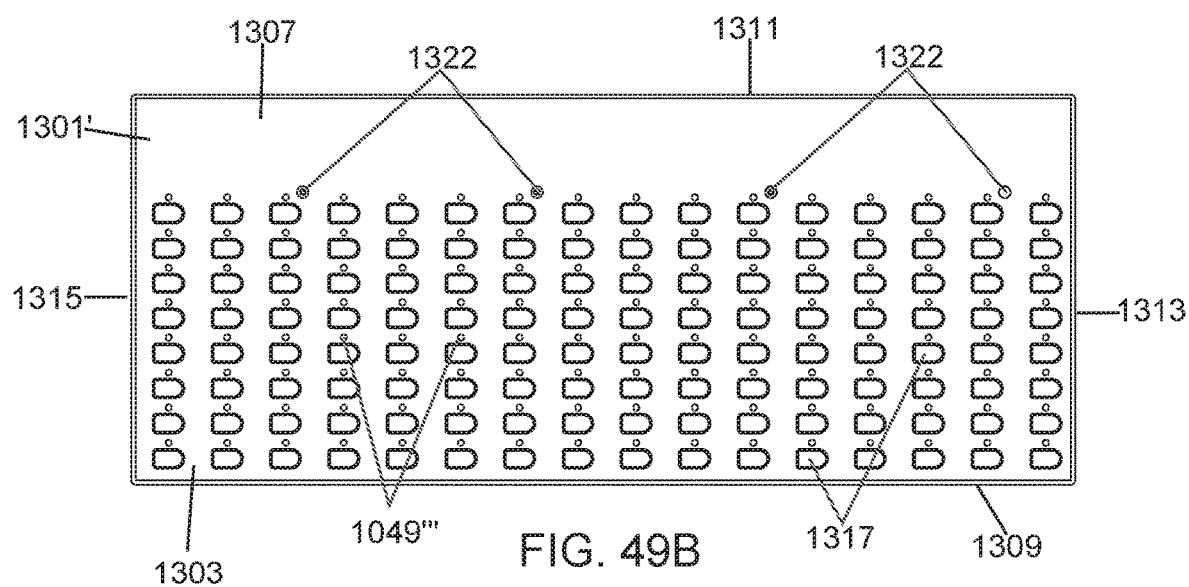

Referring to FIGS. 38-39, 43-43B and 49B, exemplary sensor guide 1301' includes four interlock switches 1320, one for each of the four groups of pockets 1229a-1229d and openings 1317a-1317d to indicate to controller 1017 that a holder 1013' is docked, or not docked, at one of such positions of docking station 1015'. Two of the four interlock switches 1320 are illustrated in FIGS. 43-43B, it being understood that each other interlock switch 1320 has the same structure and operation. Interlock switches 1320 include a spring-loaded (e.g., biased) plunger 1322 which extends toward pocket 1324 in top 1021 of docking station 1015'.

FIGS. 43A and 43B illustrate sensor guide 1301' seated on docking station 1015'. In FIG. 43A a holder 1013' is docked at pockets group 1229a and no holder 1013' is docked at pockets group 1229b. In FIG. 43A, body 1019 of docked holder 1013' covers pocket 1324 in docking station 1015'. Also in FIG. 43A, plunger 1324 contacts body 1019 and closes interlock switch 1320. Closure of interlock switch 1320 generates a signal to controller 1017 indicating that a holder 1013' is docked in the associated one of the group of pockets group, in this example pockets group 1229a. Controller 1017 permits operation of indicators 1049, 1049', 1049''' for pockets 1229 and openings. 1317 for pockets group 1229a and openings group 1317a.

As illustrated in FIG. 4B, no holder 1013' is docked at pockets position 1229b and pocket 34 of docking station 1015' is uncovered by a holder 1013'. In this state, plunger 1320 is biased to extend into pocket 1324 and, consequently, interlock switch 1320 remains open. When interlock switch 1320 is open, controller 1017 disables activation of indicators 1049, 1049', 1049''' for the associated group of pockets and openings, which is pockets group 1229b and openings group 1317b in this example. Consequently, a user cannot be prompted by indicators 1049, 1049', 1049''' to load a medicament 1011 where no holder 1013' is docked.

Sensor guides 1301, 1301' may include structure to ensure that they are located in a single, repeatable position on holder 1013, 1013'. Sensor guide 1301 preferably includes legs 1316 and interference between legs 1316 and recess 1318 locates sensor guide 1301, in a single position.

Referring now to FIGS. 28-28A and 34-36 and FIGS. 42-42A and 50-52, a sensor module 1325 may be provided within sensor guide 1301, 1301' for each sensor guide opening 1317 to detect the physical presence of a medicament 1011 or other item which falls through sensor module 1325. For convenience and brevity, select modules are indicated by reference number 1325, it being understood that the other modules have the same structure and operation in the examples.

Figure 34:
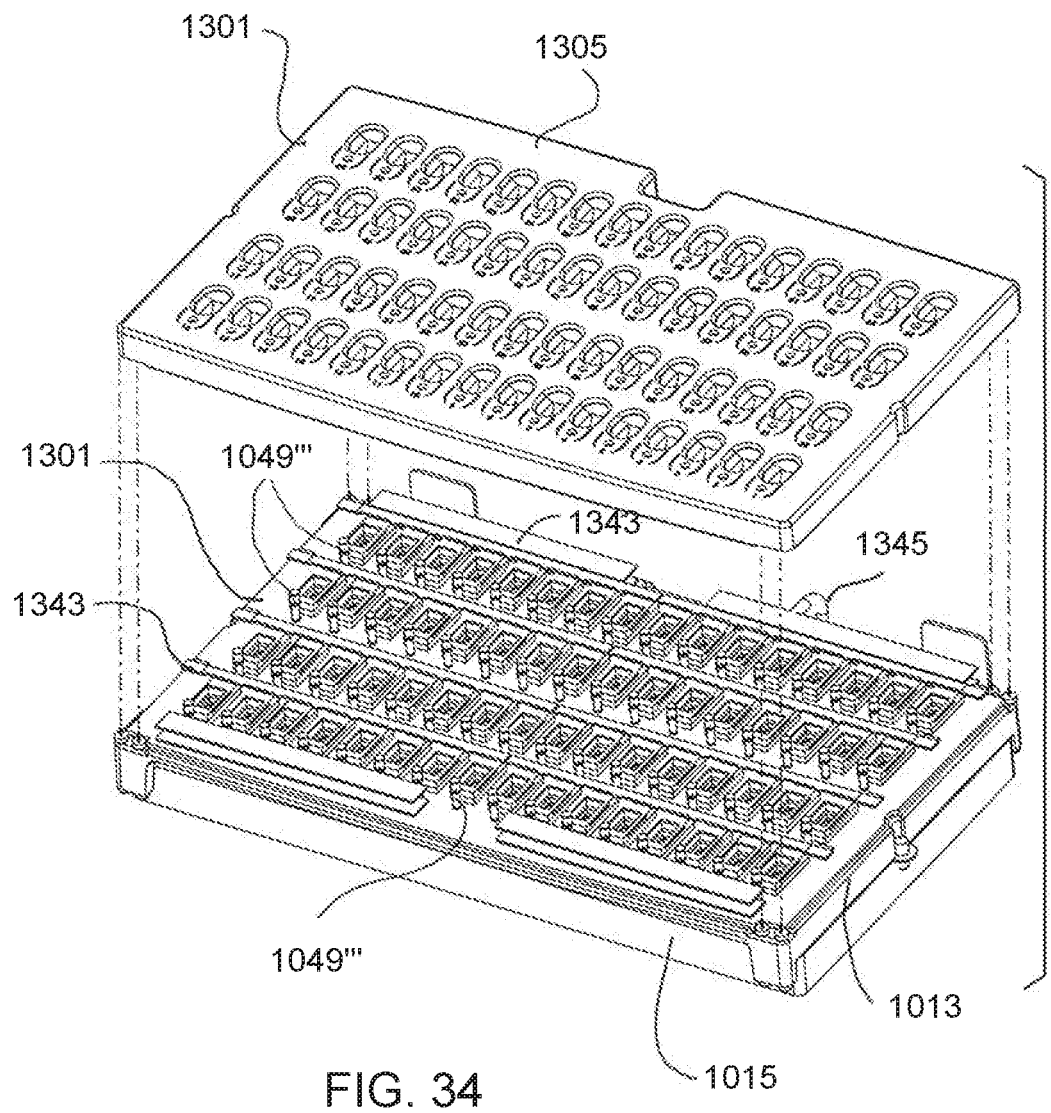
FIG. 34 is a partially exploded view of the sensor guide of FIG. 23.
Figure 35:
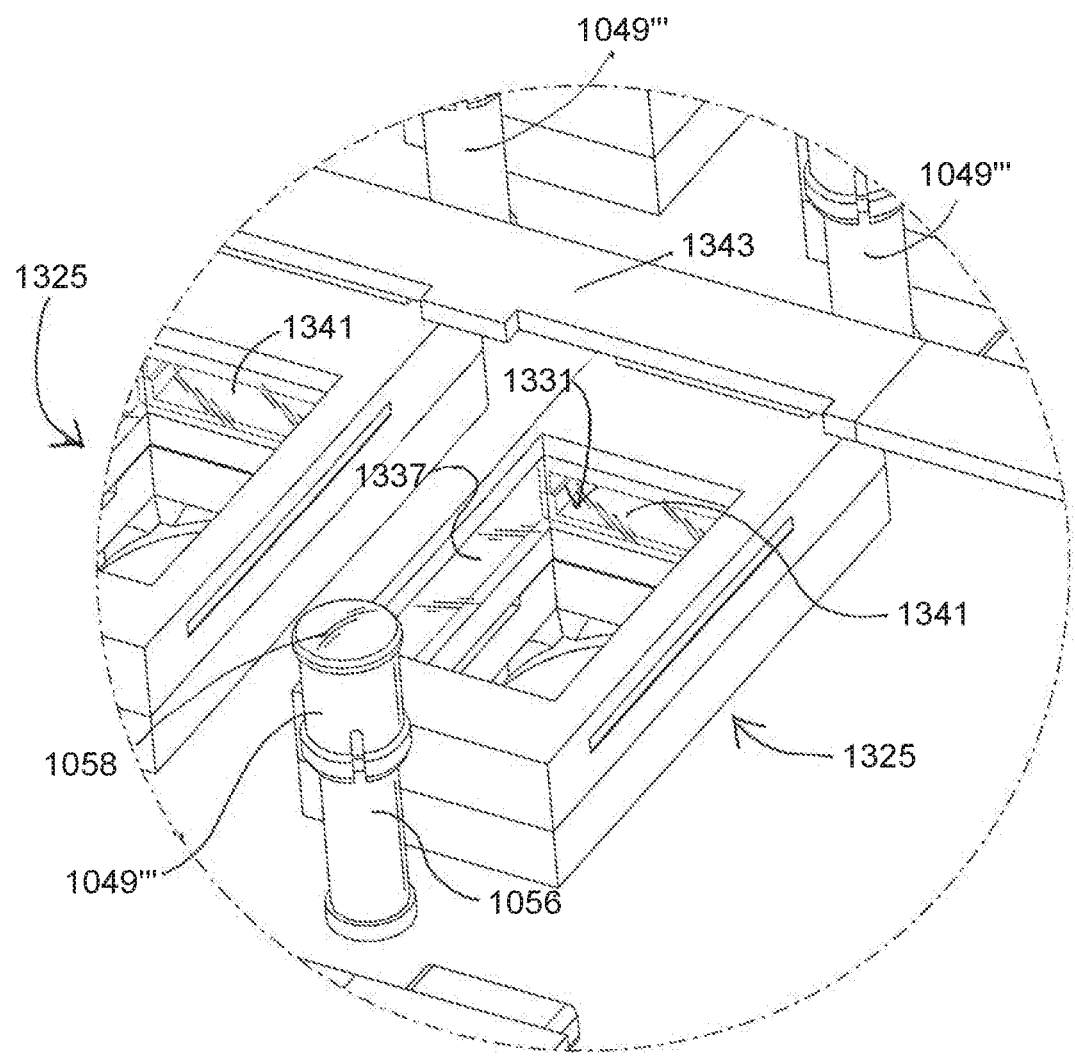
FIG. 35 is an enlarged perspective view of a portion of FIG. 23 including a sensor module.
Figure 36:
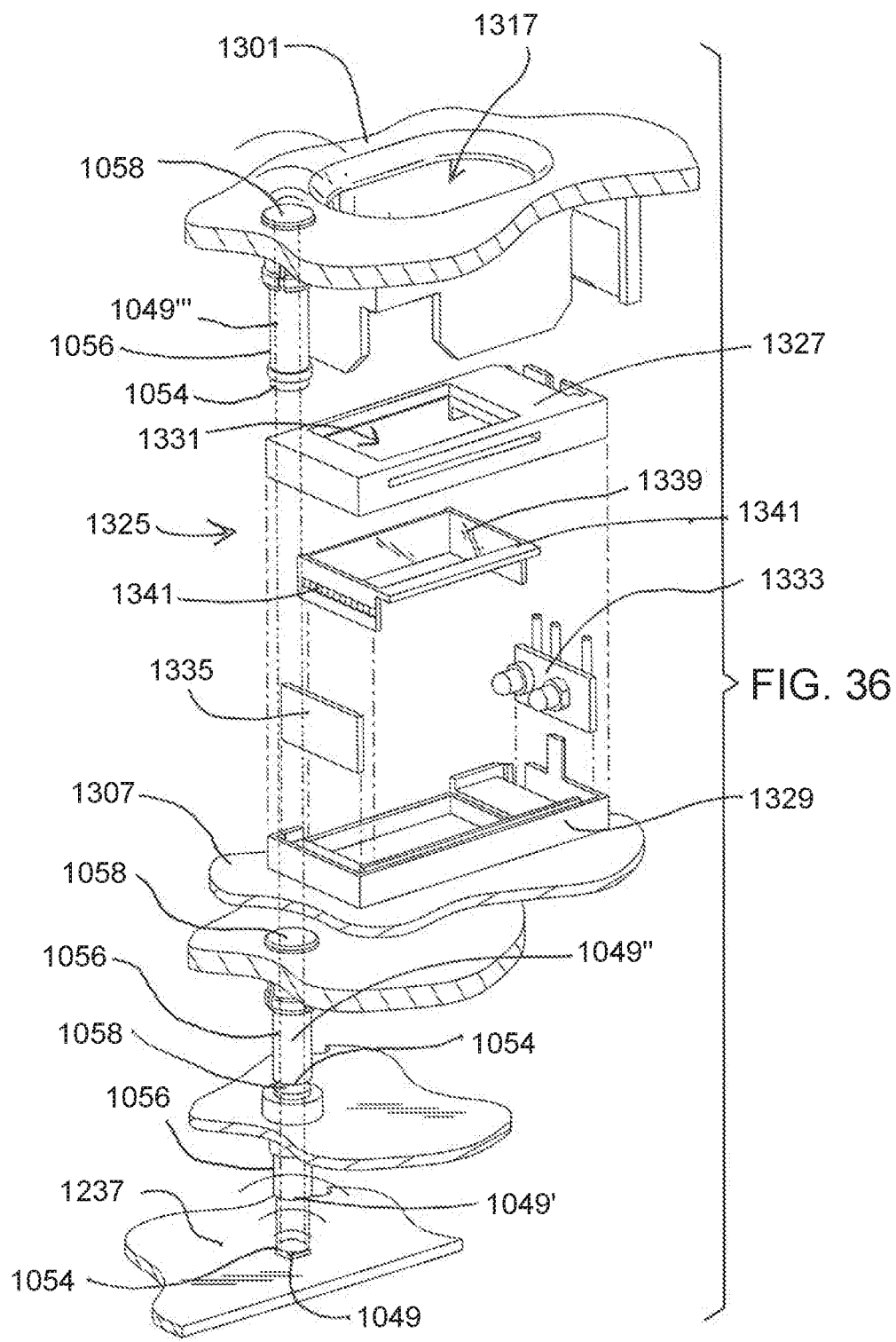
FIG. 36 is an exploded view of an exemplary sensor module of the sensor guide of FIG. 23.

As illustrated in FIG. 34, sensor guide 1301 may include 64 sensor modules 1325, one for each opening 1317. Like openings 1317, sensor modules 1325 are arranged in four rows of 16 sensor modules 1325 and each sensor module 1325 is aligned with an opening 1317.

Figure 50:
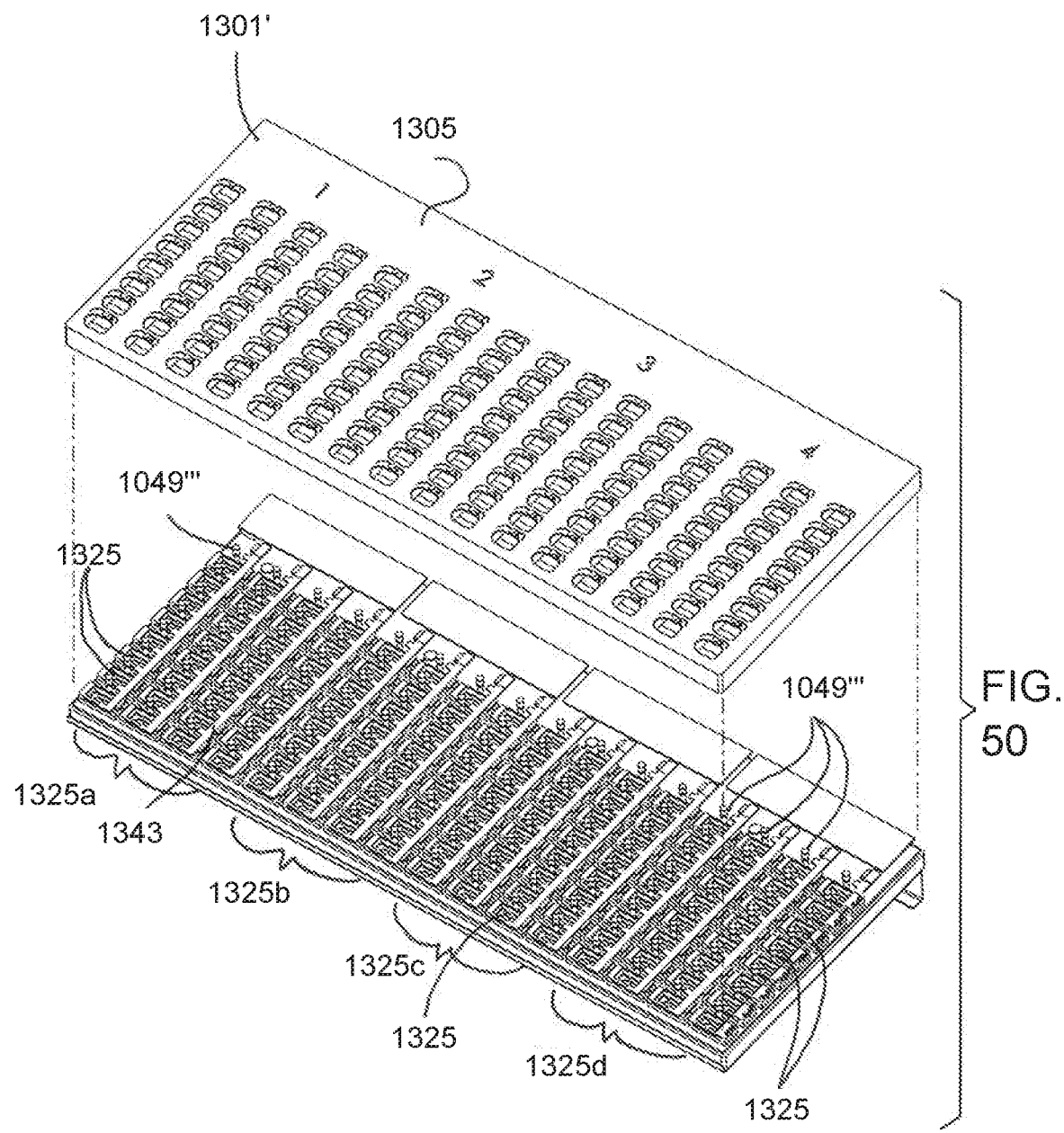
FIG. 50 is a partially exploded view of the sensor guide of FIG. 37.
Figure 51:
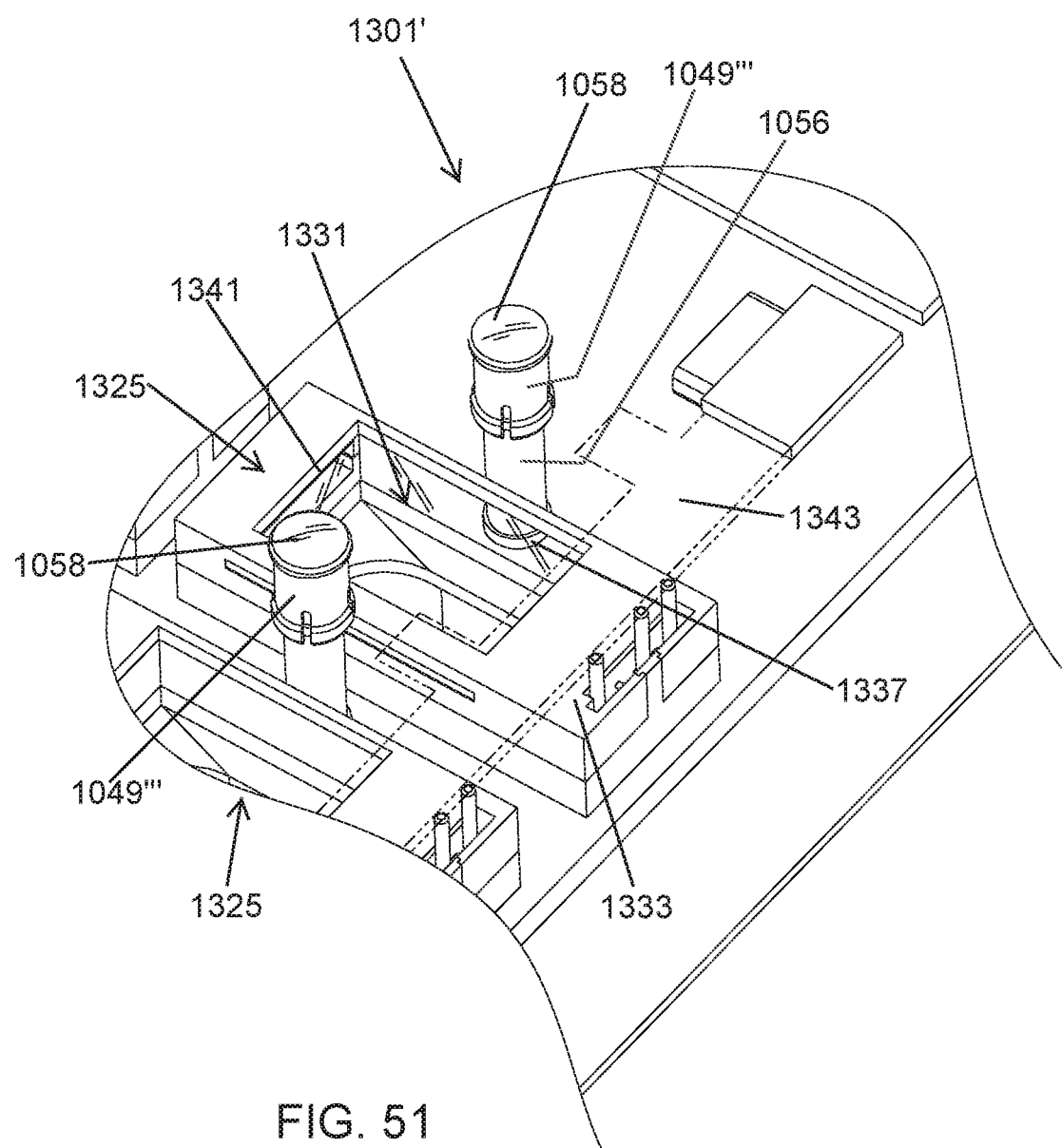
FIG. 51 is an enlarged perspective view of a portion of FIG. 50 including a sensor module.
Figure 52:
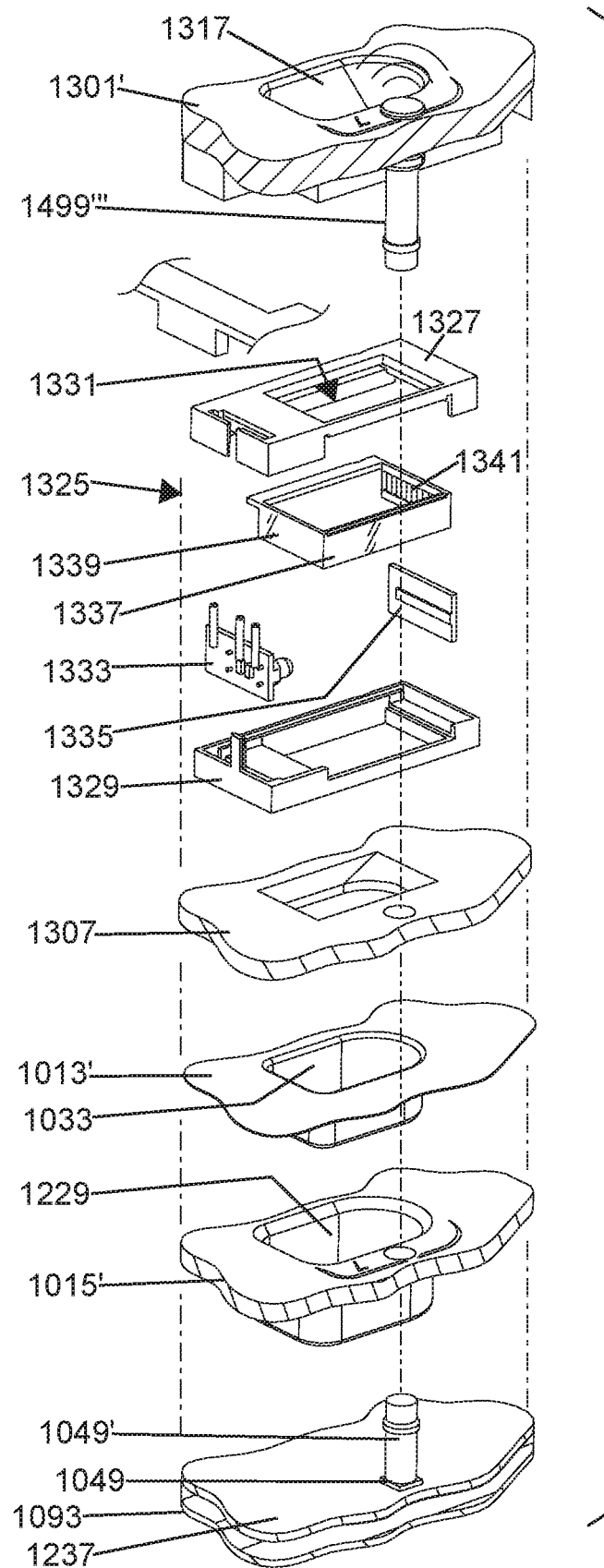
FIG. 52 is an exploded view of an exemplary sensor module of the sensor guide of FIG. 23.

As illustrated in FIG. 50, sensor guide 1301' may include 128 sensor modules 1325, one for each opening 1317. In this example, sensor modules 1325 are organized into a pattern of four groups of 32 total sensor modules (8 total rows- .times.16 total colons) 1325$a$, 1325$b$, 1325$c$, 1325$d$. Each of the four groups of sensor modules 1325 is organized into eight rows of four sensor modules 1325, one group corresponding to each group of pockets 1229$a$, 1229$b$, 1229$c$, 1229$d$. In this example, each sensor module 1325 is aligned with an opening 1317 of sensor guide 1301'.

Referring to FIGS. 28-28A, 34-37, 42-42A, and 50-52, an exemplary sensor module 1325 may include a first housing portion 1327 and a second housing portion 1329. When assembled, housing portions 1327, 1329 include an opening 1331 through which a medicament 1011 or other item passes.

A pair of infrared (IR) senders 1333 are positioned at one end of sensor module 1325 directed into opening 1331 and an infrared (IR) receiver 1335 is spaced from senders 1333 across opening 1331 at an opposite end of sensor module 1325. A lens support 1337 supports first and second lenses 1339, 1341. First lens covers IR sender 1333 and second lens covers receiver 1335 protecting sender 1333 and receiver 1335 from damage by contact with medicament 1011 or other objects. Lenses 1339, 1341 may be made of polycarbonate or other suitable IR-energy-transmissive materials. First lens 1339 preferably permits passage of IR energy from sender 1333 while blocking ambient light external to sensor guide 1301, 1301' thereby intensifying the IR energy from sender 1333. Second lens 1341 is preferably a narrow slit which permits a narrow band of IR energy to contact receiver 1335. The collective effect of lenses 1339, 1341 is to minimize false detection events that could be caused by shadows or movement of a user's hand near a sensor module 1325.

Each sensor module 1325, and IR sender and receiver 1333, 1335 may be operatively connected to circuitry in the form of a printed circuit board 1343. Circuit board 1343 may be connected to docking station 1015, 1015' via a flexible cable 1345. Docking station 1015, 1015' is operatively connected to controller 1017 permitting sensor module 1325 to send a signal to controller 1017 indicative that a medicament 1011 has been detected.

As illustrated in FIGS. 28-28A and 42-42A, during operation, IR sender 1333 emits, generates, or outputs a signal in the form of energy. The IR energy is across opening 1331 and through second lens 1341. The IR energy signal is received through second lens 1341 by IR receiver 1335. When a medicament 1011 or other item passes through opening 1331 between IR sender 1333 and IR receiver 1335, IR energy received by IR receiver 1335 is momentarily blocked. The decrease in IR energy causes sensor module 1325 to output a signal in the form of a voltage output change which is interpreted by controller 1017 as detection of a medicament 1011 or other item passing through sensor module 1323. Plural medicaments 1011 can be passed through sensor module 1325 and a separate count will be registered by controller 1017 for each medicament 1011.

Sensor module 1325 may be mounted within (i.e., inside) sensor guide 1301, 1301' in any suitable orientation. In the example of sensor guide 1301, each sensor module 1325 is oriented generally parallel to left and right sides 1313, 1315 of sensor guide 1301 whereas in the example of sensor guide 1301' sensor module 1325 is oriented generally parallel to front and rear sides 1309, 1311 of sensor guide 1301.

It is contemplated that sensor guides 1301, 1301' may be implemented in embodiments other than the illustrated sensor guides 1301, 1301'. For example, sensor guide 1301, 1301' may be an integral element of docking station 1015, 1015' or holder 1013. In such embodiments, a sensor module 1325 may be provided for each cell 1033. An appropriate data-communication connection, 1343, 1345 may be provided between each sensor module 1325 and controller 1017.

As illustrated in FIGS. 28-28A and 42-42A, sensor guide opening walls 1319 may extend below sensor guide bottom 1307 and be sized to nest within a corresponding cell 1033 of holder 1013, 1013'. In such an embodiment, each sensor guide wall 1319 extends into the corresponding cell 1033 of holder 1013, 1013' and nests into wall 1035 of cell 1033 providing a continuous guiding surface from opening 1317 through and into cell 1033 thus assuring that a medicament 1011 or other item can only enter the cell 1033 of holder 1013, 1013' aligned with each opening 1317 of sensor guide 1301, 1301'. Such an embodiment would be particularly useful when spacing between sensor guide 1301, 1301' and holder 1013, 1013' is desired. The continuous guide surface formed by walls 1035, 1319 would prevent unwanted bouncing of a medicament 1011 from one cell 1033 to another cell 1033 which could occur when a medicament 1011 or other item is loaded into a cell 1033. Such an embodiment would also help to position sensor guide 1301, 1301'' in the single, repeatable position on holder 1013, 1013'.

Sensor guide 1301, 1301' further includes at least one indicator 1049''' for each cell 1033, of Which indicator 1049''' is representative. (The symbol ''' refers to triple prime.) For purposes of simplicity and brevity, each indicator 1049''' of sensor guide 1301, 1301' is indicated by reference number 1049''', it being understood that each indicator 1049''' has the same structure and operation in the example.

Indicators 1049''' are preferably provided in a pattern which matches the pattern of cells 1033 and indicators 1049', 1049'' of docking station 1015, 1015'' and holder 1013 indicators 1049''' such that at least one indicator 1049''' is provided for (i.e., associated with) each opening 1317 and cell 1033. In the example, each indicator 1049''' is located through sensor guide 1301, 1301' body 1303 from the top 1305 of sensor guide 1301, 1301' to the bottom 1307 of the sensor guide 1301, 1301'.

In the example of sensor guide 1301, indicators 1049''' are organized into four rows of 16 indicators 1049''' corresponding to the pattern of cells 1033 of holder 1013 and openings 1317 of sensor guide 1301 and positioned so as to be below each opening 1317 and approximately centered on each opening 1317. As illustrated in FIGS. 28-28A, each exemplary indicator 1049, 1049', 1049'', 1049''' for each respective cell 1033 is in axial alignment when holder 1013 is docked at docking station 1015 and sensor guide 1301 is docked or mounted on top of holder 1013.

Exemplary sensor guide 1301' includes indicators 1049' organized into four groups of 32 total indicators 1049''' for a total of 128 indicators 1049''' in the same manner as indicators 1049, 1049' of docking station 1015. Each of the four groups of indicators 1049''' is organized into eight rows of four indicators 1049''', one group corresponding to each group of pockets 1229a-129d and openings 1317a-1317d. As with indicators 1049, 1049' of docking station 1501', indicators 1049''' are positioned so as to be above each opening 1317 and approximately centered on each opening 1317. As illustrated in FIGS. 42-42A and 50-52, each indicator 1049, 1049', 1049''' for each respective cell 1033 is in axial alignment when holder 1013' is docked at docking station 1015' and sensor guide 1301' is docked or mounted on top of holder 1013'.

In the example, each indicator 1049''' may be a visible indicator in the form of a selectively-operable light pipe of the type described in connection with indicators 1049' and 1049" of docking station 1015, 1015' and holder 1013 and the description of such indicators 1049', 1049" is incorporated herein by reference. When sensor guide 1301, 1301' is seated on a docked holder 1013, 1013', indicator 1049''' is aligned with indicators 1049, 1049', 1049" (all a visible information source) and receives light, a type of visible information, from such indicators. In the examples, light (i.e., visible information) enters the inlet 1054 of indicator 1049'''' and is communicated through indicator body 1056 to outlet 1058. Since each set of indicators 1049 1049', 1049" (for holder 1013), 1049''' is aligned when in condition for operation, indicators 1049, 1049', 1049", and 1049''' communicate the light through sensor guide 1301, 1301' so that light is visible to user along top wall 1305 of sensor guide 1301, 1301' next to, or proximate, an opening 1317 of sensor guide 1301, 1301'.

The preferred light energy provided by indicators 1049, 1049', 1049", and 1049''' may be viewable to a user on the holder 1013, 1013' top 1305 proximate each cell 1033 to indicate the cell 1033 into which a medicament 1011 or other item is to be placed. The presence or absence of light energy can be seen by the user at the moment the medicament 1011 or other item enters opening 1317 so that the user has a confidence level that the medicament 1011 was placed into the correct opening 1317. Such confidence level is heightened further by detection of the medicament 1011 or other item by sensor guide 1301, 1301'.

Sensor guides 1301, 1301' may be made of any suitable material or combination of materials. Preferably, body 1303 is made of plastic material construction for reasons of ease of manufacture, low weight, ease of cleaning, and cost. Indicators 1049''' are preferably light pipe-type indicators but may comprise other types of indicators. For example, indicators may be LEDs, liquid crystal displays (LCD) or other visible indicators.

As previously mentioned, systems 1010, 1010" may be used without a sensor guide 1301, 1301'. Sensor guide 1301, 1301' may be seated in its cradle 1106 or against docking station 1015' and deactivated or systems 1010, 1010' may be provided without a sensor guide 1301, 1301'. For example, system 1010' for loading holders 1013' of a blister-package-type container can be used without a sensor guide 1301' by simply placing a medicament 1011 directly into a cell 1033 indicated by indicators 1049, 1049'.

Controller 1017 is operable to selectively operate indicators 1049, 1049', 1049", and 1049''' associated with each cell 1033 when holder 1013, 1013' is docked at docking station 1015, 1015' and sensor guide 1301, 1301' is seated on holder 1013, 1013'. Each set of indicators 1049, 1049', 1049", and 1049''' corresponding to each opening 1317, cell 1033, and/or pocket 1229 represents a visible information source. Selective operation of indicators 1049, 1049', 1049", and 1049''' proximate to a cell 1033 or sensor guide opening 1317 prompts the technician, pharmacist, or other user to place each medicament 1011 into the cell 1033 or opening 1317 associated with the activated indicators 1049, 1049', 1049", and 1049'''.

As with systems 10, 10', indicators 1049, 1049', 1049", and 1049''' comprise a type of pick-to-light/place-to-light system. Thus, if a medicament 1011 is to be loaded in the cells 1033 designated by human-readable indicia 1047 as cells 1, 3, 6, 9, 12, 15, 18, 21, 24, and 27, each of the indicators 1049, 1049', 1049", and 1049''' next to such cells 1033 may be activated communicating to the technician, pharmacist, or other user the specific cells 1033 which should contain that medicament 1011. In other embodiments, indicators 1049, 1049', 1049", and 1049''' may be deactivated to provide the visible information. In such an embodiment, indicators 1049, 1049', 1049", and 1049''' may initially be activated. Deactivation of just the indicators 1049, 1049', 1049", and 1049''' associated with the cell 1033 into which the medicament 1011 or other item is to be placed provides the visible information. The state of indicators 1049, 1049', 1049", and 1049''' indicating that a medicament 1011 should be placed into a cell may be thought of as a "yes" state while the state of indicators 1049, 1049', 1049''' indicating that a medicament should not be placed into a cell 1033 may be thought of as a "no" state for the implicit and apparent reason that the user is being prompted to either place, or not place, a medicament 1011 into an indicated cell 1033.

Use of a pick-to-light/place-to-light system of indicators 1049, 1049', 1049", and 1049''' advantageously communicates information to the user (e.g., a technician or pharmacist) without resort to a set of written instructions. A pick-to-light/place-to-light system is far superior to written instructions because the user need not take his or her eyes off of holder 1013, 1013' to read the instructions, thereby increasing accuracy and reducing the time required to load or verify the medicaments 1011 that should be in the holder 1013, 1013'.

In further embodiments, systems 1010, 1010' may have multi-colored indicators as described in connection with FIGS. 11A, 11B, and 11C, but implemented by means of indicators 1049, 1049', 1049", and 1049'''. For example, indicator 1049 could comprise a single multi-colored indicator 1049 for each cell 1033, pocket 1229, and opening 1317. In an embodiment, a multi-colored LED lamp could be used as indicator 1049 and the voltage could be changed by controller 1017 so that indicator 1049 would emit a different color as described previously. Indicators 1049', 1049", and 1049''' would operate to communicate the color to a position on sensor guide 1301, 1301' next to the associated opening 1317 and cell 1033. The color differences could be used to communicate information of the type described above in connection with FIGS. 11A, 11B, 11C and the entire description of FIGS. 11A-11C is incorporated herein by reference.

In yet other embodiments of systems 1010, 1010', multiple sets of indicators may be provided for each cell 1033 and sensor guide opening 1317 (e.g., three sets of indicators 1049, 1049', 1049", and 1049''' for each cell 1033). Such an embodiment may operate under the control of controller 1017 in the same manner and for the same purposes as described previously in connection with FIG. 11D and the description of FIG. 11D is incorporated herein by reference.

Also as described previously, controller 1017 can control indicators 1049, 1049', 1049", and 1049''' to have a blink pattern indicating the medicament 1011 to be loaded into the associated cell 1033 through sensor guide opening 1317. A constant blink could indicate that one medicament 1011 is to be loaded into the cell, two blinks could indicate that more than one medicament 1011 is to be loaded in that cell 1033, and three blinks could indicate that a half-size medicament is to be loaded in that cell 1033. Controller 1017 can also control operation of indicators 1049, 1049', and 1049" for each cell 1033 for verification of medicaments 1011 received in each cell 1033.

Systems 1010, 1010' may include a controller 1017 as described in connection with controller 17, but with controller 1017 controlling indicators 1049, 1049', 1049", and 1049''' associated with each cell 1033 and opening 1317. For example, systems 1010, 1010' could operate with a controller 1017 including a programmable logic controller (PLC) 79 and server 107 connected thereto for purposes of controlling indicators 1049, 1049', 1049", and 1049''' as described in connection with FIGS. 12A and 12B and the description of such controller 17 embodiments is incorporated herein by reference with respect to controller 1017.

Referring to the schematic block diagram of FIG. 53, controller 1017 for use with systems 1010, 1010' is most preferably a client computer 1349 (i.e., a processing device) operably connected to data port 1109 of docking station 1015, 1015' and communication link 1111. Client computer 1349 may include memory 1113 with a program of instructions 1115 residing in memory 1113. Client computer 1349 may be connected via a communication link 1119 to a pharmacy information system (PIS) 1351 residing on server 1353. The PIS 1351 passes each prescription order to system 1010, 1010' and client computer 1349 after the prescription order is first approved by the PIS 1351. Client computer 1349 then provides overall control of system 1010, 1010'.

Controller 1017 may further be in data-transmission relationship with sensor guide 1301, 1301'. Detection of a medicament 1011 by each sensor module 1325 is used by controller 1017 to confirm that a medicament 1011 has been placed into the correct cell 1033 and to count the quantity of medicaments 1011 placed into each cell 1033 as described below.

Each system 1010, 1010' further preferably includes a video display 1125, keyboard 1127, and mouse 1129 permitting a technician, pharmacist, or other user to input and receive information from client computer 1349 of controller 1017 or PIS 1351. A biometric identification device 1130 may be provided to permit the technician, pharmacist, or other user to be identified to the system 1010 or 1010', particularly when logging on to the system. The biometric device 1130 may be a fingerprint reader, retina scanner, or other suitable device. A bar code scanner 1131 is preferably operably connected to controller 1017. Video display 1125 is preferably a touch screen display permitting a technician, pharmacist, or other user to input information to controller 1017 by simply touching her finger on a desired portion of the display 1125. Bar code scanner 1131 may be any off-the-shelf scanner capable of reading a bar code 1133 on a container 1135 provided to hold medicaments 1011. Keyboard 1127 may be an off-the-shelf QWERTY-type keyboard 1127 permitting a user to input information to controller 1017 and system 1010, 1010'.

Exemplary Operation and Use

Systems 1010, 1010' may be used with or without sensor guide 1301, 1301', although use with sensor guide 1301, 1301' provides heightened accuracy and is preferred.

Figure 24:
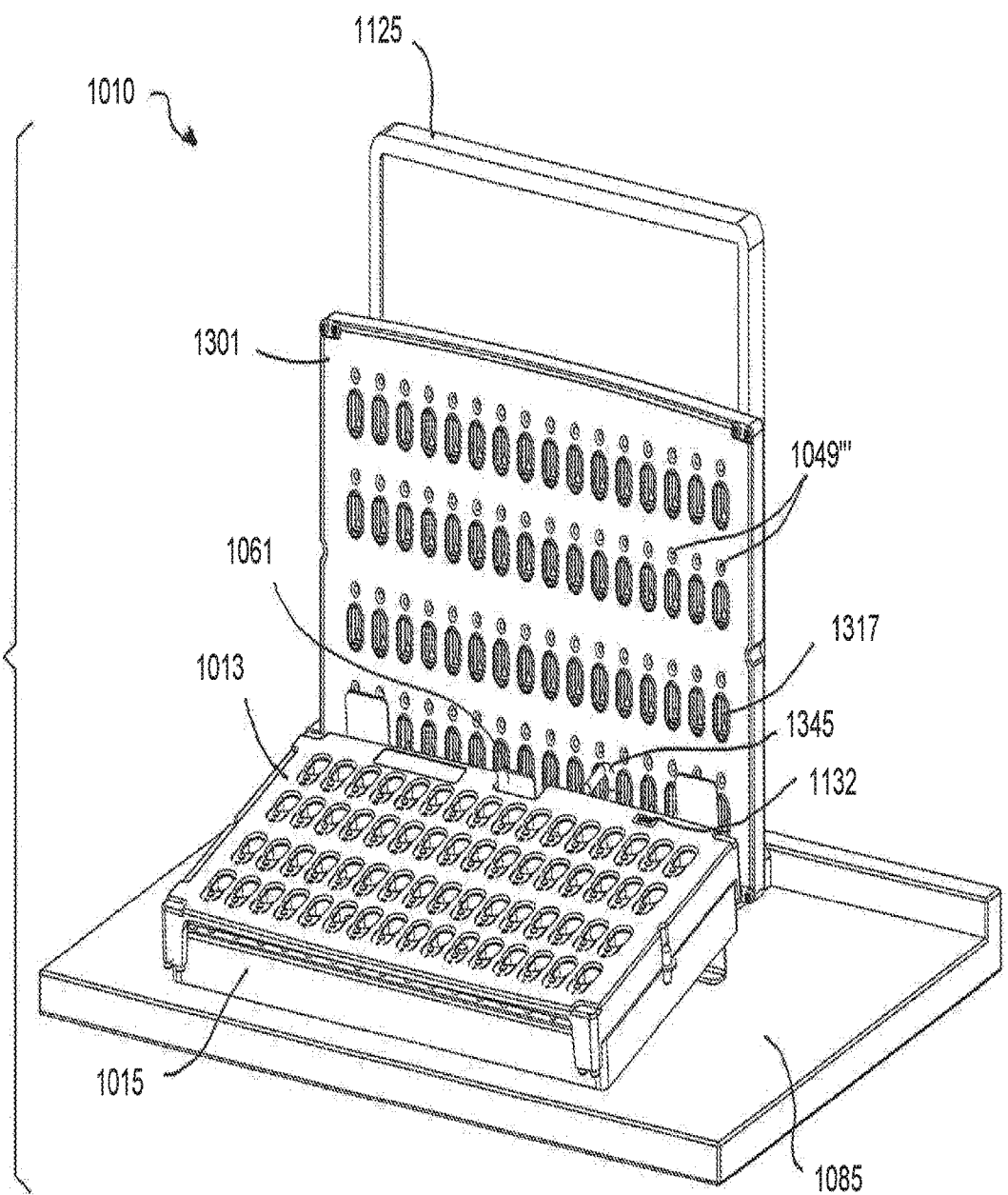
FIG. 24 is a perspective view of the medicament management system of FIG. 23, but with the sensor guide in a storage position.
Figure 25:
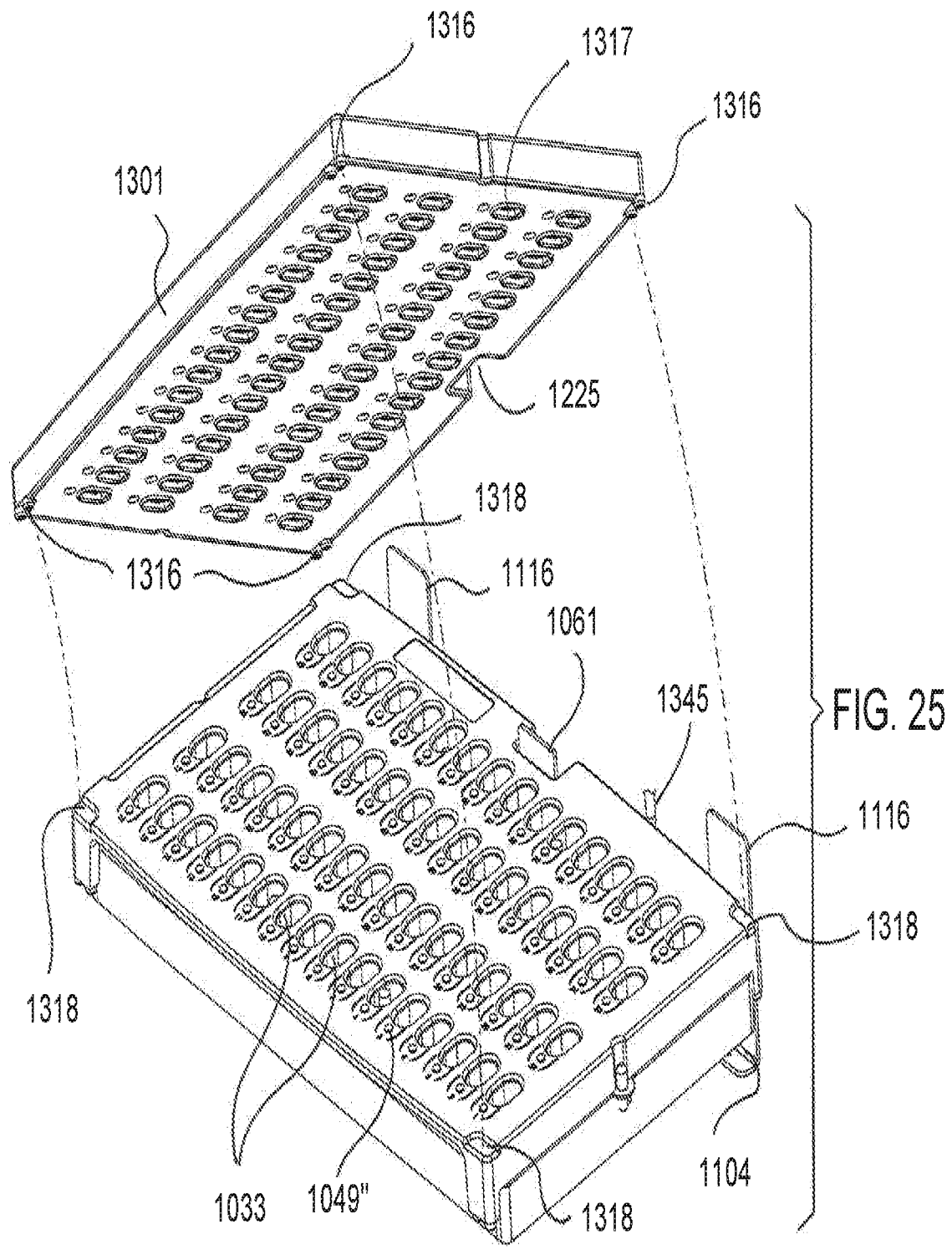
FIG. 25 is a partially exploded view of the medicament management system of FIG. 23 including a docking station, holder, and sensor guide.
Figure 26:
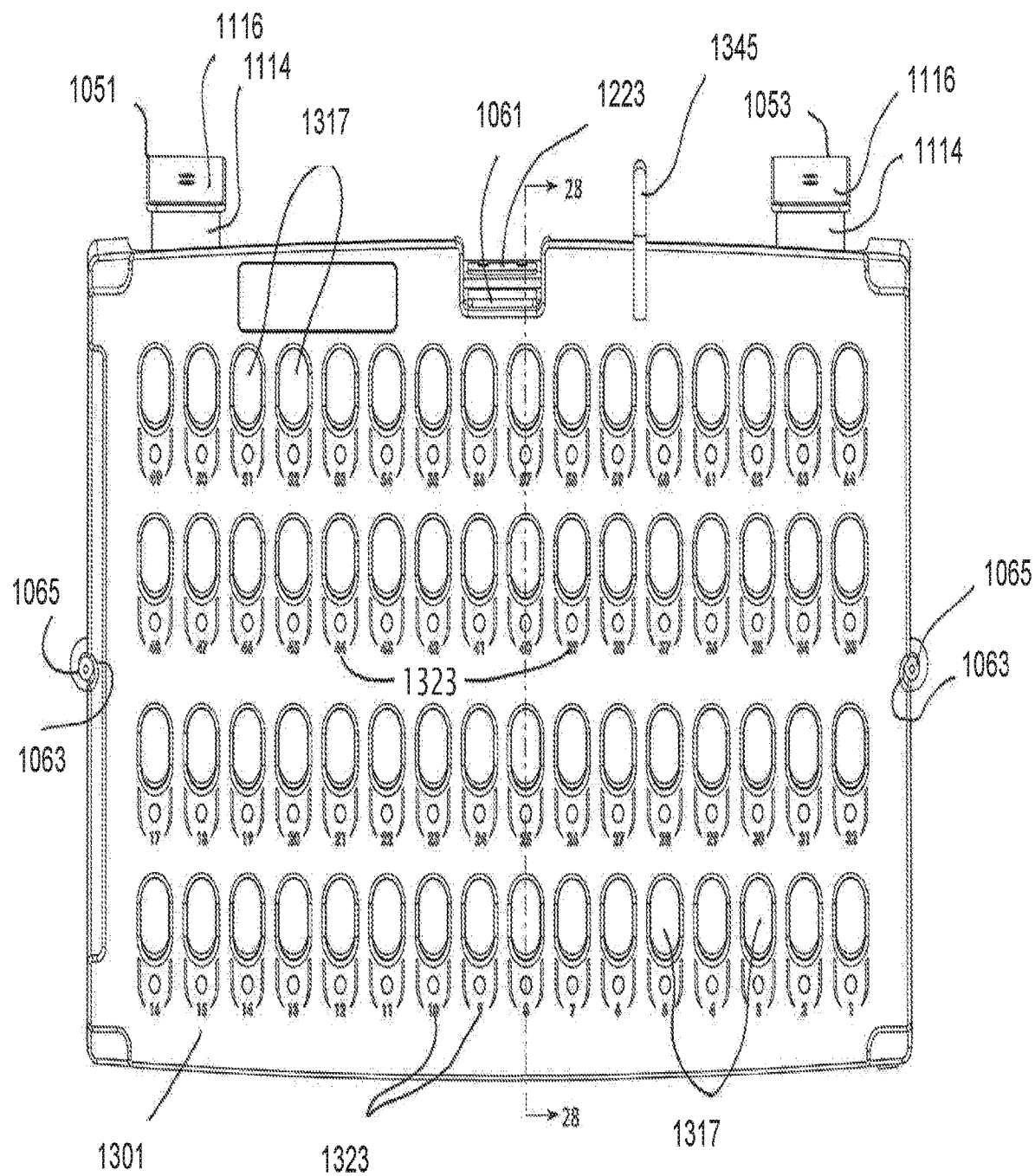
FIG. 26 is a top view of the medicament management system of FIG. 23 including a docking station, holder, and sensor guide.
Figure 27:
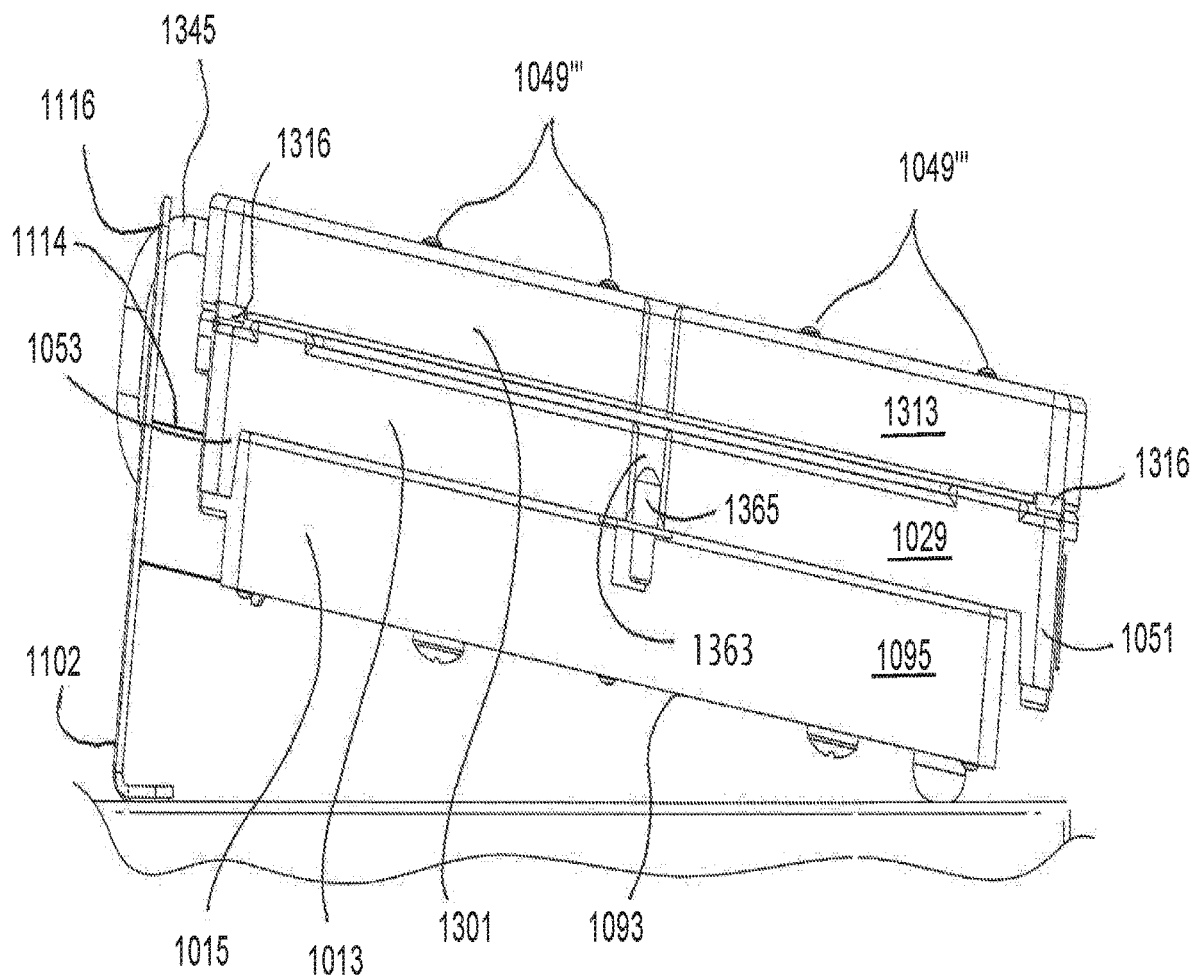
FIG. 27 is a left side elevation view of the medicament management system of FIG. 23 including a docking station, holder, and sensor guide.

In embodiments, not including a sensor guide 1301, 1301' or in which the sensor guide 1301, 130F is not activated/ utilized and is in the storage position of FIGS. 24 and 38, systems 1010, 1010' may be used as described above in connection with FIGS. 14-17, with the information presented on the video display 1125 adjusted to conform to the number and arrangement of cells 1033 of holder 1013, 1013'. The description of operation of systems 10, 10' and 1013' is incorporated by reference with respect to embodiments of systems 1010, 1010'.

More specifically, in exemplary system 1010 holder 1013 is provided with sixty four cells 1033 arranged in four rows of 16 cells 1033 identical with holder 13 and the sixty four cells 33 of holder 13. In the examples, the structure of each holder 13, 1013 and the pattern of the cells 33, 1033 is as required to conform to cells 41 of exception storage apparatus 43 of automated dispensing machine 45 as previously described. Accordingly, holder 1013 may be loaded and verified in the same manner as described for holder 13 in connection with FIGS. 14-17 with controller 1017 operating indicators 1049, 1049', 1049", and 1049''' to provide the visible information directing the user to either load a medicament 1011 into a cell 1033 or to verify that the medicament 1011 loaded in each cell 1033 is correct. The result would be a holder 1013 that has been loaded and verified as correct for transfer of the medicaments 1011 to automated dispensing machine 45 in the same manner as described in connection with systems 10, 10'.

And, container loading and verification of a holder 1013' of a blister-package-type may be loaded and verified in the same manner as described for holder 13 in connection with FIGS. 14-17 with holder 1013' docked at docking station 1015' and controller 1017 operating indicators 1049, 1049', and 1049''' to provide the "yes" or "no" state visible information directing the user by means of the "yes" state visible information to either load a medicament 1011 into a cell 1033 or to verify that the medicament 1011 loaded in each cell 1033 is correct. Once loaded and verified, holder 1013' may be closed with closure 1042 in a conventional manner for blister-package-type containers as described herein.

Use of sensor guide 1301, 1301' is illustrated in FIGS. 54-72 which represent exemplary screen displays of a type which could be displayed to a technician, pharmacist, or other user on video display 1125 for implementation of system 1010, while FIGS. 73-91 represent exemplary screen displays displayed on video display 1125 for implementation of system 1010'. The screen displays of FIGS. 54-91 are intended to represent non-limiting examples as the type and number of screen displays can be modified and the information provided in the screen displays may be customized to meet the needs of the particular pharmacy, hospital, long-term care facility or other operator.

Referring then to systems 1010, 1010', a user (e.g., a technician or pharmacist) may initiate use of system 1010, 1010' in the same manner as for system 10 by logging on to the system 1010, 1010'. Preferably, loading of holder 1013, 1013' is performed by a technician while verification of the loaded holder 1013, 1013' is performed by a registered pharmacist. (For simplicity and brevity, the person operating system 1010, 1010' is referred to as a "user.") The user may log on via a log-on screen 137 (FIG. 14) by means of keyboard 1127 entry of a password, or by means of a biometric device 1130 as described in connection with FIG. 14 with the result being that the user is recognized as a being authorized.

Figure 23:
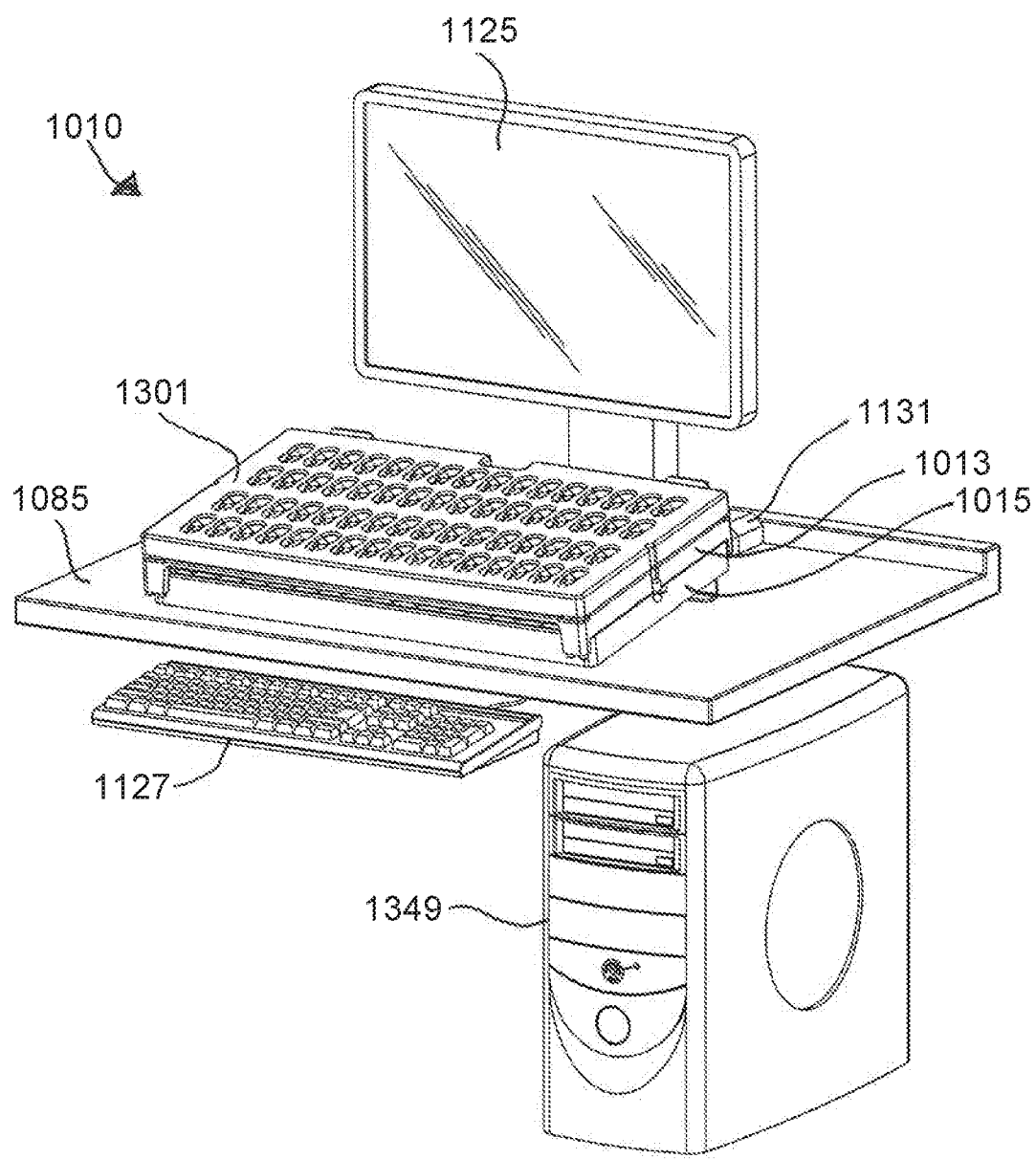
FIG. 23 is a perspective view of a further embodiment of a medicament management system including a docking station, holder, and sensor guide.
Figure 37:
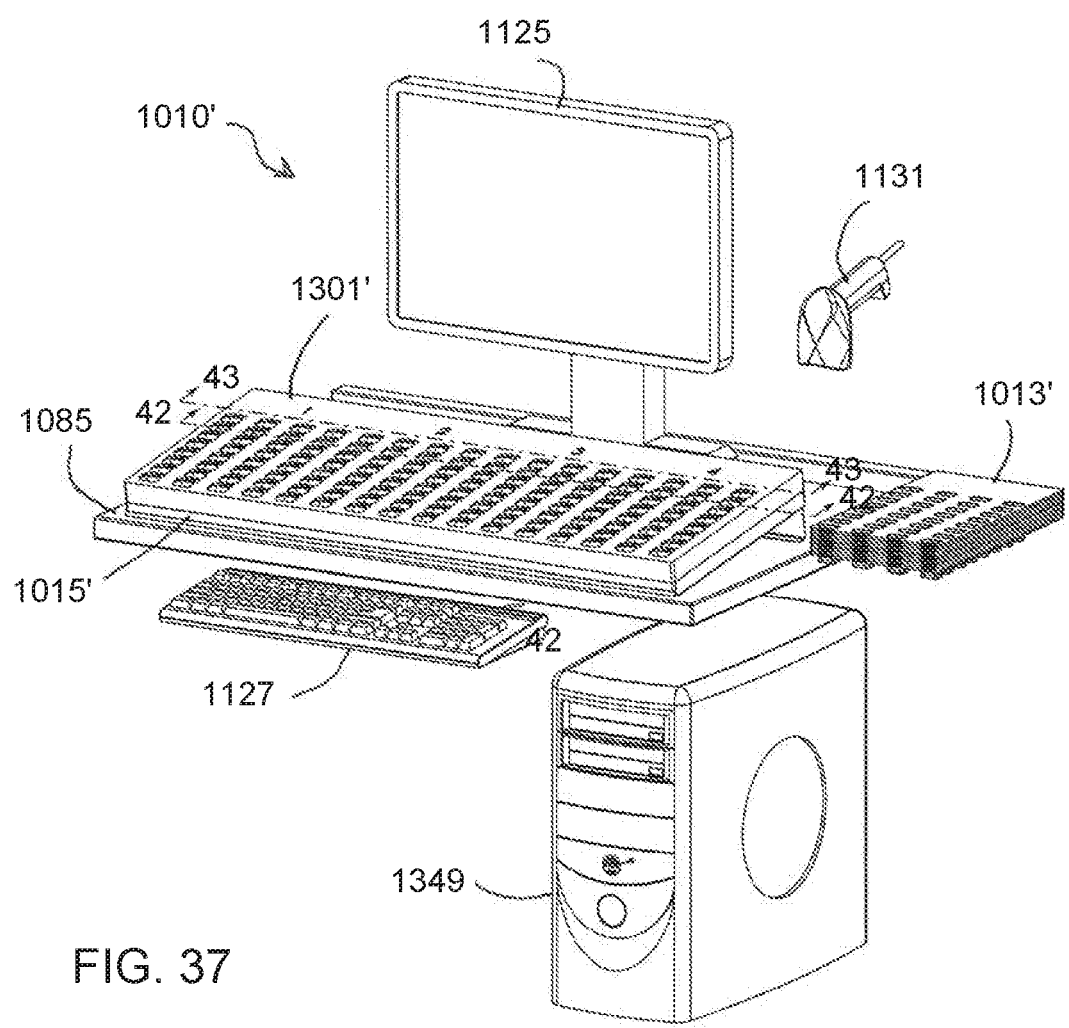
FIG. 37 is a perspective view of a further embodiment of a medicament management system including a docking station, holder, and sensor guide.
Figure 54:
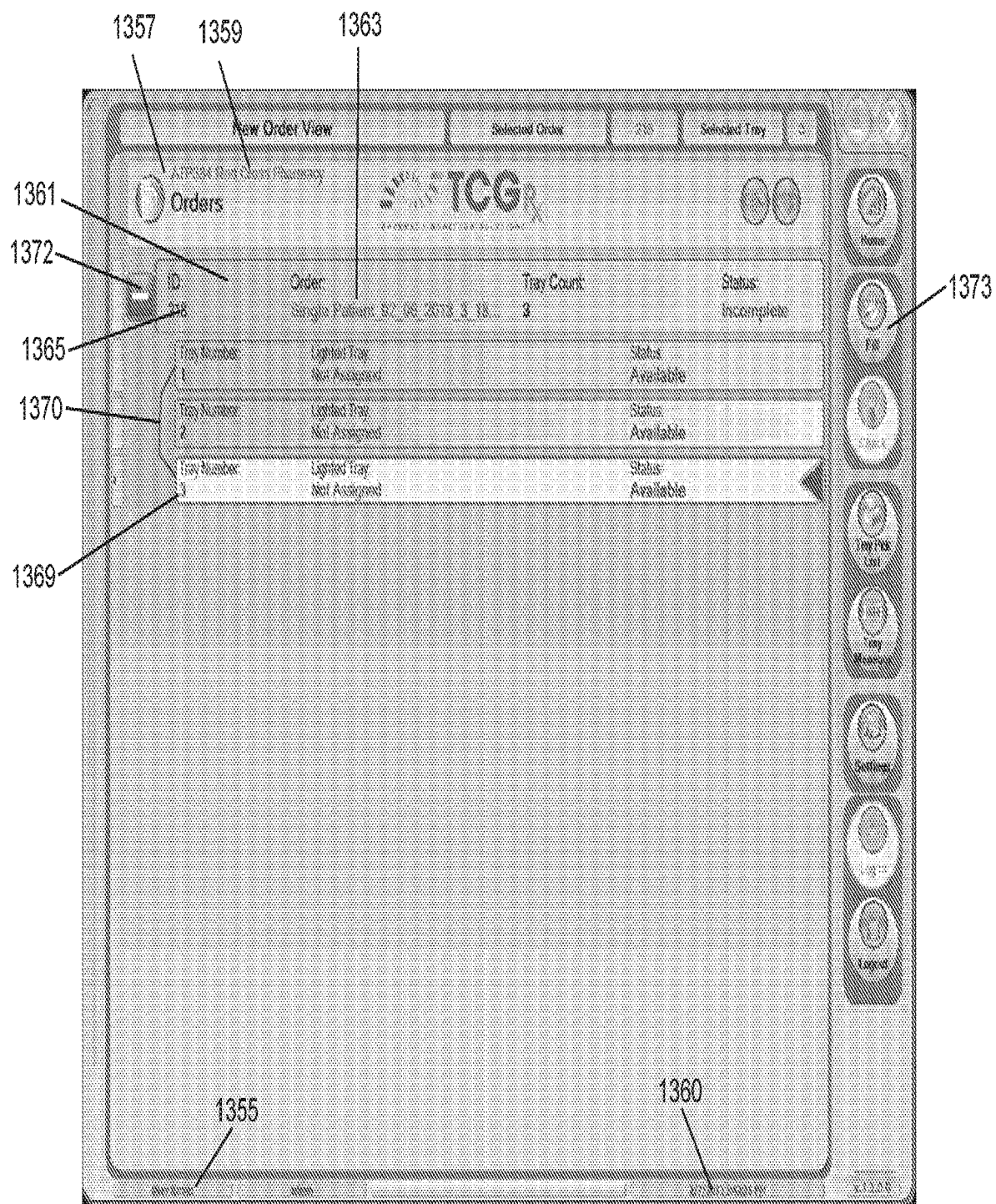
FIG. 54 is an exemplary screen display for loading a holder for the system of FIG. 23.
Figure 73:
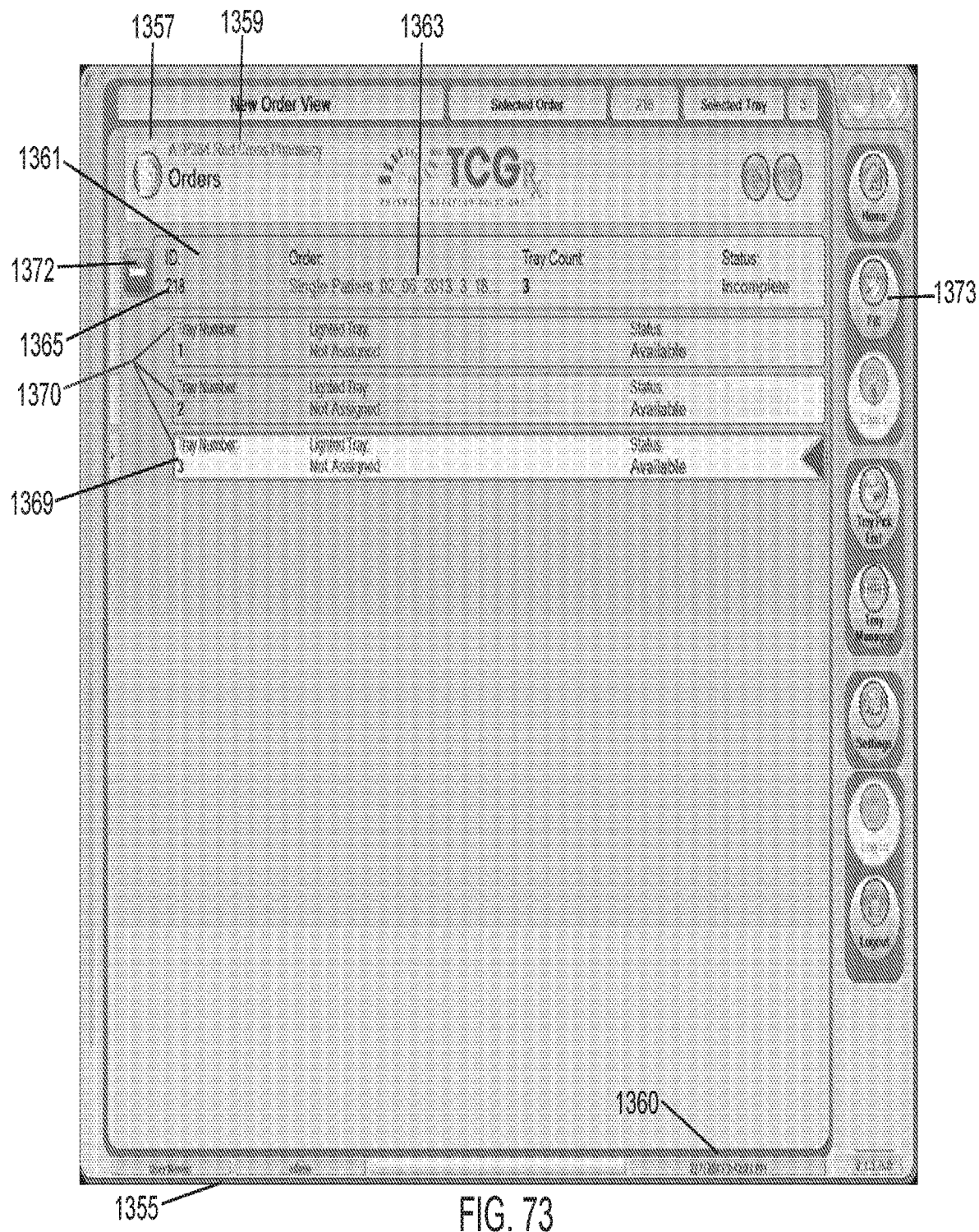
FIG. 73 is an exemplary screen display for loading a holder for the system of FIG. 37.

Referring now to FIGS. 54 and 73, if a holder 1013, 1013' is not already docked at docking station 1015, 1015' as shown in FIGS. 23 and 37, then a New Order screen 1355, 1355' (FIGS. 54, 73) may be displayed on video display 1125. The new Order screen 1355, 1355' prompts the user to initiate loading of a holder 1013, 1013' for purposes of loading automatic dispensing machine 49 or for preparation of a self-contained container 1013', potentially in fulfillment of a prescription order.

Information which may be presented on New Order screen 1355, 1355' can include an identification field 1357 identifying the operator name 1359 (e.g., Red Cross Pharmacy). Optionally, the user name, date and time-of-day on which holder 1013 is being loaded 1360 could be provided. Additional information which may be displayed in connection with New Order screen 1355, 1355' is an Order field 1361, which displays all pending prescription orders awaiting attention. In the example of FIGS. 54 and 73, a single prescription order 1363 is awaiting fulfillment. Each prescription order has previously been processed by PIS 1351 and released for fulfillment to controller 1017.

Order field 1361 may include a patient identifier and transaction code 1365 (e.g., "ID: 218" "Single Patient_02_06_2013_3_18") which indicates the transaction corresponding to loading of the holder 1013, 1013' for record-keeping purposes. In other embodiments, the name of the person for whom the prescription is intended may also be presented. New Order screen 1355, 1355' may also show holders 1013, 1013' available for fulfillment of the order, including the holder identifier 1369 (e.g., "Tray Number 3") for each holder 1013, 1013'. In the exemplary screen display examples of FIGS. 54-91, "tray" is used synonymously and interchangeably with "holder" and "container." Three holders 1013, 1013' indicated by 1370 are available to be loaded with medicaments 1011 to fulfill the prescription orders.

Preferably, the transaction code and all other information relating to loading and verification of holder 1013, 1013' is stored in a database 1371 on client computer 1349. Holder identifier 1369 may be any symbol or group of symbols capable of uniquely distinguishing one holder 1013, 1013' from another holder 1013, 1013'.

In the examples, holder identifier 1369 may be identical to an identifier embedded in RFID tag-type identification element 1081 if such an element 1081 is provided. In the examples, the holder identifier 1369 is the number "3". A unique identifier 1369 can be important if more than one identical holder 1013 is used by the pharmacy, hospital, long-term care provider or other operator. For holder 1013', unique identifier 1369 is illustrated as number "3" as illustrated in FIG. 73.

The user then touches video display 1125 next to an order in Order field 1361 to select the prescription order. In the examples of New Order screens 1355, 1355' illustrated in FIGS. 54 and 73, there is a single order pending in each illustrated Order field 1361. In FIGS. 54 and 73, the "-" symbol 1372 indicates that the selected prescription order is being processed. Alternatively, another input device, such as a mouse 1129 may be used to select the prescription order. The user further selects an available holder 1013, 1013' for the prescription order by touching display 1125 next to holder identifier 1369. The row next to holder identifier 1369 may become highlighted as illustrated in FIGS. 54 and 73. The user then touches the Fill icon 1373 to start the loading process.

Figure 55:
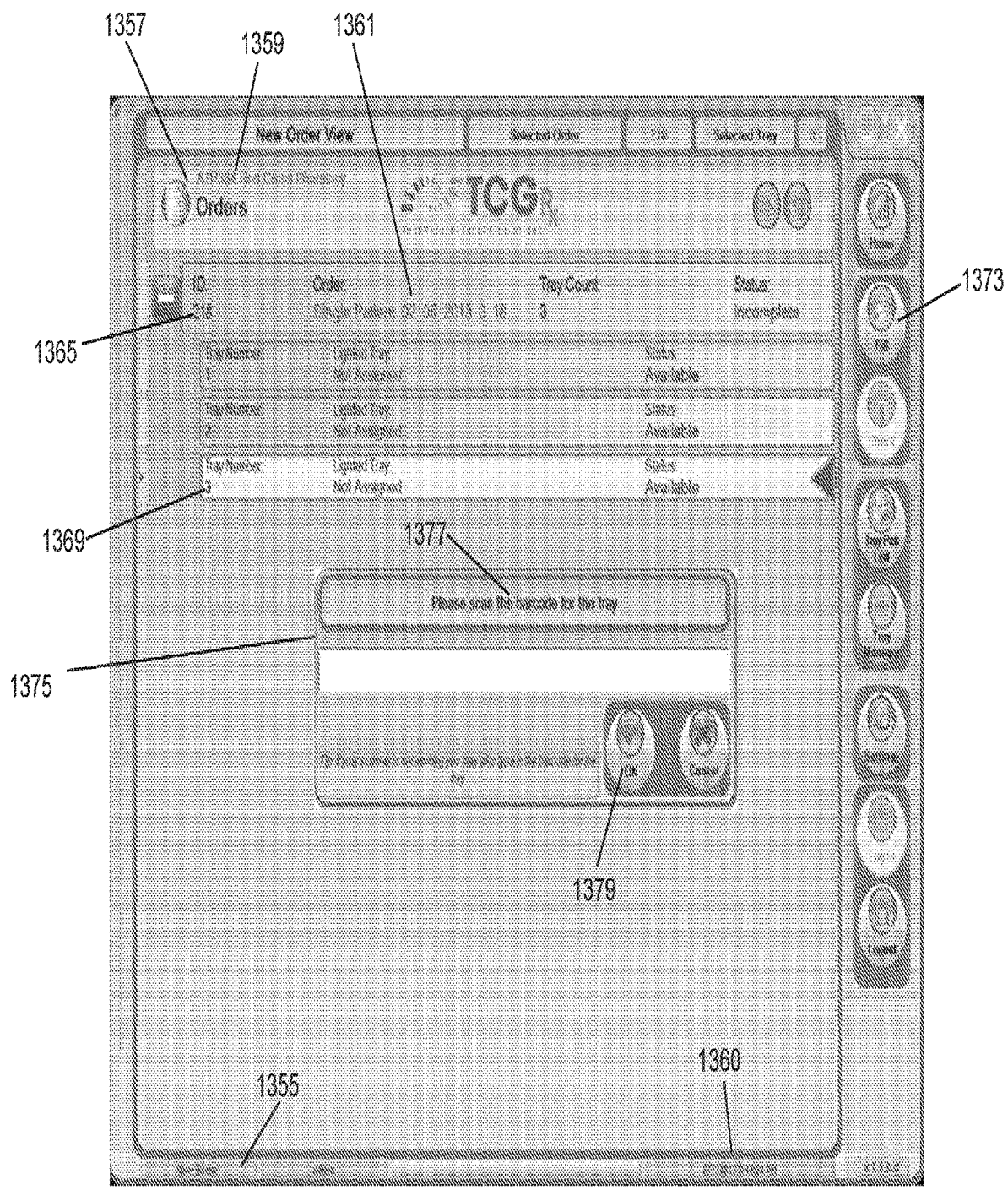
FIG. 55 is an exemplary screen display for selection of an available holder.
Figure 74:
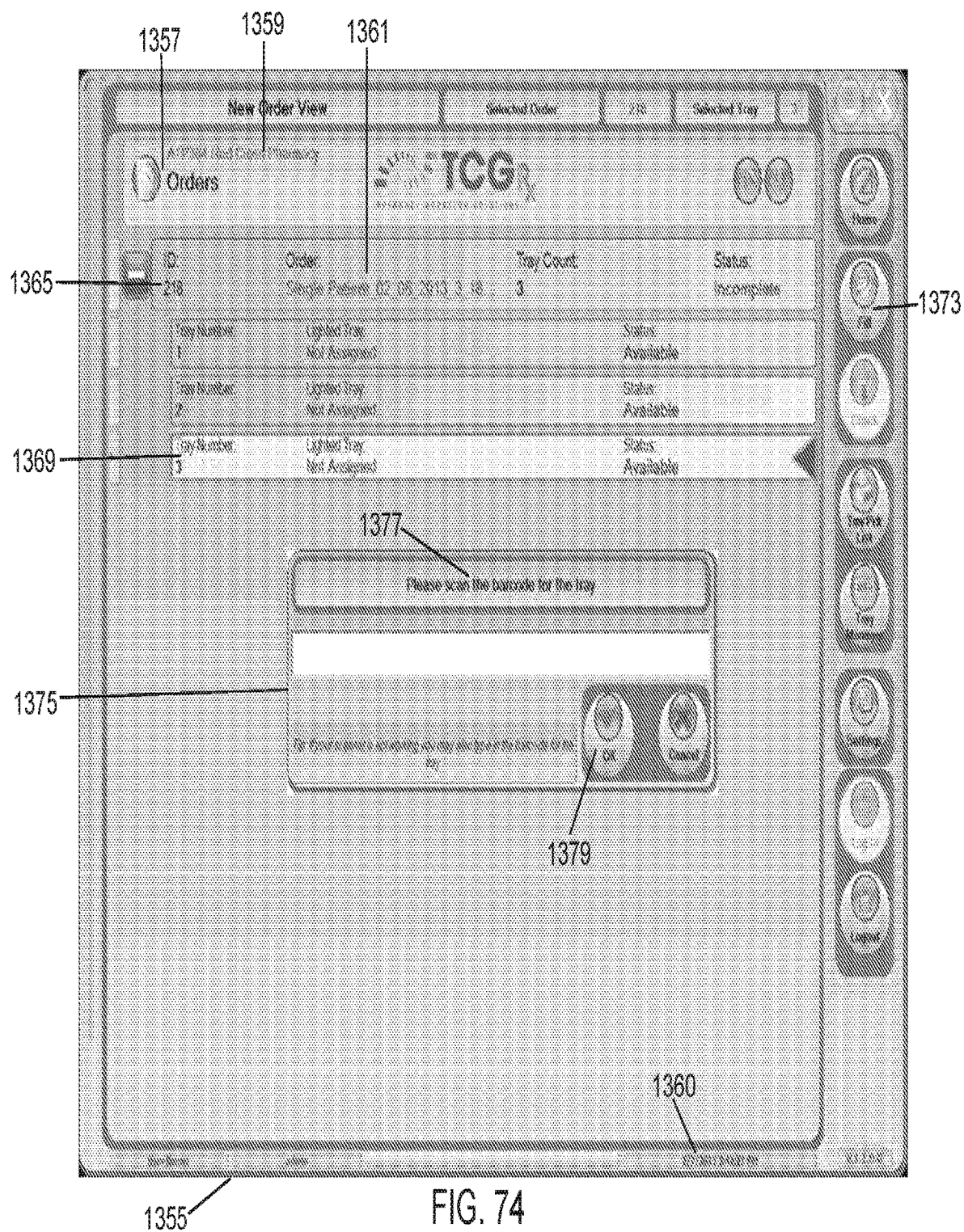
FIG. 74 is an exemplary screen display for selection of an available holder.

Referring next to FIGS. 55 and 74, the next step in the exemplary process is to physically get the holder 1013, 1013' for fulfillment of the order. Once the Fill icon 1373 is touched, an instruction field 1375 may appear on display 1125. The words "Please scan the bar code for the tray" 1377 may appear to prompt the user to scan bar code 1132 on holder 1013, 1013' with bar code reader 1131. Controller 1017 validates bar code 1132 and associates the holder 1013, 1013' with the prescription order in database 1371. The user may touch the "OK" icon 1379 following the scan to signal to controller 1017 that the bar code 1132 has been read or controller 1017 may automatically move to the next step. If the holder 1013, 1013' is not valid, then an error message (not shown) may be displayed on display 1125 and the user must obtain the correct holder 1013, 1013' or otherwise correct the error before proceeding further.

Figure 56:
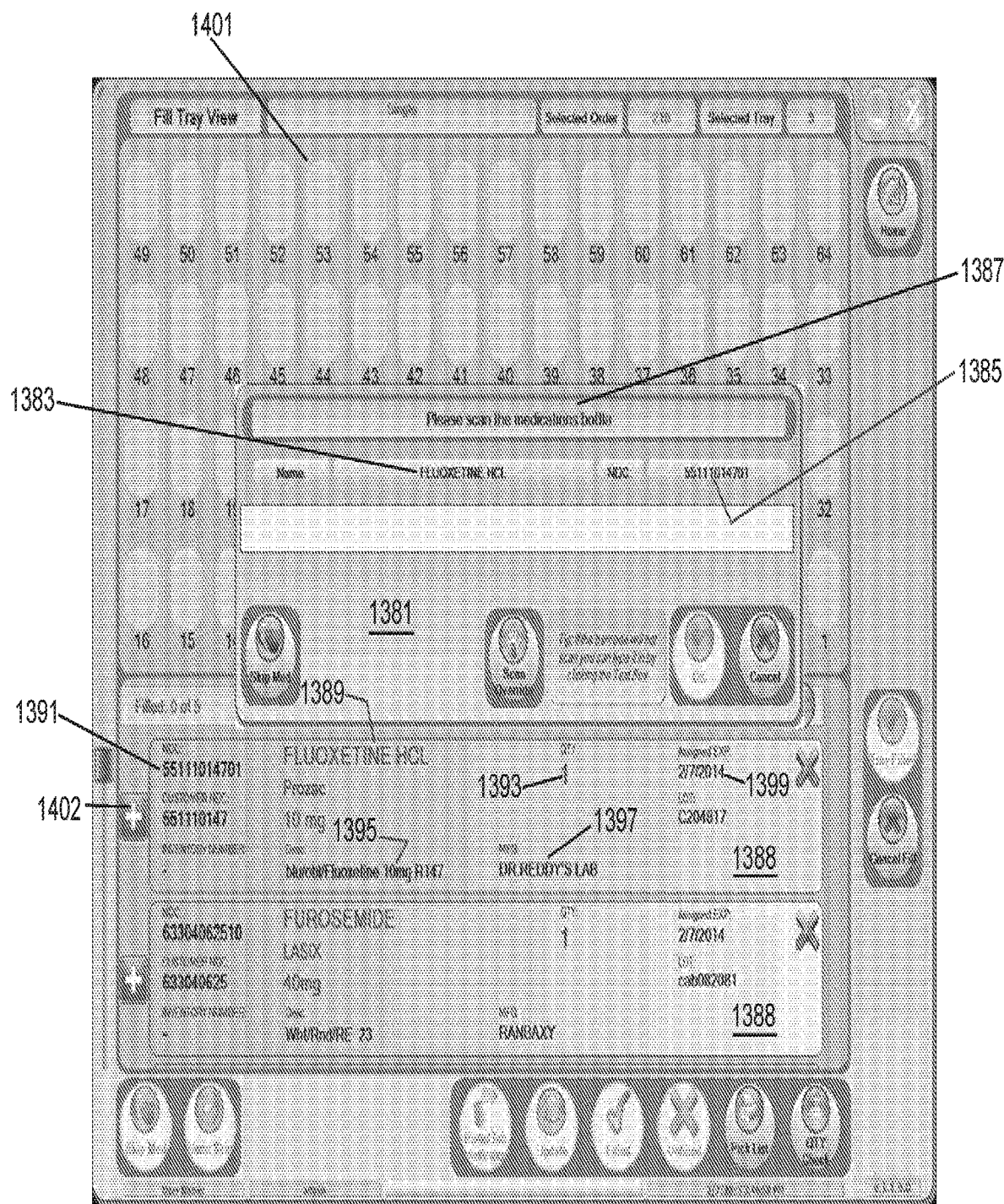
FIG. 56 is an exemplary screen display for selection of a medicament container.
Figure 75:
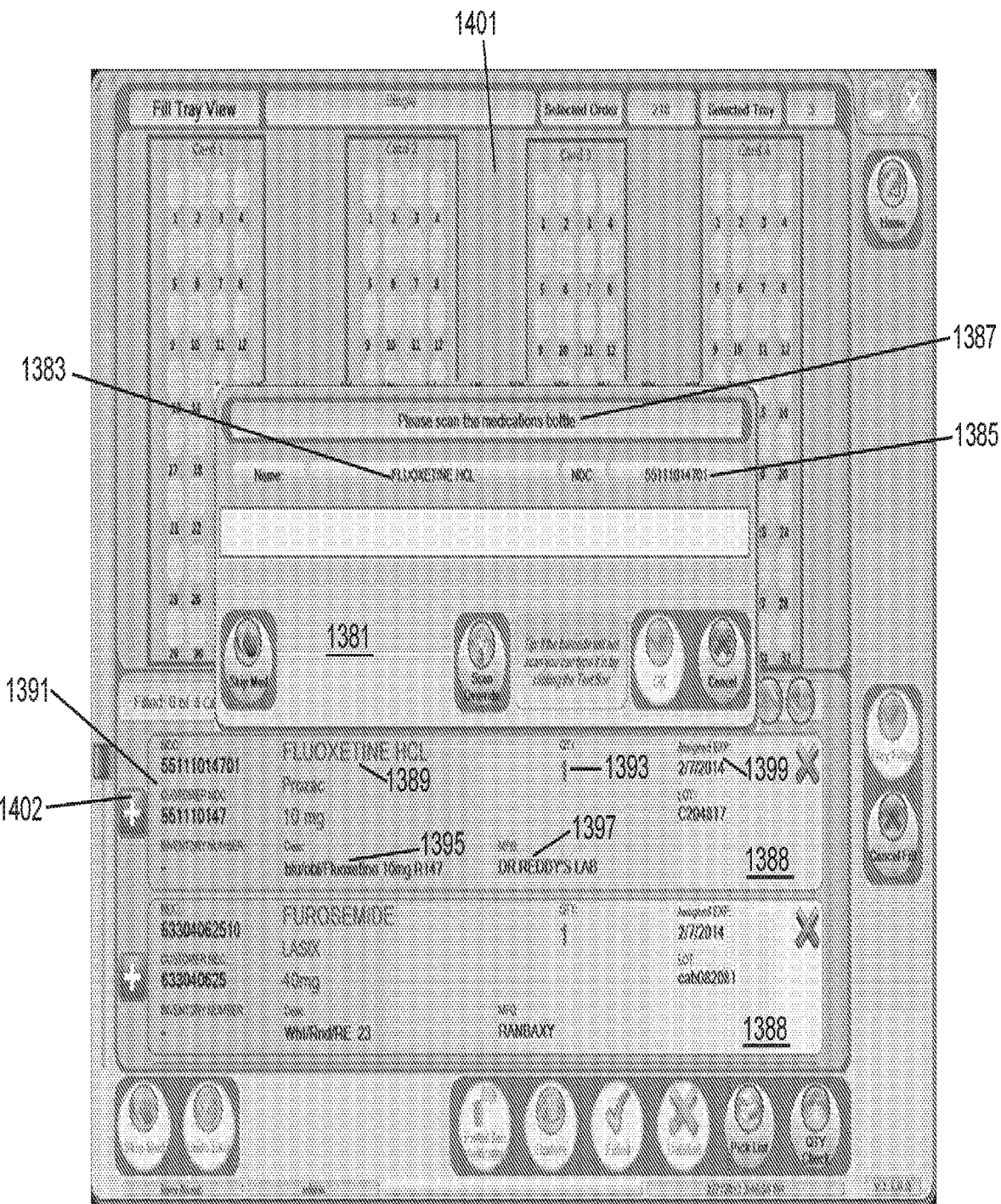
FIG. 75 is an exemplary screen display for selection of a medicament container.

Referring next to FIGS. 56 and 75, the next step in the exemplary process is to select a container 1135 (FIG. 53) of medicaments 1011 to be loaded into holder 1013, 1013'. Instructions for the prescription order residing in database 1371 include the exact type and quantity of medicament 1011 to be loaded into holder 1013, 1013' and the cell 1033 into which each medicament 1011 is to be loaded.

Instruction field 1381 may appear on display 1125 to prompt the user to select the container 1135 holding one of the types of medicaments 1011 to be loaded into holder 1013, 1013' in accordance with the order. The order may require just a single type of medicament 1011 or plural different types of medicaments 1011. Instruction field 1381 may display information identifying the type 1383 of medicament 1011 to be loaded into holder 1013, 1013' (e.g., "Fluoxetine HCL") and the National Drug Code (NDC) 1385 associated with that type of medicament 1011 (e.g., the 11 digit NDC "55111014701"). The words "Please scan the medication bottle" 1387 may appear to prompt the user to scan the bar code 1133 on container 1135.

In addition, a Medicament-identification field 1388 may appear with further information identifying the required medicament 1011 including the medicament type and strength 1389 (e.g., "Fluoxetine HCL Prozac 10 mg"), FDA and customer NDC numbers 1391 (e.g., 11-digit NDC "55111014701" and 9-digit customer NDC "551110147"), medicament 1011 quantity required 1393 (e.g., "1"), physical appearance 1395 of the medicament 1011 (e.g., "blue/obl/Fluoxetine 10 mg R147"), manufacturer name 1397 (e.g., "DR. REDDY'S LAB"), expiration date and lot number 1399 ("Assigned EXP: 2/7/2014" "Lot: C204817").

Also in the examples, a holder-view field 1401 may appear in the background for the reasons described below. Holder-view field 1401 may be a plan view graphic representation of a respective sensor guide 1301, 1301'.

The user then utilizes bar code scanner 1131 to scan bar code 1133 affixed to container 1135. The code corresponding to bar code 1133 is transmitted to controller 1017 which validates the code. The code may be validated, for example, by comparing the code embedded in bar code 1133 with an expected code in database 1371 on client computer 1349 of controller 1017 for the prescription order. If the container 1135 is not valid, then an error message (not shown) is displayed on display 1125 and the user must obtain the correct container 1135 or otherwise correct the error before proceeding further. The "+" symbol 1402 indicates that the container 1135 has not yet been validated as correct for the prescription order.

Figure 57:
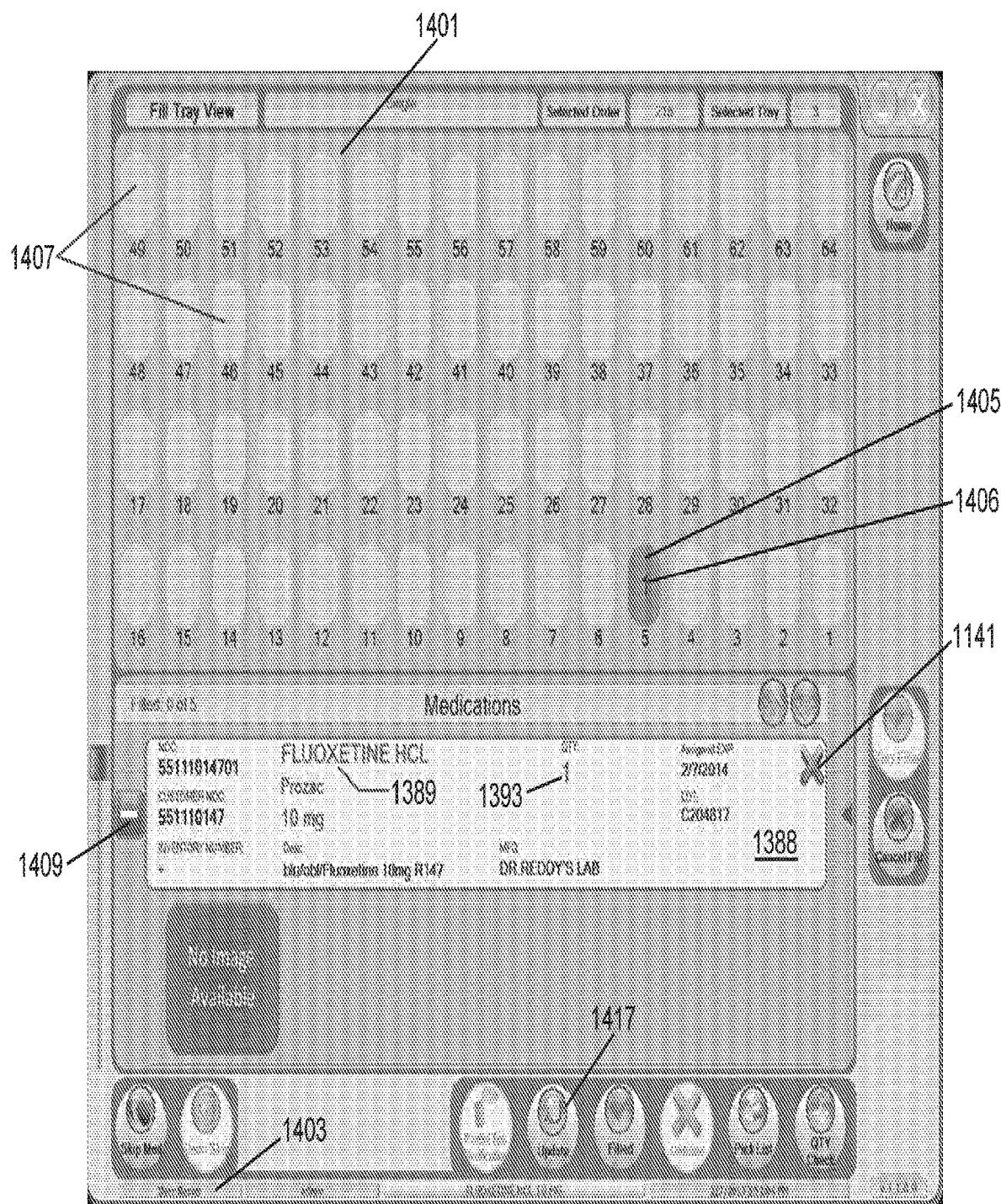
FIG. 57 is an exemplary screen display for holder filling.
Figure 76:
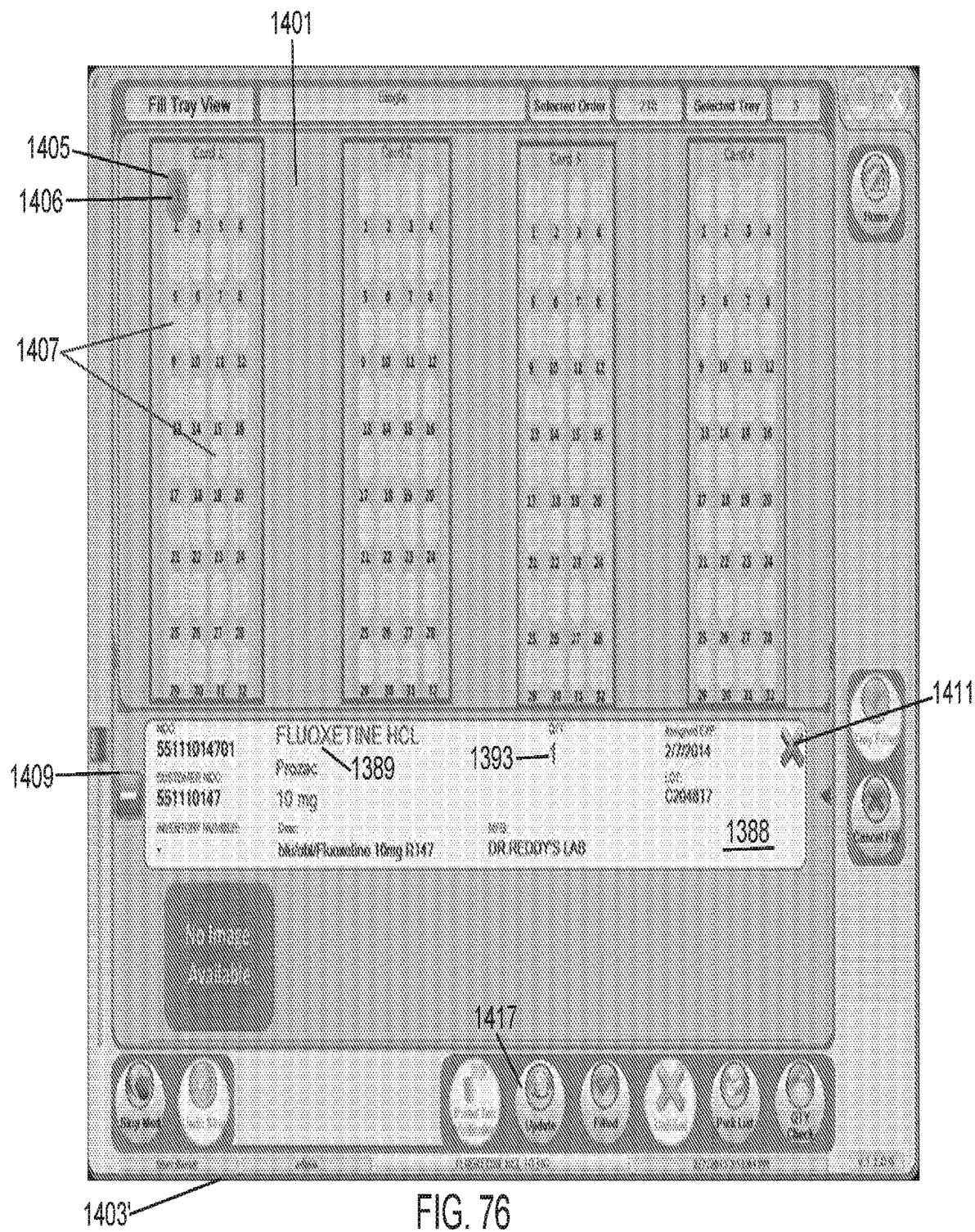
FIG. 76 is an exemplary screen display for holder filling.

Referring next to FIGS. 57 and 76, if medicament container 1135 is a valid container with the medicament 1011 required to fulfill the prescription order, then Filling screen 1403, 1403' may be displayed to assist the user with loading of the required type of medicament 1011 (e.g., Fluoxetine HCL in the examples) into holder 1013, 1013'. Holder view field 1401 is fully viewable on Filling screen 1403, 1403'. Holder view field 1401 includes a number next to each cell (e.g., 1-64 or 1-32) which corresponds to indicia 1323 next to opening 1317 on sensor guide 1301, 1301'. In the example of Filling screen 1403, Holder view field 1401 is a plan view of sensor guide 1301 and the 64 openings 1317 and aligned cells 1033 of holder 1013. In the example of Filling screen 1403', Holder view field 1401 is a generalized plan view of sensor guide 1301' and the arrangement of the 128 openings 1317 of sensor guide 1301' and the aligned cells 1033 of each separate holder 1013'. (i.e., ovals are provided corresponding to the elongate "D" shaped cells 1033 of holder 1013') In FIG. 77, the terms "Card 1", "Card 2", "Card 3", "Card 4" refer to the position of each separate holder 1301' which may be docked at docking station 1015'.

In the examples, the Fluoxetine HCL medicament 1011 corresponding to the validated container 1135 is displayed in medicament-identification field 1388. Information on any other medicaments 1011 to be loaded into holder 1013, 1013' may be turned off to avoid any possible confusion.

Filling screen 1403, 1403' provides instructions to the user regarding which sensor guide 1301, 1301' opening 1317 and cell 1033 each Fluoxetine HCL medicament 1011 is to be placed into in these examples. The instructions may include highlighting of each cell 1405 corresponding to the opening 1317 and cell 1033 into which the Fluoxetine HCL medicament 1011 is to be hand-loaded by the user. The contrast between the highlighted oval 1405 indicative of the "yes" state and un-highlighted cells 1407 indicative of the "no" state (for convenience only certain of the un-highlighted cells are indicated by 1407) enables the user to easily identify the opening 1317 and cell 1033 into which the Fluoxetine HCL medicament 1011 of the examples is to be placed.

The instructions of Filling screen 1403, 1403' may further include the quantity 1406 of medicament(s) 1011 to be placed into opening 1317 and cell 1033. This may be accomplished as illustrated in FIGS. 57 and 76 by displaying a number (e.g., "1") within the highlighted cell 1405 corresponding to the required opening 1317 and cell 1033 consistent with the quantity "1" indicated by 1393. In the example of Filling screen 1403, a quantity of one 10 mg Fluoxetine HCL is to be placed into opening 1317 and cell 1033 identified by the number "5." In the example of Filling screen 1403', a quantity of one 10 mg Fluoxetine HCL is to be placed into the holder 1013' in the Card 1 position of docking station 1015' and the holder 1013' opening 131 and cell 1033 identified by the number "1." For both Filling screens 1403, 1403' of FIGS. 57 and 76, dash "-" symbol 1409 indicates that the prescription order is being processed and that the medicament container 1135 was validated as correct. (In the screen displays, a dash "-" symbol indicates that processing is taking place whereas a "+" symbol indicates that processing is not taking presently occurring.) The "X" symbol 1411 in or next to medicament-identification field 1388 indicate that the medicament 1011 has not yet been placed into opening 1317 and cell 1033.

Simultaneous with display of Filling screen 1403, 1403', controller 1017 causes docking station 1015, 1015' to provide the visible information to the user next to each opening 1317 and cell 1033 into which the medicament 1011 is to be placed. In the example of system 1010, this may be accomplished by activating indicators 1049, 1049', 1049", and 1049''' next to opening 1317 number "5" of sensor guide 1301 and aligned cell 1033 number "5" of holder 1013. Indicators 1049, 1049', 1049", and 1049''' for more than one opening 1317 and cell 1033 may be simultaneously activated if a medicament 1011 of the same type is to be placed into more than one cell 1033 of the same holder 1013. In a further embodiment, the indicators 1049, 1049', 1049", and 1049''' for all openings 1317 and cells 1033 could be activated to provide the "no" state information while the indicators 1049, 1049', 1049", and 1049''' for the cell 1033 into which the medicament 1011 is to be placed could be deactivated, with the deactivated indicators providing the "yes" state information.

Referring to FIG. 76, in the example of system 1010', controller 1017 activates indicators 1049, 1049', and 1049''' next to opening 1317 number "1" of sensor guide 1301' and aligned cell 1033 number "1" of holder 1013' for a holder 1013' in the pockets 1229a corresponding to Card 1. If the same type of medicament 1011 is to be placed into plural openings 1317 and cells 1033, then indicators 1049, 1049', 1049''' for such openings 1317 and cells 1033 may be simultaneously activated as described above.

Accordingly, the user is provided with visible information both on Filling screen 1403, 1403' of display 1125 (FIGS. 57, 76) and from visible information sources on sensor guide 1301, 1301' indicating the opening 1317 and cell 1033 into which the medicament 1011 is to be placed. Filling screen 1403, 1403' and indicators 1049, 1049', 1049", and 1049''' make it possible for the user to correctly load the medicament 1011 without any reliance on paper instructions. The user can keep her eyes on the medicament 1011, opening 1317, cell 1033, and the visible information provided by indicators 1049, 1049', 1049", and 1049''' at the moment the medicament 1011 enters opening 1317 and cell 1033 providing a high confidence level that the medicament 1011 has been placed into the correct cell 1033.

Next, and as illustrated in FIGS. 28-28A and 42-42A, the user utilizes the visible information to actually hand-load medicament(s) 1011 into the opening 1317 and cell 1033. In the examples, the user removes one 10 mg Fluoxetine HCL medicament 1011 from container 1135. The user grips the medicament 1011 with her hand and fingers and positions the medicament 1011 just over the sensor guide opening 1317 and cell 1033 number "5" of the holder 1013 docked at the docking station 1015 in the example of system 1010 or into sensor guide opening 1317 and cell 1033 number "1" in the example of system 1010'. The user gently drops the medicament 1011 into the opening 1317 and cell 1033. Preferably, the medicament 1011 should be released as close as possible to sensor guide opening 1317. Gentle dropping avoids "bouncing" which can occur when a hard medicament 1011 strikes a hard surface, such as shuttle 1055 closing cell 1033. Bouncing could cause medicament 1011 to fall on the floor or land in an incorrect cell 1033.

FIGS. 28-28A and 42-42A illustrate entry of a medicament 1011 into a cell 1033. As illustrated, medicament 1011 first falls through opening 1317 of sensor guide 1301, 1301'. Medicament 1011 momentarily breaks the IR beam generated by senders 1333 across opening 1331 onto receiver 1335 causing a voltage drop which is detected by controller 1017 as previously described. A single breaking of the IR beam would indicate that one medicament 1011 had been placed into an opening 1317 and controller 1017 would increment one count. A count is incremented or registered for each medicament 1011 placed into opening 1317 and cell 1033. In this way, a total count of medicaments 1011 placed into each cell 1033 is created and stored in the database 1371 residing on client computer 1349.

If the detected count matches the expected count for that cell 1033, then a record is created in database 1371 that the correct quantity of medicament 1011 was placed into the cell 1033. If no other cells 1033 are required to be loaded with this type of medicament 1011, then controller 1017 may automatically change the appearance of medicament-identification field 1388 to replace the "X" symbol 1411 with a " " symbol 1415 to indicate that the medicament 1011 has been placed into the cell 1033. Plus "+" symbol 1413 indicates that the medicament 1011 required by Medicament ID field 1388 has been correctly loaded in the expected cell 1033.

Controller 1017 may immediately move to the next type of medicament 1011 to be loaded into holder 1013. Alternatively, the user may manually touch the Update icon 1417 which causes controller 1017 to move to the next type of medicament 1011 to be loaded into holder 1013. In the examples, this may be accomplished by deactivating indicators 1049, 1049', 1049", and 1049''' for, in the example, opening 1317 and cell 1033 number "5" and by un-highlighting oval 1405 on Filling screen 1403, 1403'. Then, indicators 1049, 1049', 1049", and 1049''' for the next opening 1317 and cell 1033 into which the next type of medicament 1011 is to be loaded may be activated and the corresponding cell(s) on Filling screen 1403, 1403' may be highlighted as previously described. This same process of indicator 1049, 1049', 1049", and 1049''' deactivating and activating and displaying an updated Filling screen 1403, 1403' can occur automatically without touching Update icon 1417 if controller 1017 is programmed to operate automatically.

The foregoing process is repeated until all cells 1033 of holder 1013, 1013' have been loaded.

Figure 58:
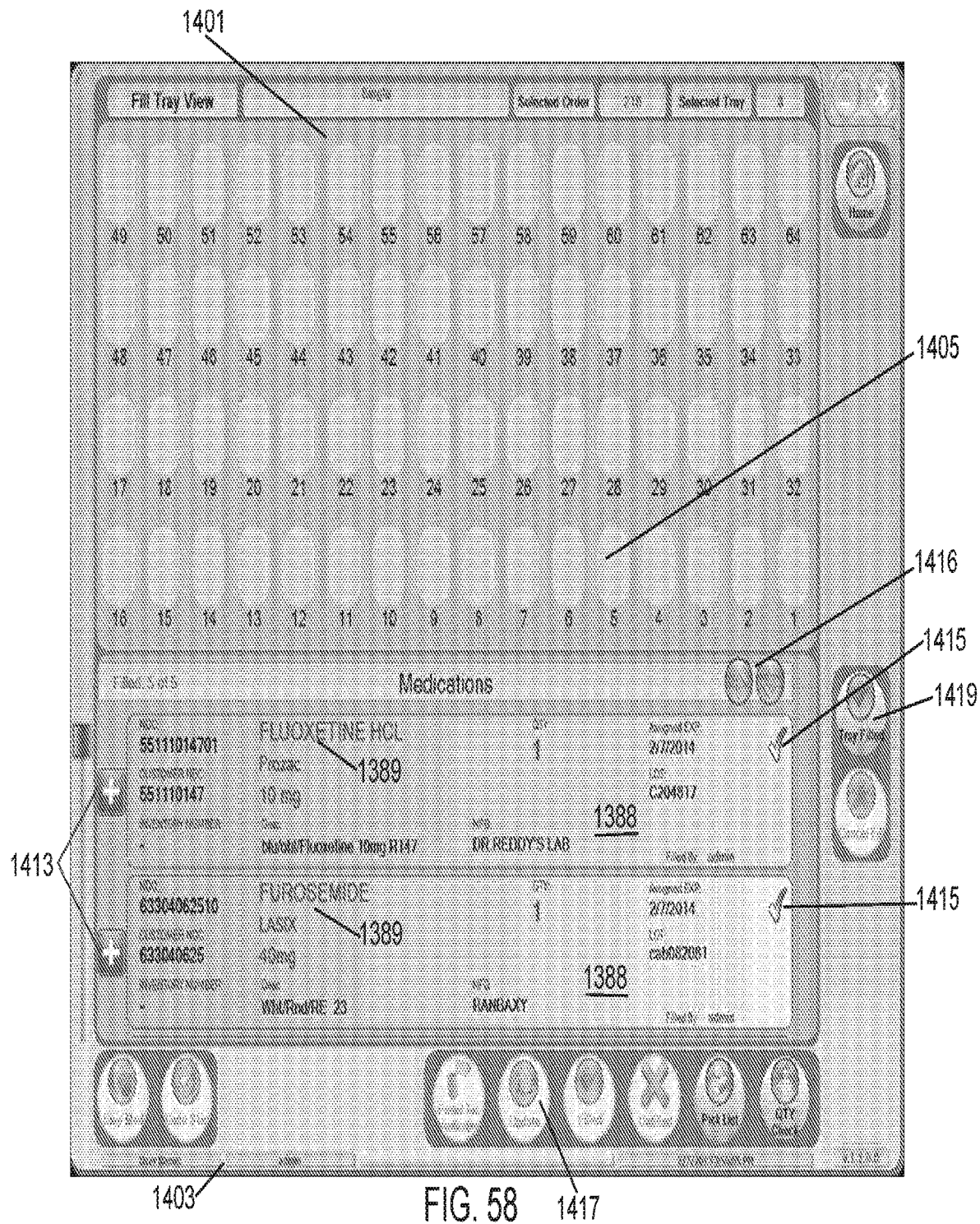
FIG. 58 is an exemplary screen display for completion of holder filling.
Figure 77:
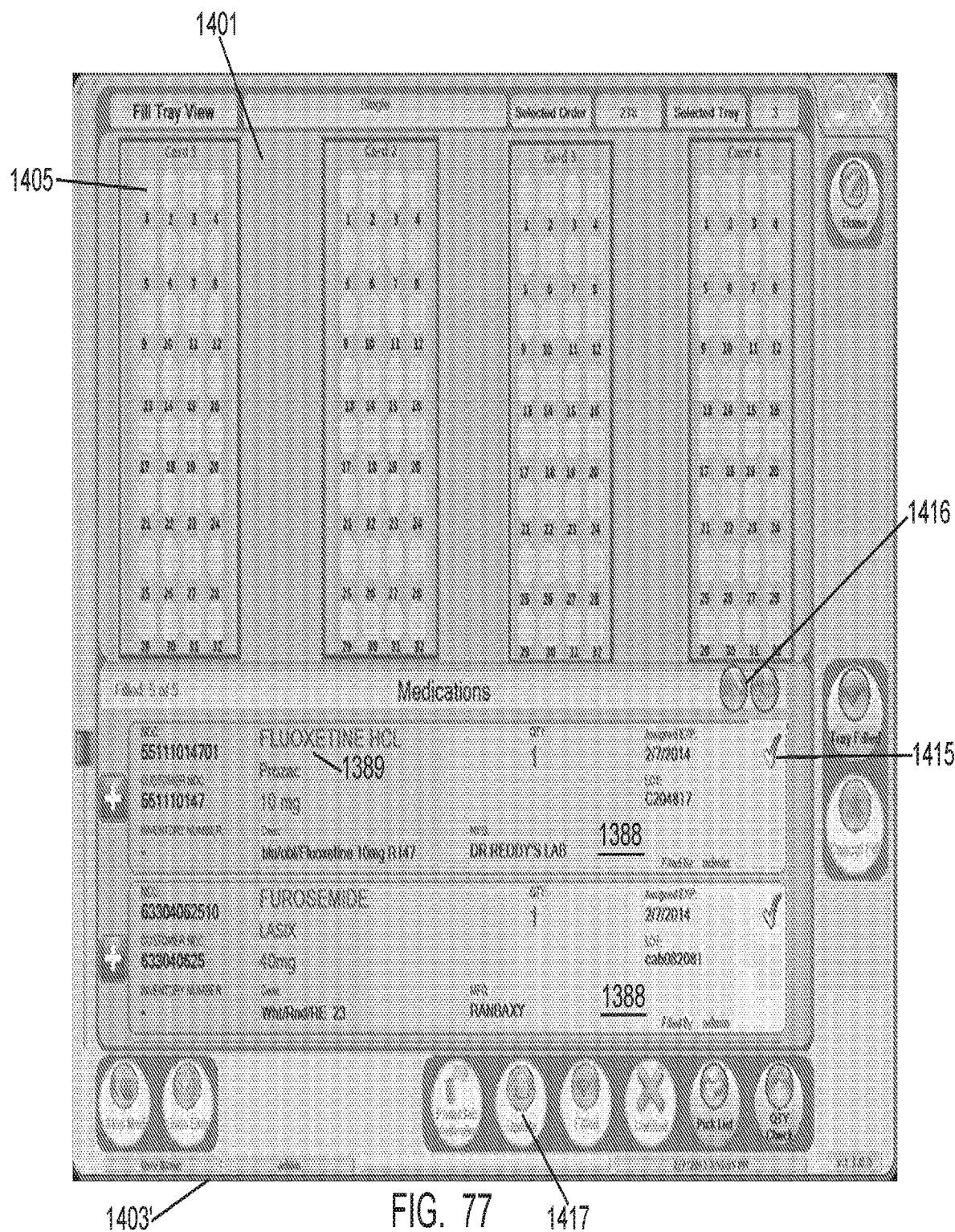
FIG. 77 is an exemplary screen display for completion of holder filling.

FIGS. 58 and 77 illustrate that the medicaments 1011 (i.e., Fluoxetine 1389 and Furosemide 1389) displayed in the two separate Medicament ID fields 1388 have been loaded with processing completed as indicated by the "+" 1413 and the operation completed " " symbols 1415. The user may scroll up or down through the medicament-identification fields 1388 using up/down scroll icons 1416 to confirm that a phis "+" symbol 1413 and " " symbol 1415 are present to indicate that the each type of medicament 1011 has been placed into each opening 1317 and cell 1033 as required by the prescription order.

Referring further to FIGS. 58 and 77, once all cells 1033 have been loaded, controller 1017 may cause "Tray Filled" icon 1419 to become highlighted and the user may touch Tray Filled icon 1419 to indicate to controller 1017 that the loading process has been completed. Touching of Tray Filled icon 1419 sends a signal to controller 1017 indicating that loading of holder 1013, 1013' has been completed.

Figure 59:
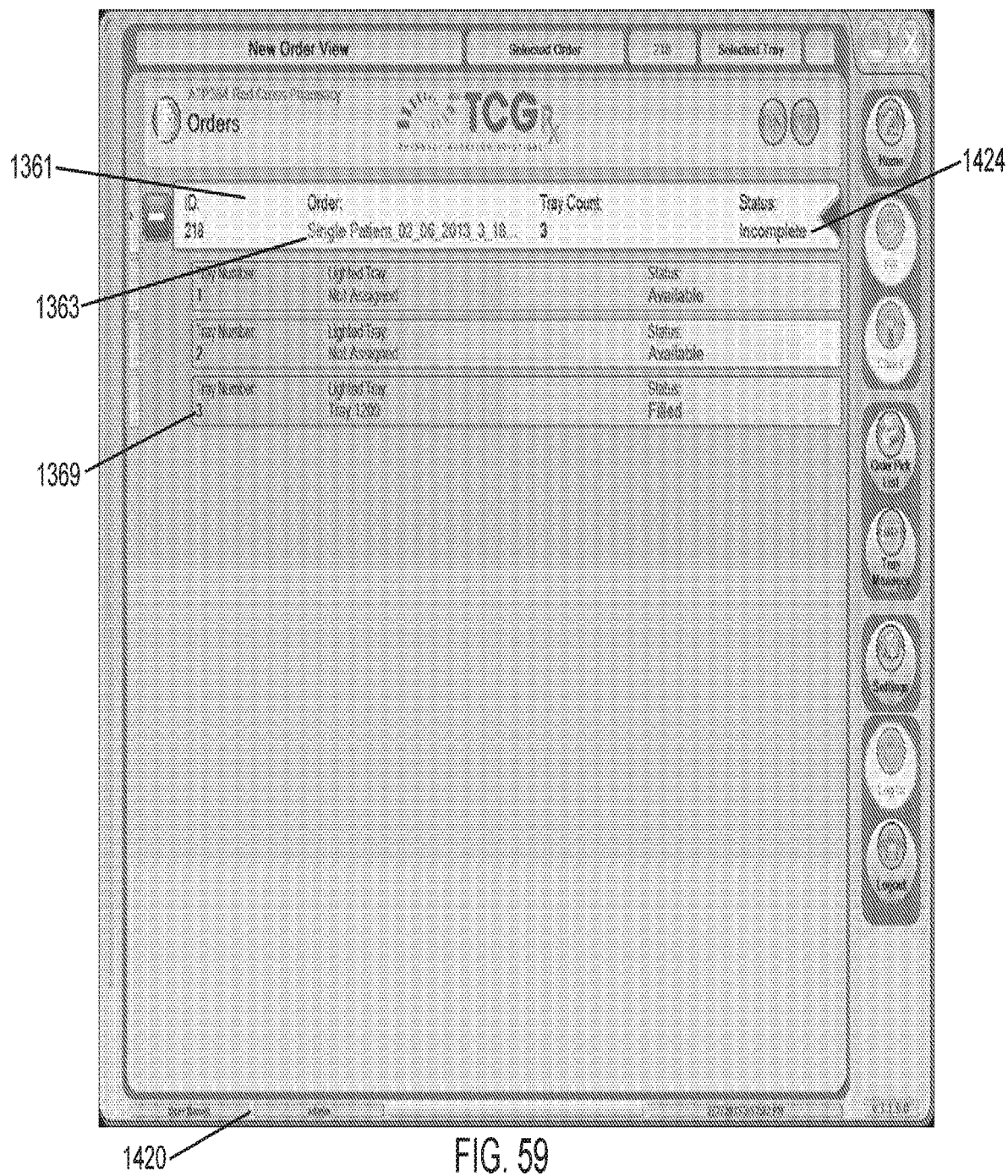
FIG. 59 is an exemplary screen display for prescription order completion.
Figure 78:
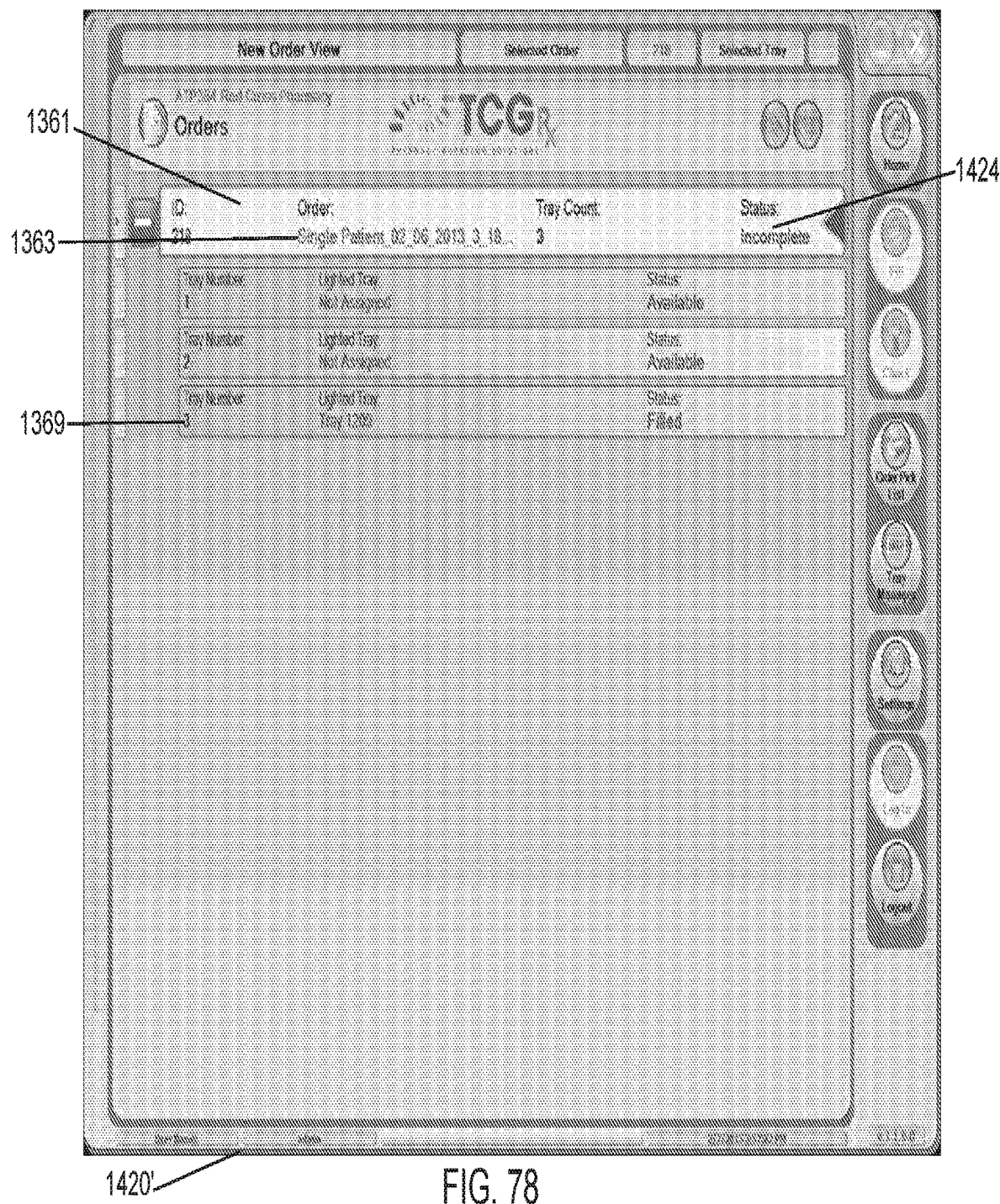
FIG. 78 is an exemplary screen display for prescription order completion.

Referring next to FIGS. 59 and 78, Filled screen 1420, 1420' is next displayed indicating the status is "filled" completing the loading process. The status of holder "3" is indicated as having been filled as indicated by the word "Filled" 1422.

Each holder 1013, 1013' may optionally be immediately verified by a pharmacist or may be undocked and stored for subsequent pharmacist verification prior to transferring medicaments 1011 from loaded holder 13 into automated dispensing machine 45 or affixing closure 1042 to holder 1013'. The status of the prescription order of Order field 1361 in FIGS. 59 and 60 is indicated as "Incomplete" 1424 because verification has not yet occurred.

Sensor guide 1301, 1301' further provides positive feedback to controller 1017 in the event that medicament 1011 is placed into the wrong opening 1317 and cell 1033 or if a greater or lesser quantity of medicaments 1011 than required has been placed into a cell 1033. The feedback is useful to help a user correct any errors that could occur when loading holder 1013, 1013'.

Figure 60:
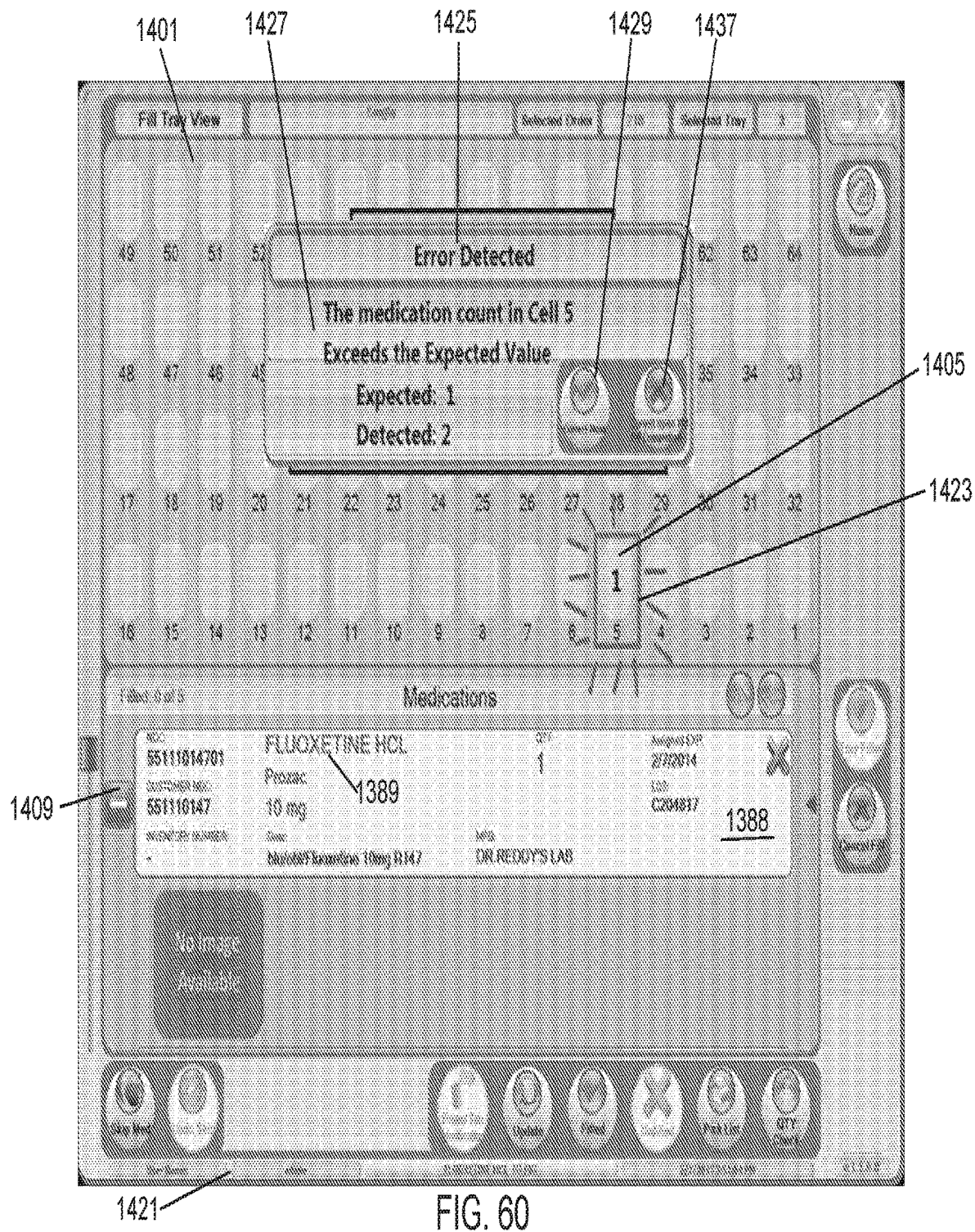
FIGS. 60-63 are exemplary screen displays for an over-count error.
Figure 79:
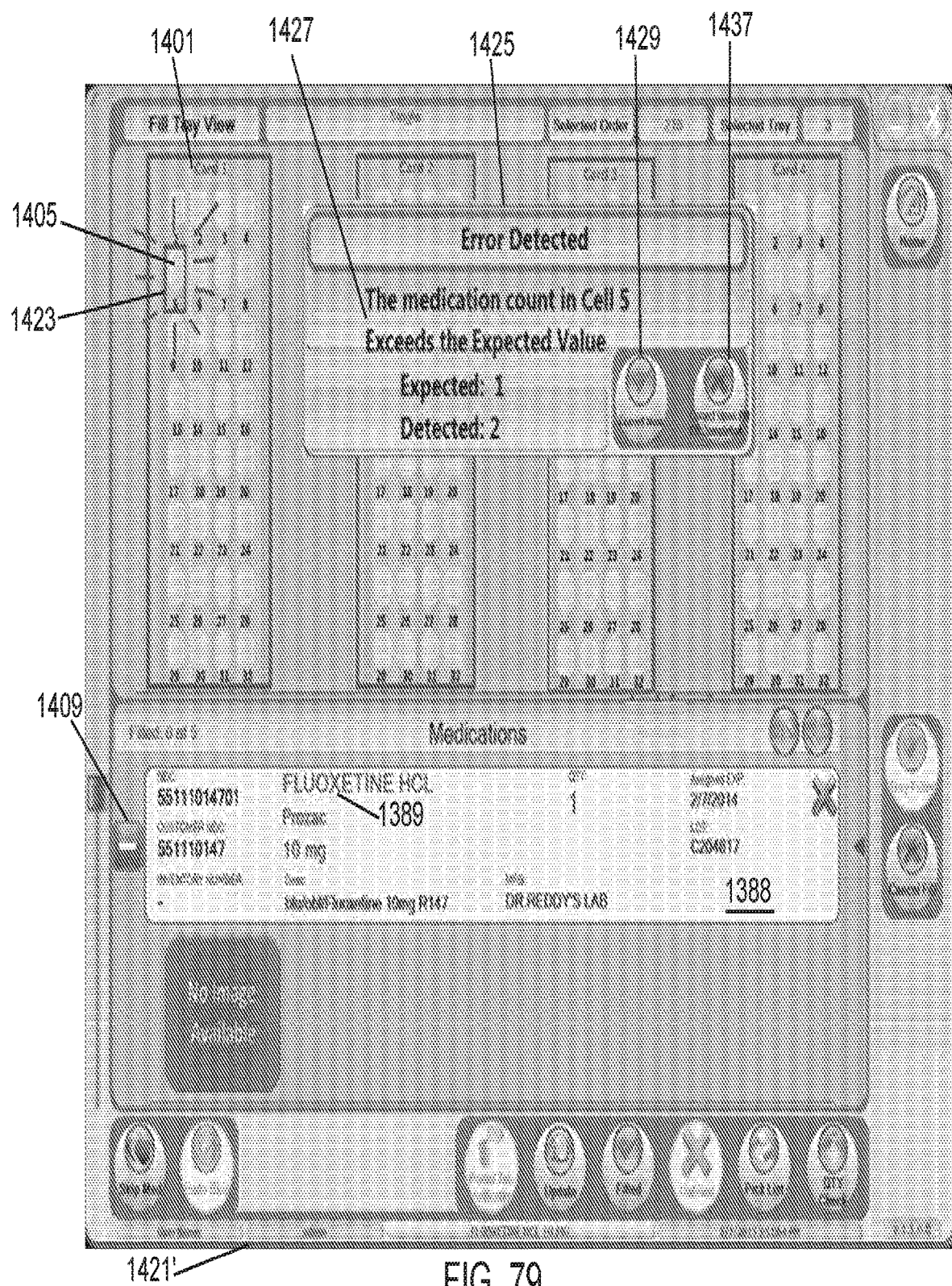
FIGS. 79-82 are exemplary screen displays for an overcount error.

Referring to FIGS. 60 and 79, if a greater than expected quantity of medicaments 1011 are detected by sensor guide 1301, 1301', then system 1010, 1010' enters an overcount mode. The signal provided by sensor module 1325 increments or registers counts by controller 1017 for the opening 1317 and cell 1033. In an overcount mode, controller 1017 may cause Overcount warning screen 1421, 1421' to be immediately displayed with the cell 1405 corresponding to the opening 1317 and cell 1033 including the excess quantity of medicaments 1011 surrounded by a blinking box 1423. An Error field 1425 including a text message 1427 describing the overcount error can be displayed.

In the examples of FIGS. 60 and 79, the text message 1427 informs the user that the quantity of medicaments 1011 in the cell 1033 designated by number "5" exceeds the expected count by one medicament 1011. In addition, controller 1017 may blink the indicators 1049, 1049', 1049", and 1049''' for the opening 1317 and cell 1033 including the overcount to indicate to the user the opening 1317 and cell 1033 requiring attention.

Referring further to FIGS. 60 and 79, in response to the Overcount warning screen 1421, 1421', the user can elect to correct the error immediately or can elect to correct the error upon completion of loading all medicaments 1011 into holder 1013, 1013'. In the examples, the user can touch the Correct Now icon 1429 or the Correct Later icon 1437.

Figure 61:
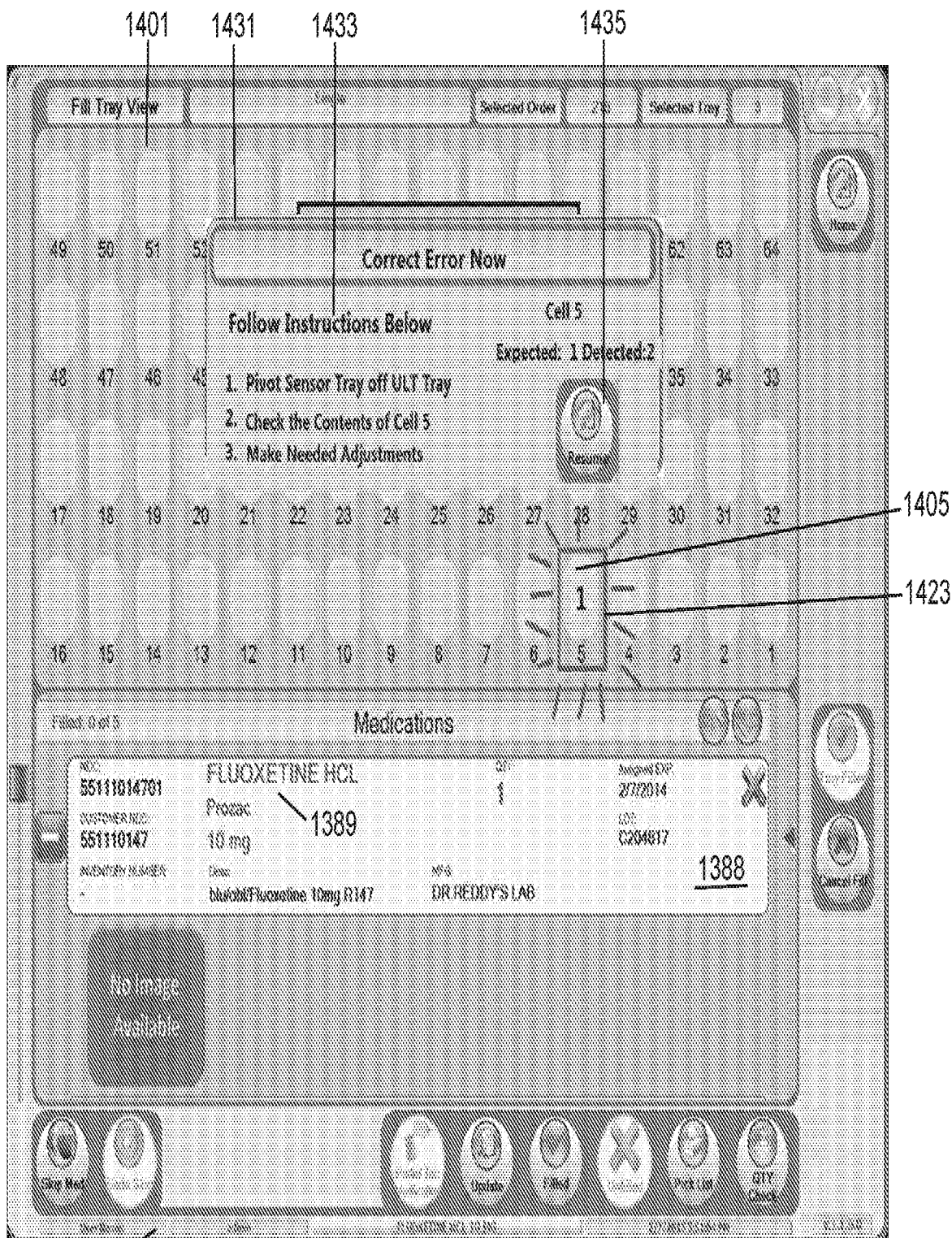
Figure 80:
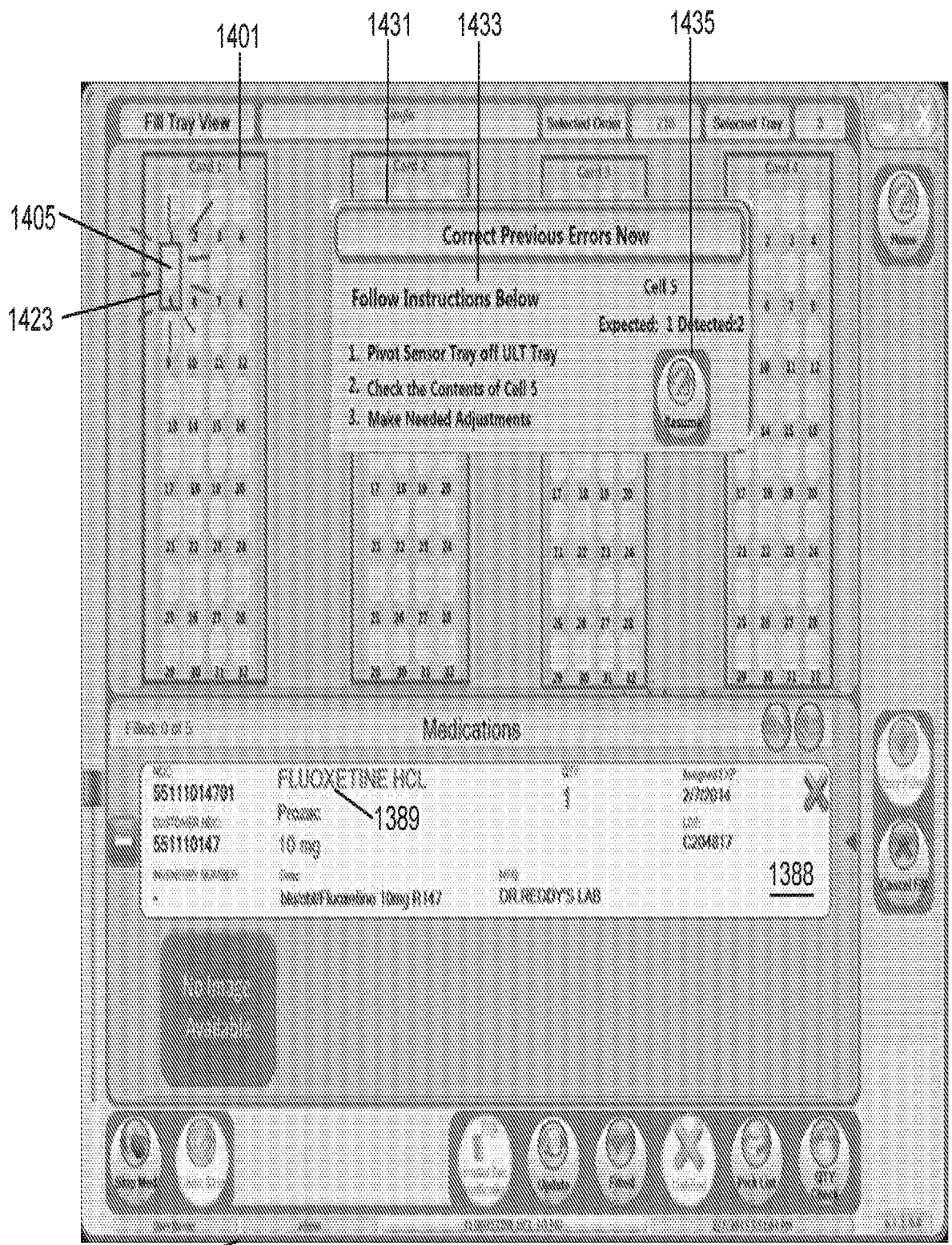
Figure 81:
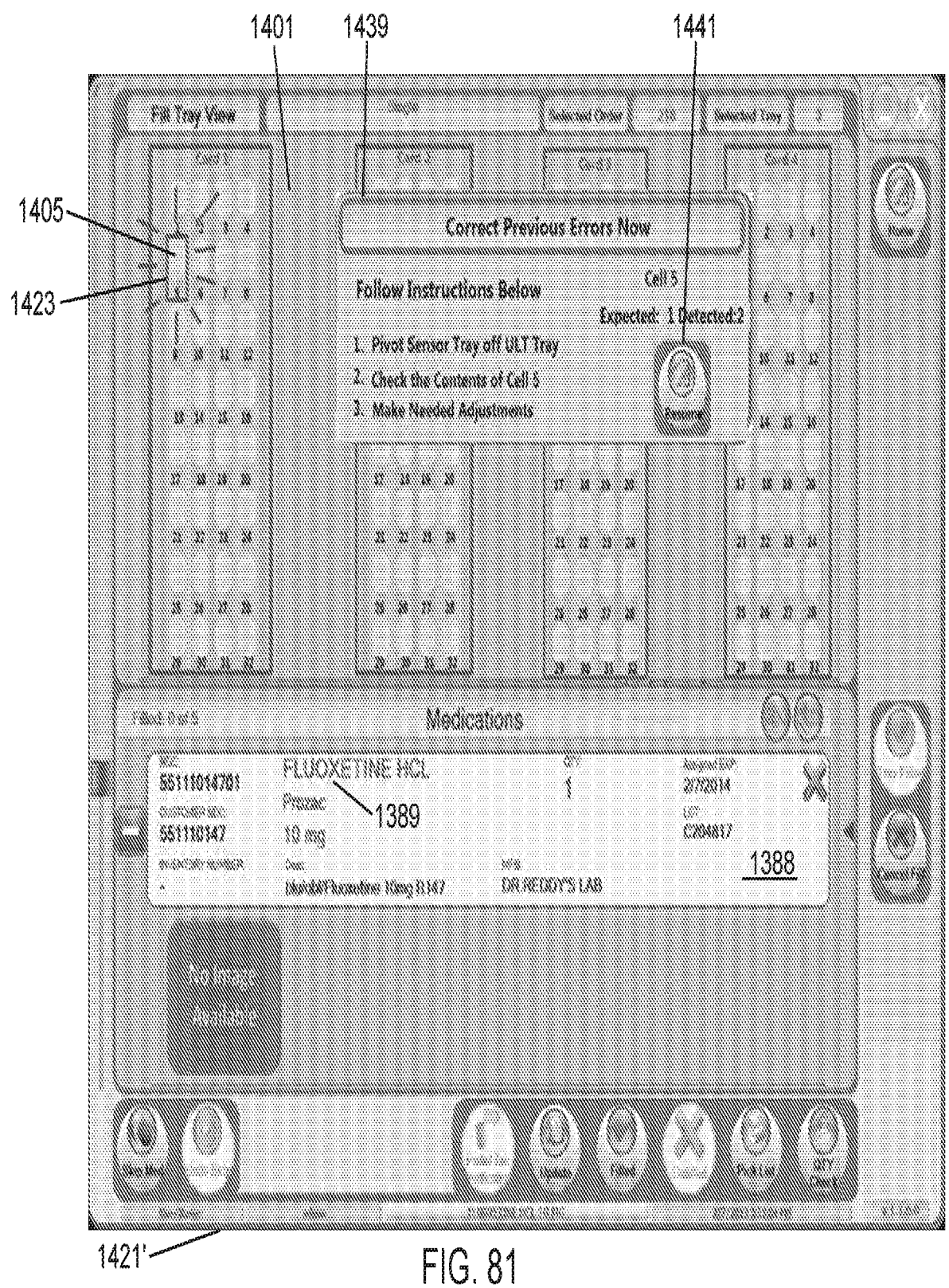

FIGS. 61 and 80 may next be displayed responsive to touching the Correct Now icon 1429. Controller 1017 may cause video display to display Correction field 1431 with instructions 1433 for correcting the error. In the examples, Correction field 1431 prompts the user to place the sensor guide 1301, 1301' in the storage position of FIGS. 24 and 38 and to inspect cell 1033 number "5" for the one medicament 1011 overcount. Once the error is corrected, the "Resume" icon 1435 may be touched indicating to controller 1017 that the error has been corrected and to proceed with loading the next cell 1033. Controller 1017 may update database 1371 to indicate that the error has been corrected. The user can then proceed to load the next cell 1033. Or, if a different type of medicament 1011 is to be loaded, controller 1017 can then cause display of the next Filling screen 1403, 1403' so that the user can load the next type of medicament 1011 into holder 1013, 1013'.

Referring again to FIGS. 60 and 79, as an alternative to immediate correction of the overcount error, the user can elect to touch Correct Later icon 1437 to correct the error upon completion of loading all medicaments 1011 into holder 1013, 1013'.

Figure 62:
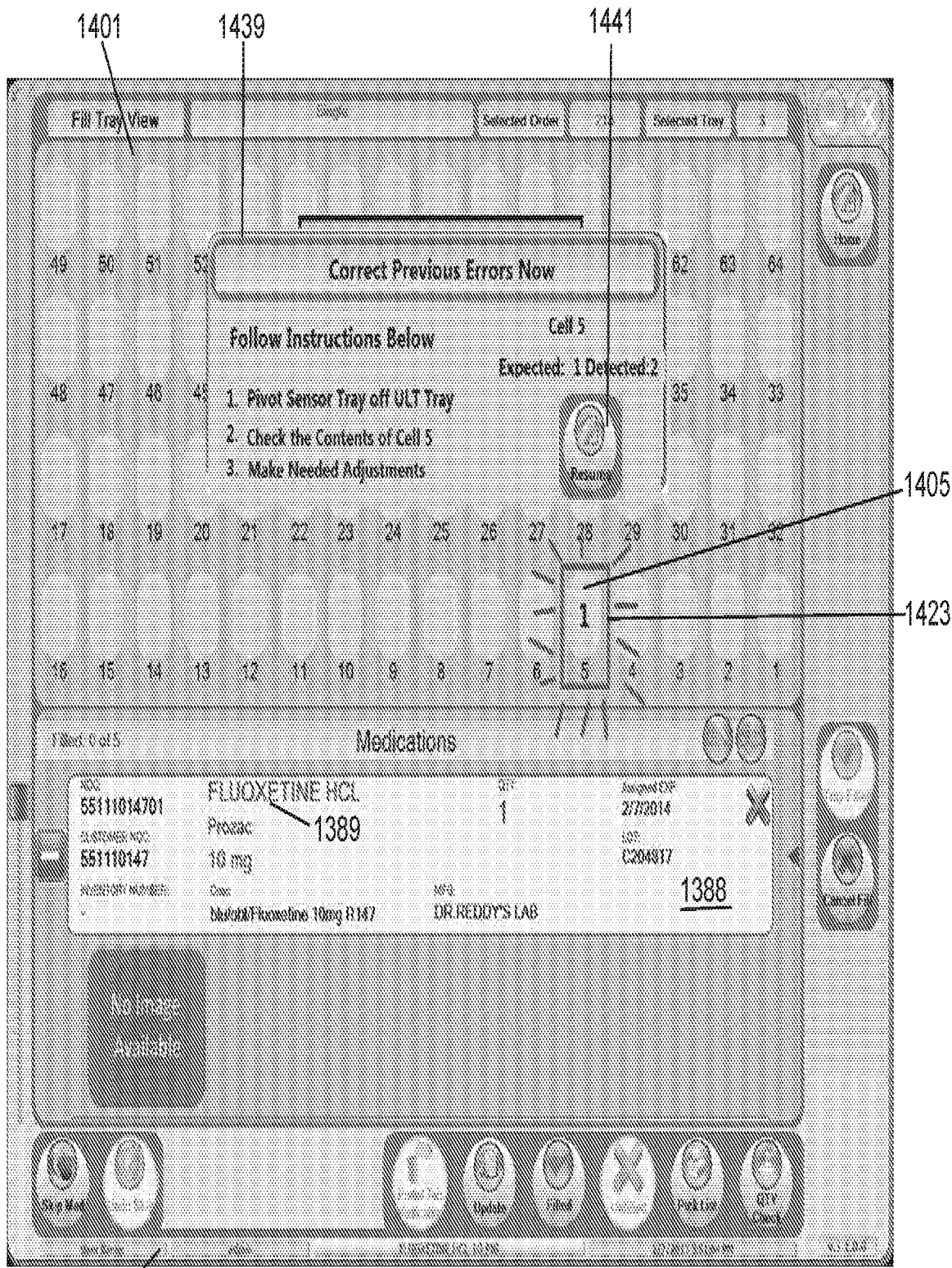
Figure 82:
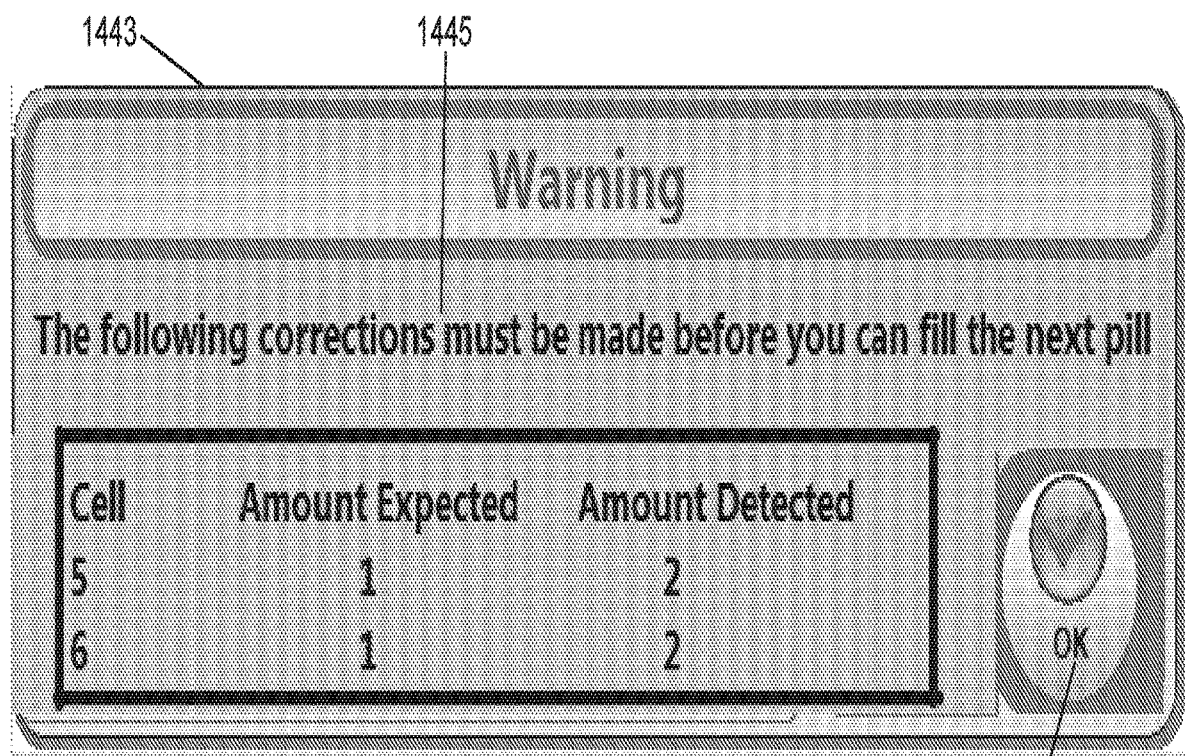

FIGS. 62 and 82 illustrate instructions which may be displayed if the Correct Later icon 1437 is selected. Once all cells 1033 have been loaded, Correction field 1439 (FIGS. 62, 82) may appear with instructions for correcting the previous error to the cell 1033 identified by number "5". In the examples, Correction field 1439 prompts the place sensor guide 1301, 1301' in the storage position (FIGS. 24, 38) and to inspect the cell 1033 identified by number "5" for a single medicament 1011 overcount. Once the overcount error is corrected, the user touches the Resume icon 1441.

Figure 63:
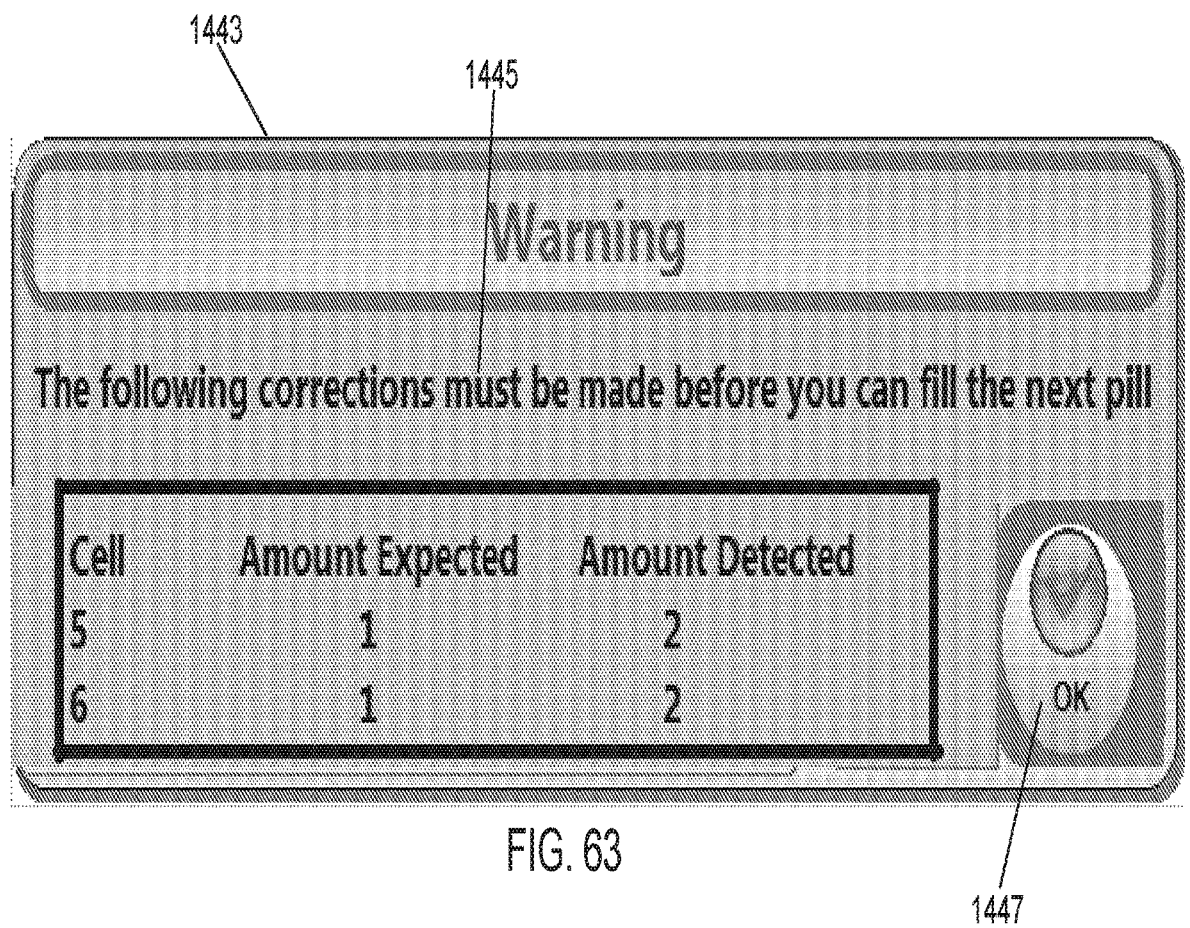

Referring now to FIGS. 63 and 82, if more than one error occurred, then controller 1017 may display Warning field 1443 notifying the user that another cell 1033 requires error correction. In the examples, instructions 1445 in Warning field 1443 prompt the user to correct an overcount in the cell 1033 designated by number "6". The user may touch OK icon 1447 whereupon Correction field 1439 (FIGS. 62, 81) is displayed prompting correction of the overcount error as preciously described. If the user does not correct the errors, then controller 1017 deactivates system 1010, 1010' requiring the user to take further action to correct the error or start over.

Figure 64:
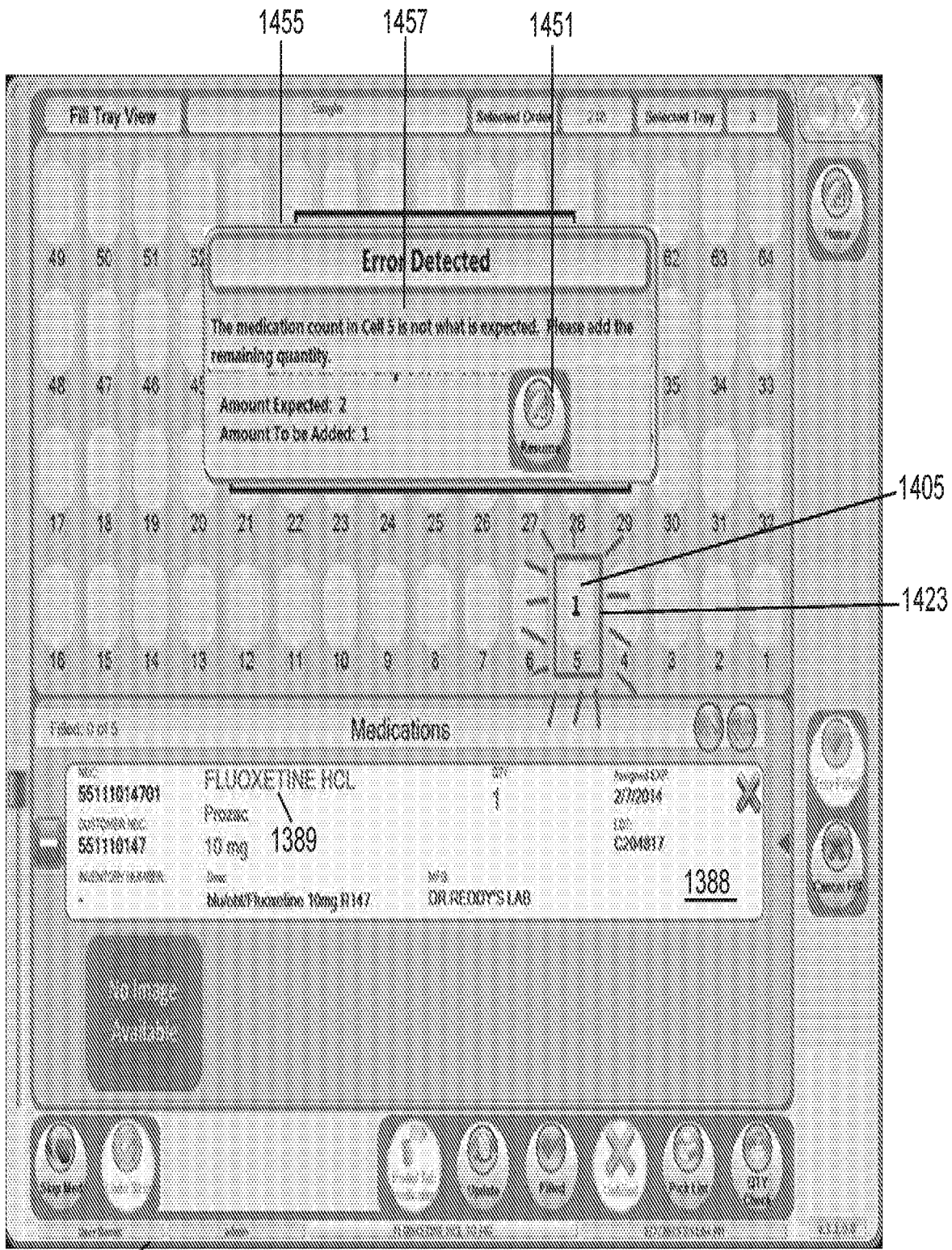
FIG. 64 is an exemplary screen display for an undercount error.
Figure 65:
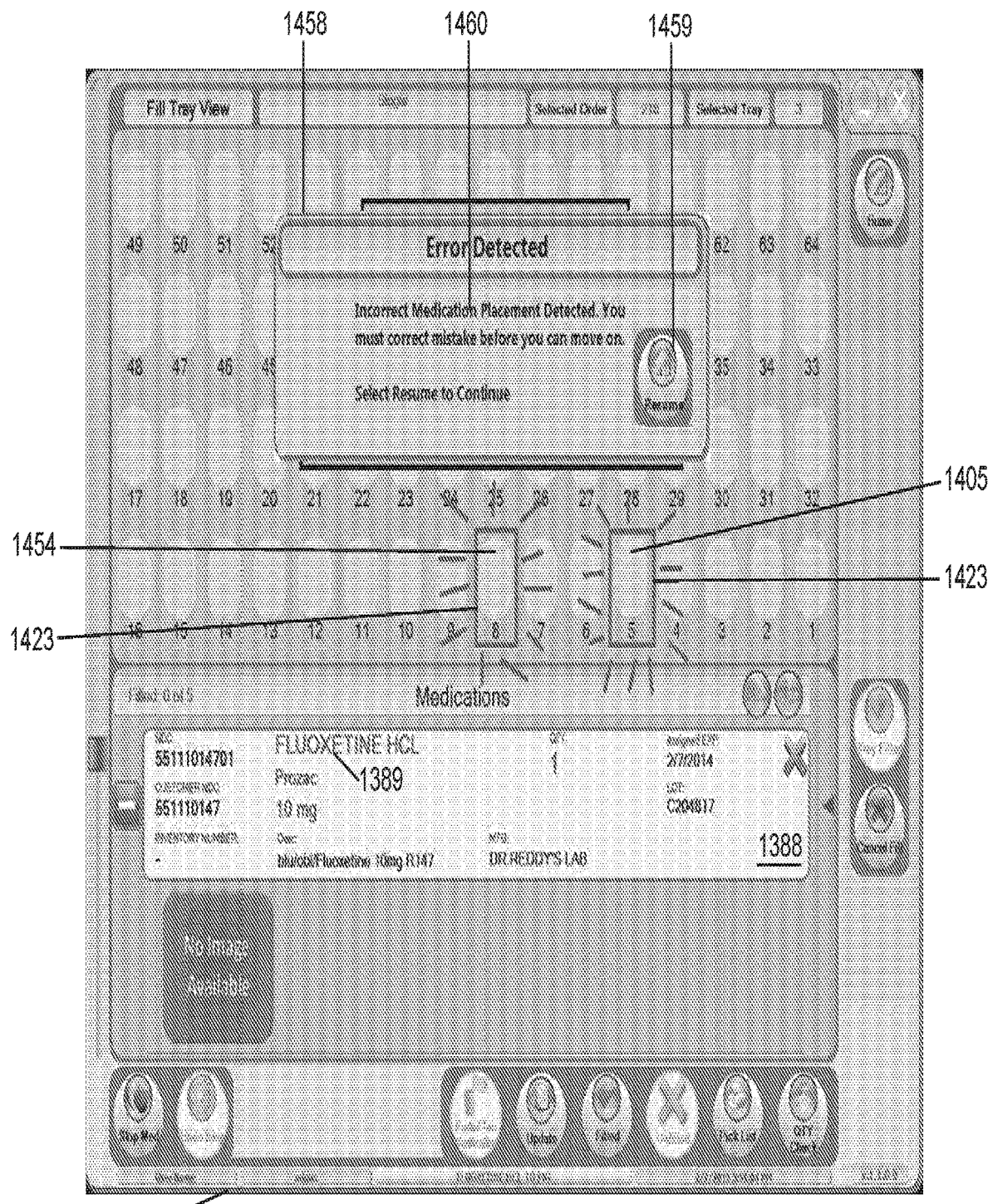
FIGS. 65-66 are exemplary screen displays for a medicament placement error.
Figure 83:
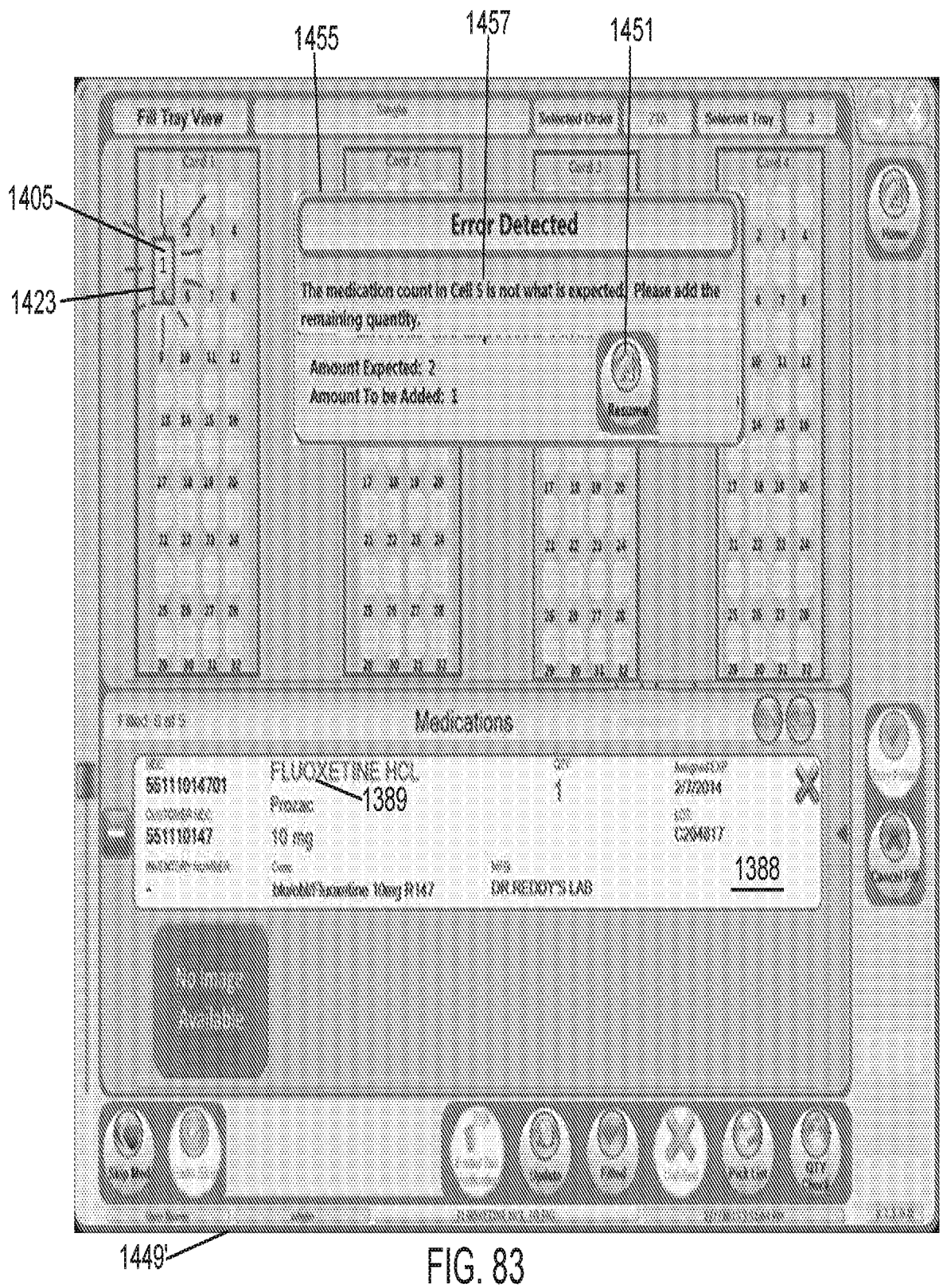
FIG. 83 is an exemplary screen display for an undercount error.
Figure 84:
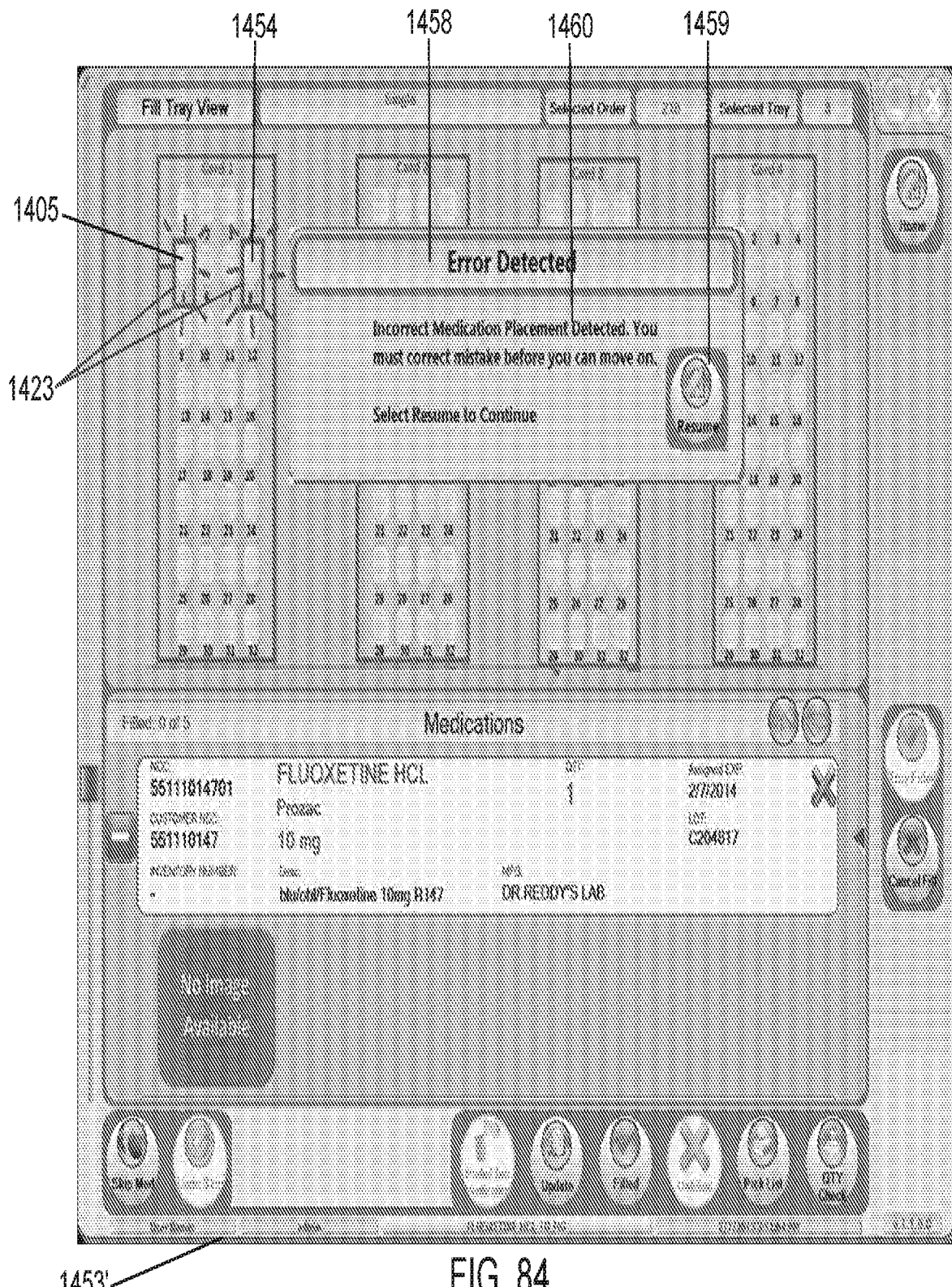
FIGS. 84-85 are exemplary screen displays for a medicament placement error.

Referring to FIGS. 64 and 83, if fewer than the expected quantity of medicaments 1011 are detected by sensor guide 1301, 1301' and controller 1017, then system 1010, 1010' enters an undercount mode. In an embodiment, an undercount can occur if the required quantity of medicaments 1011 is not detected as having been placed into the opening 1317 and cell 1033 and the user touches the Update icon 1417 (FIGS. 57, 76) to move to loading the next type of medicament 1011. In another embodiment in which controller 1017 automatically moves to the next medicament type (i.e., without touching Update icon 1417), an undercount could occur if the required quantity of medicaments 1011 is not detected as having been placed into the opening 1317 and cell 1033 within a predetermined time. A timer decremented by controller 1017 can be used to determine whether the predetermined time has elapsed before detection of the required quantity of medicaments 1011.

Referring further to FIGS. 64 and 83, in the event of an undercount, controller 1017 may cause Undercount warning screen 1449, 1449' to be displayed and can cause the cell 1405 corresponding to the opening 1317 and cell 1033 including the undercount to be surrounded by a blinking box 1423 in the same manner as described for the overcount error mode. An Error field 1455 including a text message 1457 describing the undercount error and prompting addition of the required quantity of medicaments 1011 can be displayed. In the examples, the text message 1457 prompts the user to add one medicament 1011 to the opening 1317 and cell 1033 designated by number "5". In addition, controller 1017 may blink the indicators 1049, 1049', 1049", and 1049''' for the opening 1317 and cell 1033 including the undercount to indicate to the user the opening 1317 and cell 1033 requiring attention.

In response, the user adds the required quantity of medicament(s) 1011 to the opening 1317 and cell 1033 causing detection of the added medicament(s) 1011 by sensor module 1325 and controller 1017 incrementing or registering the required counts and updating of the database 1371 for that cell 1033 to reflect loading of the correct quantity of medicaments 1011. The user then touches the Resume icon 1451 indicating to controller 1017 that the error has been corrected and to proceed with loading the next cell 1033. Controller 1017 may update database 1371 to indicate that the error has been corrected.

While not illustrated in the figures, systems 1010, 1010' may be configured to permit correction of the undercount error upon completion of loading all medicaments 1011 into holder 1013, 1013' in the same manner as previously described in connection with correction of the overcount error, but with the screen displays and information modified to indicate an undercount error. If the user does not correct the undercount error, then controller 1017 deactivates system 1010, 1010' requiring the user to take further action to correct the error or start over.

Referring now to FIGS. 65-66 and 84-85, an incorrect cell error mode is entered if the medicament 1011 is accidentally placed in an incorrect opening 1317. During routine loading, the opening 1317 and cell 1033 into which a medicament 1011 is to be placed is indicated by Filling screens 1403, 1403' and by indicators 1049, 1049', 1049", and 1049''' for the opening 1317 and cell 1033 as previously described.

If a medicament 1011 is detected by sensor guide 1301, 1301' and controller 1017 as having been placed into an opening 1317 and cell 1033 other than as indicated, then controller 1017 may cause Incorrect Cell warning screen 1453, 1453' to be displayed. Controller 1017 can further cause both the cell 1405 corresponding to the correct opening 1317 and cell 1033 and the incorrect cell 1454 corresponding to the opening 1317 and cell 1033 into which the medicament 1011 was incorrectly placed to be surrounded by a blinking box 1423 in the same manner as described for the overcount and undercount error modes. An Error field 1458 including a text message 1460 describing the undercount error and prompting addition of the required quantity of medicaments 1011 can be displayed.

Since an incorrect cell error should be corrected immediately, the correct later option for the overcount and undercount modes is not be available for the incorrect cell error correction mode. The Resume icon 1459 is touched to correct the error.

Figure 66:
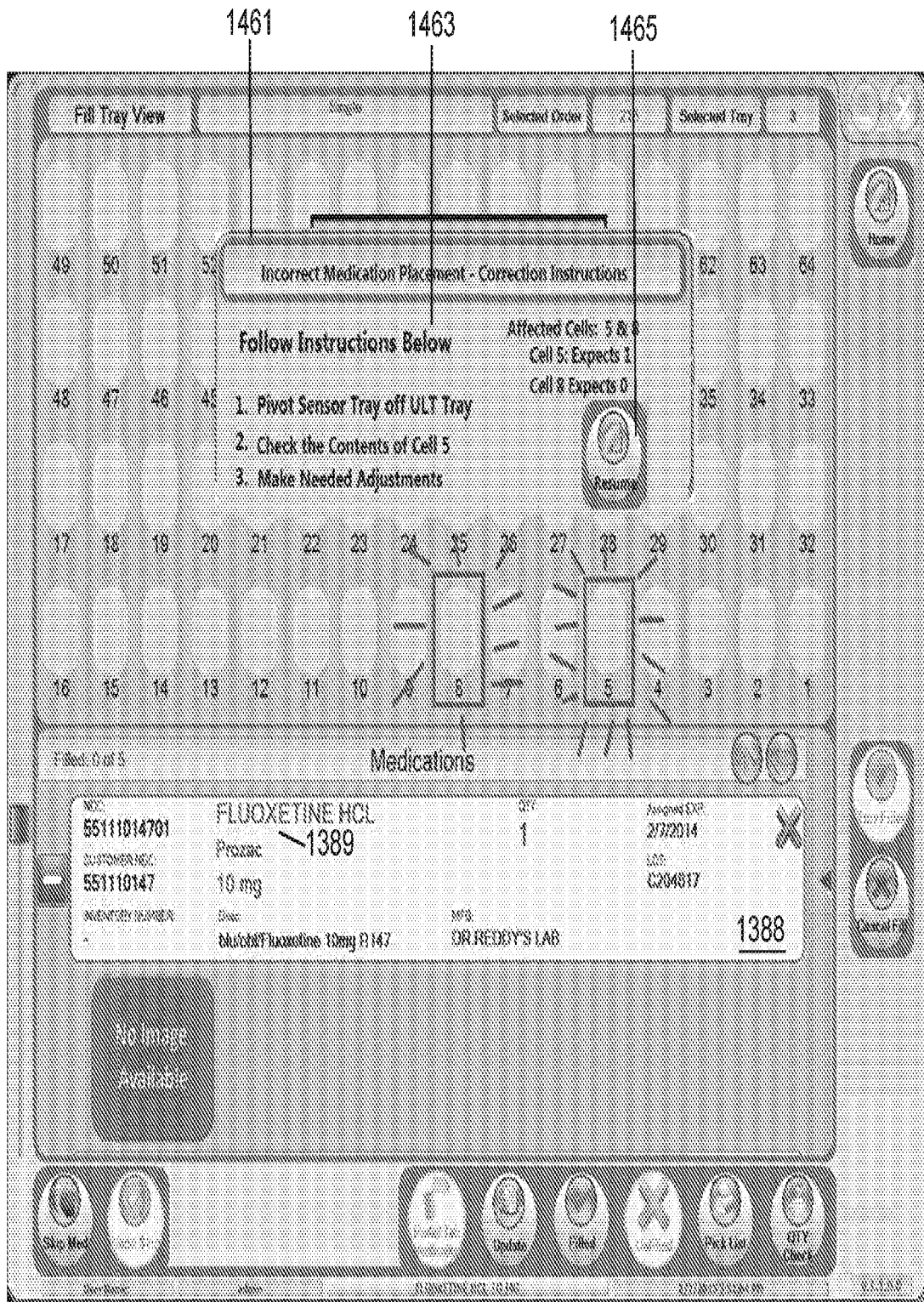
Figure 85:
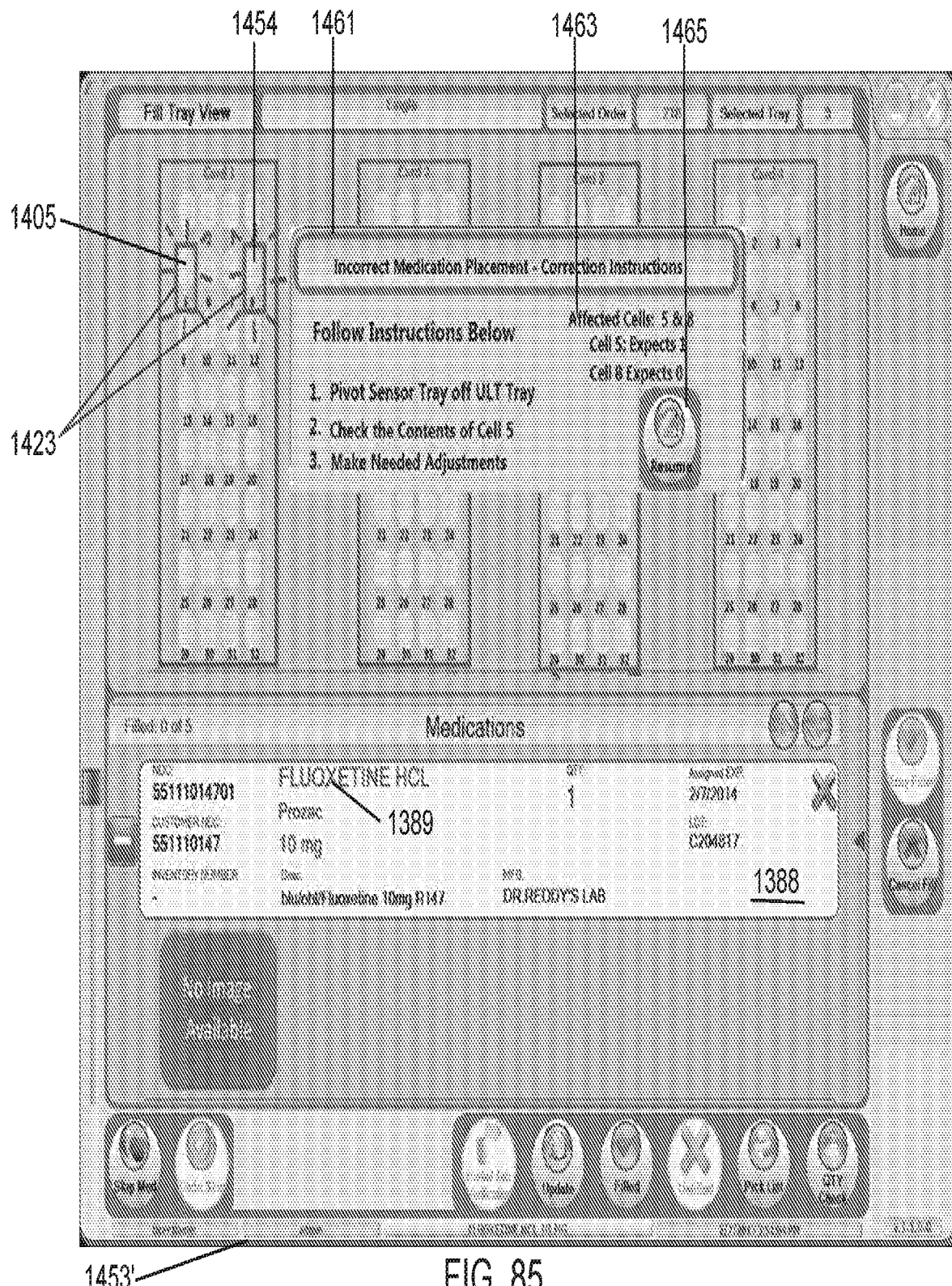

FIG. 66 or 85 may next be displayed responsive to touching the Resume icon 1459 including Correction field 1461 with instructions 1463 for correcting the error. In the examples, Correction field 1461 prompts the user to place the sensor guide 1301, 1301' in the storage position of FIGS. 24 and 38 and to inspect cell 1033 numbers 5 and 8. In the examples, the instructions 1463 inform the user that a medicament 1011 intended for cell number "5" was incorrectly placed in cell number 8.

In response, the user places the sensor guide 1301, 1301' in the storage position (FIGS. 24, 38) and reaches into the cell 1033 with her fingers to remove the incorrect medicament 1011 from cell number 8. The user can then touch the Resume icon 1465 indicating to controller 1017 that the error has been corrected and to proceed with loading the next cell 1033. Controller 1017 may update database 1371 to indicate that the error has been corrected. The user can then proceed to load the next cell 1033. Or, if a different type of medicament is to be loaded, controller 1017 can then cause display of the next Filling screen 1403, 1403' so that the user can load the next type of medicament 1011 into holder 1013, 1013'.

Referring now to FIG. 13, a storage cabinet 169 may optionally be provided to store one or more holder 1013, 1013' in the same manner as described in connection with system 10 thereby facilitating loading and verification of multiple holders.

As with systems 10, 10', each loaded holder 1013, 1013' of systems 1010, 1010' can be verified by a user who is a registered pharmacist to ensure that each cell 1033 has been loaded with the correct medicament 1011. The verification process preferably occurs without any need for use of sensor guide 1301, 1301' and sensor guide 1301, 1301' is preferably in the storage position illustrated in FIGS. 23 and 38 during verification. It will be apparent that verification for systems 1010, 1010' may be essentially the same as for systems 10, 10'.

Figure 67:
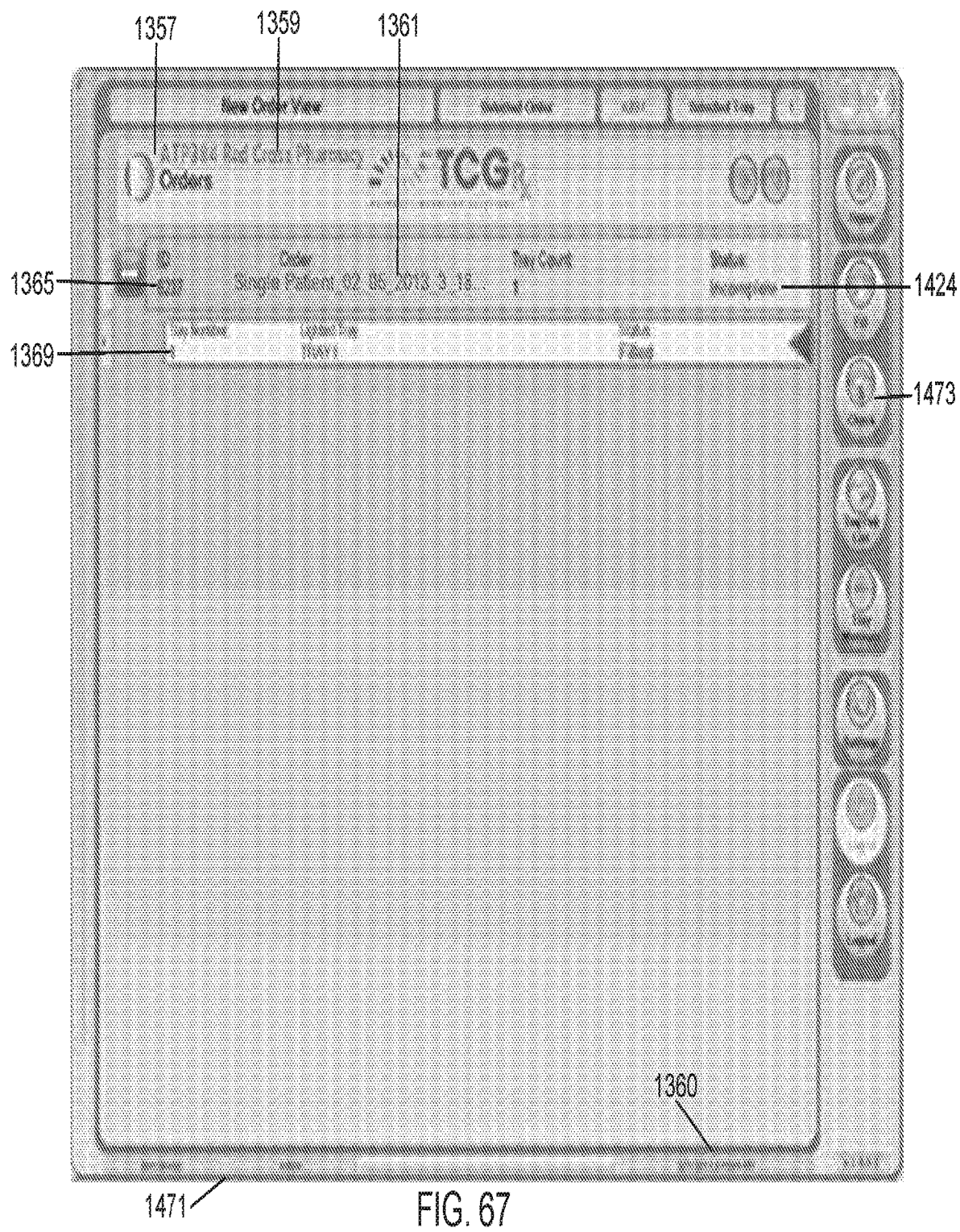
FIGS. 67-72 are exemplary screen displays for a verification process.
Figure 86:
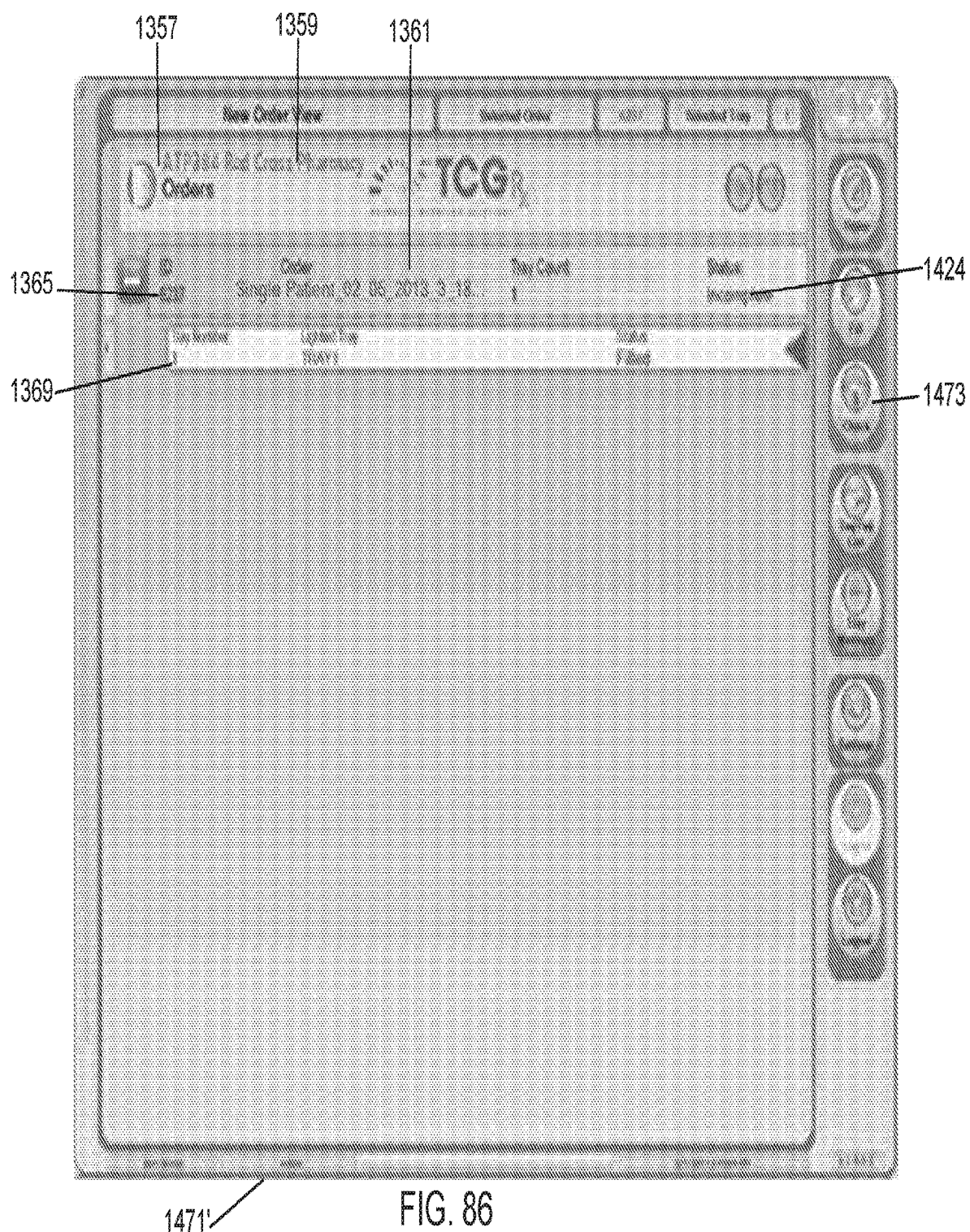
FIGS. 86-91 are exemplary screen displays for a verification process.

Referring now to FIGS. 67 and 86, verification begins by entry into a verification mode and display of Verification start screen 1471, 1471'. Holder 1013, 1013' may be docked at docking station 1015, 1015' following loading. Alternatively, holder 1013, 1013' may be retrieved, for example, from storage cabinet 169, and then docked at docking station 1015, 1015' for verification.

The information which may be presented on Verification start screen 1471, 1471' may be essentially identical to that displayed in connection with New Order screens 1355, 1355' and Filling screens 1403, 1403'. For convenience and simplicity, reference numbers for information displayed on New Order screens 1355, 1355' and Filling screens 1403, 1403' are used again to identify corresponding fields of information on Verification screens 1471, 1471'. Verification start screens 1471, 1471' may include an identification field 1357 identifying the operator name 1359 (e.g., Red Cross Pharmacy). Optionally, the user name, date and time-of-day on which holder 1013 is being loaded 1360 could be provided. Additional information which may be displayed in connection with Verification screen 1471, 1471' is an Order field 1361 which displays all pending holders 1301, 1301' awaiting verification.

In the examples of FIGS. 67 and 86, a single order 1363 is awaiting verification. Order field 1361 may include a transaction code 1365 (e.g., "ID: 6237") which indicates the transaction corresponding to loading of the holder 1013, 1013' for record-keeping purposes and may indicate the quantity 1367 of holders 1013, 1013' used to fulfill the prescription order. Verification screen 1471, 1471' may also show the holder identifier 1369 (e.g., "Tray Number 1") for each holder 1013, 1013'. The status of the prescription order of Order field 1361 in FIGS. 67 and 86 is indicated as "Incomplete" 1424 because verification has not yet occurred.

The Verification start screen 1471, 1471' prompts the user to initiate verification of a holder 1013, 1013'. The user then selects the holder 1301, 1301' for verification by touching video display 1125 next to the order in Order field 1361 or by another input device, such as a mouse 1129. The user then touches the Check icon 1473 to start the verification process.

Figure 68:
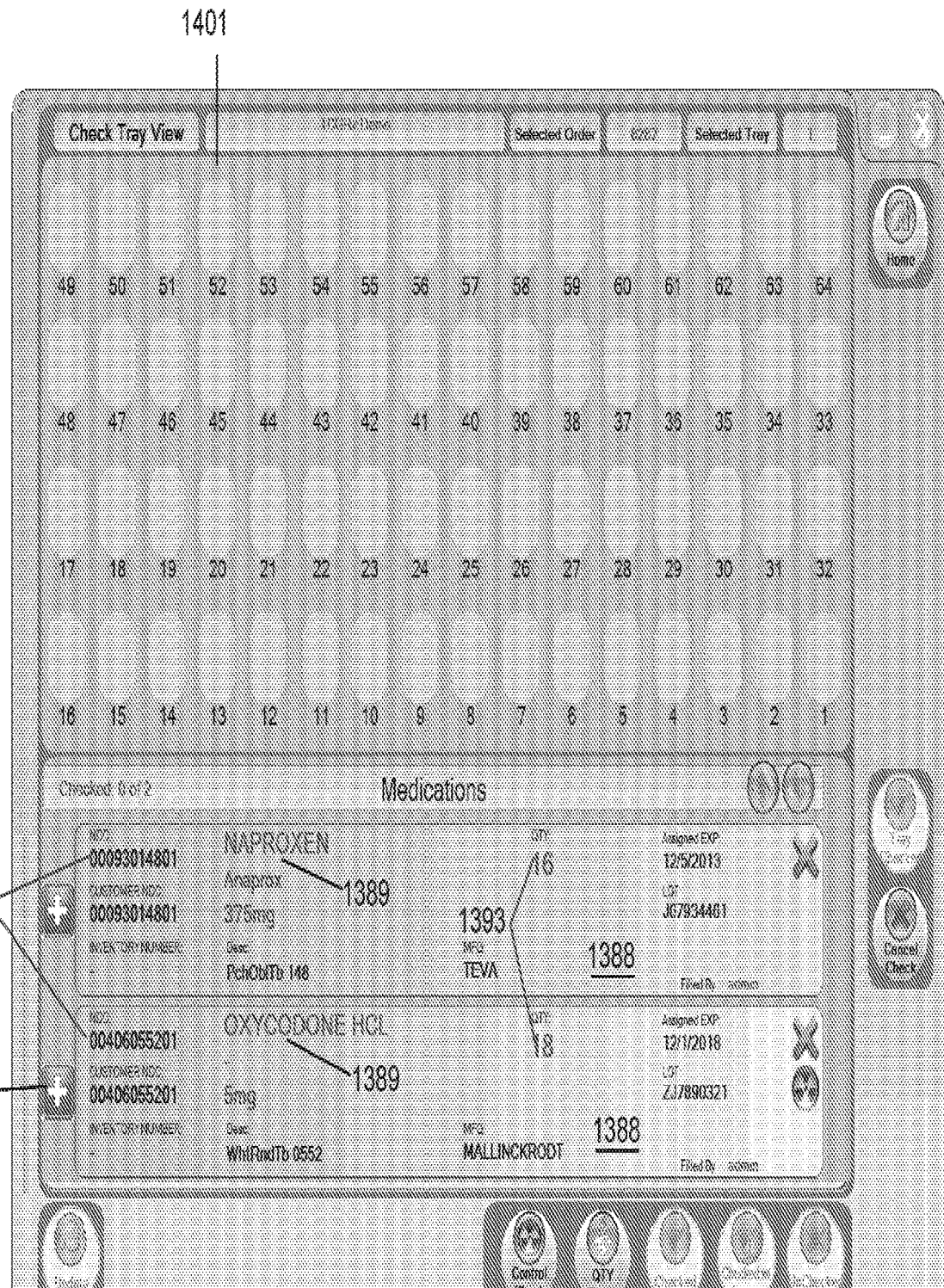
Figure 87:
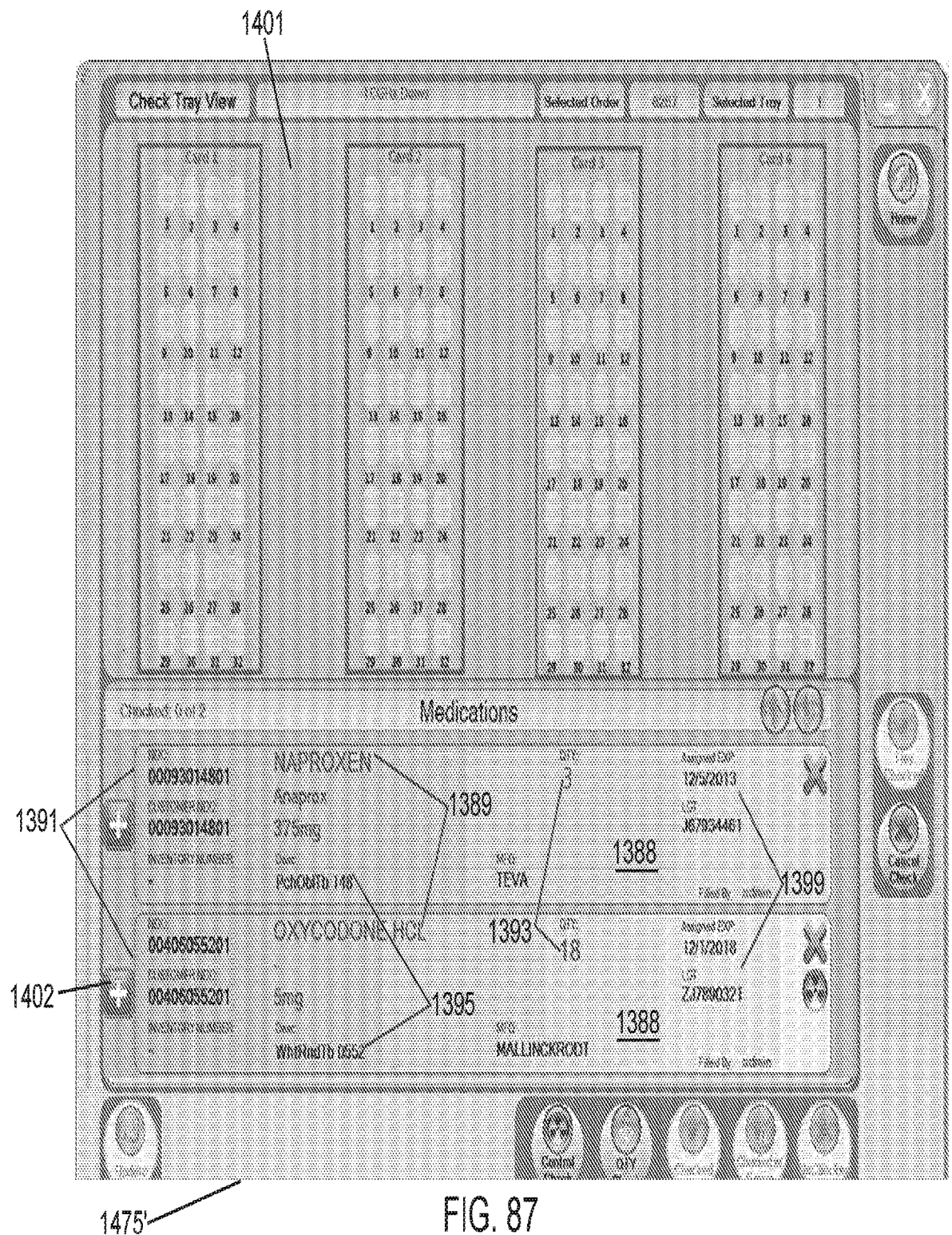

Referring next to FIGS. 68 and 87, Verification screen 1475, 1475' may be displayed for the selected holder 1013, 1013'. In the examples, Verification screen 1475, 1475' preferably includes holder-view field 1401 with a plan view of respective holders 1013, 1013'.

In addition, Medicament-identification field 1388 may appear for each medicament 1011 expected to be in holder 1013, 1013' to assist the user with the verification. Medicament-identification field 1388 may include information identifying one type of the loaded medicaments 1011 including the medicament type and strength 1389 (e.g., "Naproxen Anaprox 375 mg"), FDA and customer NDC numbers 1391 (e.g., 11-digit NDC "00093014801"), medicament 1011 quantity 1393 expected to be loaded in the holder (e.g., "24"), physical appearance 1395 of the medicament 1011 (e.g., "Pch Obl Tb 148"), manufacturer name 1397 (e.g., "TEVA"), expiration date and lot number 1399 (e.g., "Assigned EXP: 12/15/2013" "Lot: J67934461").

A second Medicament-identification field 1388 may include information identifying a second type of the loaded medicaments 1011 expected to be in holder 1013, 1013' including the medicament type and strength 1389 (e.g., "Oxycodone HCL 5 mg), FDA and customer NDC numbers 1391 (e.g., 11-digit NDC "00406055201"), medicament 1011 quantity 1393 expected to be loaded in the holder (e.g., "26"), physical appearance 1395 of the medicament 1011 (e.g., "Wht Rnd Tb 0552"), manufacturer name 1397 (e.g., "Mallinckrodt"), expiration date and lot number 1399 ("Assigned EXP: 12/1/2018" "Lot: ZJ7890321"). Plus "+" symbol 1402 indicates that verification of the medicament 1011 of Medicament ID field 1388 has not yet begun.

Preferably, the transaction code and all other information relating to loading and verification of holder 1013, 1013' is stored in a database 1371 on client computer 1349.

In order to verify that each cell 1033 holds the correct medicament 1011, the user simply selects the Medicament-identification field 1388 to be verified by touching the screen display 1125 next to the field 1388 or by using another input device such as a mouse 1129 or keyboard 1127.

Figure 69:
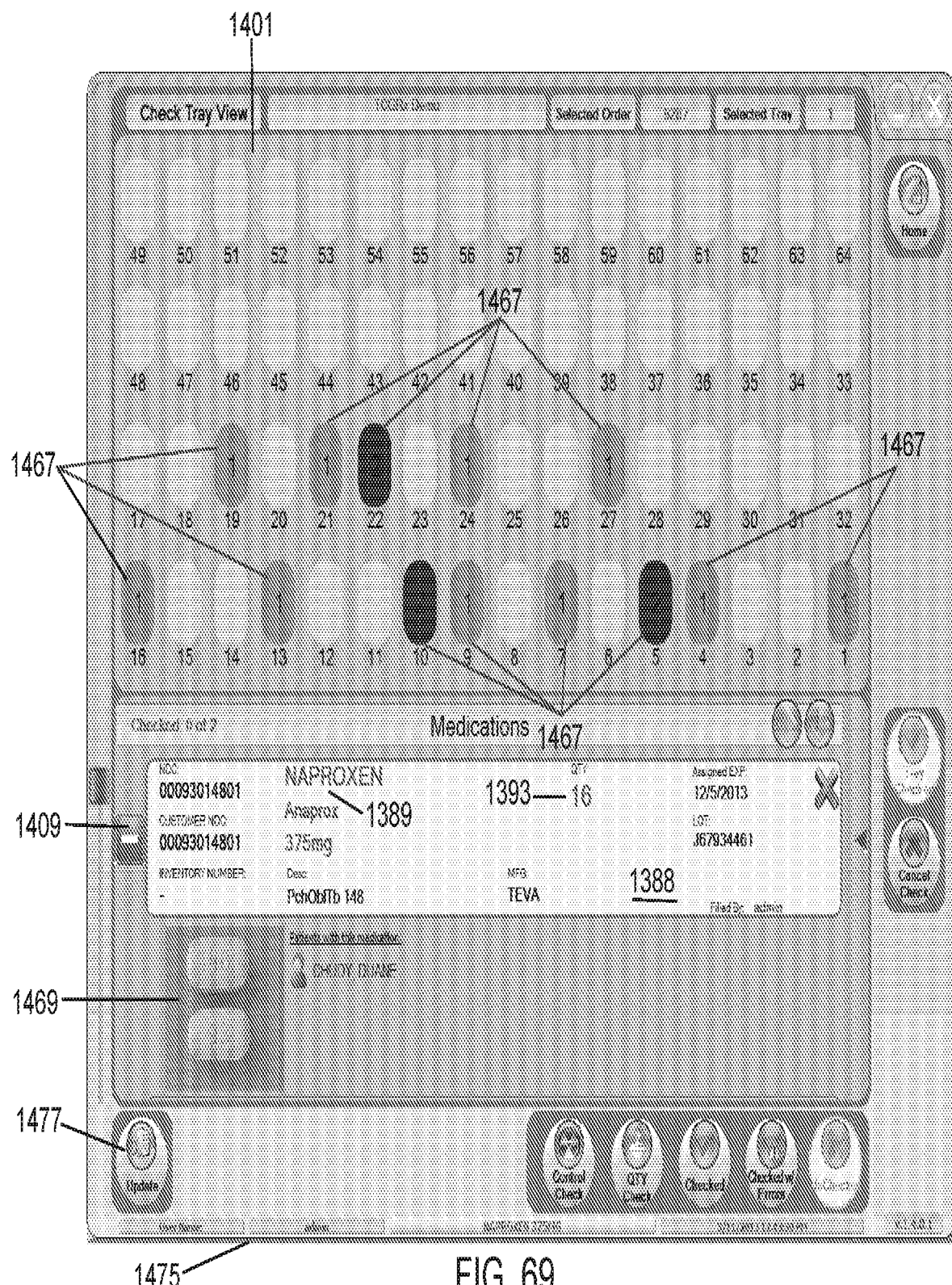
Figure 88:
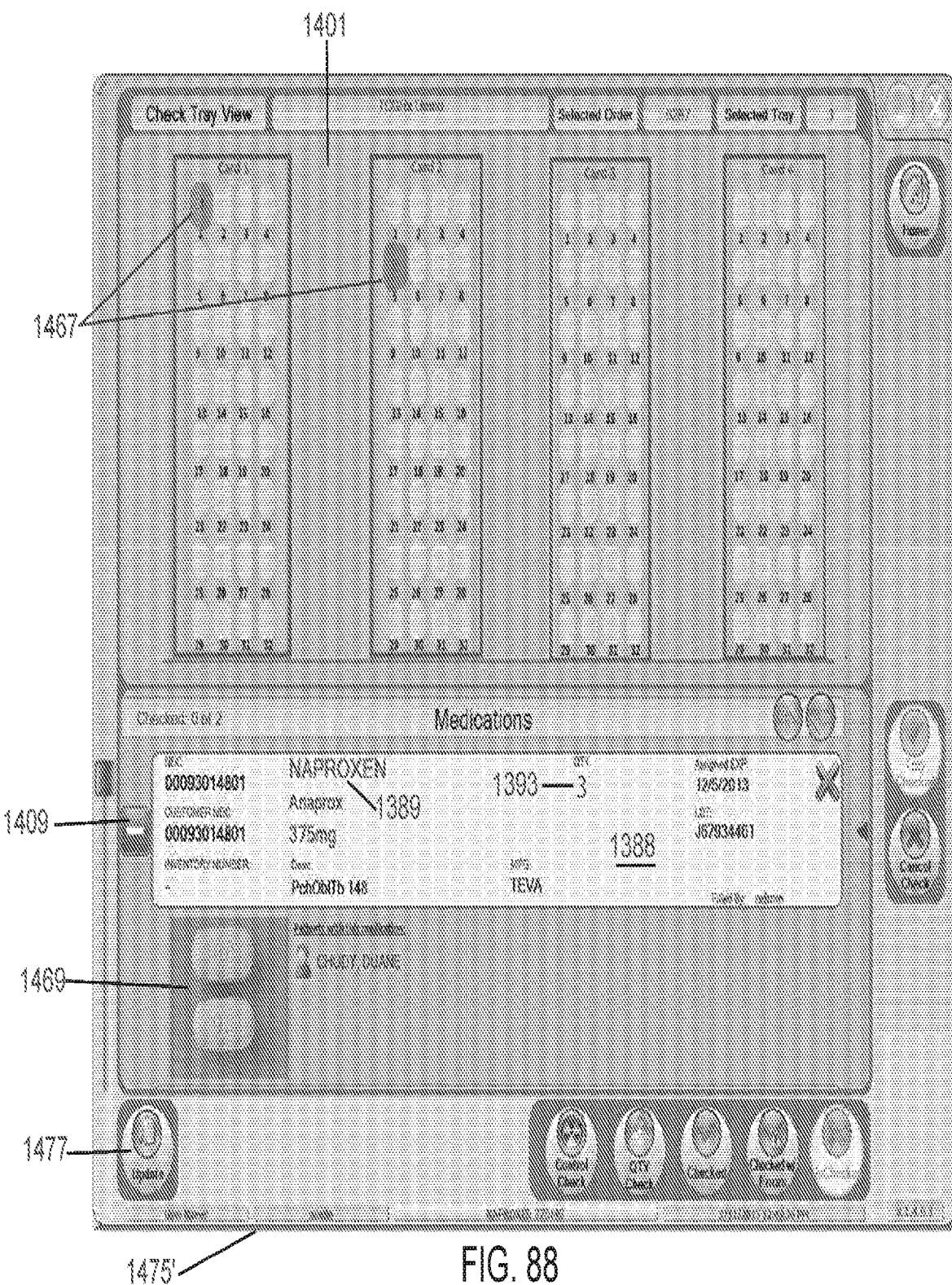

Referring next to FIGS. 69 and 88, Verification screen 1475, 1475' may be displayed responsive to selection of one of the Medicament-identification fields 1388. FIGS. 69 and 88 show examples of displayed information for verification of a total of 16 Naproxen tablets previously loaded into the openings 1317 and cells 1033 indicated by the human-readable indicia 1323 for the cells numbered "1, 4, 5, 7, 9, 10, 13, 16, 19, 21, 22, 24, 27" of holder 1013 and the single Naproxen loaded in cell numbered "1" of holder 1013'. Selection of the Naproxen tablets for verification is also indicated in the examples by highlighting the cells 1467 expected to include the Naproxen and highlighting the Medicament-identification field 1388 for Naproxen. Dash "-" symbol 1409 indicates the Medicament-identification field 1388 is being processed for verification. A reference image 1469 may be displayed to the user to assist with the verification process. The Medicament-identification field 1388 associated with the Oxycodone HCL medicaments 1011 can be turned off during verification of the Naproxen in the examples.

Also upon selection of the exemplary Medicament-identification field 1388 for the Naproxen, controller 1017 again selectively activates each indicator for the cell(s) 1033 to be verified by the pharmacist. In the example of system 1010, indicators 1049, 1049', 1049' of docking station 1015 and holder 1013 are activated and in the example of system 1010' indicators 1049, 1049' of docking station 1015' are activated. In the examples, each other indicator 1049, 1049', 1049" is inactive.

As with the loading process illustrated in FIGS. 28-28A, 42-42A, 57 and 76, this pick-to-light/place to light capability enables the user to rapidly confirm that the correct medicament 1011 has been loaded into the correct cell 1033 without the necessity for reliance on written verification instructions. The user can quickly look with her eyes into each cell 1033 and can see the medicament 1011 in the cell 1033. The user can compare the physical appearance of each medicament 1011 in each indicated cell 1033 without the necessity of reliance solely on written instructions. This process is facilitated by presentation of the reference image 1469 as the user can quickly compare the appearance of the medicament 1011 on screen Verification screen 1475, 1475' with the appearance of the medicament(s) 1011 in each highlighted cell 1033 associated with the activated indicators 1049, 1049', 1049".

Selection of the Update icon 1477 completes verification for Medicament-identification field 1388 and the exemplary Naproxen. Once all cells 1033 associated with a Medicament-identification field 1388 are verified, the user then selects the next Medicament-identification field 1388 to be verified. This process is repeated until all medicaments 1011 have been verified as called for by Verification screen 1475, 1475'.

Figure 70:
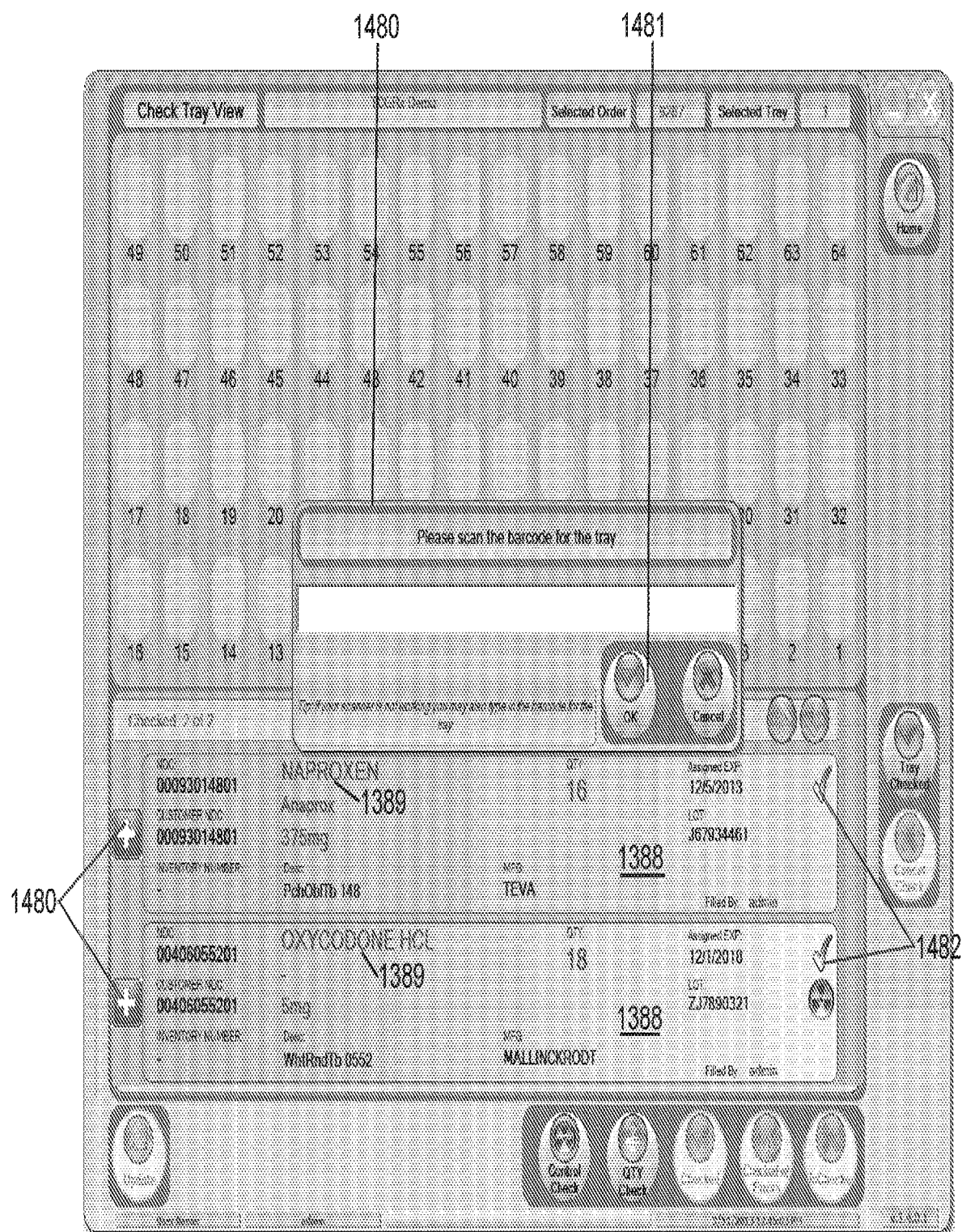
Figure 89:
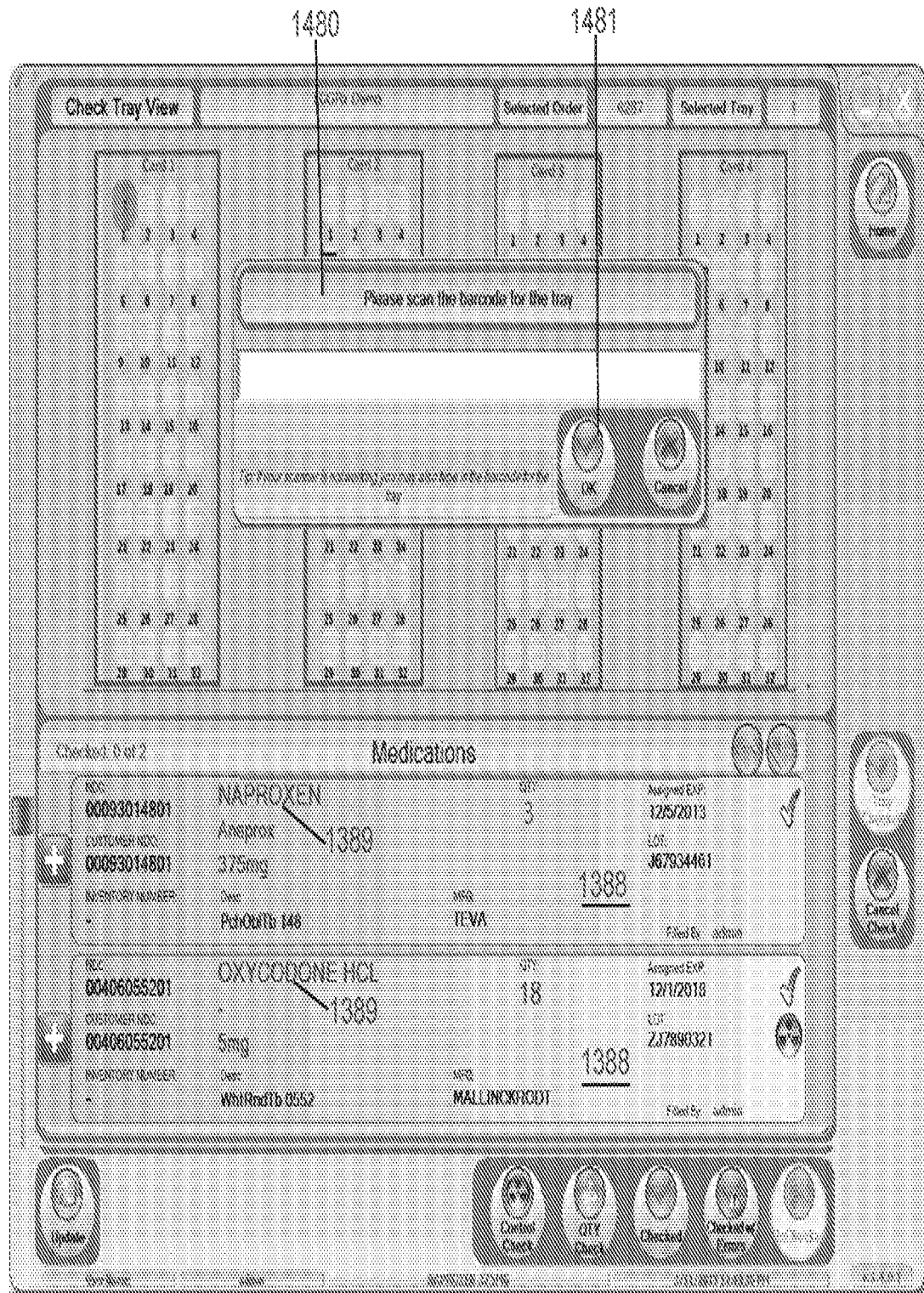

Referring next to FIGS. 70 and 89, once all Medicament-identification fields 1388 and medicaments 1011 are verified, controller 1017 displays a Barcode scan Field 1480 with instructions prompting the user to scan a bar code 1132 on the holder 1013, 1013' with bar code scanner 1131. Scanning of the bar code 1132 and touching the OK icon 1481 sends a signal to controller 1017 indicating to system 1010, 1010' that holder 1013 has been fully verified and that the medicament 1011 contents are in the correct cells 1033 ready for use with automated dispensing machine 45 or that holder 1013' has been fully verified and that the medicament 1011 contents are in the correct cells 1033 and that holder 1013' is ready to be sealed by closure 1042. Plus "+" symbol 1480 indicates that the medicaments 1011 of Medicament-identification field 1388 are no longer being processed and the symbol 1482 indicates that the medicaments of Medicament-identification field 1388 have been verified and the records of database 1371 are updated accordingly.

Figure 71:
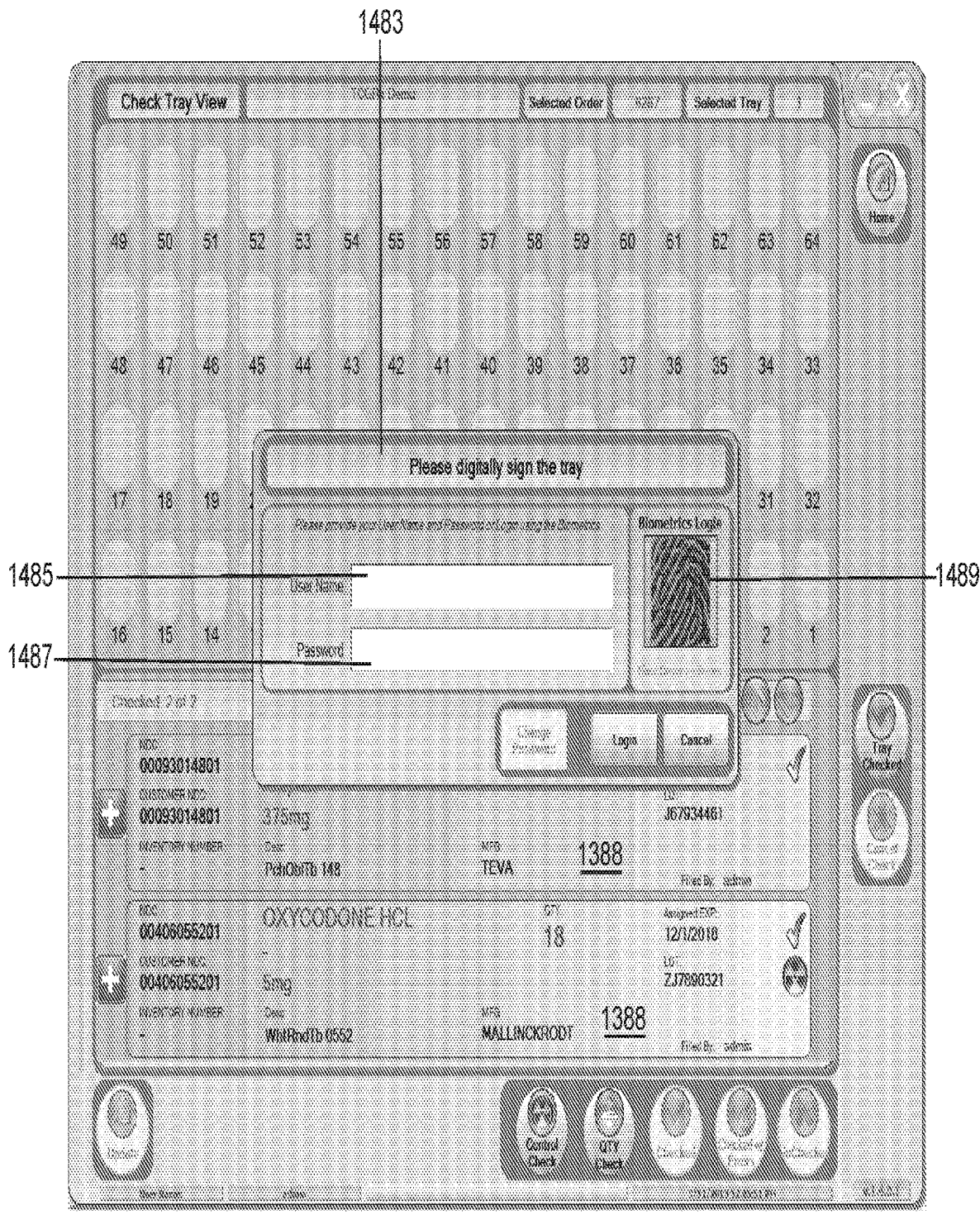
Figure 90:
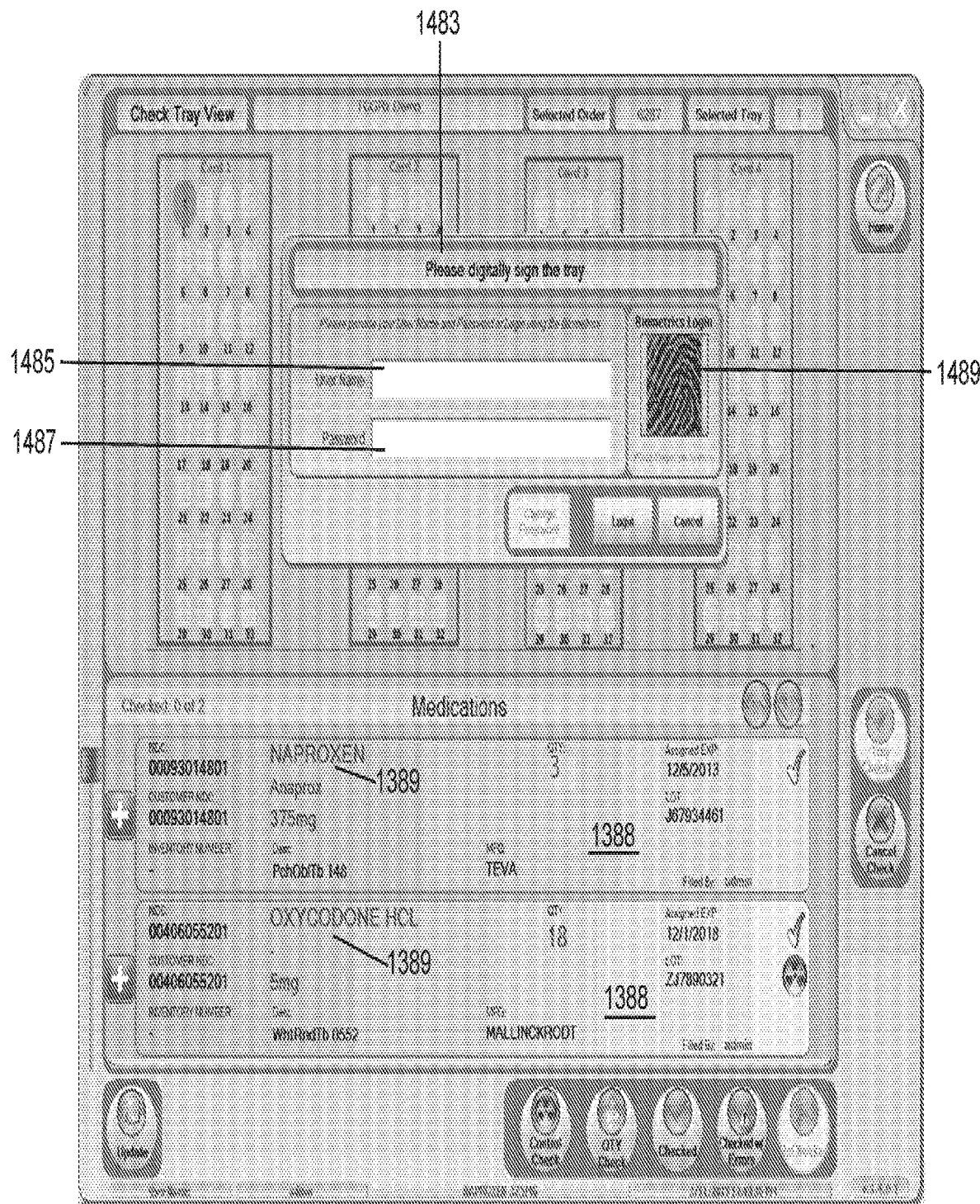

Referring next to FIGS. 71 and 90, controller 1017 displays a Digital signature field 1483 with instructions prompting the user to digitally sign the holder creating a record in database 1371 of the user responsible for the verification. The user can enter a digital signature by keying in her user name in the user name field 1485 and keying in her password in the password field 1487. Alternatively, a biometric prompt 1489 prompts the user to place her thumb on biometric scanner 1130. The biometric scan serves as the digital signature.

Figure 72:
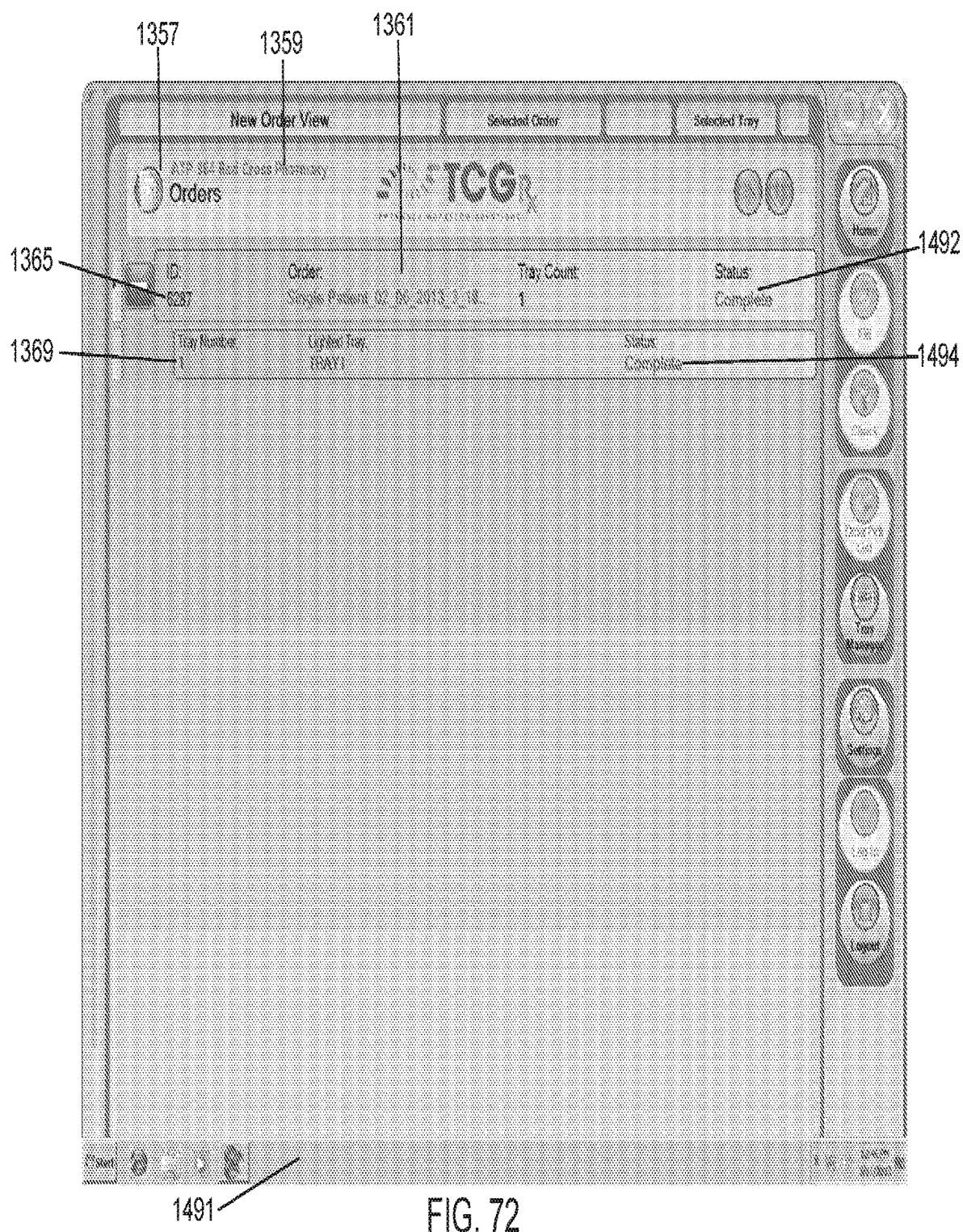
Figure 91:
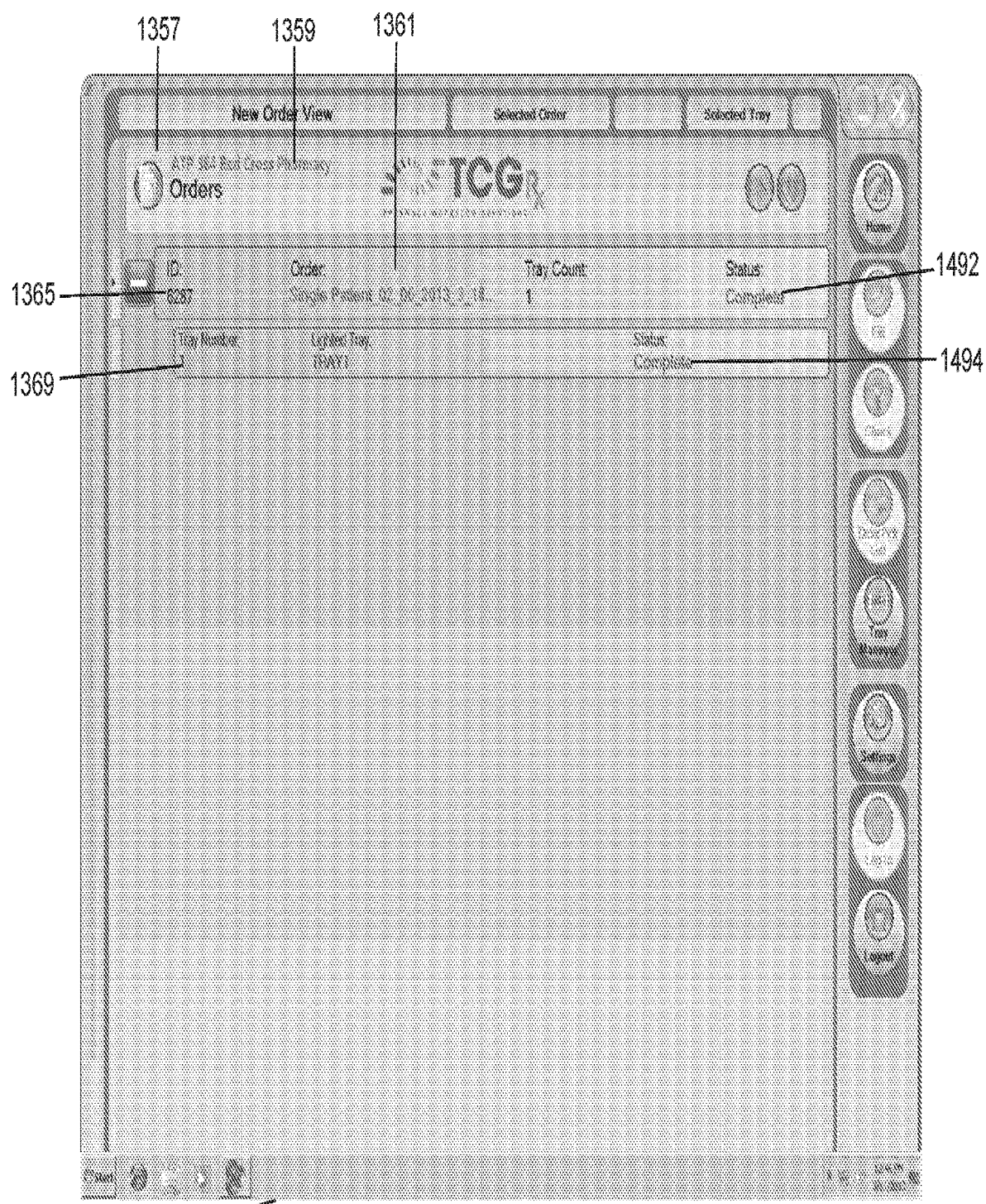

Referring to FIGS. 72 and 91, Verification complete screen 1491, 1491" may be displayed. Information identifying the prescription order may appear identical to that from Verification start screen 1471, 1471' (FIGS. 67, 86). The status of the prescription order in Order field 1361 may be indicated as Complete 1492 indicating that it has been verified as correct and the status of the holder 1013, 1013' may be indicated as Complete 1494 confirming that the medicaments 1011 in holders 1013, 1013' have been verified as correct.

A record may be made of the verified medicament 1011 contents of holder 1013, 1013' cells 1033 which may be stored in database 1371 residing on controller 1017. Such a record is useful in further confirming that the correct medicaments 1011 were loaded in holder 1013, 1013'. Each verified holder 1013 can then be stored in cabinet 169 awaiting use, or the holder 1013 and its medicament 1011 contents can be taken directly to automated dispensing machine 45 for immediate loading of medicaments 1011 into exception storage apparatus 43. Holder 1013' is preferably immediately sealed with closure 1042 and is labeled 1044 with patient-specific information or other identifying information if holder 1013' is not intended for a specific patient.

Holder 1013 of system 1010 may be utilized to transfer the organized medicaments 1011 in holder cells 1033 to an exception storage apparatus 43 of exemplary automated dispensing machine 45 of the same type as described above in connection with FIGS. 18, 19, 20, 21A, 21B, and 21C. For convenience and brevity, the structure and operation of exemplary automated dispensing machine 45 is incorporated herein by reference and will not be fully described here in connection with holder 1013. An exemplary automated dispensing machine 45 which may be used with holder 1013 is a model ATP 320, 371, or 384 dispensing machine available from. Chudy Group, LLC of Powers Lake, Wis.

Holder 1013 is a lightweight portable device which may be conveniently loaded at a workstation separate from automated dispensing machine 45. This permits holder 1013 to be loaded at a time and sequence in the work day that is convenient to the pharmacy. After loading and optional verification, holder 1013 may be easily carried by a user from the workstation or a storage cabinet 169 to exception storage apparatus 43 so that the medicaments 1011 can be accurately, quickly and easily, transferred to exception storage apparatus 43 and automated dispensing machine 45. If automated dispensing machine 45 must be shut down (i.e., deactivated to permit the transfer of medicaments 1011 to exception storage apparatus 43, then the rapid transfer of medicaments 1011 made possible by use of holder 1013 minimizes that downtime in the same manner as described above for holder 13. The transferred medicaments 1011 may then be packaged by automated dispensing machine 45 into separate pouches 202 formed (e.g., by heat-sealing or sonic welding) in a web of packaging material 204 in the same manner as illustrated in FIG. 22.

Referring then to FIGS. 18-21C, exception storage apparatus 43 is a drawer or tray-like device which can be pulled out from cabinet 191 of automated dispensing machine 45. When exception storage apparatus 43 is pulled out, automated dispensing machine 45 is temporarily shut down and is out of service and unavailable to fill prescription orders and dispense requests. Exception storage apparatus 43 illustrated in FIGS. 19-20 can be described as having a somewhat flat and narrow configuration with a plurality of cells 41 provided therein. Each cell 41 of exception storage apparatus 43 is capable of storing one medicament 1011, or a small quantity of medicaments 1011, as illustrated in FIGS. 21A-22. In the example, cells 41 include 64 total cells grouped in four rows of 16 cells, the same pattern as cells 1033 of holder 1013.

As described above, medicaments 1011 transferred to cells 41 of exception storage apparatus 43 cells 41 are indexed for movement along a track (not shown) in exception storage apparatus 43. Cells 41 are indexed forward along the track toward an opening (not shown) in the bottom of apparatus 43 so that the contents of each cell 41 fall through a cell bottom opening (not shown) and to a packaging device within automated dispensing machine 45 through chutes, hoppers or other guide structure, or by a mechanical device such as an auger. Medicaments 1011 may be discharged from cells 41 by any other suitable means including a movable gate (not shown) over a cell bottom outlet (not shown), or by a solenoid, air-powered actuator, air-jet, or mechanical arm which ejects the medicament through an upper cell inlet 209 of the type shown in FIG. 19A. The medicaments 1011 fall via chutes, guides to a packaging device or are directed to packaging device by mechanical means (e.g. an auger).

Also as described above, exemplary automated dispensing machine 45 includes a pouch-package-type packaging apparatus (not shown) within a lower portion of cabinet 191. Alternatively, packaging apparatus capable of packaging medicaments 1011 into other container types (e.g., bottles, vial, blister packages) may be utilized. A pouch-package-type packaging device includes a form-fill-seal packaging device. Packaging apparatus is preferably a "form-fill-seal" packaging device which forms a package (i.e., a pouch) in a web of packaging material 204, fills the package 202 with the medicament(s), and seals the package 202 forming a plurality of discrete packages 202, or pouches.

In the examples, one or more medicament 1011 discharged from the cassette-type storage apparatus (not shown) of automated dispensing machine 45 described previously or exception storage apparatus 43 is loaded into separate pouches 202 formed (e.g., by heat-sealing or sonic welding) in a web of packaging material 204 as illustrated in FIG. 22. Information can be printed on each pouch 202 by a printer (not shown) associated with automated dispensing machine 45 and such information can include the patient's name 206, medicament name and quantity 208, prescription number 210, date 212, instructions for taking the medicament 214 (such as time of day the medicament is to be taken) and machine-readable indicia 216 (such as a bar code) representative of the aforesaid information. As above, pouch packages 202 are ideal for use in administering medication regimens because the exact medicaments 1011 to be taken at a given time can be packaged together in a single pouch package 202, and the pouches can be organized and labeled in the exact order in which each medicament 1011 is to be taken, for example, morning, noon and evening.

Transfer of medicaments 1011 from holder cells 1033 to exception storage apparatus 43 is accomplished in the same manner as described in connection with FIGS. 21A-21C. Holder 1013 may be placed directly on top of exception storage apparatus 43 in the same manner as shown in FIG. 20 and FIGS. 21A-21C with each cell 1033 and 41 completely aligned and in registry. As previously described, holder 1013 and exception storage apparatus 43 each have 64 total cells 1033, 41 grouped in four rows of 16 cells. Human-readable indicia 211 is preferably provided on exception storage apparatus 43 (FIG. 19A) so that each cell 1033 on holder 1013 has the same indicia 1047 as indicia 211 on exception storage apparatus 43. The cell 1033 pattern and indicia 1047 of holder 13 is most preferably identical to the cell 41 pattern and indicia 211 of exception storage apparatus 43.

Referring again to FIGS. 20 and 21A-21C, the holder 1013 which is preferably verified as correct is taken to exception storage apparatus 43 of automated dispensing machine 45 by a user or pharmacist. Holder 1013 is set on top of exception storage apparatus 43 in the same manner as illustrated in FIG. 20. Legs 1051, 1053 position holder 1013 over exception storage apparatus 43 as shown, for example, in the same manner as holder 13 in FIGS. 21A-21C to ensure that holder 1013 is in the correct orientation on exception storage apparatus 43 with correct alignment of cells 1033, 41. Once aligned, holder 1013 is initially in the position shown in FIG. 21A in the same manner as holder 13.

If holder 1013 includes an identification element 1081 and automated dispensing machine 45 includes an identification element detector 84, then the detector 84 may identify holder 1013. If the correct holder 1013 is positioned over exception storage apparatus 43, the user is given a prompt signal by video display 201 to proceed with transfer of the medicaments 1011. If an incorrect holder 1013 is positioned over exception storage apparatus 43, then display 201 prompts the user to not transfer the medicaments 1011 and may present an error message and/or alarm. In addition, system 1010 may deactivate automated dispensing machine 45 preventing further operation until the correct holder 1013 is in place or the user overrides the system 1010.

Prior to medicament 1011 transfer and as shown in FIG. 21A, shuttle member 1055 is in the same position as shuttle member 55 in a "closed" position with cell 1033 outlets 1039 covered by shuttle member 1055 in the same manner as cells 33 are closed in FIG. 21A. Medicaments 1011 cannot exit cells 1033 in this closed position.

Next, the user grasps pull 1061 and moves shuttle member 1055 in the same manner as pull 61 is moved in the direction of arrow 217 in FIG. 21B. Translating movement of shuttle member 1055 partially opens cell outlets 1039 as openings 1059 in shuttle member 1055 are aligned with cell outlets 1039. As a result, medicaments 1011 begin to fall by means of gravity into the aligned cells 41 of exception storage apparatus 43 in the same manner as medicaments 11 fall from cells 33 in FIG. 21B.

Finally, the user moves shuttle member 1055 fully to the "open" position in the same manner as shuttle member 55 is moved in the direction of arrow 217 in FIG. 21C. Cells 1033 are fully open in this position causing medicaments 1011 in cells 1033 to fall into the corresponding cells 41 of exception storage apparatus 43 in the same manner as medicaments 11 fall into exception storage apparatus 43 illustrated in FIG. 21C. Exception storage apparatus 41 is now correctly loaded and is ready for dispensing and packaging of the slow mover medicaments 1011 stored in cells 41. This loading process, which is the same as shown in FIGS. 21A-21C in the example, is very rapid (less than one minute) and enables automated dispensing machine 45 to be quickly returned to service.

Holder 1013' of system 1010' is the container in which medicaments 1011 are ultimately delivered to the patient. Before or after loading of holder 1013', a label 1044 may be applied to holder 1013 as previously described (FIG. 44). Once loaded and verified, holder 1013' may be closed with closure 1042 in a conventional manner for blister-package-type containers.

Systems 1010, 1010' accurately and rapidly enable loading of medicaments 1011 in the exact order in which the medicaments 1011 are to be loaded into exception storage apparatus 43 of packaged in a container (e.g., a blister-package-type holder 1013') for use by a specific patient or for another purpose. Sensor guide 1301, 1301' provides the option for positive feedback indicative that the medicaments 1011 were loaded correctly or that an error has occurred. The use of indicators 1049, 1049', 1049", and 1049'" permits a user (e.g., a technician or pharmacist) to load and optionally verify the contents of holder 1013, 1013' without having to take his of her eyes off of the holder 1013, 1013' to read instructions thereby reducing the amount of time needed to load and optionally verify each holder 1013, 1013'.

Providing the correct medicament 1011 to the patient provides for a better level of patient care. Time saved in the fulfillment of prescription orders can be utilized for other purposes, such as counseling patients. Thus, systems 1010, 1010' provide the opportunity for improvements in patient care.

While the principles of this invention have been described in connection with specific, embodiments, it should be understood clearly that these descriptions are made only by way of example and are not intended to limit the scope of the invention.

What is claimed is:

1. A method for controlling a system for loading at least one type of medicament according to at least one prescription order, the method comprising:
    providing a tray, the tray having walls defining plural cells arranged in a pattern, each cell having an upper opening, the tray being portable;
    docking the tray in a docking station;
    providing a controller operatively associated with the docking station and with visible information sources, the visible information sources configured to generate visible information indicating at least yes and no states such that the visible information is viewable proximate the cells of the tray;
    via the controller, generating with the visible information sources the visible information such that the yes state information is visible proximate one or more cells of the tray into which a medicament is to be loaded;
    loading the medicament into the one or more cells proximate the yes state information through the upper opening of the cell;
    detecting the loading of the medicament into the one or more cells by at least one sensor associated with the one or more cells;
    repeating the generating, loading, and detecting steps until all required medicaments are loaded into the cells of the tray; and
    removing the tray from the docking station and placing the tray in an automatic dispensing machine, the automated dispensing machine being configured to automatically dispense medicaments into blister packages.

2. The method of claim 1 wherein the pattern of cells in the tray is compatible with an arrangement of cells in a blister package.

3. The method of claim 2 wherein the tray holds at least one blister package with the cells of the at least one blister package nested within the cells of the tray.

4. The method of claim 1 further comprising the step of generating a signal in response to the detecting by the at least one sensor.

5. The method of claim 4 wherein the signal is generated in response to an error in loading the medicament into an incorrect cell of the tray.

6. The method of claim 4, wherein the signal is generated in response to an incorrect number of medicaments being loaded into a cell of the tray.

7. The method of claim 1 further comprising creating a record of loading of the tray.

8. The method of claim 7 wherein the record comprises information provided by the at least one sensor.

9. The method of claim 4 wherein the signal comprises a visible change in the visible information source.

10. The method of claim 9 wherein the visible information sources comprise LEDs.

11. The method of claim 10 wherein the change in the visible information source comprises a change in state of the LED.

12. The method of claim 10 wherein the LEDs are multi-colored.

13. The method of claim 12 wherein the change in the visible information source comprises a change in the color of the LED.

14. The method of claim 6 wherein the error that is detected is a greater quantity of medicament is deposited in a cell and the signal generated is an overcount warning.

15. The method of claim 6 wherein the error that is detected is fewer than the expected quantity of medicament is deposited in a cell and the signal generated is an undercount warning.

16. The method of claim 1, further comprising the step of receiving prescription information for the at least one prescription order identifying a medicament to be loaded into the tray, the receiving step being performed prior to the generating step.

* * * * *

UNITED STATES PATENT AND TRADEMARK OFFICE
CERTIFICATE OF CORRECTION

PATENT NO. : 11,756,669 B2
APPLICATION NO. : 17/735679
DATED : September 12, 2023
INVENTOR(S) : Chudy et al.

It is certified that error appears in the above-identified patent and that said Letters Patent is hereby corrected as shown below:

In the Specification

Column 18, Line 2: Please correct "cassettes, " to read --(e.g., cassettes,--

Column 18, Line 46: Please correct "10)" to read --10')--

Column 19, Line 11: Please correct "10)" to read --10')--

Column 26, Line 67: Please correct "1049', 1049'" to read --1049', 1049'''--

Column 28, Line 34: Please correct "1013''" to read --1013'--

Column 28, Line 66: Please correct ""John Doe")" to read --(e.g., "John Doe")--

Column 31, Line 28: Please correct "1013" to read --1013'--

Column 32, Line 40: Please correct "1015, 1015" to read --1015, 1015'--

Column 35, Line 55: Please correct "1301, 1301''" to read --1301, 1301'--

Column 36, Line 44: Please correct "1049''" to read --1049'''--

Column 37, Line 13: Please correct "colons" to read --columns--

Column 38, Line 47: Please correct "1015''" to read --1015'--

Column 38, Line 64: Please correct "1049'" to read --1049'''--

Column 41, Line 67: Please correct "130F" to read --1301'--

Signed and Sealed this
Twenty-first Day of November, 2023

Katherine Kelly Vidal
*Director of the United States Patent and Trademark Office*

CERTIFICATE OF CORRECTION (continued)
U.S. Pat. No. 11,756,669 B2

Column 45, Line 43: Please correct "131" to read --1317--

Column 47, Line 33: Please correct "phis" to read --plus--